(12) United States Patent
Goyvaerts et al.

(10) Patent No.: US 12,201,610 B2
(45) Date of Patent: Jan. 21, 2025

(54) COMPOSITIONS COMPRISING ATICAPRANT

(71) Applicant: Janssen Pharmaceuticals, Inc., Titusville, NJ (US)

(72) Inventors: Nicolaas Martha Felix Goyvaerts, Beerse (BE); Mark Schmidt, Antwerp (BE); Vanina Popova, Nijlen (BE); Adam Savitz, Greenwich, CT (US); Rama Melkote, Basking Ridge, NJ (US); Wayne C. Drevets, Rancho Santa Fe, CA (US); Srihari Gopal, Belle Mead, NJ (US); Darrel Pemberton, Oud Turnhout (BE); Chakradhar Lagishetty, King of Prussia, PA (US); Iva Kezic, Antwerp (BE); Mahesh N. Samtani, Flemington, NJ (US); Tom Huybrechts, Merelbeke (BE); Geert Van der Avoort, Retie (BE); Matthieu Ravelingien, Geel (BE); Laura Martinez Marcos, Antwerp (BE); Tatiana Marcozzi, Antwerp (BE); Katarina Jokicevic, Mortsel (BE)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 0 days.

(21) Appl. No.: 18/618,520

(22) Filed: Mar. 27, 2024

(65) Prior Publication Data
US 2024/0269110 A1 Aug. 15, 2024

Related U.S. Application Data

(63) Continuation of application No. 18/179,093, filed on Mar. 6, 2023, now abandoned.

(60) Provisional application No. 63/317,471, filed on Mar. 7, 2022.

(51) Int. Cl.
| | |
|---|---|
| *A61K 9/20* | (2006.01) |
| *A61K 9/28* | (2006.01) |
| *A61K 9/48* | (2006.01) |
| *A61K 31/40* | (2006.01) |
| *A61K 45/06* | (2006.01) |
| *A61P 25/24* | (2006.01) |

(52) U.S. Cl.
CPC ............ *A61K 31/40* (2013.01); *A61K 9/2009* (2013.01); *A61K 9/2013* (2013.01); *A61K 9/2018* (2013.01); *A61K 9/2054* (2013.01); *A61K 9/2853* (2013.01); *A61K 9/4825* (2013.01); *A61K 9/4858* (2013.01); *A61K 9/4866* (2013.01); *A61K 45/06* (2013.01); *A61P 25/24* (2018.01)

(58) Field of Classification Search
CPC .......... A61K 9/14; A61K 9/141; A61K 9/145; A61K 9/16; A61K 9/1605; A61K 9/1623; A61K 9/1652; A61K 9/20; A61K 9/2004; A61K 9/2018; A61K 9/205; A61K 9/2077; A61K 9/28; A61K 9/2806
See application file for complete search history.

(56) References Cited

U.S. PATENT DOCUMENTS

| | | | |
|---|---|---|---|
| 5,457,208 A | 10/1995 | Portoghese et al. | |
| 6,391,873 B1 | 5/2002 | Jenck et al. | |
| 6,528,518 B2 | 3/2003 | Carlezon, Jr. | |
| 7,196,100 B2 | 3/2007 | Benesh et al. | |
| 7,288,543 B2 | 10/2007 | Broughton et al. | |
| 7,378,448 B2 | 5/2008 | Mitch et al. | |
| 7,381,719 B2 | 6/2008 | Blanco-Pillado et al. | |
| 7,381,750 B2 | 6/2008 | De et al. | |
| 7,396,943 B2 | 7/2008 | Benesh et al. | |
| 7,399,774 B2 | 7/2008 | Siegel et al. | |
| 7,414,132 B2 | 8/2008 | De et al. | |
| 7,531,557 B2 | 5/2009 | Mitch | |
| 7,560,463 B2 | 7/2009 | Mitch et al. | |
| 7,709,522 B2 * | 5/2010 | Buezo ................. A61P 25/18 514/429 |
| 8,063,059 B2 | 11/2011 | Hermann | |
| 8,173,695 B2 | 5/2012 | Diaz et al. | |
| 10,676,469 B2 | 6/2020 | Roberts et al. | |
| 11,266,627 B1 | 3/2022 | Schmidt et al. | |
| 11,998,525 B2 | 6/2024 | Schmidt et al. | |
| 2002/0052365 A1 | 5/2002 | Hanns et al. | |
| 2002/0132828 A1 | 9/2002 | Carroll et al. | |
| 2004/0082573 A1 | 4/2004 | Cook et al. | |
| 2006/0052439 A1 | 3/2006 | Beguin et al. | |
| 2007/0155793 A1 | 7/2007 | Benesh | |
| 2007/0213394 A1 | 9/2007 | Beguin et al. | |
| 2008/0207701 A1 | 8/2008 | Chappell et al. | |

(Continued)

FOREIGN PATENT DOCUMENTS

| | | |
|---|---|---|
| CN | 114195693 A | 3/2022 |
| WO | 02/53533 A2 | 7/2002 |

(Continued)

OTHER PUBLICATIONS

"Guidance for Industry—Q3A Impurities in New Drug Substances", Revision 2, U.S. Department of Health and Human Services, Jun. 2008, pp. 1-14.

(Continued)

Primary Examiner — Micah Paul Young
(74) Attorney, Agent, or Firm — BakerHostetler

(57) ABSTRACT

The present disclosure relates to compositions, including oral compositions in the form of tablets, comprising aticaprant and methods of using the same.

19 Claims, 29 Drawing Sheets

(56) References Cited

U.S. PATENT DOCUMENTS

| | | |
|---|---|---|
| 2008/0255152 A1 | 10/2008 | Blanco-Pillado et al. |
| 2008/0269296 A1 | 10/2008 | Blanco-Pillado et al. |
| 2009/0023785 A1 | 1/2009 | Pedregal-Tercero et al. |
| 2009/0186873 A1 | 7/2009 | Buezo et al. |
| 2009/0196824 A1 | 8/2009 | Elman et al. |
| 2010/0197669 A1 | 8/2010 | Diaz Buezo et al. |
| 2013/0303497 A1 | 11/2013 | Hansen et al. |
| 2015/0005315 A1 | 1/2015 | Carroll et al. |
| 2016/0310488 A1 | 10/2016 | Morillo et al. |
| 2018/0072654 A1 | 3/2018 | Schmidhammer et al. |
| 2018/0148432 A1 | 5/2018 | Kablaoui et al. |
| 2018/0169065 A1 | 6/2018 | Kellar et al. |
| 2019/0008806 A1* | 1/2019 | Singh ........................ A61P 25/02 |
| 2019/0023700 A1 | 1/2019 | Guerrero et al. |
| 2019/0117637 A1 | 4/2019 | Frazer et al. |
| 2019/0240293 A1 | 8/2019 | Weinstein et al. |
| 2019/0255036 A1 | 8/2019 | Kariman |
| 2019/0263781 A1 | 8/2019 | Carroll et al. |
| 2019/0298703 A1 | 10/2019 | Bhide et al. |
| 2020/0121236 A1 | 4/2020 | Gao et al. |
| 2020/0171025 A1* | 6/2020 | Parella ................. A61K 31/496 |
| 2021/0024576 A1 | 1/2021 | Aldrich et al. |
| 2021/0047310 A1 | 2/2021 | Roberts et al. |
| 2022/0370409 A1 | 11/2022 | Schmidt et al. |
| 2023/0233525 A1 | 7/2023 | Schmidt et al. |
| 2023/0277499 A1 | 9/2023 | Fernandes et al. |
| 2023/0277500 A1 | 9/2023 | Goyvaerts et al. |
| 2023/0348377 A1 | 11/2023 | Surmont et al. |

FOREIGN PATENT DOCUMENTS

| | | |
|---|---|---|
| WO | 2004/026305 A1 | 4/2004 |
| WO | 2008/021849 A2 | 2/2008 |
| WO | 2008/021851 A2 | 2/2008 |
| WO | 2008/032156 A1 | 3/2008 |
| WO | 2009/094260 | 7/2009 |
| WO | 2015/091833 A1 | 6/2015 |
| WO | 2016/156396 A1 | 10/2016 |
| WO | 2016/191763 A2 | 12/2016 |
| WO | 2017/218518 A1 | 12/2017 |
| WO | 2018/022664 A1 | 2/2018 |
| WO | 2018/022666 A1 | 2/2018 |
| WO | 2018/022668 A2 | 2/2018 |
| WO | 2018/053222 A1 | 3/2018 |
| WO | 2018/096510 A1 | 5/2018 |
| WO | 2018/170492 A1 | 9/2018 |
| WO | 2019/183556 A1 | 9/2019 |
| WO | 2020/086729 A1 | 4/2020 |
| WO | 2022/234457 A1 | 11/2022 |

OTHER PUBLICATIONS

A-Hakeim et al., "In major depression, increased serum dynorphin and kappa opioid receptor levels are positively associated with mu opioid receptor levels and immune activation and are attenuated by nicotine dependence", ResearchGate, XP093024086, Apr. 1, 2019, pp. 1-39.

Berge et al., "Pharmaceutical Salts", Journal of Pharmaceutical Sciences, Jan. 1977, vol. 66 No. 1, pp. 1-19.

Borbely et al., "Novel drug developmental strategies for treatment-resistant depression," Br. J. Pharmacol., 2022, vol. 179, pp. 1146-1186.

Chow, "Bioavailability and Bioequivalence in Drug Development", Wiley interdisciplinary reviews, Computational statistics, 2014, vol. 6, pp. 304-312.

European Clinical Trial Register Protocol for EudraCT No. 2019-000695-41, "A Phase 2a Randomized, Double-blind, Placebo-Controlled, Parallel-Group, Multi-center Study Investigating the Efficacy, Safety, Tolerability and Pharmacokinetics of JNJ-67953964 in Subjects with Major Depressive Disorder", pp. 1-7, Entry Date: Apr. 26, 2019.

Healey et al., "Pharmaceutical solvates, hydrates and amorphous forms: A special emphasis on cocrystals", Advanced Drug Delivery Reviews, Mar. 22, 2017, vol. 117, pp. 25-46.

Jones et al., "5'-Guanidinonaltrindole, a highly selective and potent K opioid receptor antagonist", European Journal of Pharmacology, May 2000, vol. 396, Issue 1, pp. 1-6.

Lieberman et al., "Pharmaceutical Dosage Forms: Disperse Systems", vols. 1-2, published by Marcel Dekker Inc., 1990, pp. 1-10.

Peckham, "Kappa opioid receptor antagonism: Are opioids the answer for treatment resistant depression?," Review of Drugs/Pharmacotherapy, 2018, vol. 8, No. 4, pp. 175-183.

Reed et al., "Kappa Opioid Receptor Antagonists as Potential Therapeutics for Mood and Substance Use Disorders". In: Handbook of Experimental Pharmacology, 2020, vol. 271, Springer, Cham., (abstract only).

Surmont, U.S. Appl. No. 18/179,025, "Pure Forms of Crystalline Aticaprant", filed Mar. 6, 2023.

Undurraga et al., "Randomized, Placebo-Controlled Trials of Antidepressants for Acute Major Depression: Thirty-Year Meta-Analytic Review", Neuropsychopharmacology, 2012, vol. 37, No. 4, pp. 851-864.

Pae et al., "Aripiprazole as Adjunctive Therapy for Patients with Major Depressive Disorder: Overview and Implications of Clinical Trial Data", CNS Drugs, 2011, vol. 25 No. 2, pp. 109-127.

Paulekuhn et al., "Trends in Active Pharmaceutical Ingredient Salt Selection based on Analysis of the Orange Book Database", J. Med. Chem., 2007, vol. 50 No. 26, pp. 6665-6672.

Petit-Demouliere et al., "Forced swimming test in mice: a review of antidepressant activity", Psychopharmacology, 2005, vol. 177, pp. 245-255.

Pizzagalli et al. "Selective kappa-opioid antagonism ameliorates anhedonic behavior: evidence from the Fast-fail Trial in Mood and Anxiety Spectrum Disorders (FAST-MAS)," Neuropsychopharmacol., 2020, vol. 45, pp. 1656-1663.

Portoghese et al., "Binaltorphimine-Related Bivalent Ligands and Their Kappa Opioid Receptor Antagonist Selectivity", J. Med. Chem., 1988, vol. 31 No. 4, pp. 1-13.

Reed et al., "Repeated Administration of Opra Kappa (LY2456302), a Novel Short-Acting, Selective KOP-r Antagonist, in Persons with and without Cocaine Dependence", Neuropsychopharmacology, 2018, No. 43, pp. 739-750.

Referencing Approved Drug Products in ANDA Submissions—Guidance for Industry, U.S. Department of Health and Human Services, Generics, Oct. 2020, pp. 1-18.

Roman et al., "Novel neuroimmunologic therapeuticsin depression: A clinical perspective on what we know so far", Brain, Behavior and Immunity, Academic Press, San Diego, CA, US, Sep. 21, 2019, vol. 83, pp. 7-21, XP085943201.

Rorick-Kehn et al., "Determining Pharmacological Selectivity of the Kappa Opioid Receptor Antagonist LY2456302 Using Pupillometry as a Translational Biomarker in Rat and Human", International Journal of Neuropsychopharmacology, 2015, pp. 1-11.

Rorick-Kehn et al., "LY2456302 is a novel, potent, orally-bioavailable small molecule kappa-selective antagonist with activity in animal models predictive of efficacy in mood and addictive disorders", Neuropharmacology, 2014, vol. 77, pp. 131-144.

Rothman et al., "An open-label study of a functional opioid K antagonist in the treatment of opioid dependence", Journal of Substance Abuse Treatment, 2000, vol. 18, pp. 277-281.

Schuckit, "Comorbidity between substance use disorders and psychiatric conditions", Addiction, 2006, vol. 101, Supp. 1, pp. 76-88.

Shippenberg et al., "Dynorphin and the pathophysiology of drug addiction", Pharmacology & Therapeutics, 2007, vol. 116 No.2, pp. 1-30.

Smith et al., "March's Advanced Organic Chemistry, Reactions Mechanisms, and Structure, 5th Edition", Molecules, 2001, vol. 6, Wiley Interscience, pp. 10164-10165.

Stahl et al., "Handbook of Pharmaceutical Salts", International Union of Pure and Applied Chemistry, Index, 2002, pp. 1-3.

Stevens, et al., "Potent and Selective Indolomorphin an Antagonists of the Kappa-Opi aid Receptor", J. Med. Chem., 2000, vol. 43, pp. 2759-2769.

(56) References Cited

OTHER PUBLICATIONS

Swerdlow et al., "Neural circuit regulation of prepulse inhibition of startle in the rat: current knowledge and future challenges", Psychophannacology, 2001, vol. 156, pp. 194-215.
Thase et al., "Adjunctive Brexpiprazole 1 and 3 mg for Patients with Major Depressive Disorder Following Inadequate Response to Antidepressants: A Phase 3, Randomized, Double-Blind Study", J Clinical Psychialiy, 2015, vol. 76 No.9, pp. 1-17.
Thase et al., "Efficacy and Safety of Adjunctive Brexpiprazole 2 mg in Major Depressive Disorder", J Clinical Psychiatry, 2015, vol. 76 No. 9, pp. 1-15.
The International Classification of Diseases, Tenth Revision (ICD-10), National Centre for Health Statistics, 2015, pp. 1-2.
Thomas et al., "Discovery of an Opioid K Receptor Selective Pure Antagonist from a Library of N-Substituted 413-Methyl-5-(3-hydroxyphenyl) morphans", J. Med. Chem., 2002, vol. 45, pp. 3524-3530.
Thomas et al., "Identification of (3R)- 7-Hydroxy-N-((1S )-1-2-methylpropy 1)-1,2,3,4-tetrahydro-3-isoquinolinecarboxamide as a Novel Potent and Selective Opioid K Receptor Antagonist", J. Med. Chem., 2003, vol. 46 No. 14, pp. 3127-3137.
Thomas, et al., "Importance of Phenolic Address Groups in Opioid Kappa Receptor Selective Antagonists", J. Med. Chem, 2004, vol. 47 No. 4, pp. 1070-1073.
U.S. Department of Health and Human Services, "National Institutes of Health NIH Publication 06-3879", Rockville, MD, 2006, pp. 1-28.
Urbano et al., "Antagonists of the kappa opioid receptor", Bioorganic & Medicinal Chemistry Letters, 2014, vol. 24, pp. 2021-2032, 2014.
US Clinical Trial Posting for NCT01913535, "Proof-of-Concept Trial of LY2456302 Augmentation of Antidepressant Therapy in Treatment-Resistant Depression", pp. 1-10, Submission Date: Apr. 7, 2015, Estimated Posting Date: Apr. 9, 2015.
US Clinical Trial Posting for NCT01913535, "Proof-of-Concept Trial of LY2456302 Augmentation of Antidepressant Therapy in Treatment-Resistant Depression", pp. 1-38, Submission Date: May 31, 2017, Posting Date: Jul. 2, 2017.
US Clinical Trial Posting for NCT01913535, "Proof-of-Concept Trial of LY2456302 Augmentation of Antidepressant Therapy in Treatment-Resistant Depression", pp. 1-5, Submission Date: Jul. 30, 2013, Estimated: Posting Date Aug. 1, 2013.
US Clinical Trial Posting for NCT03559192, "A Phase 2a Randomized, Double-blind, Placebo-Controlled, Parallel-Group, Multicenter Study Investigating the Efficacy, Safety, Tolerability and Pharmacokinetics of JNJ-67953964 in Subjects With Major Depressive Disorder", pp. 1-13, Submission Date: Dec. 4, 2018, Posting Date: Dec. 5, 2018.
US Clinical Trial Posting for NCT03559192, "A Phase 2a Randomized, Double-blind, Placebo-Controlled, Parallel-Group, Multicenter Study Investigating the Efficacy, Safety, Tolerability and Pharmacokinetics of JNJ-67953964 in Subjects With Major Depressive Disorder", pp. 1-14, Submission Date: Apr. 22, 2019, Posting Date: Apr. 23, 2019.
US Clinical Trial Posting for NCT03559192, "A Phase 2a Randomized, Double-blind, Placebo-Controlled, Parallel-Group, Multicenter Study Investigating the Efficacy, Safety, Tolerability and Pharmacokinetics of JNJ-67953964 in Subjects With Major Depressive Disorder", pp. 1-4, Submission Date: Jun. 6, 2018, Posting Date: Jun. 18, 2018.
Vidal, et al., "Assignment of Absolute Configuration on the Basis of the Conformational Effects Induced by Chiral Derivatizing Agents: The 2-Arylpyrrolidine Case", Organic Letters, 2007, vol. 9 No. 21, pp. 1-6.
Walker, et al., "Pharmacological Evidence for a Motivational Role of K-Opioid Systems in Ethanol Dependence", Neuropsychophannacology, 2008, vol. 33, pp. 643-652.
Williams et al., "Acute inhibition of kappa opioid receptors before stress blocks depression like behaviors in California mice", Progress in Neuropsychopharmacology & Biological Psychiatry, 2018, vol. 86, pp. 166-174.
Zheng et al., "Synthesis and Evaluation of 11C-LY2795050 as a k-Opioid Receptor Antagonist Radiotracer for PET Imaging", The Journal Nuclear Medicine, Mar. 2013, vol. 54, No. 3, pp. 455-4633.
Anton et al., "American College of Neuropsychopharmacology", Annual Meeting Abstracts—13, Nashville, TN, ACNP, 2007, vol. 13, Issue 3, pp. 1-12.
Avis et al., "Pharmaceutical Dosage Forms", Parenteral Medications, 1992, vol. 1-2, pp. 1-9.
Beardsley et al., "Differential effects of the novel kappa opioid receptor antagonist, JDTic, on reinstatement of cocaine seeking induced by footshock stressors vs cocaine primes and its antidepressant-like effects in rats", Psydlopharmacology, 2005, vol. 183, pp. 118-126.
Berman et al., "The Efficacy and Safety of Aripiprazole as Adjunctive Therapy in Major Depressive Disorder: A Multicenter, Randomized, Double-Blind, Placebo-Controlled Study", J Clin Psychiatry, 2007, vol. 68 Issue 6, pp. 843-853.
Blendov et al., "Reduced alcohol consumption in mice lacking preprodynorphin", Alcohol, Oct. 2006, vol. 40 No. 2, pp. 1-23.
Bortolato et al., "Kappa Opioid Receptor Activation Disrupts Prepulse Inhibition of the Acoustic Startle in Rats", Biol. Psychiatry, Jun. 2005, vol. 57 Issue 12, pp. 1-6.
Bouwknecht et al., "The stress-induced hyperthermia paradigm as a physiological animal model for anxiety: A review of pharmacological and genetic studies in the mouse", Neuroscience and Biobehavioral Reviews, 2007, vol. 31 Issue 1, pp. 1-6.
Browne et al., "Targeting opioid dysregulation in depression for the development of novel therapeutics", Pharmacol. Ther., Sep. 2019, vol. 201, pp. 51-76.
Caira M R, "Crystalline Polymorphism Of Organic Compounds", Topics In Current Chemistry, Springer, Berlin, DE, 1998, vol. 198, ISSN 0340-1022, pp. 163-208.
Carey et al., "Advanced Organic Chemistry. Part B: Reactions and Synthesis. Fourth Edition", Molecules, 2001, vol. 6, pp. 1-3.
Carroll et al., "N Substituted 4!3-Methyl-5-(3°hydroxypheny1)-7a-amidomorphans Are Potent, Selective K Opioid Receptor Antagonists", J. Med. Chem., 2006, vol. 49 No. 5, pp. 1781-1791.
Cheng et al., "Relationship Between the Inhibition Constant (K1) And the Concentration of Inhibitor which causes 50 per cent Inhibition ((150) an Enzymatic Reaction", Biochem Pharmacol., 1973, vol. 22, pp. 3099-3108.
CN114195693 English (Year: 2022).
Co-occurring Alcohol Use Disorder and Schizophrenia, Health, Retrieved from: https://athealth.com/topics/co-occurring-alcohol-use-disorder-and-schizophrenia 2/, 2013, pp. 1-9.
Cornelius et al., "Alcohol and psychiatric comorbidity", Recent Dev. Alcoholism, 2003, vol. 16, pp. 361-374.
Custodio-Patsey et al., "Sex differences in kappa opioid receptor inhibition of latent postoperative pain sensitization in dorsal horn", Neuropharmacology, 2020, vol. 163, 107726.
Delapp et al., "Determination of [35S] Guanosine-5'-O-(3-thio) Triphosphate Binding Mediated by Cholinergic Muscarinic Receptors in Membranes from Chinese Hamster Ovary Cells and Rat Striatum Using an Anti-G Protein Scintillation Proximity Assay1", Journal of Pharmacology and Experimental Therapeutics, JPET, 1999, vol. 289 No. 2, pp. 946-955.
Diagnostic and Statistical Manual of Mental Disorders, DSM-IV-TR., Revised 4th Ed., Text Revision, pp. 1-4, 2000.
Dolle et al., "Nascent Structure-Activity Relationship Study of a Diastereomeric Series of Kappa Opioid Receptor Antagonists Derived from CJ-15,208", Bioorganic & Medicinal Chemistry Letters, , Jul. 2009, vol. 19 Issue 13, pp. 1-4.
Domi et al., "Preclinical evaluation of the kappa-opioid receptor antagonist CERC-501 as a candidate therapeutic for alcohol use disorders", Neuropsychopharmacology, 2018, vol. 43, pp. 1805-1812.
El-Khalili et al., "Extended-release quetiapine fumarate (quetiapine XR) as adjunctive therapy in major depressive disorder (MOD) in patients with an inadequate response to ongoing antidepressant treahnent: a multicentre, randomized, double-blind, placebo-controlled study", International J Neuropsychophannacol., 2010, vol. 13, pp. 917-932.

(56) References Cited

OTHER PUBLICATIONS

Emmerson et al., "Characterization of Opioid Agonist Efficacy in a C6 Glioma Cell Line Expressing the μ Opioid Receptor1", J. Pharm Exp Ther., 1996, vol. 278 No. 3, pp. 1121-1127.

Fava et al., "Double-blind, placebo-controlled, proof-of-concept trial of a kappa-selective opioid receptor antagonist augmentation in treatment-resistant depression", Annals of Clinical Psychiatry: Official Journal of the American Academy of Clinical Psychiatrists, Nov. 2020, 1, vol. 32, No. 4, pp. e16-e24.

Geyer et al., "Pharmacological studies of prepulse inhibition models of sensorimotor gating deficits in schizophrenia: a decade in review", Psych opharmacology, 2001, vol. 156, pp. 117-154.

Grant et al., "Prevalence and Co-occurrence of Substance Use Disorders and Independent Mood and Anxiety Disorders", Arch Gen Psychiatry, Aug. 2004, vol. 61, pp. 807-816.

Gregg et al., "Reasons for increased substance use in psychosis", Clinical Psychology Review, 2007, vol. 27, pp. 494-510.

Impurities: Guide for Residual Solvents Q3C(R8), ICH Harmonised Guideline, pp. 1-50, Apr. 22, 2021.

International Search Report and Written Opinion received for PCT Application No. PCT/IB2022/054085, mailed on Sep. 9, 2022, pp. 1-14.

International Search Report and Written Opinion received for PCT Application No. PCT/IB2023/050170, Mailed on Feb. 23, 2023, pp. 1-15.

International Search Report and Written Opinion received for PCT Application No. PCT/IB2023/052088, Mailed on May 31, 2023, pp. 1-17.

International Search Report and Written Opinion received for PCT Application No. PCT/US2009/030811, Mailed on Apr. 8, 2009, pp. 1-9.

Jackson et al., "Effects of orally-bioavailable short-acting kappa opioid receptor-selective antagonist LY2456302 on nicotine withdrawal in mice", Neuropharmacology, 2015, pp. 270-274.

Jacobson et al., "Sex differences in the modulation of mouse nest building behavior by Kappa Opioid receptor signaling", Neuropharmacology, 2020, vol. 177, 108254, pp. 1-9.

Jacobson et al., "The kappa opioid receptor antagonist aticaprant reverses behavioral effects from unpredictable chronic mild stress in male nice", Psychopharmacology, 2020, vol. 237, pp. 3715-3728.

Jones et al., "A randomized, double-blind, placebo-controlled study of the kappa opioid receptor antagonist, CERC-501, in a human laboratory model of smoking behavior", Addiction Biology, Jun. 2019, e12799, pp. 1-9.

Knoll et al., "Anxiolytic-Like Effects of K-Opioid Receptor Antagonists in Models of Unlearned and Learned Fear in Rats", J Phrmacol. Experimental Therapeutics., 2007, vol. 323, No. 3, pp. 838-845.

Kovacs et al., "Decreased Oral Self-Administration of Alcohol in K-Opioid Receptor Knock-Out Mice", Alcoholism: Clinical and Experimental Research, May 2005, vol. 29, No. 5, pp. 730-738.

Krystal et al., "A randomized proof-of-mechanism trail applying the 'fast-fail' approach to evaluating K-opioid antagonism as a treatment for anhedonia", Nature Medicine, May 2020, vol. 26, pp. 760-768.

Krystal et al., ACNP 58th Annual Meeting: Panels, Mini-Panels and Study Groups, Neuropsychopharmacology, 2019, vol. 44, pp. 1-77.

Li et al., "A Novel 18F-labeled kappa opioid receptor antagonist as PET radiotracer: Synthesis and in vivo Evaluation", The Journal of Nuclear Medicine, May 2016, vol. 57, Supp. 2, 159, pp. 1-3.

Li et al., "Development and In Vivo Evaluation of a K-Opioid Receptor Agonist as a PET Radiotracer with Superior Imaging Characteristics", The Journal of Nuclear Medicine, Jul. 2019, vol. 60, No. 7, pp. 1023-1030.

Li et al., "Novel 18F-Labeled k-Opioid Receptor Antagonist as PET Radiotracer: Synthes and In Vivo Evaluation of 18F-LY2459989 in Nonhuman Primates", The Journal of Nuclear Medicine, Jan. 2018, vol. 69, No. 1, pp. 140-146.

Lieberman et al., "Pharmaceutical Dosage Forms: Tablets, Second Edition", Revised and Expanded, 1990, vol. 1-3, pp. 1-9.

Macrae et al., "Mercury: Visualization and analysis of crystal structures", J. Appl. Cryst., Jun. 2006, vol. 39 Part 3, pp. 1-8.

Mague, et al., "Antidepressant-Like Effects of K-Opioid Receptor Antagonists in the Forced Swim Test in Rats," The Journal of Pharmacology and Experimental Therapeutics, 2003, vol. 305, No. 1, pp. 323-330.

Marcus et al., "The Efficacy and Safety of Aripiprazole as Adjunctive Therapy in Major Depressive Disorder, A Second Multicenter, Randomized, Double-Blind, Placebo-Controlled Study", J. Clin. Psychopharmacol, Apr. 2008, vol. 28 No. 2, pp. 156-165.

Mccann, "Potential of Buprenorphine/Naltrexone in Treating Polydrug Addiction and Co-occurring Psychiatric Disorders", Clinical Pharmacology & Therapeutics, Apr. 2008, vol. 83, No. 4, pp. 627-630.

Mclaughlin et al., "K Opioid Receptor Antagonism and Prodynorphin Gene Disruption Block Stress-Induced Behavioral Responses", The Journal of Neuroscience, Jul. 2003, vol. 23, No. 13, pp. 5674-5683.

National Institute of Mental Health, "Depression, Bethesda: National Institute of Mental Health Publication No. 02-3561", 2002, pp. 1-25.

Olivier et al., "Stress-induced hyperthermia and anxiety: pharmacological validation", European Journal of Pharmacology, 2003, vol. 463, pp. 117-132.

U.S. Appl. No. 18/179,093, filed Mar. 6, 2023.

* cited by examiner

Treatment B: 1X 10 mg Formulation Concept 1 administered in the morning, after at least 10-hour overnight fasting.
Treatment C: 1X 5 mg Formulation Concept 1 administered in the morning, after at least 10-hour overnight fasting.

Treatment B: 1X 10 mg Formulation Concept 1 administered in the morning, after at least 10-hour overnight fasting.
Treatment D: 1X 10 mg Formulation Concept 1 administered in the morning, approximately 30 minutes after the start of a standardized high-fat breakfast following at least 10-hour overnight fasting.

Food effect evident at 10 mg unmilled API tablets

Treatment B: 1X 10 mg Formulation Concept 1 administered in the morning, after at least 10-hour overnight fasting.
Treatment D: 1X 10 mg Formulation Concept 1 administered in the morning, approximately 30 minutes after the start of a standardized high-fat breakfast following at least 10-hour overnight fasting.

COMPOSITIONS COMPRISING ATICAPRANT

CROSS REFERENCE TO RELATED APPLICATIONS

This application is a continuation of U.S. patent application Ser. No. 18/179,093, filed Mar. 6, 2023, which claims the benefit of U.S. Provisional Patent Application No. 63/317,471, filed on Mar. 7, 2022, the disclosure of which are incorporated by reference herein.

TECHNICAL FIELD

The present disclosure relates to compositions, including oral compositions, comprising aticaprant and methods of using the same.

BACKGROUND

Kappa opioid receptors (KOR) and their native ligand dynorphin are localized in areas of the brain that effect reward and stress and may play a key role in mood, stress, and addictive disorders. Chronic stress, substance abuse, and acute withdrawal lead to increased dynorphin expression, activating KORs and subsequent downstream signaling pathways to inhibit mesolimbic dopamine surge, contributing to negative affective states. The behavioral pharmacology of KOR antagonism has been tested in animal models of anhedonia, depression, and anxiety and found to have meaningful effects that may translate to therapeutic benefit in humans. KOR antagonists may be effective for the treatment of patients with mood disorders, perhaps by modulating the negative affective state associated with stress response.

Anhedonia is one of the core symptoms of depression. At least mild symptoms of anhedonia are present in about 90% of patients suffering from major depressive disorder (MDD). Only about 50% of patients with MDD show a meaningful response (>50% improvement to a first line antidepressant treatment), leaving many patients with substantial persistent impairment. Therapeutic strategies such as switching antidepressants and using adjuvant drug treatments can improve response, however almost 40% of patients remain symptomatic and fail to achieve full remission.

What is needed are new compounds and treatments for patients having depression and, optionally, anhedonia.

SUMMARY

In some aspects, the disclosure provides pharmaceutical compositions comprising about 2 mg to about 20 mg aticaprant and a filler, wherein the composition comprises between about 0.1% to about 90% aticaprant by weight.

In other aspects, the disclosure provides oral tablets comprising about 5 mg aticaprant, wherein the oral tablet comprises a core tablet of about 100 mg, wherein the core tablet comprises an intragranular and extragranular phase, wherein the intragranular phase comprises about 30 mg microcrystalline cellulose, about 30 mg lactose monohydrate, about 2.5 mg croscarmellose sodium, and about 0.5 mg silica, colloidal anhydrous; and wherein the extragranular phase comprises about 28.5 mg silicified microcrystalline cellulose, about 2.5 mg croscarmellose sodium, about 0.5 mg silica, colloidal anhydrous, and about 0.5 mg magnesium stearate.

In further aspects, the disclosure provides oral tablets comprising about 10 mg aticaprant, wherein the oral tablet comprises a core tablet of about 200 mg, wherein the core tablet comprises an intragranular and extragranular phase, wherein the intragranular phase comprises about 60 mg microcrystalline cellulose, about 60 mg lactose monohydrate, about 5 mg croscarmellose sodium, and about 1 mg silica, colloidal anhydrous; and wherein the extragranular phase comprises about 57 mg silicified microcrystalline cellulose, about 5 mg croscarmellose sodium, about 1 mg silica, colloidal anhydrous, and about 1 mg magnesium stearate.

In yet other aspects, the disclosure provides pharmaceutical compositions comprising between about 2 mg and 20 mg aticaprant, wherein the composition has a pharmacokinetic (PK) profile comprising one or more of the following parameters after administration of the composition to a human after at least a 10-hour fast (dose-normalized to 10 mg): (a) a mean $C_{max}$ between about 20 and 45 ng/ml; (b) a mean $AUC_{infinity}$ between about 250 and 450 h*ng/ml; (c) a mean $AUC_{last}$ between about 250 and 450 h*ng/mL; and (d) a median $t_{max}$ between about 1 to 4 hours.

In still further aspects, the disclosure provides methods for treating major depressive disorder (MDD) in a human patient, the method comprising administering to the patient a pharmaceutical composition comprising between about 2 mg and 20 mg aticaprant, wherein the patient had an inadequate response to other antidepressant therapy prior to treatment with aticaprant, and wherein the administration of the pharmaceutical composition to the patient achieves a pharmacokinetic (PK) profile comprising one or more of the following PK parameters (dose-normalized to 10 mg) after administration of the composition to a human after at least a 10-hour fast: (a) a mean $C_{max}$ between about 30 and 40 ng/ml; (b) a mean $AUC_{infinity}$ between about 300 and 430 h*ng/ml; (c) a mean $AUC_{last}$ between about 280 and 430 h*ng/ml; and (d) a median $t_{max}$ between about 1 to 4 hours.

In other aspects, the disclosure provides solid pharmaceutical compositions comprising between about 2 mg and 20 mg aticaprant, wherein the composition has a dissolution profile comprising a Q value of between about 60% and 90% at 45 minutes, under the following dissolution operating conditions: Apparatus: Paddle (USP Type 2, Ph. Eur., JP); Dissolution medium: 0.01 M hydrochloric acid; Volume: 900 mL; Temperature: 37+/−0.5° C.; Rotation Speed: 50 rpm; and Analytical Finish: UHPLC with UV detection at 247 nm.

In further aspects, the disclosure provides methods of treating major depressive disorder (MDD) in a human patient comprising administering to the patient the pharmaceutical composition, oral tablet, or solid pharmaceutical composition described herein.

BRIEF DESCRIPTION OF THE DRAWINGS

FIG. 10-B is an excerpt from FIG. 10-A for treatment weeks 0-6.

FIG. 20-B is a line graph showing MADRS change from baseline for patients with low anhedonia, i.e., SHAPS <38.

DETAILED DESCRIPTION OF ILLUSTRATIVE EMBODIMENTS

Figure 1:
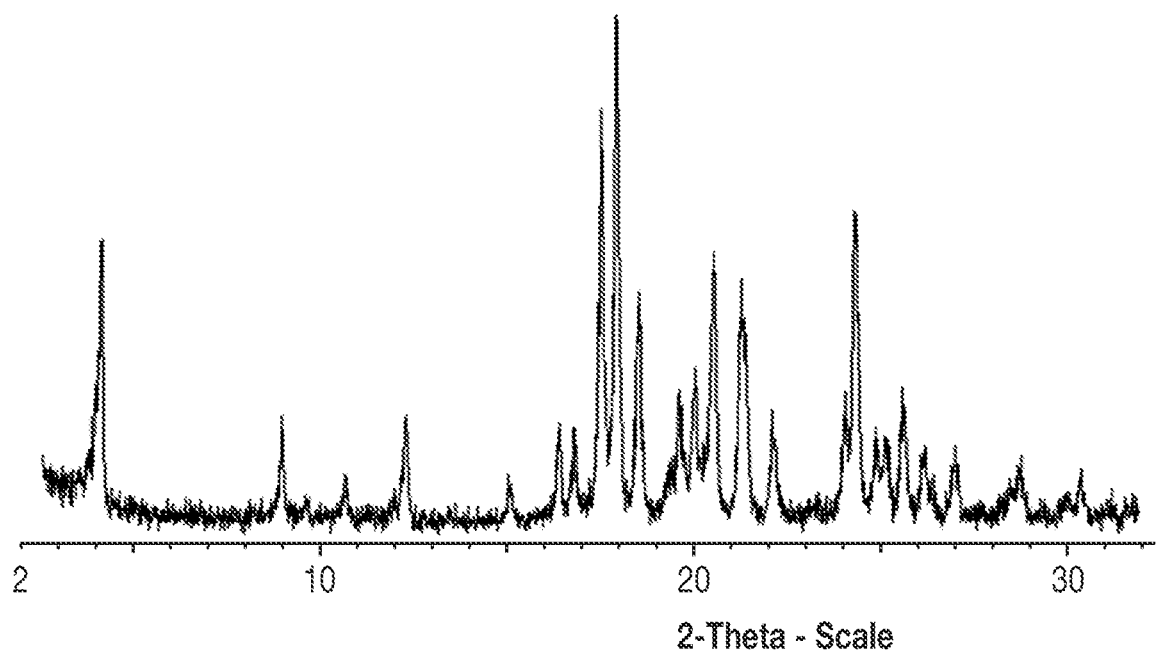
FIG. 1 is the x-ray powder diffraction (XRPD) pattern of polymorph Form III of aticaprant (transmission mode).

All individual features (e.g., particular embodiments or specific preferred features) mentioned herein may be taken in isolation or in combination with any other feature (including particular embodiment or preferred feature) mentioned herein; hence, preferred features may be taken in conjunction with other preferred features, or independently of them (and likewise with particular embodiments).

The disclosure provides compositions comprising pure crystalline Form of III aticaprant that are anhydrous and stable in the solid form.

The term "crystalline" refers to a solid form of a chemical moiety that contains a highly ordered intermolecular structure.

The term "polymorph" refers to a crystalline form of a molecule having one specific crystal structure. A crystalline compound may have one crystal form or may have two or more crystal forms, i.e., polymorphs. As is understood to those skilled in the art, polymorphs of a chemical compound may distinguished from each other by compared physicochemical properties such as solubility, dissolution rate, stability, bioavailability, among others. Polymorphs also may have different spectra selected from, without limitation, x-ray powder diffraction (XRPD), single crystal x-ray diffraction, thermogravimetric analysis (TGA), infrared spectroscopy, Raman spectroscopy, solid state nuclear magnetic resonance (NMR), differential scanning calorimetry (DSC), polarized light microscopy (PLM), hot stage microscopy, or dynamic solvent sorption.

The term "crystalline" refers to solid state form of a chemical moiety wherein the atoms, molecules, or ions are assembled in a highly ordered structure that extends in all directions. Thus, "crystalline" includes all crystalline forms of Compound I, including salts thereof. Characterization of crystalline forms may be performed by those skilled in the art including, without limitation, XRPD or DSC. Typically, the XRPD pattern contains sharp intensity peaks. This contrasts to the XRPD pattern of an amorphous form that often contains a broad, peak, without no identifying peaks. A crystalline form may be completely crystalline or partially crystalline. In some aspects, a crystalline sample may be 100% w/w crystalline. A crystalline sample may also contain solids that are amorphous. In certain aspects, a crystalline form may contain solids such that the sample is at least about 99% w/w crystalline, at least about 95% w/w amorphous, at least about 90% w/w crystalline, at least about 85% w/w crystalline, at least about 80% w/w crystalline, or the like.

The term "anhydrous" or "anhydrate" as used herein refers to a crystalline as described herein that substantially lacks water. In some aspects, an anhydrous form contains less than about 1% w/w of water. In other aspects, an anhydrous form contains less than about 0.9%, about 0.8%, about 0.7%, about 0.6%, about 0.5%, about 0.4%, about 0.3%, about 0.2%, about 0.1% w/w of water.

As provided herein, all temperature values may vary. Such variations may depend on instrument type, instrument parameters, laboratory techniques, and/or laboratory conditions. Unless otherwise defined, a recited temperature may vary. In some aspects, the temperatures noted herein vary by about 0.1°, about 0.5°, about 1°, about 2°, about 3°, about 4°, or about 5°.

Similarly, 2θ values obtained from the XRPD patterns also may vary. Such variations may depend on instrument type, instrument parameters, laboratory techniques, sample (including particle size, impurities, etc.), and/or laboratory conditions. Unless otherwise defined, the XRPD patterns and/or the 2θ peak values may vary. In certain aspects, the 2θ peak values vary (higher or lower) by about 0.05°, about 0.1°, about 0.15°, or about 0.2°. In other aspects, one or more of the 2θ peak values are higher by about 0.05°, about 0.1°, about 0.15°, or about 0.2°. In further aspects, one or more of the 2θ peak values are lower by about 0.05°, about 0.1°, about 0.15°, or about 0.2°.

As used herein, the term "corresponds to" may be used in reference to certain spectra. Thus, "corresponds to" includes a spectrum that is identical or substantially similar to another spectrum. One skilled in the art would be able to compare such spectra and determine if a spectrum corresponds to another. Thus, the term "corresponds to" is used herein to compare XRPD patterns, DSC thermograms, among others. In some aspects, one XRPD pattern corresponds to another XRPD pattern when their 2θ values are within the margin of error as described above. In other aspects, one XRPD pattern corresponds to another XRPD pattern when the peaks have the same 2θ peak value, but one or more peaks have a different height (intensity). In further aspects, one XRPD pattern corresponds to another XRPD pattern when the peaks have the same 2θ peak value, but one or more peaks have a different peak area. In yet other aspects, one XRPD pattern corresponds to another XRPD pattern when the peaks have the same 2θ peak value, but one or more peak is obscured. Such obscured peaks may be due to impurities, excipients, or the like. Such obscured peaks typically do not prevent characterization of the crystalline form.

As used herein, unless otherwise noted, the term "aticaprant" refers to 3-fluoro-4-4-2-(3,5-dimethylphenyl)pyrrolidin-1-yl-methylphenoxybenzamide, i.e., the following compound:

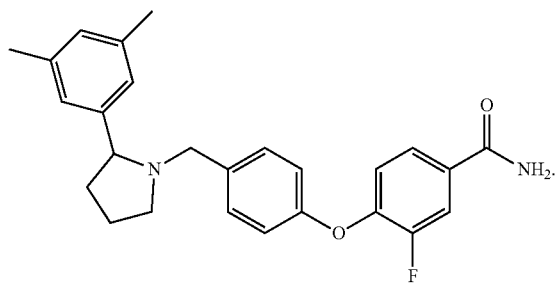 [SMILES: Cc1cc(C)cc(C2CCCN2Cc2ccc(Oc3ccc(C(N)=O)cc3F)cc2)c1]

and is also known as JNJ-67953964, 67953964-AAA, CERC-501, and LY-2456302. In some embodiments, "aticaprant" refers to the (S)-enantiomer of aticaprant, i.e., the following compound:

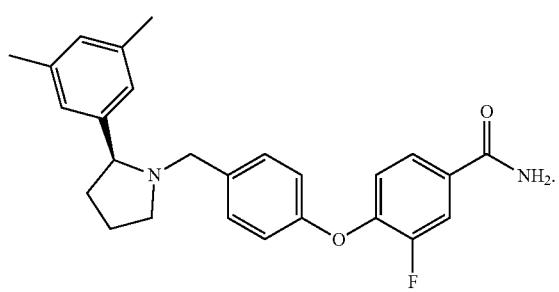 [SMILES: Cc1cc(C)cc([C@@H]2CCCN2Cc2ccc(Oc3ccc(C(N)=O)cc3F)cc2)c1]

also known as (S)-aticaprant or (S)-3-fluoro-4-4-2-(3,5-dimethylphenyl)pyrrolidin-1-yl-methylphenoxybenzamide. In other embodiments, the aticaprant used in the methods described herein is substantially free of the (R)-enantiomer, i.e., (R)-aticaprant or (R)-3-fluoro-4-4-2-(3,5-dimethylphenyl)pyrrolidin-1-yl-methylphenoxybenzamide having the following structure:

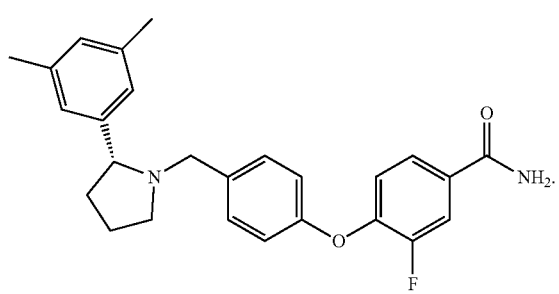 [SMILES: Cc1cc(C)cc([C@H]2CCCN2Cc2ccc(Oc3ccc(C(N)=O)cc3F)cc2)c1]

In other embodiments, the aticaprant contains less than about 10% by weight, based on the weight of aticaprant, of the (R)-enantiomer of aticaprant. In further embodiments, aticaprant contains less than about 10, about 9, about 8, about 7, about 6, about 5, about 4, about 3, about 2, about 1, about 0.5, about 0.1, about 0.005, or about 0.001% by weight, based on the weight of aticaprant, of the (R)-enantiomer of aticaprant. In yet other embodiments, the aticaprant contains about 0.001 to about 10% by weight, based on the weight of aticaprant, of the (R)-enantiomer of aticaprant. In still further embodiments, the aticaprant contains about 0.001 to about 10%, about 0.001 to about 5%, about 0.001 to about 1%, about 0.001 to about 0.5%, about 0.001 to about 0.1%, about 0.1 to about 5%, about 0.1 to about 1%, about 0.1 to about 5%, or about 0.5 to about 5% by weight, based on the weight of aticaprant.

Pharmaceutically acceptable salts of aticaprant are also contemplated by the present invention, which may be readily selected by those skilled in the art. A "pharmaceutically acceptable salt" refers a salt of aticaprant that is non-toxic, biologically tolerable, or otherwise biologically suitable for administration to the subject. See, generally, G. S. Paulekuhn, "Trends in Active Pharmaceutical Ingredient Salt Selection based on Analysis of the Orange Book Database", J. Med. Chem., 2007, 50:6665-72, S. M. Berge, "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002. Examples of pharmaceutically acceptable salts are those that are pharmacologically effective and suitable for administration to patients without undue toxicity, irritation, or allergic response.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, bromides (such as hydrobromides), iodides (such as hydroiodides), acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propane-sulfonates, naphthalene-1-sulfonates, naphthalene-2-sulfonates, and mandelates.

In some embodiments, the aticaprant is crystalline Form III of aticaprant. Crystalline Form III of aticaprant may be characterized by a number of techniques including, without limitation, x-ray diffraction and differential scanning calorimetry. In some embodiments, crystalline Form III of aticaprant is characterized by x-ray diffraction. In other embodiments, crystalline Form III of aticaprant is characterized by four or more x-ray diffraction pattern peaks at 2θ (±0.2) of 4.1°, 9.0°, 17.6°, 18.0°, or 21.4°. In further embodiments, crystalline Form III of aticaprant is characterized by four or more x-ray diffraction pattern peaks at 2θ (±0.2) of 4.1°, 9.0°, 17.6°, 18.0°, or 21.4° and one or more additional peaks at 16.4°, 20.1°, 20.3°, 24.1°, and 25.7°. In yet other embodiments, crystalline Form III of aticaprant is characterized by four or more x-ray diffraction pattern peaks at 2θ (±0.2) of 4.1°, 9.0°, 17.6°, 18.0°, or 21.4° and one or more additional peaks at 15.1°, 16.4°, 20.0°, 20.1°, 20.3°, 24.1°, 25.0°, 25.7°, 26.2°, and 28.8°. In still further embodiments, crystalline Form III of aticaprant is characterized by four or more x-ray diffraction pattern peaks at 2θ (±0.2) of 4.1°, 9.0°, 17.6°, 18.0°, or 21.4° and one or more additional peaks at 8.2°, 9.7°, 12.0°, 13.5°, 15.1°, 16.4°, 19.4°, 28.4°, 20.0°, 20.1°, 20.3°, 24.1°, 25.0°, 25.7°, 26.2°, 28.8°, and 30.0°. In other embodiments, crystalline Form III of aticaprant is characterized by four or more x-ray diffraction pattern peaks at 2θ (±0.2) of 3.1°, 19.0°, 24.0°, 24.3°, or 26.2 and one or more additional peaks of Table 1.

TABLE 1

| Position (2θ) |
| --- |
| 4.1 |
| 8.2 |
| 9.0 |
| 9.7 |
| 10.7 |
| 12.0 |
| 12.3 |
| 13.5 |
| 15.1 |
| 16.4 |
| 16.8 |
| 17.6 |
| 18.0 |
| 18.6 |
| 19.4 |
| 19.7 |
| 20.1 |
| 20.3 |
| 20.6 |
| 21.4 |
| 22.2 |
| 24.1 |
| 24.4 |
| 25.0 |
| 25.2 |
| 25.7 |
| 26.23 |
| 26.4 |
| 27.1 |
| 28.4 |
| 28.6 |
| 28.8 |
| 20.0 |
| 30.2 |
| 30.5 |
| 31.2 |
| 31.8 |
| 32.2 |
| 32.5 |
| 33.0 |
| 33.2 |
| 33.6 |
| 33.9 |
| 34.4 |
| 35.4 |
| 36.0 |
| 36.4 |
| 37.0 |
| 38.2 |
| 38.5 |
| 39.5 |

In still other embodiments, crystalline Form III of aticaprant is characterized the x-ray diffraction pattern peaks in Table 2.

TABLE 2

| Position (2θ) |
| --- |
| 4.1 |
| 8.2 |
| 9.0 |
| 9.7 |
| 12.0 |
| 13.5 |
| 15.1 |
| 16.4 |
| 17.6 |
| 18.0 |
| 19.4 |
| 19.7 |
| 20.1 |
| 20.3 |
| 21.4 |
| 24.1 |
| 25.0 |

TABLE 2-continued

| Position (2θ) |
|---|
| 25.7 |
| 26.3 |
| 28.4 |
| 28.8 |
| 30.0 |

In still other embodiments, crystalline Form III of aticaprant is characterized the x-ray diffraction pattern peaks in Table 3.

TABLE 3

| Position (2θ) |
|---|
| 4.1 |
| 8.2 |
| 9.0 |
| 9.7 |
| 10.7 |
| 12.0 |
| 12.3 |
| 13.5 |
| 15.1 |
| 16.4 |
| 16.8 |
| 17.6 |
| 18.0 |
| 18.6 |
| 19.4 |
| 19.7 |
| 20.1 |
| 20.3 |
| 20.6 |
| 21.4 |
| 22.2 |
| 24.1 |
| 24.4 |
| 25.0 |
| 25.2 |
| 25.7 |
| 26.3 |
| 26.4 |
| 27.1 |
| 28.4 |
| 28.6 |
| 28.8 |
| 30.0 |
| 30.2 |
| 30.5 |
| 31.2 |
| 31.8 |
| 32.2 |
| 32.5 |
| 33.0 |
| 33.2 |
| 33.6 |
| 33.9 |
| 34.4 |
| 35.4 |
| 36.0 |
| 36.4 |
| 37.0 |
| 38.2 |
| 38.5 |
| 39.5 |

In further embodiments, crystalline Form III of aticaprant is characterized by an x-ray powder diffraction pattern that corresponds to FIG. 1.

Figure 2:
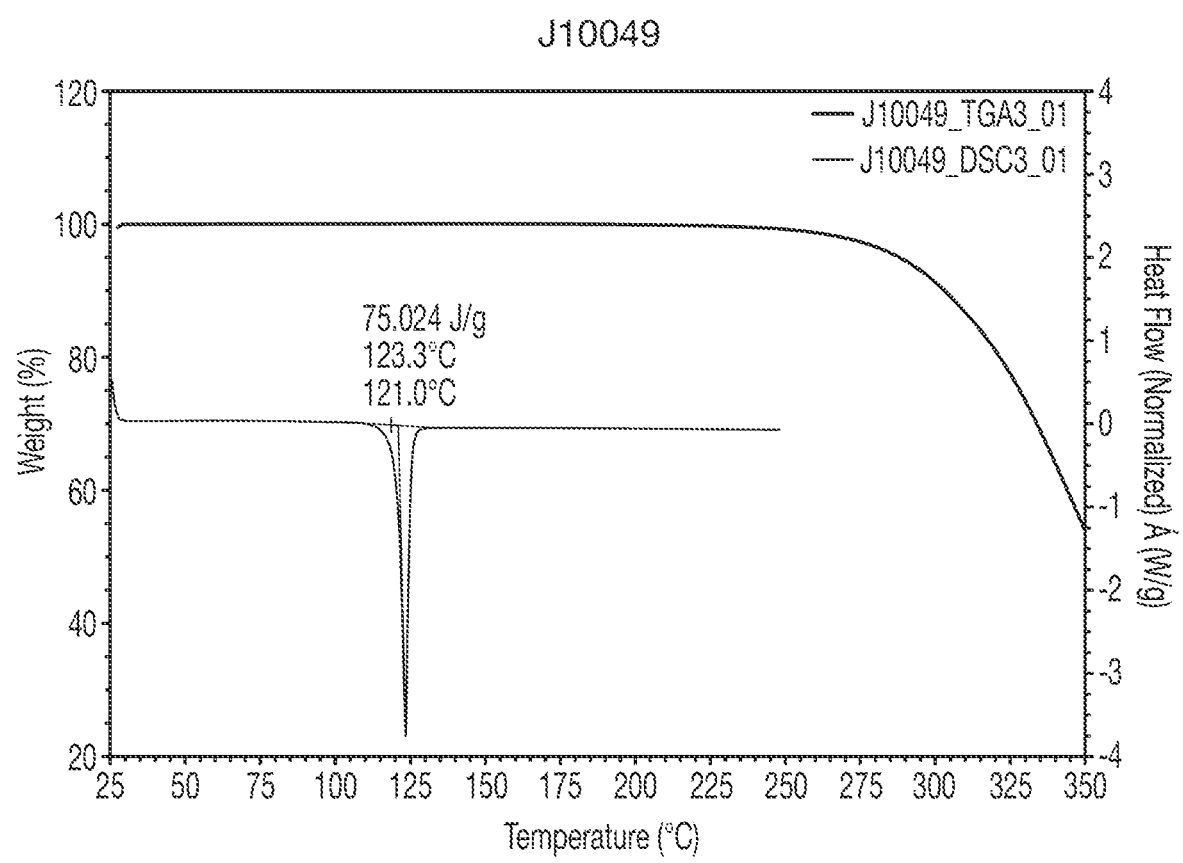
FIG. 2 is the differential scanning calorimetry (DSC) thermogram of polymorph Form III of aticaprant.

Crystalline Form III of aticaprant may also be characterized by differential scanning calorimetry. In some embodiments, the differential scanning calorimetry thermogram comprises a peak temperature ($T_m$) at about 121° C. In other embodiments, crystalline Form III of aticaprant is characterized by a differential scanning calorimetry thermogram that corresponds to FIG. 2.

Pharmaceutical Compositions

The disclosure also contemplates pharmaceutical composition comprising aticaprant and one or more pharmaceutically acceptable excipient. As used herein, the term "composition" is intended to encompass a product comprising the specified ingredients in the specified amounts, as well as any product which results, directly or indirectly, from combinations of the specified ingredients in the specified amounts. The preferred pharmaceutical composition contains crystalline Form III of aticaprant as the active ingredient intimately admixed with a pharmaceutical carrier according to conventional pharmaceutical compounding techniques, which carrier may take a wide variety of forms depending on the form of preparation desired for administration. Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain.

The amount of aticaprant present in the compositions is about 2 mg to about 60 mg. In some embodiments, the composition contains about 2 mg to about 20 mg of aticaprant. In some embodiments, the composition contains about 2, about 3, about 4, about 5, about 6, about 7, about 8, about 9, about 10, about 11, about 12, about 13, about 14, about 15, about 16, about 17, about 18, about 19, or about 20 mg of aticaprant. In other embodiments, the composition contains about 5 to about 20 mg, about 10 to about 20 mg, about 15 to about 20 mg, about 1 to about 15 mg, about 2 to about 15 mg, about 5 to about 15 mg, about 10 to about 15 mg, about 1 to about 10 mg, about 2 to about 10 mg, or about 5 to about 10 mg of aticaprant. In yet other embodiments, the effective amount of aticaprant is about 5 to about 15 mg. In further embodiments, the amount of aticaprant is about 5 or 10 mg. In other embodiments, the amount of aticaprant is about 5 mg. In still further embodiments, the amount of aticaprant is about 10 mg. The composition contains about 0.1% to about 90% by weight of aticaprant. In some embodiments, the composition contains about 0.1, about 0.5, about 1, 5, about 10, about 15, about 20, about 25, about 30, about 35, about 40, about 45, about 50, about 55, about 60, about 65, about 70, about 75, about 80, about 85, about 90% by weight, based on the weight of the composition, of aticaprant. In other embodiments, the composition contains about 0.1 to about 80, about 0.1 to about 70, about 0.1 to about 60, about 0.1 to about 50, about 0.1 to about 40, about 0.1 to about 30, about 0.1 to about 20, about 0.1 to about 10, about 0.1 to about 5, about 0.1 to about 1, about 0.1 to about 0.5, about 1 to about 90, about 1 to about 80, about 1 to about 70, about 1 to about 60, about 1 to about 50, about 1 to about 40, about 1 to about 30, about 1 to about 20, about 1 to about 10, about 1 to about 5, about 5 to about 90, about 5 to about 80, about 5 to about 70, about 5 to about 60, about 5 to about 50, about 5 to about 40, about 5 to about 30, about 5 to about 20, about 5 to about 10, about 10 to about 90, about 10 to about 80, about 10 to about 70, about 10 to about 60, about 10 to about 60, about 10 to about 50, about 10 to about 40, about 10 to about 30, about 10 to about 20, about 20 to about 90, about 20 to about 80, about 20 to about 70, about 20 to about 60, about 20 to about 50, about 20 to about 40, about 20 to about 30, about 30 to about 90, about 30 to about 80, about 30 to about 70, about 30 to about 60, about 30 to about 50, about 30 to about 40, about 40 to about 90, about 40 to about 80, about 40 to about 70, about 40 to about 60, about 40 to about 50, about 50 to about 90, about 50 to about 80, about 50 to about 70, about 50 to about 60, about 60 to about 90, about 60 to about 80, about 60 to about 70, about 70 to about 90, about 70 to about 80, or about 80 to about 90% by weight, based on the weight of the composition, of aticaprant. In further embodiments, the composition contains about 5% by weight of aticaprant. In yet other embodiments, the composition contains about 6% by weight of aticaprant. In still further embodiments, the composition contains about 7% by weight of aticaprant. In other embodiments, the composition contains about 8% by weight of aticaprant. In further embodiments, the composition contains about 9% by weight of aticaprant. In still other embodiments, the composition contains about 10% by weight of aticaprant. The amount of aticaprant for administration according to the methods described herein may be determined by one skill in the art and, unless otherwise noted, are set forth on an aticaprant free base basis. That is, the amounts indicate that amount of the aticaprant molecule administered, exclusive of, for example, solvent (such as in solvates) or counterions (such as in pharmaceutically acceptable salts).

In some embodiments, the pharmaceutical compositions have a particular pharmacokinetic (PK) profile at a specific dose. In some embodiments, the pharmaceutical compositions have a PK profile that is dose-proportional. In other embodiments, the pharmaceutical compositions have a PK profile comprising parameters, e.g., exposure parameters such as $C_{max}$ or AUC, that are dose-proportional. In further embodiments, the pharmaceutical compositions have a PK profile or PK parameter that is dose-proportional between about 1 mg to 60 mg aticaprant, between about 2 mg to 60 mg aticaprant, between about 2 mg to 40 mg aticaprant, between about 2 mg to 20 mg aticaprant, between about 2 mg to 15 mg aticaprant, between about 2 mg to 10 mg aticaprant, and between about 5 mg to 10 mg aticaprant.

Some embodiments include pharmaceutical compositions comprising aticaprant that are bioequivalent to any one of the pharmaceutical compositions described herein. In some embodiments, the pharmaceutical composition comprises between about 2 mg and about 60 mg, between about 2 mg and about 20 mg aticaprant, between about 5 mg and about 10 mg aticaprant, or about 5 mg or about 10 mg aticaprant, wherein the composition is bioequivalent to a pharmaceutical composition comprising aticaprant which when administered to a human after at least a 10-hour fast yields a PK profile that includes one or more of: a mean $C_{max}$ of between about 30 and 35 ng/ml, a mean $AUC_{infinity}$ of between about 300 and 320 ng/mL, and a median $t_{max}$ of about 1.5 hour (dose-normalized to 10 mg). Bioequivalence may be demonstrated by any method known to one skilled in the art, for example, as described in Example 9 herein, or as described in Chow, Bioavailability and Bioequivalence in Drug Development, Wiley interdisciplinary reviews, Computational statistics, 6, 4 (2014): 304-312. doi:10.1002/wics.1310.

In some embodiments, the pharmaceutical composition comprises between about 2 mg and about 20 mg aticaprant, about 5 mg aticaprant, or about 10 mg aticaprant, wherein when the pharmaceutical composition is compared to a reference composition, the 90% confidence interval of the ratio of geometric means of one or more PK parameters of the pharmaceutical composition and reference composition is within the bioequivalence limits of 80% and 125%. In some embodiments, the reference composition is a composition comprising aticaprant which when administered to a human after at least a 10-hour fast yields a PK profile that includes one or more of: a mean $C_{max}$ of between about 30 and 35 ng/ml, a mean $AUC_{infinity}$ of between about 300 and 320 ng/ml, and a median $t_{max}$ of about 1.5 hour (dose-normalized to 10 mg). In some other embodiments, the reference composition has a PK profile of any one of Treatment A, Treatment B, Treatment C, or Treatment D described in Table 69.

In some embodiments, the PK profile is based on administration of the composition, containing about 2 mg to about 60 mg aticaprant, to a human after at least a 10-hour fast. In some other embodiments, the PK profile is based on administration of the composition, containing about 2 mg to about 60 mg aticaprant, to a human about 30 minutes after the start of a high-fat meal following at least a 10-hour fast. As another example, the PK profile is based on administration of the composition, containing about 2 mg to about 20 mg aticaprant, to a human after at least a 10-hour fast. In some embodiments, the PK profile is based on administration of a composition containing about 2, about 3, about 4, about 5, about 6, about 7, about 8, about 9, about 10, about 11, about 12, about 13, about 14, about 15, about 16, about 17, about 18, about 19, or about 20 mg of aticaprant to a human. In further embodiments the PK profile is based on administration of a composition containing about 2 to about 19, about 2 to about 18, about 2 to about 16, about 2 to about 14, about 2 to about 12, about 2 to about 10, about 2 to about 8, about 2 to about 6, about 2 to about 4, about 4 to about 20, about 4 to about 18, about 4 to about 16, about 4 to about 14, about 4 to about 12, about 4 to about 10, about 4 to about 8, about 4 to about 6, about 6 to about 20, about 6 to about 18, about 6 to about 16, about 6 to about 14, about 6 to about 12, about 6 to about 10, about 6 to about 8, about 8 to about 20, about 8 to about 18, about 8 to about 16, about 8 to about 14, about 8 to about 12, about 8 to about 10, about 10 to about 20, about 10 to about 18, about 10 to about 16, about 10 to about 14, about 10 to about 12, about 12 to about 20, about 12 to about 18, about 12 to about 16, about 12 to about 14, about 14 to about 20, about 14 to about 18, about 14 to about 16, about 16 to about 20, about 16 to about 18, or about 18 to about 20 mg of aticaprant to a human.

In certain aspects, the PK profile is determined after an at least 10-hour food fast. In some embodiments, the food fast is at least about 1, about 2, about 4, about 5, about 10, about 12, about 15, about 18, about 20, about 22, 24, about 28, or about 32 hours.

For example, the PK profile may include a $C_{max}$ ranging between about 1 and about 100, about 5 and about 70, about 5 and about 65, about 5 and about 60, about 5 and about 55, about 5 and about 50, about 5 and about 45, about 10 and about 70, about 10 and about 65, about 10 and about 60, about 10 and about 55, about 10 and about 50, about 10 and about 45, about 13 and about 60, about 13 and about 55, about 13 and about 50, about 20 and about 70, about 20 and about 65, or about 20 and about 63 ng/ml (dose-normalized to 10 mg). In some embodiments, the PK profile includes a $C_{max}$ ranging between about 20 and about 45, about 22 and about 45, about 23 and about 45, or about 24 and about 44 ng/ml (dose-normalized to 10 mg) when administered after at least a 10-hour fast. In some embodiments, the PK profile includes a $C_{max}$ ranging between about 25 and about 50, about 27 and about 38, about 25 and about 40, or about 28 and about 38 ng/mL (dose-normalized to 10 mg) when administered about 30 minutes after the start of a high-fat meal following at least a 10-hour fast.

In some embodiments, the PK profile includes an $AUC_{infinity}$ ranging between about 50 and about 800, about 100 and about 500, about 100 and about 480, about 100 and about 450, about 100 and about 400, about 110 and about 500, about 110 and about 480, about 110 and about 450, about 110 and about 400, about 150 and about 700, about 200 and about 700, about 200 and about 650, about 250 and about 450, about 280 and about 420, about 290 and about 410, or about 210 and about 650 h*ng/mL (dose-normalized to 10 mg). In some embodiments, the PK profile includes an AUC$_{infinity}$ ranging between about 200 and about 400, about 210 and about 400, about 210 and about 398, about 220 and about 400, or about 220 and about 398 h*ng/ml (dose-normalized to 10 mg) when administered after at least a 10-hour fast. In some embodiments, the PK profile includes an AUC$_{infinity}$ ranging between about 300 and about 600, about 300 and 550, or about 320 and about 530 h*ng/ml (dose-normalized to 10 mg) when administered about 30 minutes after the start of a high-fat meal following at least a 10-hour fast.

In some embodiments, the PK profile includes an AUC$_{last}$ ranging between about 50 and about 800, about 100 and about 500, about 100 and about 480, about 100 and about 450, about 100 and about 400, about 110 and about 500, about 110 and about 480, about 110 and about 450, about 110 and about 400, about 150 and about 700, about 200 and about 700, about 200 and about 650, about 250 and about 450, about 280 and about 420, about 290 and about 410, or about 210 and about 650 h*ng/ml (dose-normalized to 10 mg). In some embodiments, the PK profile includes an AUC$_{last}$ ranging between about 300 and about 400 (dose-normalized to 10 mg).

In some embodiments, the PK profile incudes a t$_{max}$ ranging between about 0.5 and about 5, between about 1 and about 4.5, about 1 and about 4, about 1 and about 3, about 1 and about 2.5, or about 1 and about 2 hours. In some embodiments, the PK profile includes a t$_{max}$ that ranges between about 1 and about 2.5, about 1 and about 2, or about 1 and about 3 hours when administered after at least a 10-hour fast. In some embodiments, the PK profile includes a t$_{max}$ that ranges between about 1 and about 4 hours when administered after about 30 minutes after the start of a high-fat meal following at least a 10-hour fast.

In some embodiments, the PK profile incudes a tin ranging between about 5 and about 60, about 5 and about 55, about 5 and about 50, about 5 and about 45, about 5 and about 40, about 9 and about 60, about 9 and about 55, about 9 and about 50, about 9 and about 45, or about 9 and about 40 hours.

In some embodiments, the PK profile includes a 2 ranging between about 0.010 and about 0.080, about 0.010 and about 0.075, about 0.010 and about 0.070, about 0.015 and about 0.080, about 0.015 and about 0.075, about 0.015 and about 0.070, about 0.015 and about 0.065, about 0.015 and about 0.060, about 0.015 and about 0.055, or about 0.015 and about 0.050 l/hour.

In some other embodiments, the PK profile includes a CL/F ranging between about 10 and about 90, about 10 and about 85, about 10 and about 80, about 10 and about 75, about 10 and about 70, about 10 and about 60, about 10 and about 50, about 15 and about 90, about 15 and about 80, about 15 and about 70, about 15 and about 60, about 15 and about 50, about 20 and about 90, about 20 and about 80, about 20 and about 75, about 20 and about 70, about 20 and about 60, or about 20 and about 50 L/h.

In some other embodiments, the PK profile includes a Vd/F ranging between about 400 and about 6000, about 400 and about 5500, about 400 and about 5000, about 400 and about 4000, about 400 and about 3500, about 400 and about 3400, about 450 and about 3500, about 450 and about 3000, about 500 and about 3500, about 500 and about 3000, about 400 and about 2000, about 400 and about 1500, about 400 and about 1200, about 550 and about 3500, about 550 and about 3000, about 600 and about 3500, about 600 and about 3000, about 600 and about 2500, or about 450 and about 1200 L.

For example, the PK profile may include a mean C$_{max}$ between about 20 and 45 ng/ml when dose-normalized to 10 mg. In some embodiments, the mean C$_{max}$ is about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, or about 55 ng/ml (dose-normalized to 10 mg). In other embodiments, the mean C$_{max}$ is about 20 to about 40, about 20 to about 35, about 20 to about 30, about 20 to about 25, about 25 to about 45, about 25 to about 40, about 25 to about 35, about 25 to about 30, about 30 to about 45, about 30 to about 40, about 30 to about 35, about 35 to about 45, about 35 to about 40, or about 40 to about 45 ng/ml (dose-normalized to 10 mg). In further embodiments, the mean C$_{max}$ is between about 30 and 35 ng/ml, about 31 and 35 ng/ml, or about 31 and 34 ng/ml (dose-normalized to 10 mg) when administered after at least a 10-hour fast. In further embodiments, the mean C$_{max}$ is between about 35 and 40, about 36 and 39, or about 37 and 38 ng/mL (dose-normalized to 10 mg) when administered about 30 minutes after the start of a high-fat meal following at least a 10-hour fast.

The PK profile also may have a mean AUC$_{infinity}$ between about 250 and 450 h*ng/ml (dose-normalized to 10 mg). In some embodiments, the AUC$_{infinity}$ is about 250, about 260, about 270, about 280, about 290, about 300, about 310, about 320, about 330, about 340, about 350, about 360, about 370, about 380, about 390, about 400, about 410, about 420, about 430, about 440, or about 450 h*ng/ml (dose-normalized to 10 mg). In other embodiments, the mean AUC$_{infinity}$ is about 250 to about 400, about 250 to about 375, about 250 to about 350, about 250 to about 325, about 250 to about 300, about 250 to about 275, about 275 to about 450, about 275 to about 425, about 275 to about 400, about 275 to about 375, about 275 to about 350, about 275 to about 325, about 275 to about 300, about 300 to about 450, about 300 to about 425, about 300 to about 400, about 300 to about 390, about 300 to about 380, about 300 to about 370, about 300 to about 360, about 300 to about 350, about 300 to about 340, about 300 to about 330, about 300 to about 320, about 300 to about 310, about 325 to about 450, about 325 to about 425, about 325 to about 400, about 325 to about 375, about 325 to about 350, about 350 to about 450, about 350 to about 425, about 350 to about 400, about 350 to about 375, about 375 to about 450, about 375 to about 425 to about 375 to about 400, about 400 to about 450, about 400 to about 425, or about 425 to about 450 h*ng/ml (dose-normalized to 10 mg). In further embodiments, the mean AUC$_{infinity}$ is between about 300 and 320 h*ng/ml (dose-normalized to 10 mg) when administered after at least a 10-hour fast. In further embodiments, the mean AUC$_{infinity}$ is between about 320 and 530 h*ng/ml (dose-normalized to 10 mg) when administered about 30 minutes after the start of a high-fat meal following at least a 10-hour fast.

In other aspects, the pharmaceutical composition has a PK profile comprising a mean AUC$_{last}$ between about 250 and 450 h*ng/mL (dose-normalized to 10 mg). In some embodiments, the AUC$_{last}$ is about 250, about 260, about 270, about 280, about 290, about 300, about 310, about 320, about 330, about 340, about 350, about 360, about 370, about 380, about 390, about 400, about 410, about 420, about 430, about 440, or about 450 h*ng/mL. In other embodiments, the mean $AUC_{last}$ is about 250 to about 400, about 250 to about 375, about 250 to about 350, about 250 to about 325, about 250 to about 300, about 250 to about 275, about 275 to about 450, about 275 to about 425, about 275 to about 400, about 275 to about 375, about 275 to about 350, about 275 to about 325, about 275 to about 300, about 300 to about 450, about 300 to about 425, about 300 to about 400, about 300 to about 390, about 300 to about 380, about 300 to about 370, about 300 to about 360, about 300 to about 350, about 300 to about 340, about 300 to about 330, about 300 to about 320, about 300 to about 310, about 325 to about 450, about 325 to about 425, about 325 to about 400, about 325 to about 375, about 325 to about 350, about 350 to about 450, about 350 to about 425, about 350 to about 400, about 350 to about 375, about 375 to about 450, about 375 to about 425 to about 375 to about 400, about 400 to about 450, about 400 to about 425, or about 425 to about 450 h*ng/mL (dose-normalized to 10 mg). In further embodiments, the PK profile has a mean $AUC_{last}$ of between about 280 and 310 h*ng/ml (dose-normalized to 10 mg).

In still further aspects, the pharmaceutical composition has a PK profile comprising a median $t_{max}$ between about 1 to 4 hours. In some embodiments, the median $t_{max}$ is about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, or about 4 hours. In other embodiments, the median $t_{max}$ is about 1 to about 3.5, about 1 to about 3, about 1 to about 2.5, about 1 to about 2, about 1 to about 1.5, about 1.5 to about 4, about 1.5 to about 3.5, about 1.5 to about 3, about 1.5 to about 2.5, about 1.5 to about 2, about 2 to about 4, about 2 to about 3.5, about 2 to about 3, about 2 to about 2.5, about 2.5 to about 4, about 2.5 to about 3.5, about 2.5 to about 3, about 3 to about 4, about 3 to about 3.5, or about 3.5 to about 4 hours. In further embodiments, the median $t_{max}$ is about 1.5 hours.

In some embodiments, the pharmaceutical composition comprises a PK profile of Treatment A, Treatment B, Treatment C, or Treatment D, as shown in Table 69.

In some embodiments, the pharmaceutical composition has a PK profile including a mean $C_{max}$ of about 30, about 31, about 32, about 33, about 34, or about 35 ng/ml when administered after at least a 10-hour fast (dose-normalized to 10 mg). In some embodiments, the pharmaceutical composition comprises has a PK profile including a mean $C_{max}$ of about 31.2 ng/ml with standard deviation of about 6.9 ng/ml (dose-normalized to 10 mg). In some embodiments, the pharmaceutical composition comprises about 10 mg aticaprant and has a PK profile including a mean $C_{max}$ of about 34.1 ng/ml with standard deviation of about 10.0 ng/ml when administered after at least a 10-hour fast. In some embodiments, the pharmaceutical composition comprises about 5 mg aticaprant and has a PK profile including a mean $C_{max}$ of about 17.0 ng/mL with standard deviation of about 4.48 ng/mL when administered after at least a 10-hour fast.

In some embodiments, the pharmaceutical composition has a PK profile including a mean $C_{max}$ of about 36, about 37, about 38, about 39, or about 35 ng/ml when administered about 30 minutes after the start of a high-fat meal following at least a 10-hour fast (dose-normalized to 10 mg). In some embodiments, the pharmaceutical composition comprises about 10 mg aticaprant and has a PK profile including a mean $C_{max}$ of about 37.7 ng/ml with a standard deviation of about 9.18 ng/ml when administered about 30 minutes after the start of a high-fat meal following at least a 10-hour fast.

In some embodiments, the pharmaceutical composition has a PK profile comprising a mean $AUC_{infinity}$ of about 300, about 305, about 310, about 315, or about 320 h*ng/mL when administered after a least a 10-hour fast (dose-normalized to 10 mg).

In some embodiments, the pharmaceutical composition has a PK profile comprising a mean $AUC_{infinity}$ of about 400, about 420, about 425, about 430, about 440, or about 450 h*ng/ml when administered about 30 minutes after the start of a high-fat meal following at least a 10-hour fast (dose-normalized to 10 mg).

In some embodiments, the pharmaceutical composition has a PK profile comprising a median $t_{max}$ of about 1.0, about 1.1, about 1.2, about 1.3, about 1.4, about 1.5, about 1.6, about 1.7, about 1.8, about 1.9, or about 2.0 hours when administered after at least a 10-hour fast. In some embodiments, the pharmaceutical composition has a PK profile comprising a median $t_{max}$ of about 1.5 hours when administered after at least a 10-hour fast.

In some embodiments, the pharmaceutical composition has a PK profile comprising a median $t_{max}$ of about 2.5, about 2.6, about 2.7, about 2.8, about 2.9 or about 3.0 hours when administered about 30 minutes after the start of a high-fat meal following at least a 10-hour fast. In some embodiments, the pharmaceutical composition has a PK profile comprising a median $t_{max}$ of about 2.75 hours when administered about 30 minutes after the start of a high-fat meal following at least a 10-hour fast.

As noted, the compositions contain a pharmaceutically acceptable excipient, one of which may be a filler. In some embodiments, the filler is the filler is microcrystalline cellulose, lactose monohydrate, or silicified microcrystalline cellulose, or a combination thereof. In other embodiments, the filler is microcrystalline cellulose. In further embodiments, the filler is lactose monohydrate. In yet other embodiments, the filler is silicified microcrystalline cellulose. The composition comprises between about 10% to about 99.9% filler by weight, based on the weight of the composition. In some embodiments, the composition contains about 10, about 15, about 20, about 25, about 30, about 35, about 40, about 45, about 50, about 55, about 60, about 65, about 70, about 75, about 80, about 81, about 82, about 83, about 84, about 85, about 86, about 87, about 88, about 89, about 90, about 91, about 92, about 93, about 94, about 95, about 96, about 97, about 98, about 99, or about 99.9% by weight, based on the weight of the composition, of a filler In other embodiments, the composition comprises about 10 to about 90, about 10 to about 80, about 10 to about 70, about 10 to about 60, about 10 to about 50, about 10 to about 40, about 10 to about 30, about 10 to about 20, about 20 to about 99.9, about 20 to about 90, about 20 to about 80, about 20 to about 70, about 20 to about 60, about 20 to about 50, about 20 to about 40, about 20 to about 30, about 30 to about 99.9, about 30 to about 90, about 30 to about 80, about 30 to about 70, about 30 to about 60, about 30 to about 50, about 30 to about 40, about 40 to about 99.9, about 40 to about 90, about 40 to about 80, about 40 to about 70, about 40 to about 60, about 40 to about 50, about 50 to about 99.9, about 50 to about 90, about 50 to about 80, about 50 to about 70, about 50 to about 60, about 60 to about 99.9, about 60 to about 90, about 60 to about 80, about 60 to about 70, about 70 to about 99.9, about 70 to about 90, about 70 to about 80, about 80 to about 99.9, about 80 to about 90, or about 90 to about 99.9% by weight, based on the weight of the composition, of a filler. In further embodiments, the composition comprises about 90% by weight, based on the weight of the composition, of the filler. In other embodiments, the composition comprises about 88.5% by weight, based on the weight of the composition, of the filler.

The aticaprant to filler ratio is between about 0.005 and about 9 by weight. In some embodiments, the aticaprant to filler ratio is about 0.008 and 0.8 about by weight. In other embodiments, the aticaprant to filler ratio is about 0.005 to about 8, about 0.005 to about 7, about 0.005 to about 6, about 0.005 to about 5, about 0.005 to about 4, about 0.005 to about 3, about 0.005 to about 2, about 0.005 to about 1, about 0.005 to about 0.5, about 0.005 to about 0.1, about 0.005 to about 0.05, about 0.005 to about 0.01, about 0.01 to about 9, about 0.01 to about 8, about 0.01 to about 7, about 0.01 to about 6, about 0.01 to about 5, about 0.01 to about 4, about 0.01 to about 3, about 0.01 to about 2, about 0.01 to about 1, about 0.01 to about 0.5, about 0.01 to about 0.1, about 0.01 to about 0.05, about 0.05 to about 9, about 0.05 to about 8, about 0.05 to about 7, about 0.05 to about 6, about 0.05 to about 5, about 0.05 to about 4, about 0.05 to about 3, about 0.05 to about 2, about 0.05 to about 1, about 0.05 to about 0.5, about 0.05 to about 0.1, about 0.1 to about 9, about 0.1 to about 8, about 0.1 to about 7, about 0.1 to about 6, about 0.1 to about 5, about 0.1 to about 4, about 0.1 to about 3, about 0.1 to about 2, about 0.1 to about 1, about 0.1 to about 0.5, about 1 to about 9, about 1 to about 8, about 1 to about 6, about 1 to about 5, about 1 to about 4, about 1 to about 3, about 1 to about 2, about 2 to about 9, about 2 to about 8, about 2 to about 7, about 2 to about 6, about 2 to about 5, about 2 to about 4, about 2 to about 3, about 3 to about 9, about 3 to about 8, about 3 to about 7, about 3 to about 6, about 3 to about 5, about 3 to about 4, about 4 to about 9, about 4 to about 8, about 4 to about 7, about 4 to about 6, about 4 to about 4, about 5 to about 9, about 5 to about 8, about 5 to about 7, about 5 to about 6, about 6 to about 9, about 6 to about 8, about 6 to about 7, about 7 to about 9, about 7 to about 8, or about 8 to about 9 by weight. In further embodiments, the aticaprant to filler ratio is about 0.056 by weight.

The composition may further comprise one or more of a filler, disintegrant, glidant, lubricant, solvent, coloring agent, binder, buffers, preservatives, penetration agents, wetting agents, surfactants, solubilizing agents, thickening agents, colorants, antioxidants, emulsifying agents, isotonizing agents, suspending agents, and/or viscosity increasing agents.

In some embodiments, the composition further comprises one or more of a disintegrant. Examples of disintegrants useful in the compositions include, e.g., the disintegrant is croscarmellose sodium. The composition comprises between about 0.5% to about 50% by weight, based on the weight of the composition, of the disintegrant. In some embodiments, the composition comprises about 0.5, about 1, about 2, about 3, about 4, about 5, about 6, about 7, about 8, about 9, about 10, about 15, about 20, about 25, about 30, about 35, about 40, about 45, or about 50% by weight, based on the weight of the composition, of the disintegrant. In other embodiments, the composition comprises about 0.5 to about 40%, about 0.5 to about 30%, about 0.5 to about 20%, about 0.5 to about 10%, about 0.5 to about 5%, about 0.5 to about 4%, about 0.5 to about 3%, about 0.5 to about 2%, about 0.5 to about 1%, about 5 to about 50%, about 5 to about 40%, about 5 to about 30%, about 5 to about 20%, about 5 to about 10%, about 10 to about 50%, about 10 to about 40%, about 10 to about 30%, about 10 to about 20%, about 20 to about 50%, about 20 to about 40%, about 20 to about 30%, about 30 to about 50%, about 30 to about 40%, or about 40 to about 50% by weight, based on the weight of the composition of the disintegrant. In further embodiments, the composition comprises about 5% by weight, based on the weight of the composition, of the disintegrant. The aticaprant to disintegrant ratio is between about 0.1 and 10 by weight. In some embodiments, the aticaprant to disintegrant ratio is about 0.1, about 0.5, about 1, about 2, about 3, about 4, about 5, about 6, about 7, about 8, about 9, or about 10 by weight. In other embodiments, the aticaprant to disintegrant ratio is about 0.1 to about 8, about 0.1 to about 7, about 0.1 to about 6, about 0.1 to about 5, about 0.1 to about 4, about 0.1 to about 3, about 0.1 to about 2, about 0.1 to about 1, about 0.1 to about 0.5, about 0.5 to about 10, about 0.5 to about 9, about 0.5 to about 8, about 0.5 to about 7, about 0.5 to about 6, about 0.5 to about 5, about 0.5 to about 4, about 0.5 to about 3, about 0.5 to about 2, about 0.5 to about 1, about 1 to about 10, about 1 to about 9, about 1 to about 8, about 1 to about 7, about 1 to about 6, about 1 to about 5, about 1 to about 4, about 1 to about 3, about 1 to about 2, about 2 to about 10, about 2 to about 9, about 2 to about 8, about 2 to about 7, about 2 to about 6, about 2 to about 5, about 2 to about 4, about 2 to about 3, about 3 to about 10, about 3 to about 9, about 3 to about 8, about 3 to about 7, about 3 to about 6, about 3 to about 5, about 3 to about 4, about 4 to about 10, about 4 to about 9, about 4 to about 8, about 4 to about 7, about 4 to about 6, about 4 to about 5, about 5 to about 10, about 5 to about 9, about 5 to about 8, about 5 to about 7, about 5 to about 6, about 6 to about 10, about 6 to about 9, about 6 to about 8, about 6 to about 7, about 7 to about 10, about 7 to about 9, about 7 to about 8, about 8 to about 10, about 8 to about 9, about 9 to about 10 by weight. In further embodiments, the aticaprant to disintegrant ratio is about 5 by weight. In other embodiments, the aticaprant to disintegrant ratio is about 1 by weight.

In other embodiments, the composition further comprises one or more of a glidant. Examples of glidants useful in the compositions include, e.g., silica, colloidal anhydrous. The composition comprises between about 0.1% to about 10% glidant by weight, based on the weight of the composition. In some embodiment, the composition contains about 0.1, about 0.5, about 1, about 2, about 3, about 4, about 5, about 6, about 7, about 8, about 9, or about 10% by weight, based on the weight of the composition, of the glidant. In other embodiments, the composition contains about 0.1 to about 9, about 0.1 to about 8, about 0.1 to about 7, about 0.1 to about 6, about 0.1 to about 5, about 0.1 to about 4, about 0.1 to about 3, about 0.1 to about 2, about 0.1 to about 1, about 0.1 to about 0.5, about 0.5 to about 10, about 0.5 to about 9, about 0.5 to about 8, about 0.5 to about 7, about 0.5 to about 6, about 0.5 to about 5, about 0.5 to about 4, about 0.5 to about 3, about 0.5 to about 2, about 0.5 to about 1, about 1 to about 10, about 1 to about 9, about 1 to about 8, about 1 to about 7, about 1 to about 6, about 1 to about 5, about 1 to about 4, about 1 to about 3, about 1 to about 2, about 2 to about 10, about 2 to about 9, about 2 to about 8, about 2 to about 7, about 2 to about 6, about 2 to about 5, about 2 to about 4, about 2 to about 3, about 3 to about 10, about 3 to about 9, about 3 to about 8, about 3 to about 7, about 3 to about 6, about 3 to about 5, about 3 to about 4, about 4 to about 10, about 4 to about 9, about 4 to about 8, about 4 to about 7, about 4 to about 6, about 4 to about 5, about 5 to about 10, about 5 to about 9, about 5 to about 8, about 5 to about 7, about 5 to about 6, about 6 to about 10, about 6 to about 9, about 6 to about 8, about 6 to about 7, about 7 to about 10, about 7 to about 9, about 7 to about 8, about 8 to about 10, about 8 to about 9, or about 9 to about 10% by weight, based on the weight of the composition, of the glidant. In further embodiments, the composition contains about 1% by weight, based on the weight of the composition, of the glidant. The aticaprant to glidant ratio is between 0.5 and 50 by weight. In some embodiments, the aticaprant to glidant ratio is about 0.5, about 1, about 2, about 3, about 4, about 5, about 6, about 7, about 8, about 9, about 10, about 15, about 20, about 25, about 30, about 35, about 40, about 45, or about 50 by weight. In other embodiments, the aticaprant to glidant ratio is about 0.5 to about 50, about 0.5 to about 45, about 0.5 to about 40, about 0.5 to about 35, about 0.5 to about 30, about 0.5 to about 25, about 0.5 to about 20, about 0.5 to about 15, about 0.5 to about 10, about 0.5 to about 5, about 0.5 to about 1, about 1 to about 50, about 1 to about 45, about 1 to about 40, about 1 to about 35, about 1 to about 30, about 1 to about 25, about 1 to about 20, about 1 to about 15, about 1 to about 10, about 1 to about 5, about 5 to about 50, about 5 to about 45, about 5 to about 40, about 5 to about 35, about 5 to about 30, about 5 to about 25, about 5 to about 20, about 5 to about 15, about 5 to about 10, about 10 to about 50, about 10 to about 45, about 10 to about 40, about 10 to about 35, about 10 to about 30, about 10 to about 25, about 10 to about 20, about 10 to about 15, about 20 to about 50, about 20 to about 40, about 20 to about 30, about 30 to about 50, about 23 to about 40, about 40 to about 50, or about 45 to about 50 by weight. In further embodiments, the aticaprant to glidant ratio is about 5 by weight.

In further embodiments, the composition further comprises one or more of a lubricant. Examples of lubricants useful in the compositions include, e.g., the lubricant is magnesium stearate. The composition comprises between about 0.05% to about 5% lubricant by weight, based on the weight of the composition. In some embodiments, the composition comprises about 0.05, about 0.1, about 0.5, about 1, about 1.5, about 2, about 2.5, about 3, about 3.5, about 4, about 4.5 or about 5% by weight, based on the weight of the composition, of lubricant. In other embodiments, the composition comprises about 0.05 to about 4.5, about 0.05 to about 4, about 0.05 to about 3, about 0.05 to about 2, about 0.05 to about 1, about 0.05 to about 0.5, about 0.05 to about 0.1, about 0.1 to about 5, about 0.1 to about 4, about 0.1 to about 3, about 0.1 to about 2, about 0.1 to about 1, about 0.1 to about 0.5, about 0.5 to about 5, about 0.5 to about 4, about 0.5 to about 3, about 0.5 to about 2, about 0.5 to about 1, about 1 to about 5, about 1 to about 4, about 1 to about 3, about 1 to about 2, about 2 to about 5, about 2 to about 4, about 2 to about 3, about 3 to about 5, about 3 to about 4, or about 4 to about 5% by weight, based on the weight of the composition, of lubricant. In further embodiments, the composition comprises about 0.5% by weight, based on the weight of the composition, of the lubricant. The aticaprant to lubricant ratio is between about 1 and about 100 by weight. In some embodiments, the aticaprant to lubricant ratio is about 1, about 5, 10, about 15, about 20, about 25, about 30, about 35, about 40, about 45, about 50, about 55, about 60, about 65, about 70, about 75, about 80, about 85, about 90, about 95, or about 100 by weight. In other embodiments, the aticaprant to lubricant ratio is 1 to about 90, about 1 to about 80, about 1 to about 70, about 1 to about 60, about 1 to about 50, about 1 to about 40, about 1 to about 30, about 1 to about 20, about 1 to about 10, about 1 to about 5, about 5 to about 100, about 1 to about 90, about 1 to about 80, about 1 to about 70, about 1 to about 60, about 1 to about 50, about 1 to about 40, about 1 to about 30, about 1 to about 20, about 1 to about 10, about 1 to about 5, about 5 to about 100, 5 to about 90, about 5 to about 80, about 5 to about 70, about 5 to about 60, about 5 to about 50, about 5 to about 40, about 5 to about 30, about 5 to about 20, about 5 to about 10, about 10 to about 100, about 10 to about 90, about 10 to about 80, about 10 to about 70, about 10 to about 60, about 10 to about 50, about 10 to about 40, about 10 to about 30, about 10 to about 20, about 20 to about 100, about 20 to about 90, about 20 to about 80, about 20 to about 70, about 20 to about 60, about 20 to about 50, about 20 to about 40, about 20 to about 30, about 30 to about 100, about 30 to about 90, about 30 to about 80, about 30 to about 70, about 30 to about 60, about 30 to about 50, about 30 to about 40, about 40, to about 100, about 40 to about 90, about 40 to about 80, about 40 to about 70, about 40 to about 60, about 40 to about 50, about 50 to about 100, about 50 to about 90, about 50 to about 80, about 50 to about 70, about 50 to about 60, about 60 to about 100, about 60 to about 90, about 60 to about 80, about 60 to about 70, about 70 to about 100, about 70 to about 90, about 70 to about 80, about 80 to about 100, about 80 to about 90, or about 90 to about 100 by weight. In further embodiments, the aticaprant to lubricant ratio is about 10 by weight.

In some aspects, the composition comprises one or more of an aticaprant to filler ratio between 0.005 and 9 by weight; an aticaprant to disintegrant ratio between 0.1 and 10 by weight; an aticaprant to glidant ratio between 0.5 and 50 by weight; and an aticaprant to lubricant ratio between 1 and 100 by weight.

In other aspects, the composition comprises one or more of an aticaprant to filler ratio of about 0.06 by weight; an aticaprant to disintegrant ratio of about 1 by weight; an aticaprant to glidant ratio of about 5 by weight; and an aticaprant to lubricant ratio of about 10 by weight.

In further aspects, the composition comprises about 5% by weight of aticaprant, about 88.5% by weight of filler, about 5% by weight of disintegrant by weight, about 1% by weight of glidant, and about 0.5% by weight of lubricant, based on the weight of the composition.

Desirably, the composition is formulated as a solid composition. In some embodiments, the solid composition is a tablet, capsule, or caplet. In other embodiments, the solid composition is a tablet such as an oral tablet. In further embodiments, the solid composition is a capsule such as an oral capsule. In yet other embodiments, the solid composition is a caplet such as an oral caplet. Optionally, the solid compositions are coated. For example, the coating is an enteric coating. By doing so, the coating provides a film coat on the solid composition. In some embodiments, the film coat comprises a coating powder. In other embodiments, the film coat comprises Opadry II Orange. In further embodiments, the coating powder is Opadry II Orange.

The tablet may comprise one or more layers. In some embodiments, the tablet comprises a core tablet and a film coat to provide a film coated tablet. The ratio of the film coat to core tablet is between about 0.03 to 10 by weight. In some embodiments, the ratio of the film coat to core tablet is about 0.03, 0.05, 0.08, 0.1, 0.5, 1, 2, 3, 4, 5, 6, 7, 8, 9, or 10 by weight, based on the weight of the composition. In other embodiments, the ratio of the film coat to core tablet is about 0.03 to about 9, about 0.03 to about 8, about 0.03 to about 7, about 0.03 to about 6, about 0.03 to about 6, about 0.03 to about 5, about 0.03 to about 4, about 0.03 to about 3, about 0.03 to about 2, about 0.03 to about 1, about 0.03 to about 0.5, about 0.03 to about 0.1, about 0.05 to about 10, 0.05 to about 9, about 0.05 to about 8, about 0.05 to about 7, about 0.05 to about 6, about 0.05 to about 6, about 0.05 to about 5, about 0.05 to about 4, about 0.05 to about 3, about 0.05 to about 2, about 0.05 to about 1, about 0.05 to about 0.5, about 0.05 to about 0.1, about 0.1 to about 10, 0.1 to about 9, about 0.1 to about 8, about 0.1 to about 7, about 0.1 to about 6, about 0.1 to about 6, about 0.1 to about 5, about 0.1 to about 4, about 0.1 to about 3, about 0.1 to about 2, about 0.1 to about 1, about 0.1 to about 0.5, 0.5 to about 9, about 0.5 to about 8, about 0.5 to about 7, about 0.5 to about 6, about 0.5 to about 6, about 0.5 to about 5, about 0.5 to about 4, about 0.5 to about 3, about 0.5 to about 2, about 0.5 to about 1, about 1 to about 10, 1 to about 9, about 1 to about 8, about 1 to about 7, about 1 to about 6, about 1 to about 6, about 1 to about 5, about 1 to about 4, about 1 to about 3, about 1 to about 2, about 2 to about 10, about 2 to about 9, about 2 to about 8, about 2 to about 7, about 2 to about 6, about 2 to about 6, about 2 to about 5, about 2 to about 4, about 2 to about 3, about 3 to about 10, about 3 to about 9, about 3 to about 8, about 3 to about 7, about 3 to about 6, about 3 to about 6, about 3 to about 5, about 3 to about 4, about 4 to about 10, about 4 to about 9, about 4 to about 8, about 4 to about 7, about 4 to about 6, about 4 to about 5, about 5 to about 10, about 5 to about 9, about 5 to about 8, about 5 to about 7, about 5 to about 6, about 6 to about 10, about 6 to about 9, about 6 to about 8, about 6 to about 7, about 7 to about 10, about 7 to about 9, about 7 to about 8, about 8 to about 10, about 8 to about 9, or about 9 to about 10.

The core tablet may contain one or more phases. In some embodiments, the core tablet comprises a first phase such as an intragranular phase. In other embodiments, the core tablet comprises a second phase such as an extragranular phase. In further embodiments, the core tablet comprises intragranular and extragranular phases.

The ratio of the intragranular phase to extragranular phase in the core tablet is between about 1.5 and about 3 by weight. In some embodiments, the ratio of the intragranular phase to extragranular phase in the core tablet is about 1.5, about 1.6, about 1.7, about 1.8, about 1.9, about 2, about 2.1, about 2.2, about 2.3, about 2.4, about 2.5, about 2.6, about 2.7, about 2.8, about 2.9, or about 3 by weight. In other embodiments, the ratio of the intragranular phase to extragranular phase in the core tablet is about 1.5 to about 2.8, about 1.5 to about 2.5, about 1.5 to about 2.3, about 1.5 to about 2, about 1.5 to about 1.8, about 1.8 to about 3, about 1.8 to about 2.8, about 1.8 to about 2.5, about 1.8 to about 2.3, about 2 to about 3, about 2 to about 2.8, about 2 to about 2.5, about 2 to about 2.3, about 2 to about 2.1, about 2.1 to about 3, about 2.1 to about 2.8, about 2.1 to about 2.5, about 2.1 to about 2.3, about 2.3 to about 3, about 2.3 to about 2.8, about 2.3 to about 2.5, about 2.5 to about 3, about 2.5 to about 2.8, and about 2.8 to about 3 by weight. In further embodiments, the ratio of the intragranular phase to extragranular phase in the core tablet is about 2.1 by weight.

As for the composition, the solid composition contains aticaprant and one or more pharmaceutically acceptable excipients. In some aspects, the intragranular phase comprises aticaprant, a filler, a disintegrant, and a glidant. In other aspects, the intragranular phase comprises one filler. In further aspects, the intragranular phase comprises two fillers.

The intragranular phase comprises about 10 to about 120 mg of the filler. In some embodiments, the intragranular phase comprises about 10, about 20, about 30, about 40, about 50, about 60, about 70, about 80, about 90, about 100, about 110, or about 120 mg of the filler. In other embodiments, the intragranular phase comprises about 10 to about 110, about 10 to about 100, about 10 to about 90, about 10 to about 80, about 10 to about 70, about 10 to about 60, about 10 to about 50, about 10 to about 40, about 10 to about 30, about 10 to about 20, about 20 to about 120, about 20 to about 110, about 20 to about 100, about 20 to about 90, about 20 to about 80, about 20 to about 70, about 20 to about 60, about 20 to about 50, about 20 to about 40, about 20 to about 30, about 30 to about 120, about 30 to about 110, about 30 to about 100, about 30 to about 90, about 30 to about 80, about 30 to about 70, about 30 to about 60, about 30 to about 50, about 30 to about 40, about 40 to about 120, about 40 to about 110, about 40 to about 100, about 40 to about 90, about 40 to about 80, about 40 to about 70, about 40 to about 60, about 40 to about 50, about 50 to about 120, about 50 to about 110, about 50 to about 100, about 50 to about 90, about 50 to about 80, about 50 to about 70, about 50 to about 60, about 60 to about 120, about 60 to about 110, about 60 to about 100, about 60 to about 90, about 60 to about 80, about 60 to about 70, about 70 to about 120, about 70 to about 110, about 70 to about 100, about 70 to about 90, about 70 to about 80, about 80 to about 120, about 80 to about 110, about 80 to about 100, about 80 to about 90, about 90 to about 120, about 90 to about 110, about 90 to about 100, about 100 to about 120, about 100 to about 110, or about 110 to about 120. In further embodiments, the intragranular phase contains about 60 mg of filler. In yet other embodiments, the intragranular phase contains about 30 mg of microcrystalline cellulose. In still further embodiments, the intragranular phase contains about 30 mg of lactose monohydrate. In other embodiments, the intragranular phase contains about 60 mg of microcrystalline cellulose. In further embodiments, the intragranular phase contains about 60 mg of lactose monohydrate.

The intragranular phase comprises an aticaprant to filler ratio of between about 0.008 and 0.8 by weight. In some embodiments, the intragranular phase contains an aticaprant to filler ratio of about 0.008, about 0.005, about 0.001, about 0.01, about 0.05, about 0.1, about 0.2, about 0.3, about 0.4, about 0.5, about 0.6, about 0.7, or about 0.8 by weight. In other embodiments, the intragranular phase comprises an aticaprant to filler ratio of about 0.008 to about 0.7, about 0.008 to about 0.6, about 0.008 to about 0.5, about 0.008 to about 0.6, about 0.008 to about 0.5, about 0.008 to about 0.4, about 0.008 to about 0.3, about 0.008 to about 0.2, about 0.008 to about 0.1, about 0.008 to about 0.05, about 0.008 to about 0.01, about 0.01 to about 0.8, about 0.01 to about 0.7, 0.01 to about 0.6, about 0.01 to about 0.5, about 0.01 to about 0.4, about 0.01 to about 0.5, about 0.01 to about 0.4, about 0.01 to about 0.3, about 0.01 to about 0.2, about 0.01 to about 0.1, about 0.01 to about 0.05, about 0.05 to about 0.8, about 0.05 to about 0.9, about 0.05 to about 0.8, about 0.05 to about 0.7, about 0.05 to about 0.6, about 0.05 to about 0.6, about 0.05 to about 0.5, about 0.05 to about 0.4, about 0.05 to about 0.3, about 0.05 to about 0.2, about 0.05 to about 0.1, about 0.1 to about 0.8, about 0.1 to about 0.7, about 0.1 to about 0.6, about 0.1 to about 0.5, about 0.1 to about 0.4, about 0.1 to about 0.3, about 0.1 to about 0.2, about 0.2 to about 0.8, about 0.2 to about 0.7, about 0.2 to about 0.6, about 0.2 to about 0.5, about 0.2 to about 0.4, about 0.2 to about 0.3, about 0.3 to about 0.8, about 0.3 to about 0.7, about 0.3 to about 0.6, about 0.3 to about 0.5, about 0.3 to about 0.4, about 0.4 to about 0.8, about 0.4 to about 0.7, about 0.4 to about 0.6, about 0.4 to about 0.5, about 0.5 to about 0.8, about 0.5 to about 0.7, about 0.5 to about 0.6, about 0.6 to about 0.8, about 0.6 to about 0.7, or about 0.7 to about 0.8 by weight. In further embodiments, the intragranular phase comprises an aticaprant to filler ratio of about 0.08 by weight.

The intragranular phase also may contain a disintegrant. In some embodiments, the intragranular phase contains about 1 to about 10 mg of the disintegrant. In other embodiments, the intragranular phase contains about 1, about 1.5, about 2, about 2.5, about 3, about 3.5, about 4, about 4.5, about 5, about 5.5, about 6, about 6.5, 7, about 7.5, about 8, about 8.5, about 9, about 9.5 or about 10 mg of the disintegrant. In further embodiments, the intragranular phase contains about 1 to about 9, about 1 to about 8, about 1 to about 7, about 1 to about 6, about 1 to about 5, about 1 to about 4, about 1 to about 3, about 1 to about 2, about 2 to about 10, about 2 to about 9, about 2 to about 8, about 2 to about 7, about 2 to about 6, about 2 to about 5, about 2 to about 4, about 2 to about 3, about 2.5 to about 10, about 2.5 to about 9, about 2.5 to about 8, about 2.5 to about 7, about 2.5 to about 6, about 2.5 to about 5, about 2.5 to about 4, about 2.5 to about 3, about 3 to about 10, about 3 to about 9, about 3 to about 8, about 3 to about 7, about 3 to about 6, about 3 to about 5, about 3 to about 4, about 4 to about 10, about 4 to about 9, about 4 to about 8, about 4 to about 7, about 4 to about 6, about 4 to about 5, about 5 to about 10, about 5 to about 9, about 5 to about 8, about 5 to about 7, about 5 to about 6, about 6 to about 10, about 6 to about 9, about 6 to about 8, about 6 to about 7, about 7 to about 10, about 7 to about 9, about 7 to about 8, about 8 to about 10, about 8 to about 9, or about 0 to about 10. In yet other embodiments, the intragranular phase contains about 2.5 mg of the disintegrant. In still further embodiments, the intragranular phase contains about 5 mg of the disintegrant. In other embodiments, the intragranular phase contains about 2.5 mg of croscarmellose sodium. In further embodiments, the intragranular phase contains about 5 mg of croscarmellose sodium.

The intragranular phase may further contain a glidant. In some embodiments, the intragranular phase contains about 0.1 to about 5 mg of a glidant. In other embodiments, the intragranular phase contains about 0.1, about 0.5, about 1, about 1.5, about 2, about 2.5, about 3, about 3.5, about 4, about 4.5, or about 5 mg of a glidant. In further embodiments, the intragranular phase contains about 0.1 to about 4, about 0.1 to about 3, about 0.1 to about 2, about 0.1 to about 1, about 0.1 to about 0.5, about 0.5 to about 5, about 0.5 to about 4, about 0.5 to about 3, about 0.5 to about 2, about 0.5 to about 1, about 1 to about 5, about 1 to about 4, about 1 to about 3, about 1 to about 2, about 2 to about 5, about 2 to about 4, about 2 to about 3, about 3 to about 5, about 3 to about 4, or about 4 to about 5 mg of a glidant. In yet other embodiments, the intragranular phase contains about 0.5 mg of the glidant. In still further embodiments, the intragranular phase contains about 1 mg of the glidant. In other embodiments, the intragranular phase contains about 0.5 mg of silica, colloidal anhydrous. In further embodiments, the intragranular phase contains about 1 mg of silica, colloidal anhydrous.

The intragranular phase has an aticaprant to disintegrant ratio of between about 0.2 and 20 by weight; In some embodiments, the intragranular phase has an aticaprant to disintegrant ratio of about 0.2, about 0.3, about 0.4, about 0.5, about 0.6, about 0.7, about 0.8, about 0.9, about 1, about 1.1, about 1.2, about 1.3, about 1.4, about 1.5, about 1.6, about 1.7, about 1.8, about 1.9, about 2, about 3, about 4, about 5, about 6, about 7, about 8, about 9, about 10, about 11, about 12, about 13, about 14, about 15, about 16, about 17, about 18, about 19, or about 20 by weight. In other embodiments, the intragranular phase comprises an aticaprant to disintegrant ratio of about 0.2 to about 18, about 0.2 to about 16, about 0.2 to about 14, about 0.2 to about 12, about 0.2 to about 10, about 0.2 to about 8, about 0.2 to about 6, about 0.2 to about 4, about 0.2 to about 3, about 0.2 to about 2, about 0.2 to about 1, about 0.2 to about 0.5, about 0.5 to about 20, about 0.5 to about 18, about 0.5 to about 16, about 0.5 to about 14, about 0.5 to about 12, about 0.5 to about 10, about 0.5 to about 8, about 0.5 to about 6, about 0.5 to about 4, about 0.5 to about 2, about 0.5 to about 1, about 1 to about 20, about 1 to about 18, about 1 to about 16, about 1 to about 14, about 1 to about 12, about 1 to about 10, about 1 to about 8, about 1 to about 6, about 1 to about 4, about 1 to about 3, about 1 to about 2, about 1 to about 1.5, about 2 to about 20, about 2 to about 18, about 2 to about 16, about 2 to about 14, about 2 to about 12, about 2 to about 10, about 2 to about 8, about 2 to about 6, about 2 to about 4, about 4 to about 20, about 4 to about 18, about 4 to about 16, about 4 to about 14, about 4 to about 12, about 4 to about 10, about 4 to about 6, about 4 to about 8, about 4 to about 6, about 5 to about 20, about 6 to about 18, about 6 to about 16, about 6 to about 14, about 6 to about 12, about 6 to about 10, about 6 to about 8, about 8 to about 20, about 8 to about 18, about 8 to about 16, about 8 to about 14, about 8 to about 12, about 8 to about 10, about 10 to about 20, about 10 to about 18, about 10 to about 16, about 10 to about 14, about 10 to about 12, about 12 to about 20, about 12 to about 18, about 12 to about 16, about 12 to about 14, about 14 to about 20, about 14 to about 18, about 14 to about 16, about 16 to about 20, about 16 to about 18, or about 18 to about 20 by weight. In further embodiments, the intragranular phase comprises an aticaprant to disintegrant ratio of about 2 by weight.

The intragranular phase comprises an aticaprant to glidant ratio of between about 1 and 100 by weight. In some embodiments, the intragranular phase comprises an aticaprant to glidant ratio of about 1, about 5, about 10, about 15, about 20, about 30, about 40, about 50, about 60, about 70, about 80, about 90, or about 100 by weight. In other embodiments, the intragranular phase comprises an aticaprant to glidant ratio of about 1 to about 80, about 1 to about 60, about 1 to about 40, about 1 to about 20, about 1 to about 15, about 1 to about 10, about 1 to about 5, about 2 to about 80, about 2 to about 60, about 2 to about 40, about 2 to about 20, about 2 to about 15, about 2 to about 10, about 2 to about 5, about 5 to about 80, about 5 to about 60, about 5 to about 40, about 5 to about 20, about 5 to about 15, about 5 to about 10, about 10 to about 80, about 10 to about 60, about 10 to about 40, about 10 to about 20, about 20 to about 80, about 20 to about 60, about 20 to about 40, about 40 to about 80, about 40 to about 60, or about 60 to about 80 by weight. In further embodiments, the intragranular phase comprises an aticaprant to glidant ratio of 10 by weight.

The extragranular phase comprises one or more of a filler, a disintegrant, a glidant, and a lubricant. In some embodiments, the extragranular phase comprises a filler. In other embodiments, the extragranular phase comprises a disintegrant. In further embodiments, the extragranular phase comprises a glidant. In yet other embodiments, the extragranular phase comprises a lubricant.

The extragranular phase may comprise a filler. In some embodiments, the extragranular phase contains one filler. In other embodiment, the extragranular phase contains about 10 to about 80 mg of a filler. In further embodiments, the extragranular phase contains about 10, about 15, about 20, about 25, about 30, about 35, about 40, about 45, about 50, about 55, about 60, about 70, or about 80 mg of a filler. In still other embodiments, the extragranular phase contains about 10 to about 70, about 10 to about 60, about 10 to about 50, about 10 to about 40, about 10 to about 30, about 10 to about 20, about 10 to about 15, about 15 to about 80, about 15 to about 70, about 15 to about 60, about 15 to about 50, about 15 to about 40, about 15 to about 30, about 15 to about 20, about 20 to about 80, about 20 to about 70, about 20 to about 60, about 20 to about 50, about 20 to about 40, about 20 to about 30, about 25 to about 80, about 25 to about 70, about 25 to about 60, about 25 to about 50, about 25 to about 40, about 25 to about 30, about 30 to about 80, about 30 to about 70, about 30 to about 60, about 30 to about 50, about 30 to about 40, about 35 to about 80, about 35 to about 70, about 35 to about 60, about 35 to about 50, about 35 to about 40, about 40 to about 80, about 40 to about 70, about 40 to about 60, about 40 to about 50, about 40 to about 80, about 40 to about 70, about 45 to about 80, about 45 to about 70, about 45 to about 60, about 45 to about 50, about 50 to about 80, about 50 to about 70, about 50 to about 60, about 50 to about 55, about 55 to about 80, about 55 to about 70, about 55 to about 60, about 60 to about 80, about 60 to about 70, about 65 to about 80, about 65 to about 80, about 70 to about 80, or about 75 to about 80 mg of a filler. In yet further embodiments, the extragranular phase contains about 28.5 mg of the filler. In other embodiments, the extragranular phase contains about 28.5 of silicified microcrystalline cellulose. In further embodiments, the extragranular phase contains about 57 mg of the filler. In still other embodiments, the extragranular phase contains about 57 mg of silicified microcrystalline cellulose.

The extragranular phase may additionally contain a disintegrant. In some embodiments, the disintegrant is croscarmellose sodium. In other embodiments, the extragranular phase contains about 1 to about 10 mg of a disintegrant. In further embodiments, the extragranular phase contains about 1, about 2, about 2.5, about 3, about 4, about 5, about 6, about 7, about 7.5, about 8, about 9, or about 10 mg of a disintegrant. In yet other embodiments, the extragranular phase contains about 1 to about 10, about 1 to about 9, about 1 to about 8, about 1 to about 7, about 1 to about 6, about 1 to about 5, about 1 to about 4, about 1 to about 3, about 1 to about 2.5, about 1 to about 2, about 2 to about 10, about 2 to about 9, about 2 to about 8, about 2 to about 7, about 2 to about 6, about 2 to about 5, about 2 to about 4, about 2 to about 3, about 2.5 to about 10, about 2.5 to about 9, about 2.5 to about 8, about 2.5 to about 7, about 2.5 to about 6, about 2.5 to about 5, about 2.5 to about 4, about 2.5 to about 3, about 3 to about 10, about 3 to about 9, about 3 to about 8, about 3 to about 7, about 3 to about 6, about 3 to about 5, about 3 to about 4, about 4 to about 10, about 4 to about 9, about 4 to about 8, about 4 to about 7, about 4 to about 6, about 4 to about 5, about 5 to about 10, about 5 to about 9, about 5 to about 8, about 5 to about 7, about 5 to about 6, about 6 to about 10, about 6 to about 9, about 6 to about 8, about 6 to about 7, about 7 to about 10, about 7 to about 9, about 7 to about 8, about 7.5 to about 10, about 7.5 to about 9, about 7.5 to about 8, about 8 to about 10, about 8 to about 9, or about 9 to about 10 mg of a disintegrant. In still further embodiments, the extragranular phase contains about 2.5 mg of a disintegrant. In other embodiments, the extragranular phase contains about 5 mg of a disintegrant. In further embodiments, the extragranular phase contains about 2.5 mg of croscarmellose sodium. In still other embodiments, the extragranular phase contains about 5 mg of croscarmellose sodium.

The extragranular phase comprises a filler to disintegrant ratio of between about 1 and 100 by weight. In some embodiments, the extragranular phase comprises a filler to disintegrant ratio of 1, 5, 10, 20, 30, 40, 50, 60, 70, 80, 90, or 100 by weight. In further embodiments, the extragranular phase comprises a filler to disintegrant ratio of about 1 to about 90, about 1 to about 80, about 1 to about 70, about 1 to about 60, about 1 to about 50, about 1 to about 40, about 1 to about 30, about 1 to about 20, about 1 to about 10, about 1 to about 5, about 5 to about 100, about 5 to about 80, about 5 to about 60, about 5 to about 40, about 5 to about 20, about 5 to about 15, about 10 to about 80, about 10 to about 60, about 10 to about 40, about 10 to about 20, about 10 to about 15, about 20 to about 100, about 20 to about 80, about 20 to about 60, about 20 to about 40, about 40 to about 100, about 40 to about 80, about 40 to about 60, about 60 to about 100, about 60 to about 80, or about 80 to about 100 by weight. In yet other embodiments, the extragranular phase comprises a filler to disintegrant ratio of about 11.4.

The extragranular phase further may contain a glidant. In some embodiments, the glidant is silica, colloidal anhydrous. In other embodiments, the extragranular phase contains about 0.1 to about 5 mg of the glidant. In further embodiments, the extragranular phase contains about 0.1, 0.25, 0.5, 0.75, 1, 2, 3, 4, or 5 mg of a glidant. In yet other embodiments, the extragranular phase contains about 0.1 to about 4, about 0.1 to about 3, about 0.1 to about 2, about 0.1 to about 1, about 0.1 to about 0.5, about 0.5 to about 5, about 0.5 to about 4, about 0.5 to about 3, about 0.5 to about 2, about 0.5 to about 1, about 1 to about 5, about 1 to about 4, about 1 to about 3, about 1 to about 2, about 2 to about 5, about 2 to about 4, about 2 to about 3, about 3 to about 5, about 3 to about 4, or about 4 to about 5 mg of a glidant. In still further embodiments, the extragranular phase contains about 0.5 mg of a glidant. In other embodiments, the extragranular phase contains about 1 mg of a glidant. In further embodiments, the extragranular phase contains about 0.5 mg of silica, colloidal anhydrous. In yet other embodiments, the extragranular phase contains about 1 mg of silica, colloidal anhydrous.

The extragranular phase comprises a filler to glidant ratio of between about 5 and 500 by weight. In other embodiments, the extragranular phase comprises a filler to glidant ratio of about 5, about 10, about 25, about 50, about 100, about 150, about 200, about 250, about 300, about 350, about 400, about 450, or about 500. In further embodiments, the extragranular phase comprises a filler to glidant ratio of about 5 to about 400, about 5 to about 300, about 5 to about 200, about 5 to about 100, about 5 to about 75, about 5 to about 50, about 10 to about 500, about 10 to about 400, about 10 to about 300, about 10 to about 200, about 10 to about 100, about 10 to about 50, about 25 to about 500, about 25 to about 400, about 25 to about 300, about 25 to about 200, about 25 to about 100, about 25 to about 75, about 25 to about 50, about 50 to about 500, about 50 to about 400, about 50 to about 300, about 50 to about 200, about 50 to about 100, about 100 to about 500, about 100 to about 400, about 100 to about 300, about 100 to about 200, about 200 to about 500, about 200 to about 400, about 200 to about 300, about 300 to about 500, about 300 to about 400, or about 400 to about 500 by weight. In still further embodiments, the extragranular phase comprises a filler to glidant ratio of about 57.

The extragranular phase may also contain a lubricant. In some embodiments, the lubricant is magnesium stearate. In other embodiments, the extragranular phase contains about 0.1 to about 5 mg of the lubricant. In further embodiments, the extragranular phase contains about 0.1, 0.25, 0.5, 0.75, 1, 2, 3, 4, or 5 mg of a lubricant. In yet other embodiments, the extragranular phase contains about 0.1 to about 4, about 0.1 to about 3, about 0.1 to about 2, about 0.1 to about 1, about 0.1 to about 0.5, about 0.5 to about 5, about 0.5 to about 4, about 0.5 to about 3, about 0.5 to about 2, about 0.5 to about 1, about 1 to about 5, about 1 to about 4, about 1 to about 3, about 1 to about 2, about 2 to about 5, about 2 to about 4, about 2 to about 3, about 3 to about 5, about 3 to about 4, or about 4 to about 5 mg of a lubricant. In still further embodiments, the extragranular phase contains about 0.5 mg of a lubricant. In other embodiments, the extragranular phase contains about 1 mg of a lubricant. In further embodiments, the extragranular phase contains about 0.5 mg of magnesium stearate. In yet other embodiments, the extragranular phase contains about 1 mg of magnesium stearate.

The extragranular phase comprises a filler to lubricant ratio of between about 5 and 500 by weight. In other embodiments, the extragranular phase comprises a filler to lubricant ratio of about 5, about 10, about 25, about 50, about 100, about 150, about 200, about 250, about 300, about 350, about 400, about 450, or about 500. In further embodiments, the extragranular phase comprises a filler to lubricant ratio of about 5 to about 400, about 5 to about 300, about 5 to about 200, about 5 to about 100, about 5 to about 75, about 5 to about 50, about 10 to about 500, about 10 to about 400, about 10 to about 300, about 10 to about 200, about 10 to about 100, about 10 to about 50, about 25 to about 500, about 25 to about 400, about 25 to about 300, about 25 to about 200, about 25 to about 100, about 25 to about 75, about 25 to about 50, about 50 to about 500, about 50 to about 400, about 50 to about 300, about 50 to about 200, about 50 to about 100, about 100 to about 500, about 100 to about 400, about 100 to about 300, about 100 to about 200, about 200 to about 500, about 200 to about 400, about 200 to about 300, about 300 to about 500, about 300 to about 400, or about 400 to about 500 by weight. In still further embodiments, the extragranular phase comprises a filler to lubricant ratio of about 57.

In some embodiments, the intragranular phase comprises one or more of: an aticaprant to filler ratio of between about 0.008 and 0.8 by weight; an aticaprant to disintegrant ratio of between about 0.2 and 20 by weight; and an aticaprant to glidant ratio of between about 1 and 100 by weight.

In some embodiments, the extragranular phase comprises one or more of: a filler to disintegrant ratio of between about 1 and 100 by weight; a filler to glidant ratio of between about 5 and 500 by weight; and a filler to lubricant ratio of between about 5 and 500 by weight. In other embodiments, the extragranular phase comprises a filler to disintegrant ratio of about 11.4 by weight. In further embodiments, the extragranular phase comprises a filler to glidant ratio of about 57 by weight. In yet other embodiments, the extragranular phase comprises a filler to lubricant ratio of about 57 by weight.

In other aspects, the core tablet comprises about 5% aticaprant by weight, about 88.5% filler by weight, about 5% disintegrant by weight, about 1% glidant by weight, and about 0.5% lubricant by weight.

The oral tablet may be of weight that is suitable for administration by a patient. In some embodiments, the oral tablet has a core tablet of about 10 to about 1000 mg. In other embodiments, the core tablet is about 10, about 25, about 50, about 100, about 200, about 300, about 400, about 500, about 600, about 700, about 800, about 900, or about 1000 mg. In further embodiments, the core tablet is about 10 to about 900, about 10 to about 800, about 10 to about 700, about 10 to about 600, about 10 to about 500, about 10 to about 400, about 10 to about 300, about 10 to about 200, about 10 to about 100, about 10 to about 50, about 25 to about 1000, about 25 to about 900, about 25 to about 800, about 25 to about 700, about 25 to about 600, about 25 to about 500, about 25 to about 400, about 25 to about 300, about 25 to about 200, about 25 to about 100, about 25 to about 75, about 50 to about 1000, about 50 to about 900, about 50 to about 800, about 50 to about 700, about 50 to about 600, about 50 to about 500, about 50 to about 400, about 50 to about 300, about 50 to about 200, about 50 to about 100, about 100 to about 1000, about 100 to about 900, about 100 to about 800, about 100 to about 700, about 100 to about 600, about 100 to about 500, about 100 to about 400, about 100 to about 300, about 100 to about 200, about 200 to about 1000, about 200 to about 900, about 200 to about 800, about 200 to about 700, about 200 to about 600, about 200 to about 500, about 200 to about 400, about 200 to about 300, about 500 to about 1000, about 500 to about 800, about 500 to about 600, about 800 to about 1000, or about 800 to about 900 mg. In yet other embodiments, the core tablet is about 100 mg. In still further embodiments, the oral tablet comprises a core tablet of about 200 mg.

In some aspects, the core tablet contains a disintegrant. For example, the core tablet contains about 5 to about 100 mg of a disintegrant. In some embodiments, the core tablet contains about 5, about 10, about 20, about 30, about 40, about 50, about 60, about 70, about 80, about 90, or about 100 mg of a disintegrant. In other embodiments, the core tablet contains about 5 to about 80, about 5 to about 60, about 5 to about 40, about 5 to about 20, about 5 to about 15, about 5 to about 10, about 10 to about 100, about 10 to about 80, about 10 to about 60, about 10 to about 40, about 10 to about 20, about 20 to about 100, about 20 to about 80, about 20 to about 60, about 20 to about 40, about 40 to about 100, about 40 to about 80, about 40 to about 60, about 60 to about 100, about 60 to about 80, or about 80 to about 100 mg of a disintegrant. In further embodiments, the core tablet contains about 5 mg of the disintegrant. In yet other embodiments, the core tablet contains about 10 mg of the disintegrant.

In other aspects, the core tablet contains a glidant. For example, the core tablet contains about 1 to about 100 mg of a glidant. In some embodiments, the core tablet contains about 1, about 2, about 3, about 4, about 5, about 10, about 20, about 30, about 40, about 50, about 60, about 70, about 80, about 90, or about 100 mg of a glidant. In other embodiments, the core tablet contains about 1 to about 100, about 1 to about 80, about 1 to about 60, about 1 to about 40, about 1 to about 20, about 1 to about 10, about 1 to about 5, about 2 to about 100, about 2 to about 80, about 2 to about 60, about 2 to about 40, about 2 to about 20, about 2 to about 10, about 2 to about 5, about 5 to about 80, about 5 to about 60, about 5 to about 40, about 5 to about 20, about 5 to about 15, about 5 to about 10, about 10 to about 100, about 10 to about 80, about 10 to about 60, about 10 to about 40, about 10 to about 20, about 20 to about 100, about 20 to about 80, about 20 to about 60, about 20 to about 40, about 40 to about 100, about 40 to about 80, about 40 to about 60, about 60 to about 100, about 60 to about 80, or about 80 to about 100 mg of a glidant. In further embodiments, the core tablet contains about 1 mg of the glidant. In yet other embodiments, the core tablet contains about 2 mg of the glidant.

In further aspects, the core tablet contains a lubricant. For example, the core tablet contains about 0.5 to about 100 mg of a lubricant. In some embodiments, the core tablet contains about 0.5, about 1, about 2, about 3, about 4, about 5, about 10, about 20, about 30, about 40, about 50, about 60, about 70, about 80, about 90, or about 100 mg of a lubricant. In other embodiments, the core tablet contains about 0.5 to about 80, about 0.5 to about 60, about 0.5 to about 40, about 0.5 to about 20, about 0.5 to about 10, about 0.5 to about 5, about 0.5 to about 1, about 1 to about 100, about 1 to about 80, about 1 to about 60, about 1 to about 40, about 1 to about 20, about 1 to about 10, about 1 to about 5, about 2 to about 100, about 2 to about 80, about 2 to about 60, about 2 to about 40, about 2 to about 20, about 2 to about 10, about 2 to about 5, about 5 to about 80, about 5 to about 60, about 5 to about 40, about 5 to about 20, about 5 to about 15, about 5 to about 10, about 10 to about 100, about 10 to about 80, about 10 to about 60, about 10 to about 40, about 10 to about 20, about 20 to about 100, about 20 to about 80, about 20 to about 60, about 20 to about 40, about 40 to about 100, about 40 to about 80, about 40 to about 60, about 60 to about 100, about 60 to about 80, or about 80 to about 100 mg of a lubricant. In further embodiments, the core tablet contains about 0.5 mg of the lubricant. In yet other embodiments, the core tablet contains about 1 mg of the lubricant.

In further aspects, the core tablet contains a filler. For example, the core tablet contains about 1 to about 200 mg of a filler. In some embodiments, the core tablet contains about 1, about 2, about 3, about 4, about 5, about 10, about 20, about 30, about 40, about 50, about 60, about 70, about 80, about 90, about 100, about 110, about 120, about 130, about 140, about 150, about 160, about 170, about 180, about 190, or about 200 mg of a filler. In other embodiments, the core tablet contains about 1 to about 180, about 1 to about 160, about 1 to about 140, about 1 to about 120, 1 to about 100, about 1 to about 80, about 1 to about 60, about 1 to about 40, about 1 to about 20, about 1 to about 10, about 1 to about 5, about 2 to about 200, about 2 to about 180, about 2 to about 160, about 2 to about 140, about 2 to about 120, about 2 to about 100, about 2 to about 80, about 2 to about 60, about 2 to about 40, about 2 to about 20, about 2 to about 10, about 2 to about 5, about 5 to about 200 m, about 5 to about 180, about 5 to about 160, about 5 to about 140, about 5 to about 120, about 5 to about 100, about 5 to about 80, about 5 to about 60, about 5 to about 40, about 5 to about 20, about 5 to about 15, about 5 to about 10, about 10 to about 200, about 10 to about 180, about 10 to about 160, about 10 to about 140, about 10 to about 120, about 10 to about 100, about 10 to about 80, about 10 to about 60, about 10 to about 40, about 10 to about 20, about 20 to about 200, about 20 to about 180, about 20 to about 160, about 20 to about 140, about 20 to about 120, about 20 to about 100, about 20 to about 80, about 20 to about 60, about 20 to about 40, about 40 to about 200, about 40 to about 180, about 40 to about 160, about 40 to about 140, about 40 to about 120, bout 40 to about 100, about 40 to about 80, about 40 to about 60, about 60 to about 200, about 60 to about 180, about 60 to about 160, about 60 to about 140, about 60 to about 120, about 60 to about 100, about 60 to about 200, about 60 to about 180, about 60 to about 160, about 60 to about 140, about 60 to about 120, about 60 to about 100, about 60 to about 80, about 80 to about 200, about 80 to about 180, about 80 to about 160, about 80 to about 140, about 80 to about 120, about 80 to about 100 mg, about 100 to about 200, about 100 to about 180, about 100 to about 160, about 100 to about 140, about 100 to about 120, about 120 to about 200, about 120 to about 180, about 120 to about 160, about 120 to about 140, about 140 to about 200, about 140 to about 180, about 140 to about 160, about 160 to about 200, about 160 to about 180, or about 180 to about 200 mg of a filler. In further embodiments, the core tablet contains about 88.5 mg of the filler. In yet other embodiments, the core tablet contains about 177 mg of the filler.

In some preferred embodiments, the oral tablet comprises a core tablet of about 100 mg and comprising about 5 mg aticaprant, about 5 mg disintegrant, about 88.5 mg filler, about 1 mg glidant, and about 0.5 mg lubricant.

In other preferred embodiments, oral tablet comprising a core tablet of about 200 mg, the core tablet comprising about 10 mg aticaprant, about 10 mg disintegrant, about 177 mg filler, about 2 mg glidant, and about 1 mg lubricant.

As noted above, the core tablet may be coated with a film coat. In some embodiments, the oral tablet comprises about 3 mg of film coat. In other embodiments, the oral tablet comprises about 6 mg of film coat.

In some aspects, the film coated oral tablet comprises about 80 to about 99.9% by weight of the core tablet and about 0.1 to about 20% by weight, based on the weight of the film coated oral tablet, of the core tablet. In some embodiments, the film coated oral tablet comprises about 80, about 81, about 82, about 83, about 84, about 85, about 86, about 87, about 88, about 89, about 90, about 91, about 92, about 93, about 94, about 95, about 96, about 97, about 98, about 99, or 99.9% by weight, based on the weight of the film coated oral tablet. In other embodiments, the film coated oral tablet comprises about 80 to about 99, about 80 to about 96, about 80 to about 94, about 80 to about 92, about 80 to about 90, about 80 to about 88, about 80 to about 86, about 80 to about 84, about 80 to about 82, about 82 to about 99, about 82 to about 96, about 82 to about 94, about 82 to about 92, about 82 to about 90, about 82 to about 88, about 82 to about 86, about 82 to about 84, about 84 to about 99, about 84 to about 99, about 84 to about 96, about 84 to about 94, about 84 to about 92, about 84 to about 90, about 84 to about 88, about 84 to about 86, about 86 to about 99, about 86 to about 96, about 86 to about 94, about 86 to about 92, about 86 to about 90, about 86 to about 88, about 88 to about 99, about 88 to about 96, about 88 to about 94, about 88 to about 92, about 88 to about 90, about 90 to about 99, about 90 to about 96, about 90 to about 94, about 90 to about 92, about 92 to about 99, about 92 to about 96, about 92 to about 94, about 94 to about 99, about 94 to about 96, about 96 to about 99, or about 98 to about 99% by weight, based on the weight of the film coated oral tablet, of the core tablet. In further embodiments, the film coated oral tablet comprises about 97% core tablet by weight, based on the weight of the film coated oral tablet. In yet other embodiments, the film coated oral tablet comprises about 0.1 to about 20% by weight, based on the weight of the film coated oral tablet, of film coat. In still further embodiments, film coated oral tablet comprises about 0.1, about 0.5, about 1, about 2, about 3, about 4, about 5, about 6, about 7, about 8, about 9, about 10, about 11, about 12, about 13, about 14, about 15, about 16, about 17, about 18, about 19, or about 20% by weight, based on the weight of the film coated oral tablet, of the film coat. In other embodiments, the film coated oral tablet comprises about 0.1 to about 18, about 0.1 to about 16, about 0.1 to about 14, about 0.1 to about 12, about 0.1 to about 10, about 0.1 to about 8, about 0.1 to about 6, about 0.1 to about 4, about 0.1 to about 2, about 0.1 to about 1, about 0.5 to about 20, about 0.5 to about 18, about 0.5 to about 16, about 0.5 to about 14, about 0.5 to about 12, about 0.5 to about 10, about 0.5 to about 8, about 0.5 to about 6, about 0.5 to about 4, about 0.5 to about 2, about 1 to about 20, about 1 to about 18, about 1 to about 16, about 1 to about 14, about 1 to about 12, about 1 to about 10, about 1 to about 8, about 1 to about 6, about 1 to about 4, about 1 to about 2, about 2 to about 20, about 2 to about 18, about 2 to about 16, about 2 to about 14, about 2 to about 12, about 2 to about 10, about 2 to about 8, about 2 to about 8, about 2 to about 6, about 2 to about 4, about 4 to about 20, about 4 to about 18, about 4 to about 16, about 4 to about 12, about 4 to about 10, about 4 to about 8, about 4 to about 6, about 6 to about 20, about 6 to about 18, about 6 to about 16, about 6 to about 14, about 6 to about 12, about 6 to about 10, about 6 to about 8, about 8 to about 20, about 8 to about 18, about 8 to about 16, about 8 to about 14, about 8 to about 12, about 8 to about 10, about 10 to about 20, about 10 to about 18, about 10 to about 16, about 10 to about 14, about 10 to about 12, about 12 to about 20, about 12 to about 18, about 12 to about 16, about 12 to about 14, about 14 to about 20, about 14 to about 18, m about 14 to about 16, about 16 to about 20, about 16 to about 18, or about 18 to about 20% by weight, based on the weight of the film coated oral tablet, of the film coat. In further embodiments, the film coated oral tablet comprises about 3% by weight, based on the weight of the film coated oral tablet, of the film coat. In yet other embodiments, the film coated oral tablet comprises about 97% core tablet by weight and about 3% film coat by weight, based on the weight of the film coated oral tablet.

In some embodiments, the disclosure provides oral tablets comprising about 5 mg aticaprant, wherein the oral tablet comprises a core tablet of about 100 mg, wherein the core tablet comprises an intragranular and extragranular phase, wherein the intragranular phase comprises about 30 mg microcrystalline cellulose, about 30 mg lactose monohydrate, about 2.5 mg croscarmellose sodium, and about 0.5 mg silica, colloidal anhydrous; and wherein the extragranular phase comprises about 28.5 mg silicified microcrystalline cellulose, about 2.5 mg croscarmellose sodium, about 0.5 mg silica, colloidal anhydrous, and about 0.5 mg magnesium stearate.

In other embodiments, the disclosure provides oral tablets comprising about 10 mg aticaprant, wherein the oral tablet comprises a core tablet of about 200 mg, wherein the core tablet comprises an intragranular and extragranular phase, wherein the intragranular phase comprises about 60 mg microcrystalline cellulose, about 60 mg lactose monohydrate, about 5 mg croscarmellose sodium, and about 1 mg silica, colloidal anhydrous; and wherein the extragranular phase comprises about 57 mg silicified microcrystalline cellulose, about 5 mg croscarmellose sodium, about 1 mg silica, colloidal anhydrous, and about 1 mg magnesium stearate.

The solid compositions may also have a desirable dissolution profile that provide the desired release of aticaprant. In some embodiments, the solid composition contains about 2 mg and 20 mg of aticaprant and has a dissolution profile comprising a Q value of between about 60% and 90% at 45 minutes, under the dissolution operating conditions of (i) apparatus: Paddle (USP Type 2, Ph. Eur., JP), (ii) dissolution medium: 0.01 M hydrochloric acid, (iii) volume: 900 mL, (iv) temperature: 37±0.5° C., (v) rotation speed: 50 rpm, and (vi) analytical finish: UHPLC with UV detection at 247 nm. In some embodiments, the Q value is about 60, about 61, about 62, about 63, about 64, about 65, about 66, about 67, about 68, about 69, about 70, about 71, about 72, about 73, about 74, about 75, about 75, about 76, about 77, about 78, about 79, about 80, about 81, about 82, about 83, about 84, about 85, about 86, about 87, about 88, about 89, about 90, about 91, about 92, about 93, about 94, or about 95% at 45 minutes. In other embodiments, the Q value is about 60 to about 85, about 60 to about 80, about 60 to about 75, about 60 to about 70, about 70 to about 90, about 70 to about 85, about 70 to about 80, about 70 to about 75, about 75 to about 90, about 75 to about 85, about 75 to about 80, about 80 to about 90, about 80 to about 85, or about 85 to about 90% at 45 minutes. In further embodiments, the Q value is between about 70% and 80% at 45 minutes. In other aspects, the Q value is about 75% at 45 minutes.

Advantageously, aticaprant may be administered once daily, or the total daily dosage may be administered in divided doses of two, three or four times daily. In some embodiments, the composition containing aticaprant is administered once daily. In other embodiments, the oral tablet containing aticaprant is administered once daily. In further embodiments, the solid pharmaceutical composition containing aticaprant is administered once daily.

As described herein, in particular, the patient had an inadequate response to other antidepressant therapy prior to treatment with aticaprant. Thus, in a particular embodiment, the disclosure relates to aticaprant, for use as described herein, wherein the patient had an inadequate response to other antidepressant therapy prior to treatment with aticaprant. In a further particular embodiment, the disclosure also relates to the use of aticaprant in the manufacture of a medicament, as described herein, wherein the patient had an inadequate response to other antidepressant therapy prior to treatment with of aticaprant. In a further particular embodiment, the disclosure further relates to a package or pharmaceutical product as described herein, wherein the patient had an inadequate response to other antidepressant therapy prior to treatment with aticaprant. Such antidepressant therapy can be in particular selected from a selective serotonin reuptake inhibitor (SSRI), serotonin-norepinephrine reuptake inhibitor (SNRI), or a combination thereof.

As described herein, aticaprant may be used as adjunctive treatment, or in other words, in conjunction, as an add-on, or in combination with one or more antidepressants, for example, the patient may be already, or also, administered one or more antidepressants. Thus, in a further particular embodiment, the disclosure relates to aticaprant, for use as described herein, comprising administration of aticaprant, as adjunctive treatment with an effective amount of one or more antidepressants. In a further particular embodiment, the disclosure relates to aticaprant, for use as described herein, comprising administration of aticaprant, in conjunction with an effective amount of one or more antidepressants. In a further particular embodiment, the disclosure relates to aticaprant, for use as described herein, comprising administration of aticaprant, in combination with an effective amount of one or more antidepressants. In a further particular embodiment, the disclosure also relates to the use of aticaprant, in the manufacture of a medicament, as described herein, wherein the treatment comprises administration of an effective amount of aticaprant, as adjunctive treatment with an effective amount of one or more antidepressants. In a further particular embodiment, the disclosure also relates to the use of aticaprant, as described herein, wherein the treatment comprises administration of an effective amount of aticaprant, in conjunction with an effective amount of one or more antidepressants. In a further particular embodiment, the disclosure also relates to the use of aticaprant, as described herein, wherein the treatment comprises administration of an effective amount of aticaprant, in combination with an effective amount of one or more antidepressants. In a further particular embodiment, the disclosure further relates to a package or pharmaceutical product as described herein, wherein the instructions for treatment direct the administration of an effective amount of aticaprant, as adjunctive treatment with an effective amount of one or more antidepressants. In a further particular embodiment, the disclosure further relates to a package or pharmaceutical product as described herein, wherein the instructions for treatment direct the administration of an effective amount of aticaprant, in conjunction with an effective amount of one or more antidepressants. In a further particular embodiment, the disclosure further relates to a package or pharmaceutical product as described herein, wherein the instructions for treatment direct administration of an effective amount of aticaprant, in combination with an effective amount of one or more antidepressants. Such one or more antidepressants can be selected from a selective serotonin reuptake inhibitor (SSRI), serotonin-norepinephrine reuptake inhibitor (SNRI), or a combination thereof.

As already described, the disclosure relates to aticaprant, for use as described herein. In a particular embodiment, aticaprant is S-aticaprant. In a further embodiment of the disclosure, aticaprant, in particular S-aticaprant, for use as described herein, is to be administered in an amount of about 2 to about 35 mg, more in particular, of about 10 mg. In a yet further embodiment, aticaprant, in particular S-aticaprant, for use as described herein, is administered orally. Furthermore, in a further particular embodiment, the disclosure relates to aticaprant, in particular S-aticaprant, for use as described herein, administered once daily. The disclosure also relates to the use of aticaprant, in the manufacture of a medicament, as described herein. In a particular embodiment, aticaprant is S-aticaprant. In a further embodiment of the use as described herein, about 2 to about 35 mg aticaprant, is to be administered, more in particular, about 10 mg. In a yet further embodiment of the use, aticaprant is to be administered orally. Furthermore, in a further particular embodiment of the use aticaprant in particular S-aticaprant, is to be administered once daily. In a further particular embodiment, the disclosure further relates to a package or pharmaceutical product as described herein, wherein aticaprant is in particular S-aticaprant. In a further embodiment of the package or pharmaceutical product as described herein, the instructions for treatment direct administration of about 2 to about 35 mg aticaprant, more in particular, about 10 mg. In a yet further embodiment of the package or pharmaceutical product as described herein, the instructions for treatment direct aticaprant, in particular S-aticaprant, is for oral administration. Furthermore, in a further particular embodiment of the package or pharmaceutical product, as described herein, the instructions for treatment direct aticaprant, in particular S-aticaprant, is for once daily administration.

Advantageously, administration of aticaprant, does not result in weight gain during treatment, including clinically relevant weight gain. Thus, in a further particular embodiment, the disclosure relates to aticaprant, for use as described herein, wherein the patient does not experience weight gain during the treatment with aticaprant. In a further particular embodiment, the disclosure relates to a use as defined herein, wherein the patient does not experience weight gain during the treatment with aticaprant. In a further particular embodiment, the disclosure further relates to a package or pharmaceutical product as described herein, wherein the patient does not experience weight gain during the treatment with aticaprant. The body weight of the patient can in particular be assessed at the time of the initial administration of aticaprant.

It was also unexpectedly observed that, based on assessment at the time of initial administration, the patient does not experience a decrease in sexual functioning during the treatment with aticaprant. Thus, in further particular embodiment, the disclosure relates to aticaprant, for use as described herein, wherein the patient does not experience a decrease in sexual functioning during the treatment with aticaprant. In a further particular embodiment, the disclosure relates to a use as described herein, wherein the patient does not experience a decrease in sexual functioning during the treatment with aticaprant. In a further particular embodiment, the disclosure relates to a package or pharmaceutical product as described herein, wherein the patient does not experience a decrease in sexual functioning during the treatment with aticaprant. Such term "sexual functioning" comprises sexual drive, sexual arousal, vaginal lubrication, erection, orgasm achievement, or orgasm satisfaction. Sexual satisfaction can be assessed by methods known to the skilled person, for example, by applying the Arizona Sexual Experience Scale (ASEX).

As already described, the patient has anhedonia. In certain aspects, the anhedonia is moderate. In other aspects, the anhedonia is severe. Anhedonia can be measured, through an anhedonia scale, for example, the Snaith Hamilton Pleasure Scale (SHAPS). Thus, in a particular embodiment, the disclosure relates to aticaprant, for use as described herein, wherein the anhedonia of the patient is reduced by at least 40%, as measured by the change from baseline in total score in an anhedonia scale following 6 weeks of the treatment with aticaprant, more in particular, the anhedonia of the patient is reduced within about 3 weeks to about 6 weeks as measured by the change from baseline in total score in an anhedonia scale. In a further particular embodiment, the anhedonia scale is the Snaith Hamilton Pleasure Scale (SHAPS). Thus, in a particular embodiment, the disclosure relates to the use as described herein, wherein the anhedonia of the patient is reduced by at least 40%, as measured by the change from baseline in total score in an anhedonia scale following 6 weeks of the treatment with aticaprant, more in particular, the anhedonia of the patient is reduced within about 3 weeks to about 6 weeks as measured by the change from baseline in total score in an anhedonia scale. In a further particular embodiment, the anhedonia scale is the Snaith Hamilton Pleasure Scale (SHAPS). In a further particular embodiment, the disclosure relates to the package or pharmaceutical product as described herein, wherein the anhedonia of the patient is reduced by at least 40%, as measured by the change from baseline in total score in an anhedonia scale following 6 weeks of the treatment with aticaprant, more in particular, the anhedonia of the patient is reduced within about 3 weeks to about 6 weeks as measured by the change from baseline in total score in an anhedonia scale. In a further particular embodiment, the anhedonia scale is the Snaith Hamilton Pleasure Scale (SHAPS).

Treatment Methods

In one aspect of the present invention, methods are provided for treating patients having a more severe type of depression, i.e., major depressive disorder, using the compounds, compositions, e.g., solid compositions, and tablets, e.g., oral tablets, described herein. The patient also may be experiencing anhedonia. Because MDD alone is difficult to treat, treatment patients having anhedonia are even more problematic since their ability to gauge pleasure is impaired. Thus, such patients often receive inadequate treatment due to ineffective medications, repeated and unnecessary medical appointments, lack of patient compliance, overall patient frustration, among others. Further, antidepressants are known to have a variety of side effects such as weight gain, metabolic side effects, extrapyramidal symptoms, akathisia, cognitive impairment, among others. Thus, patients may choose to refrain from or stop taking antidepressants to avoid or prevent any side-effects.

The methods described herein are effective in managing the patient's depression and anhedonia using aticaprant. Desirably, the methods successfully permit the patient to manage their depression while simultaneously reducing anhedonia. In particular embodiments, the patients treated according to the described methods have moderate to severe anhedonia. The term "anhedonia" as used herein refers to the lack of or decreased ability to experience pleasure in daily activities. The term anhedonia includes loss of pleasure in sensory experiences (i.e., touch, taste, smell), as well as social interactions. In some embodiments, anhedonia and depressed mood are diagnostic criteria for a major depressive episode as part of MDD. Anhedonia also describes deficits in one or more components of reward-related behavior, also known as the pleasure cycle, such as wanting, liking, and learning. The pleasure cycle can be divided into three phases: the appetitive phase (dominated by wanting), the consummatory phase (dominated by liking), and the satiety phase (dominated by learning). The appetitive phase is characterized by the initial energy expenditure to attain a reward; the consummatory phase is enjoyment of the reward; and the satiety phase is characterized by learning and feedback integration.

To assess a potential effect on anhedonia, an anhedonia scale may be used. For example, the Snaith-Hamilton Pleasure Scale (SHAPS) analysis is a validated scale for the measurement of anhedonia. The SHAPS is a subject completed scale in which subjects score whether or not they experience pleasure in performing a list of activities or experiences. The SHAPS is a self-reported 14-item instrument, developed for the assessment of hedonic capacity. Subjects score whether they experience pleasure in performing a list of activities or experiences. Subjects can rate the answers as 1-4 where 1 indicates "Definitely agree", 2 indicates "Agree", 3 indicates "Disagree" and 4 indicates "Definitely disagree". The subject's item responses are summed to provide a total score ranging from 14 to 56. A higher total SHAPS score indicates higher levels of current anhedonia. Physician/clinical judgment can be used to assess anhedonia separately or in conjunction with an anhedonia scale.

In some embodiments, the patient has moderate anhedonia. In other embodiments, the patient has severe anhedonia. An assessment of moderate or severe anhedonia is typically determined physician/clinical judgment and/or by one or more tests that provide insight into whether a patient has anhedonia. For example, the severity of the anhedonia may be determined using the SHAPS method. In some embodiments, a patient with moderate or severe anhedonia is considered to have a high level of anhedonia. For example, a patient with a SHAPS score of 38 or greater is considered to have moderate to severe anhedonia that can be considered a high level of anhedonia. In some embodiments, a high level of anhedonia is reflected by a SHAPS score of at least about 40, about 42, about 44, about 46, about 48, about 50, about 52, about 54, about 56, about 58, or higher. A patient with mild or no anhedonia would be considered to have a low level of anhedonia that is assessed by physician/clinical judgment and/or one or more tests. For example, a patient with a SHAPS score of less than 38 is considered to have low anhedonia. In certain embodiments, a patient with mild anhedonia may have a SHAPS score of 20 to less than 38, for example, a SHAPS score of 20 to about 36, about 22 to about 36, about 24 to about 36, about 26 to about 36, about 26 to about 34, about 26 to about 32, about 26 to about 30, about 26 to about 28, about 28 to about 36, about 28 to about 36, about 30, to about 36, about 32 to about 36, about 34 to about 36, about 20 to about 34, about 22 to about 34, about 24 to about 34, about 26 to about 32, about 26 to about 30, about 26 to about 28, about 28 to about 36, about 28 to about 34, about 28 to about 32, about 28 to about 30, about 30 to about 36, about 30 to about 34, about 30 to about 32, about 32 to about 36, about 32 to about 34, or about 34 to about 36. Typically, a SHAPS score of less than 20 can be considered to correspond to normal hedonic functioning, and for purposes of this disclosure, would fall into the low category of anhedonia, e.g., a SHAPS score of less than 38.

In some embodiments, the patient's anhedonia is reduced from a high level of anhedonia to a low level of anhedonia. In yet other embodiments, the patient's anhedonia is reduced by at least about 40%, as measured by the change from baseline in total score in an anhedonia scale following treatment with aticaprant. In yet other embodiments, the patient's anhedonia is reduced by at least about 40%, about 50%, about 60%, about 70%, about 80%, about 90%, or about 95%, as measured by the change from baseline in total score in an anhedonia scale following treatment with aticaprant. In still further embodiments, In yet other embodiments, the patient's anhedonia is reduced by about 40 to about 90%, about 50 to about 90%, about 60 to about 90%, about 70 to about 90%, about 80 to about 90%, about 40 to about 80%, about 50 to about 80%, about 60 to about 80%, about 70 to about 80%, about 40 to about 70%, about 50 to about 70%, about 60 to about 70%, about 40 to about 60%, about 50 to about 60%, or about 50 to about 60%, as measured by the change from baseline in total score in an anhedonia scale following treatment with aticaprant. In other embodiments, the patient's anhedonia is ameliorated, i.e., reduced by 100%, as measured by the change from baseline in total score in an anhedonia scale following treatment with aticaprant.

Reduction of anhedonia after initiating treatment with aticaprant may be measured relative to the anhedonia of the patient as measured before treatment with aticaprant, i.e., a baseline anhedonia measurement. In doing so, the treating clinician is able to calculate the change of anhedonia from the baseline to the real time anhedonia measurement at any point after treatment with aticaprant. Thus, standard methods for measuring anhedonia may be used, such as an anhedonia scale, e.g., SHAPS.

Desirably, a baseline anhedonia measurement is obtained no more than about 1 week before initiating treatment with aticaprant. In some embodiments, a baseline anhedonia measurement is obtained about 7 days, about 6 days, about 5 days, about 4 days, about 3 days, about 2 days, or about 1 day before treatment with aticaprant. In further embodiments, a baseline anhedonia measurement is obtained about 24 hours, about 18 hours, about 12 hours, about 8 hours, about 4 hours, about 2 hours, about 1 hours, about 30 minutes, or about 15 minutes before initiating treatment with aticaprant.

The patient's change of anhedonia will depend on several factors including, without limitation, anhedonia severity, patient's sensitivity to aticaprant, other pharmaceutical agents being administered, among others. In some embodiments, the patient's anhedonia is reduced after about 3 weeks of treatment with aticaprant. In other embodiments, the patient's anhedonia is reduced after about 3 weeks of treatment with aticaprant. In further embodiments, the patient's anhedonia is reduced after about 3 weeks to about 6 weeks, and, in certain embodiments, through week 6, of treatment with aticaprant. In certain embodiments, the patient's anhedonia is reduced by at least about 40%, as measured by the change from baseline in total score in an anhedonia scale following about 6 weeks of the treatment with aticaprant. In further embodiments, the anhedonia of the patient is reduced within about 3 weeks, and in some embodiments within about 3 weeks to about 6 weeks, as measured by the change from baseline in total score in an anhedonia scale and/or by physician/clinical judgement.

The methods described herein were found to not only improve the patient's depression and anhedonia symptoms, but resulted in fewer antidepressant side effects. Doing so resulted in less absenteeism (i.e., more visits or interactions with physicians), greater cognitive functioning, improvements in health-related quality of life, more interest and engagement in everyday activities, improvement in family and inter-personal relationships, ability to function in the workplace, fewer hospitalizations, among others.

In some embodiments, the disclosure provides methods for treating MDD in a human patient by administering to the patient a pharmaceutical composition comprising between about 2 mg and 20 mg aticaprant, wherein the patient had an inadequate response to other antidepressant therapy prior to treatment with aticaprant. In some embodiments, administration of the pharmaceutical composition to the patient achieves a pharmacokinetic (PK) profile comprising one or more of the PK parameters noted above (dose-normalized to 10 mg) after administration of the composition to a human after at least a 10-hour fast.

As used herein, unless otherwise noted, the terms "subject" and "patient" refer to a human, who has been the object of treatment, observation or experiment. Preferably, the patient has experienced and/or exhibited at least one symptom of the disease or disorder to be treated and/or prevented. In some embodiments, the patient is an adult. As used herein, the term "adult" as used herein refers to a human that is about 18 years of age or older. In certain aspects, the patient is an elderly adult, i.e., greater than or equal to 65 years of age.

As used herein, unless otherwise noted, the terms "treating", "treatment" and the like, shall include the management and care of a subject or patient (preferably mammal, more preferably human) for the purpose of combating a disease, condition, or disorder and includes the administration of a compound described herein to prevent the onset of the symptoms or complications, alleviate one or more of the symptoms or complications, or eliminate the disease, condition, or disorder.

As used herein, the term "depression" (also referred to as depressive disorder) includes major depressive disorder, persistent depressive disorder, seasonal affective disorder, postpartum depression, premenstrual dysphoric disorder, situational depression, anhedonia, melancholic, mid-life depression, late-life depression, bipolar depression, depression due to identifiable stressors, treatment resistant depression, or combinations thereof. In certain embodiments, the depression is major depressive disorder. In other embodiments, the major depressive disorder is with melancholic features or anxious distress. In further embodiments, the depression is treatment-resistant depression. In other embodiments, the depression is major depressive disorder with suicidal ideation.

As known in the art, a patient is considered to have major depressive disorder if exhibiting five or more symptoms during the same two week period that are a change from previous functioning; depressed mood and/or loss of interest/pleasure must be present; excluding symptoms clearly attributable to another medical condition. See, e.g., Table 4.

TABLE 4

1. Depressed mood: Most of the day, nearly every day; may be subjective (e.g., feels sad, empty, hopeless) or observed by others (e.g., appears tearful); in children and adolescents, can be irritable mood
2. Loss of interest/pleasure: Markedly diminished interest/pleasure in all (or almost all) activities most of the day, nearly every day; may be subjective or observed by others
3. Weight loss or gain: Significant weight loss (without dieting) or gain (change of >5% body weight in a month), or decrease or increase in appetite nearly every day; in children, may be failure to gain weight as expected TABLE 4-continued 4. Insomnia or hypersomnia: Nearly every day
5. Psychomotor agitation or retardation: Nearly every day and observable by others (not merely subjectively restless or slow)
6. Fatigue: Or loss of energy, nearly every day
7. Feeling worthless or excessive/inappropriate guilt: Nearly every day; guilt may be delusional; not merely self-reproach or guilt about being sick
8. Decreased concentration: Nearly every day; may be indecisiveness; may be subjective or observed by others
9. Thoughts of death/suicide" Recurrent thoughts of death (not just fear of dying), recurrent suicidal ideation without specific plan, or suicide attempt, or a specific plan for suicide In some embodiments, to be diagnosed with MDD, the following criteria also are met:

1. Symptoms cause clinically significant distress or impairment in social, occupational, or other important areas of functioning
2. Episode not attributable to physiological effects of a substance or another medical condition
3. Episode not better explained by schizoaffective disorder, schizophrenia, schizophreniform disorder, delusional disorder, or other specified and unspecified schizophrenia spectrum and other psychotic disorders
4. No history of manic or hypomanic episode Major depressive disorder may be categorized as mild, moderate, or severe. In some embodiments, the MDD is mild. In other embodiments, the MDD is moderate. In further embodiments, the MDD is severe. As used herein, "mild MDD" applies to a patient having few, if any, symptoms in excess of those required to make the diagnosis, the intensity of the symptoms is distressing but manageable, and the symptoms result in minor impairment in social or occupational functioning. The mild MDD may be a single episode (ICD-10 F32.0) or a recurrent episode (ICD-10 F33.0). "Moderate MDD" applies to a patient having a number of symptoms, intensity of symptoms, and/or functional impairment are between those specified for "mild" and "severe." The moderate MDD may be a single episode (ICD-10 F32.1) or a recurrent episode (ICD-10 F33.1). "Severe MDD" applies to a patient where the number of symptoms is substantially in excess of that required to make the diagnosis, the intensity of symptoms is seriously distressing and unmanageable, and the symptoms markedly interfere with social and occupational functioning, and urgent symptom control is necessary. In some embodiments, the severe MDD may be a single episode (ICD-10 F32.2) or a recurrent episode (ICD-10 F33.2). In other embodiments, MDD is classified according to the DSM-5 definition of Table 5.

TABLE 5

| DSM-5 Criteria for MDD | |
|---|---|
| 1. Depressed Mood | At least 1 |
| 2. Loss of interest/pleasure (anhedonia) | |
| 1. Weight loss or gain | At least 5 |
| 2. Sleep problems | |
| 3. Psychomotor agitation or retardation | |
| 4. Guilt or worthlessness | |
| 5. Decreased concentration | |
| 6. Suicidality | |
| 7. Fatigue | |
| 1. Symptoms cause significant distress or impairment | Must have all 4 |
| 2. Not attributable to medical condition | |
| 3. Exclude schizophrenia disorders | |
| 4. No hx of mania or hypomania | |

Several scales are known in the art that may be utilized to diagnose or monitor patients with MDD. Examples of these scales include, without limitation, the Montgomery-Åsberg Depression Rating Scale (MADRS), Clinical Global Impression-Severity (CGI-S) scale, Symptoms of Major Depressive Disorder Scale (SMDDS), Self-Assessment of Treatment Experience (SATE) scale, and Massachusetts General Hospital (MGH) Antidepressant Treatment Response Questionnaire (ATRQ), i.e., MGH-ATRQ.

In some embodiments, MADRS is utilized to diagnose and/or monitor the patient. MADRS is a 10-item rating scale that is used in antidepressant studies. It is clinician-administered and designed to be used in subjects with MDD to measure the overall severity of depressive symptoms. The MADRS scale is validated, reliable, and acceptable to regulatory health authorities as a primary scale to determine efficacy in major depression. In some embodiments, MADRS is administered using the Structured Interview Guide for the MADRS (SIGMA). The scale consists of 10 items, each of which is scored from 0 (item not present or normal) to 6 (severe or continuous presence of the symptoms), summed for a total possible score of 60. Higher scores represent a more severe condition. The MADRS evaluates apparent sadness, reported sadness, inner tension, sleep appetite, concentration, lassitude, inability to feel (interest level), pessimistic thoughts, and suicidal thoughts.

In other embodiments, CGI-S is utilized to diagnose and/or monitor the patient's depression. CGI-S is a scale that rates the severity of the subject's illness at the time of assessment, relative to the clinician's past experience with subjects who have the same diagnosis and improvement with treatment. CGI-S provides an overall clinician-determined summary measure of severity of subject's illness that considers all available information, including knowledge of subject's history, psychosocial circumstances, symptoms, behavior, and impact of symptoms on subject's ability to function. CGI-S evaluates severity of psychopathology on scale of 0 to 7. Subject is assessed on severity of mental illness at time of rating according to: 0=not assessed; 1=normal (not at all ill); 2=borderline mentally ill; 3=mildly ill; 4=moderately ill; 5=markedly ill; 6=severely ill; 7=among most extremely ill patients.

In further embodiments, SMDDS is utilized to diagnose and/or monitor the patient's depression. SMDDS is a subjective rating of the patient. The SMDDS is a 16-item PRO measure. Each item is rated by the subject according to a 5-point Likert scale. Subjects respond to each question using a rating scale between 0 ("Not at all" or "Never") to 4 ("Extremely" or "Always"). The total score ranges from 0 to 60. The SMDDS uses a 7-day recall period and verbal rating scales. Higher score indicates more severe depressive symptomatology.

In yet other embodiments, SATE is utilized to diagnose and/or monitor the patient's depression. SATE is a one to three questionnaire administered when the subject is unable to complete other evaluations, i.e., away from the clinical setting such as at home. SATE is useful to evaluate improvement or deterioration of depressive symptoms of the subjects over a short period of time. For rating overall depression, subject selected one option out of Improved, not changed or got worse; for depression improvement, subject selected one option out of slightly improved, much improved, very much improved and for depression worsen subject selected slightly worse, much worse, very much worse. See, Table 6.

TABLE 6

SATE Questionnaire

Question 1: Since starting this study medication, overall would you say your depression is:
Improved
Got worse
Not changed
If the subject selects answer 1 (Improved), following question is asked:
Question 2: How much did your depression improve?
Slightly improved
Much improved
Very much improved
If the subject selects answer 3 (Got worse), following question is asked:
Question 3: How much did your depression worsen?
Slightly worse
Much worse
Very much worse The MGH-ATRQ is a self-rated scale used to determine treatment resistance in patient's having MDD. This questionnaire examines the antidepressant treatment history, using specific anchor points to define the adequacy of both dose and duration of each antidepressant trial, and the degree of symptomatic improvement. The MGH-ATRQ permits determining treatment resistance in depression and is known to those skilled in the art.

In certain embodiments, the patient had an inadequate response to other antidepressant therapy. "Inadequate response" as used herein refers to a patient experiencing a less than about 50% reduction in depressive symptom severity from the start of initiating treatment. Typically, the inadequate response is during a current/active episode of the depression. In some embodiments, an inadequate response refers to a patient experiencing about 26 to less than about 50% reduction in depressive symptom severity from the start of initiating treatment. In other embodiments, an inadequate response refers to a patient experiencing about 26 to about 49, about 26 to about 45, about 26 to about 40, about 26 to about 35, about 26 to about 30, about 30 to about 49, about 30 to about 45, about 30 to about 40, about 30 to about 35, about 35 to about 49, about 35 to about 45, about 35 to about 40, about 40 to about 49, or about 40 to about 45% reduction in depressive symptom severity from the start of initiating treatment. A patient's response may be measured by one or more scales described herein and/or by physician/clinical judgment. In some embodiments, an inadequate response is measured by MGH-ATRQ, MADRS, or SHAPS. In further embodiments, an inadequate response is measured by MGH-ATRQ.

To the extent a patient is said to have a partial response to treatment, this refers to some minor to moderate symptomatic improvement since the initiation of treatment, but some of the initial symptoms are still present and troubling to the patient and these persistent symptoms still affect behavior and function. For instance, the patient's motivation, productivity, and interest in his or her usual activities may still be impaired.

The term "other antidepressant therapy" as used herein refers to an antidepressant medication or non-pharmacological treatment that is used to treat patients having depression. In some aspects, the other antidepressant therapy is an antidepressant medication. In other aspects, the other antidepressant therapy is a non-pharmacological treatment. In further aspects, the other antidepressant therapy is an antidepressant medication other than aticaprant.

The antidepressant medication is any pharmaceutical agent which can be used to treat depression. Suitable examples include, without limitation, mono-amine oxidase inhibitors, tricyclics, tetracyclics, non-cyclics, triazolopyridines, selective serotonin reuptake inhibitors (SSRI), serotonin receptor antagonists, serotonin noradrenergic reuptake inhibitors (SNRI), noradrenergic and specific serotonergic agents, noradrenaline reuptake inhibitors, or antipsychotics (typical or atypical antipsychotics). Examples of monoamine oxidase inhibitors include phenelzine, tranylcypromine, moclobemide, and the like. Examples of tricyclics include imipramine, amitriptyline, desipramine, nortriptyline, doxepin, protriptyline, trimipramine, clomipramine, amoxapine, and the like. Examples of tetracyclics includes maprotiline, and the like. Examples of non-cyclics include nomifensine, and the like. Examples of triazolopyridines include trazodone, and the like. Examples of SSRIs include fluoxetine, sertraline, paroxetine, citalopram, citalopram, escitalopram, fluvoxamine, and the like. Examples of serotonin receptor antagonists include nefazadone, and the like. Examples of SNRIs include venlafaxine, milnacipran, desvenlafaxine, duloxetine, levomilnacipran and the like. Examples of noradrenergic and specific serotonergic agents include mirtazapine, and the like. Examples of noradrenaline reuptake inhibitors include reboxetine, edivoxetine and the like. Examples of typical antipsychotics include phenothiazines (e.g., chlorpromazine, thioridazine, fluphenazine, perphenazine, trifluoperazine, levomepromazin), thioxanthenes (e.g., thiothixene, flupentixol), butyrophenones (e.g., haloperidol), dibenzoxazepines (e.g., loxapine), dihydroindolones (e.g., molindone), substituted benzamides (e.g., sulpride, amisulpride), and the like. Examples of atypical antipsychotics include paliperidone, clozapine, risperidone, olanzapine, quetiapine, zotepine, ziprasidone, iloperidone, perospirone, blonanserin, sertindole, ORG-5222, sonepiprazole, aripiprazole, nemonapride, SR-31742, CX-516, SC-111, NE-100, divalproate (mood stabilizer) and the like. In further embodiments, the antidepressant medication includes natural products such as Kava-Kava, St. John's Wort, and the like or dietary supplements such as s-adenosylmethionine, and the like. In yet other embodiments, the antidepressant medication includes neuropeptides such as thyrotropin-releasing hormone and the like or compounds targeting neuropeptide receptors such as neurokinin receptor antagonists and the like. In still further embodiments, the antidepressant medication is a hormone such as triiodothyronine, and the like. In other embodiments, the antidepressant medication is SSRI, SNRI, or a combination thereof. Preferably, the antidepressant is a SSRI that is escitalopram, sertraline, paroxetine, fluoxetine or citalopram. In other embodiments, the antidepressant medication is a SNRI that is venlafaxine, duloxetine, vortioxeine or desvenlafaxine.

The non-pharmacologic treatment for use herein may be selected by one skilled in the art. In some embodiments, the non-pharmacologic treatment is psychotherapy, transcranial magnetic stimulation, or the like.

Therapeutically effective amounts/dosage levels and dosage regimens for the other antidepressant therapy may be readily determined by one of ordinary skill in the art. For example, therapeutic dosage amounts and regimens for pharmaceutical agents approved for sale are publicly available, for example as listed on packaging labels, in standard dosage guidelines, in standard dosage references such as the Physician's Desk Reference (Medical Economics Company or online at http://www.pdrel.com) or other sources.

In some embodiments, other antidepressant therapy may include one antidepressant medication. In other embodiments, other antidepressant therapy includes two or more antidepressant medications. In further embodiments, other antidepressant therapy includes two antidepressant medications. In yet other embodiments, other antidepressant therapy includes three antidepressant medications. The attending physician would be able to select suitable antidepressant therapies for use as described herein.

In certain embodiments, the patient was receiving treatment with other antidepressant therapy prior to receiving aticaprant. In some embodiments, the patient was receiving treatment with other antidepressant therapy that comprised a SSRI, SNRI, or a combination thereof. In other embodiments, the patient stopped treatment with other antidepressant therapy before initiating treatment with aticaprant.

Also encompassed by the methods described herein include adjunctive treatment with an effective amount of one or more antidepressants. As used herein, the term "adjunctive treatment" and "adjunctive therapy" shall mean treatment of a patient in need thereof by administering aticaprant in combination with one or more antidepressant(s), wherein aticaprant and the antidepressant(s) are administered by any suitable means, simultaneously, sequentially, separately, or in a single pharmaceutical formulation.

In some aspects, aticaprant is administered adjunctively with other antidepressant(s) currently being administered to the patient, including current antidepressant(s) to which the patient had an inadequate response, i.e., the antidepressant failed to treat the patient's depression. In other embodiments, aticaprant is administered adjunctively with an antidepressant(s) not previously administered to the patient, i.e., a new antidepressant. In still other embodiments, aticaprant is administered in a regimen with an antidepressant(s) previously administered to the patient.

Where aticaprant and other antidepressant(s) are administered in separate dosage forms, the number of dosages administered per day for each active compound may be the same or different and more typically different. The antidepressant may be dosed as prescribed by the attending physician and/or by its label and aticaprant is dosed as described herein. Typically, a patient is under concurrent treatment with both an antidepressant and aticaprant, where both are administered by their prescribed dosing regimens. The aticaprant and antidepressant(s) may be administered according to simultaneous or alternating regimens, at the same or different times during the course of the therapy, concurrently in divided or single forms.

Aticaprant and the antidepressant(s) may be administered via the same or different routes of administration. Examples of suitable methods of administration include, but are not limited to, oral, intravenous (iv), intranasal (in) intramuscular (im), subcutaneous (sc), transdermal, buccal, or rectal. In some embodiments, aticaprant is administered orally.

Treatment with aticaprant as described herein has several advantages over the treatments in the art. In some embodiments, the patient does not experience many of the side effects that are associated with other antidepressants, i.e., antidepressants other than aticaprant. In certain aspects, the patient does not experience weight gain during the treatment with aticaprant. As used herein, the term "weight gain" refers to an increase in the weight of patient, relative to the weight of the patient before taking aticaprant or the weight of the patient that is assessed at the time of the initial administration of aticaprant. In certain embodiments, the patient may actually see a decrease in overall weight, relative to the weight of the patient before taking aticaprant. In further embodiments, the patient's weight is stable, i.e., does not increase or decrease. In some embodiments, the patient does not experience a clinically relevant weight gain which is characterized as a weight increase of $\geq 7\%$.

This is contrary to many other antidepressants where weight gain, including clinically relevant weight gain, is a common, but unfortunate, side-effect.

In further aspects, the patient does not experience a decrease in sexual functioning during the treatment with aticaprant. As used herein, the term "decrease in sexual functioning" refers to reducing or lessening of one or more components of the human sex drive, i.e., sexual functioning. In some embodiments, the sexual functioning comprises one or more of sexual drive, sexual arousal, vaginal lubrication, erection, orgasm achievement, or orgasm satisfaction. In other embodiments, the sexual functioning comprises sexual drive. In further embodiments, the sexual functioning comprises vaginal lubrication satisfaction. In further embodiments, the sexual functioning comprises orgasm achievement. In yet other embodiments, the sexual functioning comprises orgasm satisfaction. Desirably, the patient's sexual functioning is assessed at the time of initial administration of aticaprant. Thus, the patient's sexual functioning while taking aticaprant can be compared to the patient's sexual functioning before administration of aticaprant. Sexual functioning may be assessed by using standard scales and techniques such as the Arizona Sexual Experience Scale (ASEX). The ASEX is used to investigate whether aticaprant has a further positive or negative effect on sexual function. The ASEX is 5 item rating scale administered to patients that quantifies sexual drive, sexual arousal, vaginal lubrication or penile erection, ability to reach orgasm and satisfaction. Scores range from 5 to 30, and two different versions of the scale are available (males and females).

Other scales may be utilized to determine the effectiveness of the methods used herein to treat the patient. Examples include the Cognitive and Physical Functioning Questionnaire (CPFQ), Karolinska Sleepiness Scale (KSS), and Temporal Experience of Pleasure Scale (TEPS). The CPFQ is a brief self-report scale that provides additional information regarding the impact of adjunctive treatment on aspects of cognitive and executive function including attention, memory and mental acuity. Subjects with MDD are often reported to have difficulties with functioning in this area. The KSS is a subject-reported assessment used to rate sleepiness on a scale of 1 to 9, ranging from "extremely alert" (1) to "very sleepy, great effort to keep awake, fighting sleep" (9). The TEPS includes 18 items, 2 subscales designed to distinguish between anticipatory and consummatory pleasure.

The methods described herein include administering an effective amount of aticaprant to the patient. The term "effective amount" as used herein, means that amount of active compound or pharmaceutical agent that elicits the biological or medicinal response in a human that is being sought by a researcher, medical doctor or other clinician, which includes alleviation of one or more of the symptoms of the disease or disorder being treated. In some embodiments, aticaprant is utilized in an effective amount as determined by the attending physician. In other embodiments, other antidepressant(s) is utilized in an effective amount either separately or in combination with aticaprant.

EMBODIMENTS

The invention provides also the following non-limiting embodiments:

Embodiment 1 is a pharmaceutical composition comprising about 2 mg to about 20 mg aticaprant and a filler, wherein the composition comprises between about 0.1% to about 90% aticaprant by weight.

Embodiment 2 is the pharmaceutical composition of Embodiment 1, further comprising one or more of: a disintegrant, a glidant, a lubricant, a solvent, a coloring agent, and a binder.

Embodiment 3 is the pharmaceutical composition of Embodiment 1 or 2, wherein the composition comprises between about 10% to about 99.9% filler by weight.

Embodiment 4 is the pharmaceutical composition of any one of Embodiments 1-3, wherein the composition comprises a disintegrant.

Embodiment 5 is the pharmaceutical composition of Embodiment 4, wherein the composition comprises between about 0.5% to about 50% disintegrant by weight.

Embodiment 6 is the pharmaceutical composition of any one of Embodiments 1-5, wherein the composition comprises a glidant.

Embodiment 7 is the pharmaceutical composition of Embodiment 6, wherein the composition comprises between about 0.1% to about 10% glidant by weight.

Embodiment 8 is the pharmaceutical composition of any one of Embodiments 1-7, wherein the composition comprises a lubricant.

Embodiment 9 is the pharmaceutical composition of Embodiment 8, wherein the composition comprises between about 0.05% to about 5% lubricant by weight.

Embodiment 10 is the pharmaceutical composition of any one of Embodiments 1-9, wherein the composition comprises one or more of: an aticaprant to filler ratio between 0.005 and 9 by weight; an aticaprant to disintegrant ratio between 0.1 and 10 by weight; an aticaprant to glidant ratio between 0.5 and 50 by weight; and an aticaprant to lubricant ratio between 1 and 100 by weight.

Embodiment 11 is the pharmaceutical composition of any one of Embodiments 1-10, wherein the composition comprises about 5% aticaprant by weight, about 88.5% filler by weight, about 5% disintegrant by weight, about 1% glidant by weight, and about 0.5% lubricant by weight.

Embodiment 12 is the pharmaceutical composition of any one of Embodiments 1-11, wherein the composition is an oral tablet.

Embodiment 13 is the pharmaceutical composition of Embodiment 12, wherein the oral tablet is a film coated oral tablet comprising (a) a core tablet and (b) a film coat.

Embodiment 14 is the pharmaceutical composition of Embodiment 13, wherein the ratio of the film coat to core tablet is between about 0.03 to 10 by weight.

Embodiment 15 is the pharmaceutical composition of Embodiment 13 or 14, wherein the film coat comprises a coating powder.

Embodiment 16 is the pharmaceutical composition of any one of Embodiments 13-15, wherein the core tablet comprises an intragranular and an extragranular phase.

Embodiment 17 is the pharmaceutical composition of Embodiment 16, wherein the ratio of intragranular to extragranular phase in the core tablet is between about 1.5 and 3.

Embodiment 18 is the pharmaceutical composition of Embodiment 16, wherein the intragranular phase comprises aticaprant, a filler, a disintegrant, and a glidant.

Embodiment 19 is the pharmaceutical composition of Embodiment 18, wherein the intragranular phase comprises one or more of: an aticaprant to filler ratio of between about 0.008 and 0.8 by weight; an aticaprant to disintegrant ratio of between about 0.2 and 20 by weight; and an aticaprant to glidant ratio of between about 1 and 100 by weight.

Embodiment 20 is the pharmaceutical composition of Embodiment 16 or 17, wherein the extragranular phase comprises a filler, a disintegrant, a glidant, and a lubricant.

Embodiment 21 is the pharmaceutical composition of Embodiment 20, wherein the extragranular phase comprises one or more of: a filler to disintegrant ratio of between about 1 and 100 by weight; a filler to glidant ratio of between about 5 and 500 by weight; and a filler to lubricant ratio of between about 5 and 500 by weight.

Embodiment 22 is the pharmaceutical composition of any one of Embodiments 13-21, wherein the film coated oral tablet comprises about 97% core tablet by weight and about 3% film coat by weight and wherein the core tablet comprises about 5% aticaprant by weight, about 88.5% filler by weight, about 5% disintegrant by weight, about 1% glidant by weight, and about 0.5% lubricant by weight.

Embodiment 23 is the pharmaceutical composition of any one of Embodiments 1-22, wherein the composition is an oral tablet comprising a core tablet of about 100 mg, the core tablet comprising about 5 mg aticaprant, about 5 mg disintegrant, about 88.5 mg filler, about 1 mg glidant, and about 0.5 mg lubricant.

Embodiment 24 is the pharmaceutical composition of Embodiment 23, further comprising about 3 mg of film coat.

Embodiment 25 is the pharmaceutical composition of any one of Embodiments 1-24, wherein the composition is an oral tablet comprising a core tablet of about 200 mg, the core tablet comprising about 10 mg Aticaprant, about 10 mg disintegrant, about 177 mg filler, about 2 mg glidant, and about 1 mg lubricant.

Embodiment 26 is the pharmaceutical composition of Embodiment 25, further comprising about 6 mg of film coat.

Embodiment 27 is the pharmaceutical composition of any of Embodiments 1-26, wherein the filler is selected from: microcrystalline cellulose, lactose monohydrate, and silicified microcrystalline cellulose.

Embodiment 28 is the pharmaceutical composition of any of Embodiments 2-27, wherein the disintegrant is croscarmellose sodium.

Embodiment 29 is the pharmaceutical composition of any of Embodiments 2-28, wherein the glidant is silica, colloidal anhydrous.

Embodiment 30 is the pharmaceutical composition of any of Embodiments 2-29, the lubricant is magnesium stearate.

Embodiment 31 is the pharmaceutical composition of any of Embodiments 15-30, wherein the coating powder is Opadry II Orange.

Embodiment 32 is an oral tablet comprising about 5 mg aticaprant, wherein the oral tablet comprises a core tablet of about 100 mg, wherein the core tablet comprises an intragranular and extragranular phase, wherein the intragranular phase comprises about 30 mg microcrystalline cellulose, about 30 mg lactose monohydrate, about 2.5 mg croscarmellose sodium, and about 0.5 mg silica, colloidal anhydrous; and wherein the extragranular phase comprises about 28.5 mg silicified microcrystalline cellulose, about 2.5 mg croscarmellose sodium, about 0.5 mg silica, colloidal anhydrous, and about 0.5 mg magnesium stearate.

Embodiment 33 is the oral tablet of Embodiment 32, further comprising about 3 mg film coat.

Embodiment 34 is the oral tablet of Embodiment 33, wherein the film coat comprises Opadry II Orange.

Embodiment 35 is an oral tablet comprising about 10 mg aticaprant, wherein the oral tablet comprises a core tablet of about 200 mg, wherein the core tablet comprises an intragranular and extragranular phase, wherein the intragranular phase comprises about 60 mg microcrystalline cellulose, about 60 mg lactose monohydrate, about 5 mg croscarmellose sodium, and about 1 mg silica, colloidal anhydrous; and wherein the extragranular phase comprises about 57 mg silicified microcrystalline cellulose, about 5 mg croscarmellose sodium, about 1 mg silica, colloidal anhydrous, and about 1 mg magnesium stearate.

Embodiment 36 is the oral tablet of Embodiment 35, further comprising 3 mg film coat.

Embodiment 37 is the oral tablet of Embodiment 36, wherein the film coat comprises Opadry II Orange.

Embodiment 38 is a pharmaceutical composition comprising between about 2 mg and 20 mg aticaprant, wherein the composition has a pharmacokinetic (PK) profile comprising one or more of the following parameters after administration of the composition to a human after at least a 10-hour fast (dose-normalized to 10 mg):
  a. a mean $C_{max}$ between about 30 and 40 ng/ml;
  b. a mean $AUC_{infinity}$ between about 300 and 430 h*ng/ml;
  c. a mean $AUC_{last}$ between about 280 and 430 h*ng/ml;
  d. a median $t_{max}$ between about 1 to 4 hours.

Embodiment 39 is the pharmaceutical composition of Embodiment 38, wherein the mean $C_{max}$ is between about 30 and 35 ng/ml.

Embodiment 40 is the pharmaceutical composition of Embodiment 38 or 39, wherein the mean $AUC_{infinity}$ is between about 300 and 320 h*ng/mL.

Embodiment 41 is the pharmaceutical composition of any one of Embodiments 38-40, wherein the mean $AUC_{last}$ is between about 280 and 310 h*ng/mL.

Embodiment 42 is the pharmaceutical composition of any one of Embodiments 38-41, wherein the median $t_{max}$ is about 1.5 hours.

Embodiment 43 is the pharmaceutical composition of any one of Embodiments 38-42, wherein the composition is an oral tablet.

Embodiment 44 is the pharmaceutical composition of any one of Embodiments 38-43, wherein the composition further comprises one or more of: a filler, a disintegrant, a glidant, a lubricant, a binder, and a coloring agent.

Embodiment 45 is the pharmaceutical composition of any one of Embodiments 38-44, wherein the composition comprises between about 0.1% and 90% aticaprant by weight.

Embodiment 46 is the pharmaceutical composition of any one of Embodiments 38-45, wherein the composition comprises about 5 mg aticaprant or about 10 mg aticaprant.

Embodiment 47 is the pharmaceutical composition of any one of Embodiments 38-46, wherein the composition comprises one or more of: an aticaprant to filler ratio between 0.005 and 9 by weight; an aticaprant to disintegrant ratio between 0.1 and 10 by weight; an aticaprant to glidant ratio between 0.5 and 50 by weight; and an aticaprant to lubricant ratio between 1 and 100 by weight.

Embodiment 48 is the pharmaceutical composition of any one of Embodiments 38-47, wherein the composition wherein the composition comprises about 5% aticaprant by weight, about 88.5% filler by weight, about 5% disintegrant by weight, about 1% glidant by weight, and about 0.5% lubricant by weight.

Embodiment 49 is a method for treating major depressive disorder (MDD) in a human patient, the method comprising administering to the patient a pharmaceutical composition comprising between about 2 mg and 20 mg aticaprant, wherein the patient had an inadequate response to other antidepressant therapy prior to treatment with aticaprant, and wherein the administration of the pharmaceutical composition to the patient achieves a pharmacokinetic (PK) profile comprising one or more of the following PK parameters (dose-normalized to 10 mg) after administration of the composition to a human after at least a 10-hour fast:

e. a mean $C_{max}$ between about 30 and 40 ng/ml;
f. a mean $AUC_{infinity}$ between about 300 and 430 h*ng/ml;
g. a mean $AUC_{last}$ between about 280 and 430 h*ng/ml;
h. a median $t_{max}$ between about 1 to 4 hours.

Embodiment 50 is the method of Embodiment 49, wherein the mean $C_{max}$ is between about 30 and 35 ng/mL.

Embodiment 51 is the method of Embodiment 49 or 50, wherein the mean $AUC_{infinity}$ is between about 300 and 320 h*ng/mL.

Embodiment 52 is the method of any one of Embodiments 49-51, wherein the mean $AUC_{last}$ is between about 280 and 310 h*ng/mL.

Embodiment 53 is the method of any one of Embodiments 49-52, wherein the median $t_{max}$ is about 1.5 hours.

Embodiment 54 is the method of any one of Embodiments 49-53, wherein the composition is an oral tablet.

Embodiment 55 is the method of any one of Embodiments 49-54, wherein the composition further comprises one or more of: a filler, a disintegrant, a glidant, a lubricant, a binder, and a coloring agent.

Embodiment 56 is the method of any one of Embodiments 49-55, wherein the composition comprises between about 0.1% and 90% aticaprant by weight.

Embodiment 57 is the method of any one of Embodiments 49-56, wherein the composition comprises between about 10% and 99.9% filler by weight.

Embodiment 58 is the method of any one of Embodiments 49-57, wherein the composition comprises one or more of: an aticaprant to filler ratio between 0.005 and 9 by weight; an aticaprant to disintegrant ratio between 0.1 and 10 by weight; an aticaprant to glidant ratio between 0.5 and 50 by weight; and an aticaprant to lubricant ratio between 1 and 100 by weight.

Embodiment 59 is the method of any one of Embodiments 49-58, wherein the composition wherein the composition comprises about 5% aticaprant by weight, about 88.5% filler by weight, about 5% disintegrant by weight, about 1% glidant by weight, and about 0.5% lubricant by weight.

Embodiment 60 is the method of any one of Embodiments 49-59, wherein the patient has anhedonia.

Embodiment 61 is the method of any one of Embodiments 49-60, wherein the pharmaceutical composition comprises about 5 mg aticaprant.

Embodiment 62 is the method of any one of Embodiments 49-60, wherein the pharmaceutical composition comprises about 10 mg aticaprant.

Embodiment 63 is the method of any one of Embodiments 49-60, wherein the other antidepressant therapy comprised one or more antidepressants.

Embodiment 64 is the method of Embodiment 63, wherein the one or more antidepressants comprised a SSRI, SNRI, or a combination thereof.

Embodiment 65 is the method of any one of Embodiments 49-64, wherein the aticaprant is S-aticaprant.

Embodiment 66 is the method of any one of Embodiments 49-65, further comprising treatment with an effective amount of one or more antidepressants.

Embodiment 67 is the method of Embodiment 66, wherein the one or more antidepressants is a SSRI, SNRI, or combination thereof.

Embodiment 68 is the method of any one of Embodiments 49-67, wherein the pharmaceutical composition comprising aticaprant is administered once daily.

Embodiment 69 is a solid pharmaceutical composition comprising between about 2 mg and 20 mg aticaprant, wherein the composition has a dissolution profile comprising a Q value of between about 60% and 90% at 45 minutes, under the following dissolution operating conditions:
Apparatus: Paddle (USP Type 2, Ph. Eur., JP)
Dissolution medium: 0.01 M hydrochloric acid
Volume: 900 mL
Temperature: 37+/−0.5 degrees Celsius
Rotation Speed: 50 rpm
Analytical Finish: UHPLC with UV detection at 247 nm.

Embodiment 70 is the solid pharmaceutical composition of Embodiment 69, wherein the composition comprises about 5 mg or about 10 mg aticaprant.

Embodiment 71 is the solid pharmaceutical composition of Embodiment 69 or 70, wherein the Q value is between about 70% and 80% at 45 minutes.

Embodiment 72 is the solid pharmaceutical composition of Embodiment 71, wherein the Q value is about 75% at 45 minutes.

Embodiment 73 is the solid pharmaceutical composition of any one of Embodiments 69-72, wherein the composition is an oral tablet.

Embodiment 74 is the solid pharmaceutical composition of any one of Embodiments 69-73, wherein the composition further comprises one or more of: a filler, a disintegrant, a glidant, a lubricant, a binder, and a coloring agent.

Embodiment 75 is the solid pharmaceutical composition of any one of Embodiments 69-74, wherein the composition comprises between about 0.1% and 90% aticaprant by weight.

Embodiment 76 is the solid pharmaceutical composition of any one of Embodiments 69-75, wherein the composition comprises between about 10% and 99.9% filler by weight.

Embodiment 77 is the solid pharmaceutical composition of any one of Embodiments 69-76, wherein the composition comprises one or more of: an aticaprant to filler ratio between 0.005 and 9 by weight; an aticaprant to disintegrant ratio between 0.1 and 10 by weight; an aticaprant to glidant ratio between 0.5 and 50 by weight; and an aticaprant to lubricant ratio between 1 and 100 by weight.

Embodiment 78 is the solid pharmaceutical composition of any one of Embodiments 69-77, wherein the composition wherein the composition comprises about 5% aticaprant by weight, about 88.5% filler by weight, about 5% disintegrant by weight, about 1% glidant by weight, and about 0.5% lubricant by weight.

Embodiment 79 is a method of treating major depressive disorder (MDD) in a human patient comprising administering to the patient the pharmaceutical composition of any one of Embodiments 1-32 or 38-48, the oral tablet of any of Embodiments 33-37, or the solid pharmaceutical composition of any of Embodiments 69-78.

Embodiment 80 is a method of Embodiment 79, wherein the patient has anhedonia.

Embodiment 81 is the method of any one of Embodiments 79-80, wherein the pharmaceutical composition, the oral tablet, or the solid pharmaceutical composition comprises about 5 mg aticaprant.

Embodiment 82 is the method of any one of Embodiments 79-81, wherein the pharmaceutical composition, the oral tablet, or the solid pharmaceutical composition comprises about 10 mg aticaprant.

Embodiment 83 is the method of any one of Embodiments 79-82, wherein the patient had an inadequate response to other antidepressant therapy prior to the treatment with aticaprant.

Embodiment 84 is the method of Embodiment 83 wherein the other antidepressant therapy comprised one or more antidepressants.

Embodiment 85 is the method of Embodiment 84, wherein the one or more antidepressants comprised a SSRI, SNRI, or a combination thereof.

Embodiment 86 is the method of any one of Embodiments 79-85, wherein the aticaprant is S-aticaprant.

Embodiment 87 is the method of any one of Embodiments 79-86, further comprising treatment with an effective amount of one or more antidepressants.

Embodiment 88 is the method of Embodiment 87, wherein the one or more antidepressants is a SSRI, SNRI, or combination thereof.

Embodiment 89 is the method of any one of Embodiments 79-88, wherein the pharmaceutical composition, the oral tablet, or the solid pharmaceutical composition comprising aticaprant is administered once daily.

Embodiment 90 is a method of treating major depressive disorder in a human patient, comprising administering a pharmaceutical composition comprising aticaprant and one or more pharmaceutically acceptable excipients to the human patient, wherein the patient had a previous inadequate response to other antidepressant therapy and wherein the pharmaceutical composition is administered orally once daily with or without food.

Embodiment 91 is the method of Embodiment 90, wherein the pharmaceutical composition is an oral tablet.

Embodiment 92 is the method of Embodiment 90 or 91, wherein the pharmaceutical composition comprises about 5 mg to 10 mg aticaprant, about 5 mg aticaprant, or about 10 mg aticaprant.

Embodiment 93 is the method of any one of Embodiments 90-92 wherein the other antidepressant therapy comprised one or more antidepressants.

Embodiment 94 is the method of Embodiment 93, wherein the one or more antidepressants comprised a SSRI, SNRI, or a combination thereof.

Embodiment 95 is the method of any one of Embodiments 90-94, wherein the aticaprant is S-aticaprant or the aticaprant is crystalline aticaprant.

Embodiment 96 is the method of any one of Embodiments 90-95, further comprising treatment with an effective amount of one or more antidepressants.

Embodiment 97 is the method of Embodiment 96, wherein the one or more antidepressants is a SSRI, SNRI, or combination thereof.

Embodiment 98 is the method of any one of Embodiments 90-97, wherein the patient has anhedonia, optionally moderate to severe anhedonia.

Embodiment 99 is the method of any one of Embodiments 90-98, wherein the pharmaceutical composition comprises one or more of: a filler, a disintegrant, a glidant, a lubricant, a binder, and a coloring agent.

Embodiment is 100 is the method of Embodiment 99, wherein the filler is selected from: microcrystalline cellulose, lactose monohydrate, and silicified microcrystalline cellulose; the disintegrant is croscarmellose sodium; the glidant is silica, colloidal anhydrous; and the lubricant is magnesium stearate.

Embodiment 101 is the method of any one of Embodiments 90-100, wherein the pharmaceutical composition comprises between about 0.1% and 90% aticaprant by weight.

Embodiment 102 is the method of any one of Embodiments 90-101, wherein the pharmaceutical composition comprises between about 10% and 99.9% filler by weight.

Embodiment 103 is the method of any one of Embodiments 90-102, wherein the pharmaceutical composition is a film coated oral tablet, comprising (i) a film coat and (ii) a core tablet, wherein the core tablet comprises about 5% aticaprant by weight, about 88.5% filler by weight, about 5% disintegrant by weight, about 1% glidant by weight, and about 0.5% lubricant by weight.

Embodiment 104 is the method of wherein the film coated oral tablet comprises about 97% core tablet by weight and about 3% film coat by weight.

Embodiment 105 is the method of any one of Embodiments 90-104, wherein the pharmaceutical composition is an oral tablet comprising about 10 mg aticaprant, wherein the oral tablet comprises a core tablet of about 200 mg, wherein the core tablet comprises an intragranular and extragranular phase, wherein the intragranular phase comprises about 60 mg microcrystalline cellulose, about 60 mg lactose monohydrate, about 5 mg croscarmellose sodium, and about 1 mg silica, colloidal anhydrous; and wherein the extragranular phase comprises about 57 mg silicified microcrystalline cellulose, about 5 mg croscarmellose sodium, about 1 mg silica, colloidal anhydrous, and about 1 mg magnesium stearate.

The following Examples are set forth to aid in the understanding of the invention, and are not intended and should not be construed to limit in any way the invention set forth in the claims which follow thereafter.

| | Abbreviations |
|---|---|
| ABV | Alcohol-by-Volume |
| AE | Adverse Event |
| ALT | Alanine Aminotransferase |
| Anti-HEV (IgM) | Anti-hepatitis E Virus (Immunoglobulin M) |
| ASEX | Arizona Sexual Experiences Scale |
| AST | Aspartate Transaminase |
| ATRQ | Antidepressant Treatment History Questionnaire |
| AV | Atrioventricular |
| BMI | Body Mass Index |
| CGI-S | Clinical Global Impression-Severity |
| CI | Confidence Interval |
| CPFQ | Cognitive and Physical Functioning Questionnaire |
| CSF | Cerebrospinal Fluid |
| C-SSRS | Columbia Suicide Severity Rating Scale |
| CYP | cytochrome P450 |
| DSC | Differential Scanning Calorimetry |
| DSM | Diagnostic and Statistical Manual of Mental Disorders |
| ECG | Electrocardiogram |
| eITT | Enriched Intent-To-Treat (population) |
| FAS | Full Safety Analysis Set |
| fITT | Full Intent-To-Treat (population) |
| FSH | Follicle Stimulating Hormone |
| G17 | Gastrin-17 |
| GI | Gastrointestinal |
| HAM-A \| HDRS-17 | Hamilton Depression Rating Scale |
| HCV | Hepatitis C Virus |
| HbsAg | Hepatitis b Surface Antigen |
| β-hCG | β-human Chorionic Gonadotropin |
| HAM-A6 | 6 Item Subscale from HAM-A |
| HIV | Human Immunodeficiency Virus |
| HPA | Hypothalamus Pituitary Adrenal |
| Hp IgG | Helicobacter IgG antibodies |
| ICH | International Conference on Harmonisation |
| KOR | Kappa Opioid Receptor |
| KSS | Karolinska Sleepiness Scale |
| LBBB | Left Bundle Branch Block |
| LC-MS/MS | Liquid Chromatography/Mass Spectrometry/Mass Spectrometry |
| LOQ | Limit of Quantification |
| LS | Least Squares |
| LSD | Lysergic Acid Diethylamide |
| MADRS | Montgomery Asberg Depression Rating Scale |
| MDD | Major Depressive Disorder |
| mDSC | Modulated Differential Scanning Calorimetry |
| MedDRA | Medical Dictionary for Regulatory Activities |

-continued

| Abbreviations | |
|---|---|
| MINI | Mini International Neuropsychiatric Interview |
| MMRM | Mixed-effects Model for Repeated Measures |
| MOR | Mu Opioid Receptor |
| NSAID | Nonsteroidal Anti-Inflammatory Drug |
| PCP | Phencyclidine |
| PGI | Pepsinogen I |
| PGII | Pepsinogen II |
| PK | Pharmacokinetic |
| PPI | Proton Pump Inhibitor |
| PRO | Patient Reported Outcome |
| QD | Once Daily |
| RH | Relative Humidity |
| RT | Toom Temperature |
| SATE | Self-Assessment of Treatment Experience |
| SD | Standard Deviation |
| SHAPS | Snaith-Hamilton Pleasure Scale |
| SIGH-A | Structured Interview Guide for the Hamilton Anxiety scale |
| SIGMA | The Structured Interview Guide for the MADRS |
| SMDDS | Symptoms of Major Depressive Disorder Scale |
| SNRI | Serotonin-Norepinephrine Reuptake Inhibitor |
| SSRI | Selective Serotonin Reuptake Inhibitor |
| TEAE | Treatment-Emergent Adverse Event |
| THF | Tetrahydrofuran |
| TSH | Thyroid-Stimulating Hormone |
| ULN | Upper Limit of Normal |
| USP | United States Pharmacopeia |
| XRPD | X-ray Powder Diffraction |

Example 1: Instrument and Methodology Details

A. X-Ray Powder Diffraction (XRPD)

Bruker AXS D8 Advance

XRPD diffractograms were collected on a Bruker D8 diffractometer using Cu Kα radiation (40 kV, 40 mA) and a θ-2θ goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively.

Samples were run under ambient conditions as flat plate specimens using powder as received. The sample was prepared on a polished, zero-background (510) silicon wafer by gently pressing onto the flat surface or packed into a cut cavity. The sample was rotated in its own plane.

The details of the standard Pharmorphix data collection method are:

Angular range: 2 to 42° 2θ

Step size: 0.05° 2θ

Collection time: 0.5 s/step (total collection time: 6.40 min)

When required other methods for data collection are used with details as shown in Table 7.

TABLE 7

| Additional D8 XRPD methods 4 Minute Method | |
|---|---|
| Angular Range | 2 to 31° 2θ |
| Step Size | 0.06° 2θ |
| Time per Step | 0.5 s/step |

PANalytical Empyrean

XRPD diffractograms were collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel$^{3D}$ detector, placed on the diffracted beam, was fitted with a receiving slit and 0.04 rad Soller slits. The software used for data collection was X'Pert Data Collector using X'Pert Operator Interface. The data were analyzed and presented using Diffrac Plus EVA or High-Score Plus.

Samples were prepared and analyzed in either a metal or Millipore 96 well-plate in transmission mode. X-ray transparent film was used between the metal sheets on the metal well-plate and powders (approximately 1-2 mg) were used as received. The Millipore plate was used to isolate and analyze solids from suspensions by adding a small amount of suspension directly to the plate before filtration under a light vacuum.

The scan mode for the metal plate used the gonio scan axis, whereas a 2θ scan was utilized for the Millipore plate.

The details of the standard screening data collection method are:

Angular range: 2.5 to 32.0° 2θ

Step size: 0.0130° 2θ

Collection time: 12.75 s/step (total collection time of 2.07 min)

The software used for data collection was X'Pert Data Collector and the data analyzed and presented using Diffrac Plus EVA.

B. Differential Scanning calorimetry (DSC)

TA Instruments Q2000

DSC data were collected on a TA Instruments Q2000 equipped with a 50 position auto-sampler. Typically, 0.5-3 mg of each sample, in a pin-holed aluminum pan, was heated at 10° C./min from 25° C. to 275° C. A purge of dry nitrogen at 50 mL/min was maintained over the sample.

Modulated temperature DSC was carried out using an underlying heating rate of 2° C./min and temperature modulation parameters of +0.636° C. (amplitude) every 60 seconds.

The instrument control software was Advantage for Q Series and Thermal Advantage and the data were analyzed using Universal Analysis or TRIOS.

TA Instruments Discovery DSC

DSC data were collected on a TA Instruments Discovery DSC equipped with a 50 position auto-sampler. Typically, 0.5-3 mg of each sample, in a pin-holed aluminum pan, was heated at 10° C./min from 25° C. to 275° C. A purge of dry nitrogen at 50 mL/min was maintained over the sample.

The instrument control software was TRIOS and the data were analyzed using TRIOS or Universal Analysis.

C. Chemical Purity Determination by HPLC

Purity analysis was performed on an Agilent HP1100/Infinity II 1260 series system equipped with a diode array detector and using OpenLAB software. The full method details are provided in Table 8.

TABLE 8

| HPLC method for chemical purity determinations | |
|---|---|
| Parameter | Value |
| Type of method | Reverse phase with gradient elution |
| Sample Preparation | 0.2 mg/ml in acetonitrile:water 1:1 |
| Column | Supelco Ascentis Express C18 2.7 μm 100 × 4.6 mm |

TABLE 8-continued

| HPLC method for chemical purity determinations | |
|---|---|
| Column Temperature (° C.) | 25 |
| Injection (µL) | 5 |
| Detection: Wavelength, Bandwidth (nm) | 255, 90 |
| Flow Rate (ml/min) | 2 |
| Phase A | 0.1% TFA in water |
| Phase B | 0.085% TFA in acetonitrile |

| | Time (min) | % Phase A | % Phase B |
|---|---|---|---|
| Timetable | 0 | 95 | 5 |
| | 6 | 5 | 95 |
| | 6.2 | 95 | 5 |
| | 8 | 95 | 5 |

Example 2—Preparation of the Aticaprant THF Solvate

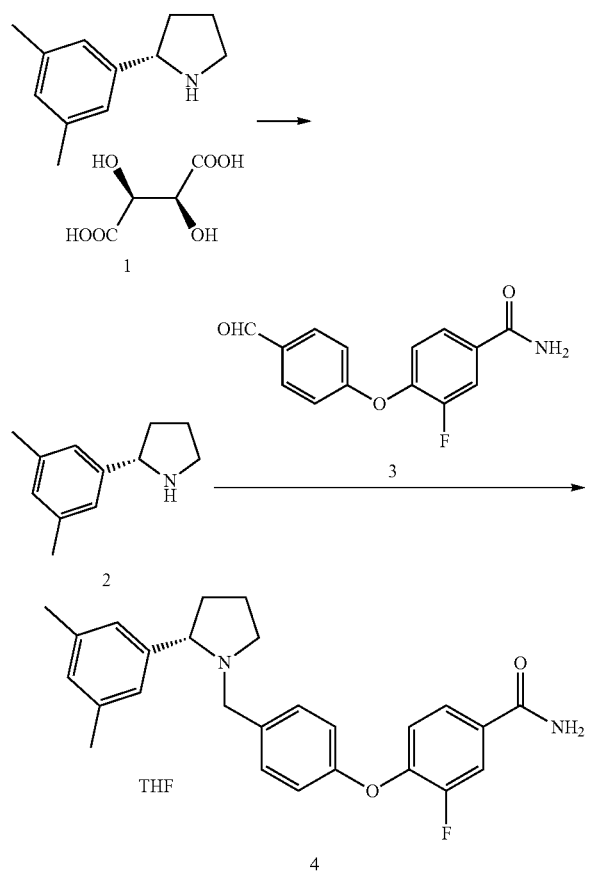

Aqueous sodium hydroxide was added to compound 1 in 2-methyltetrahydrofuran. After phase separation, compound 2, i.e., the free base of compound 1, in 2-MeTHF was solvent switched to tetrahydrofuran (THF). Reductive amination of compound 3 using compound 2 was carried out by adding sodium triacetoxyborohydride and THF. Upon reaction completion, the reaction mixture was washed with saturated sodium bicarbonate and sodium chloride. The organic phase containing crude compound 4 was concentrated and ethanol and water were added. The product was crystallized using THF, ethanol, and water to produce compound 4 as a solid.

Charge 7.3 L/kg water into a reactor. Charge 6.6 L/kg 2-MeTHF into the reactor. Charge 1.15 mol/mol of compound 1 into the reactor. Dose 2.3 mol/mol 50% aq. NaOH into the reactor over a minimum 20 minutes at 22° C. while stirring. Rinse with 1.0 L/kg water into the reactor. Stir for minimum 30 minutes at 22° C. Settle for minimum 30 minutes. Separate and discard the lower aqueous layer. Concentrate under vacuum to minimal volume at maximum 45° C. Charge portions of THF to the reactor and distill back to minimal volume to complete the solvent switch. Adjust the reactor to 20° C. Charge 5.0 L/kg THF into the reactor. Charge 1.00 mole compound 3 into the reactor. Charge 10.0 L/kg THF into the reactor. Adjust R1 to 32° C. and stir for minimum 1 hour. Adjust the reactor to 15° C. Charge 1.50 mole/mole NaBH(OAc)$_3$ in portions into the reactor at 15° C. Stir for minimum 1 hour at 15° C. Dose 5.0 L/kg water at 15° C. to the reactor. Dose 3.05 mole/mole 50% aq. NaOH at 15° C. to the reactor and stir for minimum 2 hours. Rinse with 0.5 L/kg water. Settle for minimum 30 minutes. Separate and discard the lower aqueous layer. Charge 6.2 L/kg 20% aq. NaCl at 15° C. to the reactor and stir for minimum 30 minutes. Settle for minimum 30 minutes. Separate and discard the lower aqueous layer. Concentrate under vacuum to 8.0 L/kg at maximum 45° C. Adjust the reactor to 25° C. Charge 8.0 L/kg EtOH (2% MeOH) and 8.0 L/kg water at 25° C. to the reactor. Dose 2.0 L/kg water at 25° C. over minimum 2.5 hours. Charge 0.03 kg/kg of crude compound 4 seeds to the reactor at 25° C. Stir for minimum 2 hours at 25° C. Charge 6.0 L/kg water at 25° C. to the reactor over minimum 7.5 hours. Cool to 2.5° C. over minimum 7 hours. Stir for minimum 6 hours at 2.5° C. Isolate the product and wash with THF/EtOH/water 1:1:2 (volume ratio). Dry the product at 25° C.

Example 3—Preparation of Pure Aticaprant

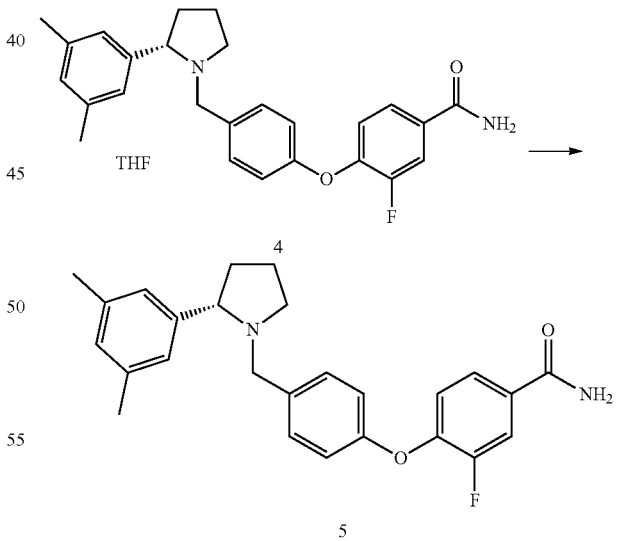

Charge 1.0 mol of crude compound 4 into a dissolution reactor. Add 1.91 L/mol of 2-MeTHF. Add 2.39 L/mole n heptane. Stir the contents of the reactor. Adjust temperature to 42° C. and stir for minimum 10 minutes until full dissolution. Filter the solution over a polish filter into a crystallization reactor to remove insoluble matter that might be present. Rinse the polish filter. Stir for minimum 10 minutes at 40° C. Cool to 20° C. over minimum 1 hour. Stir for minimum 10 minutes at 20° C. Dose 1.23 L/mol n-heptane over a minimum 30 minutes at 20° C. Stir for a minimum 10 minutes at 20° C. Seed with 0.02 mole/mole JNJ 67953964 AAA at 20° C. Stir for a minimum 8 hours at 20° C. Dose 3.68 L/mol of n-heptane over a minimum 12 hours at 20° C. Stir for a minimum 2 hours at 20° C. Cool to 10° C. over a minimum 3 hours. Stir for a minimum 4 hours at 10° C. Isolate compound 5. Wash the wet cake with 2-MeTHF/n-heptane (25/75 w/w %). Dry compound 5 at 50° C.

Characterization was performed on compound 5 and the results are shown in Table 9.

TABLE 9

Characterization data for Form III

| | |
|---|---|
| XRPD | Crystalline |
| HPLC Purity | 99.3% |
| DSC | Endo. 121.0° C., 75 J/g. |
| | Degradation not observed |
| TGA | No weight loss observed before degradation. |
| | Degradation onset ~250° C. |
| GVS | 0.4% max uptake at 90% RH |
| | No hysteresis observed |
| | XRPD unchanged after GVS |

Figure 3:
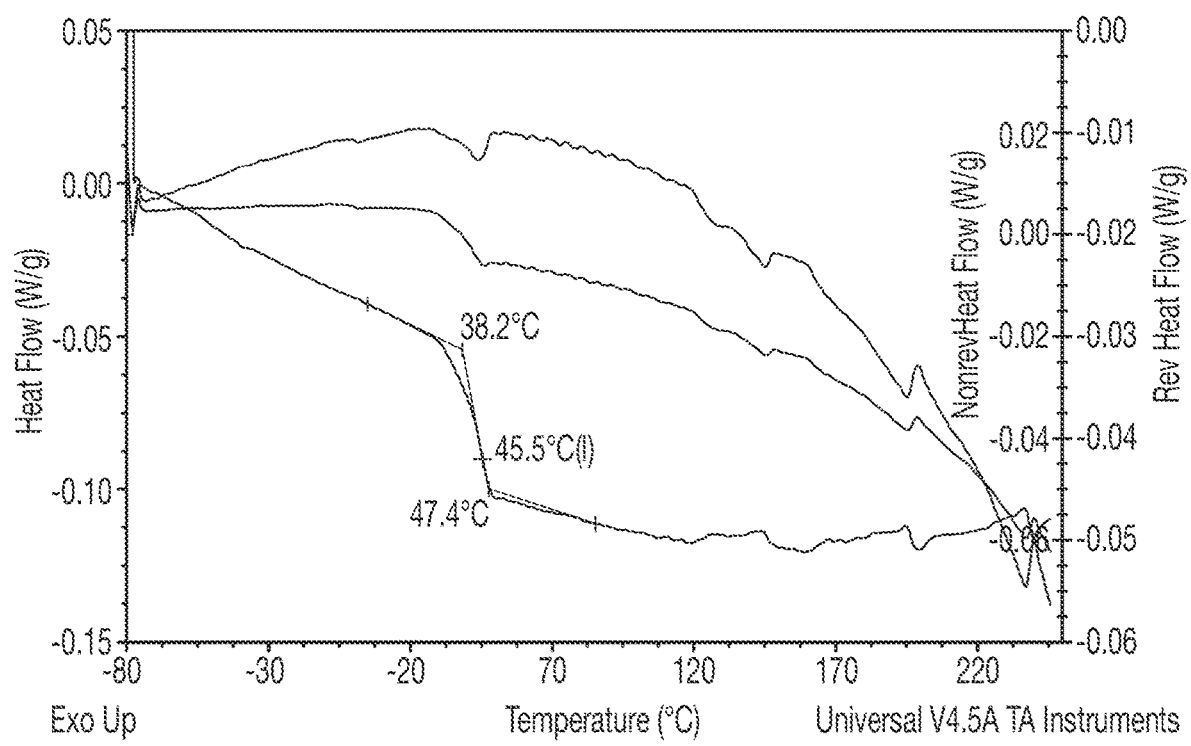
FIG. 3 is the mDSC thermogram of polymorph Form III of aticaprant.

Form III of aticaprant was found to be crystalline by XRPD. $^1$H NMR showed that the material was consistent with the proposed structure, with the presence of residual ethyl acetate. Ion chromatography showed that there were no cations/anions present, and HPLC showed 99.8% purity. The DSC (heating from 20 to 131° C. at 10° C./min) showed a peak temperature at 121° C. See, FIG. 3.

Example 4—Tablets Containing Aticaprant

Figure 24:
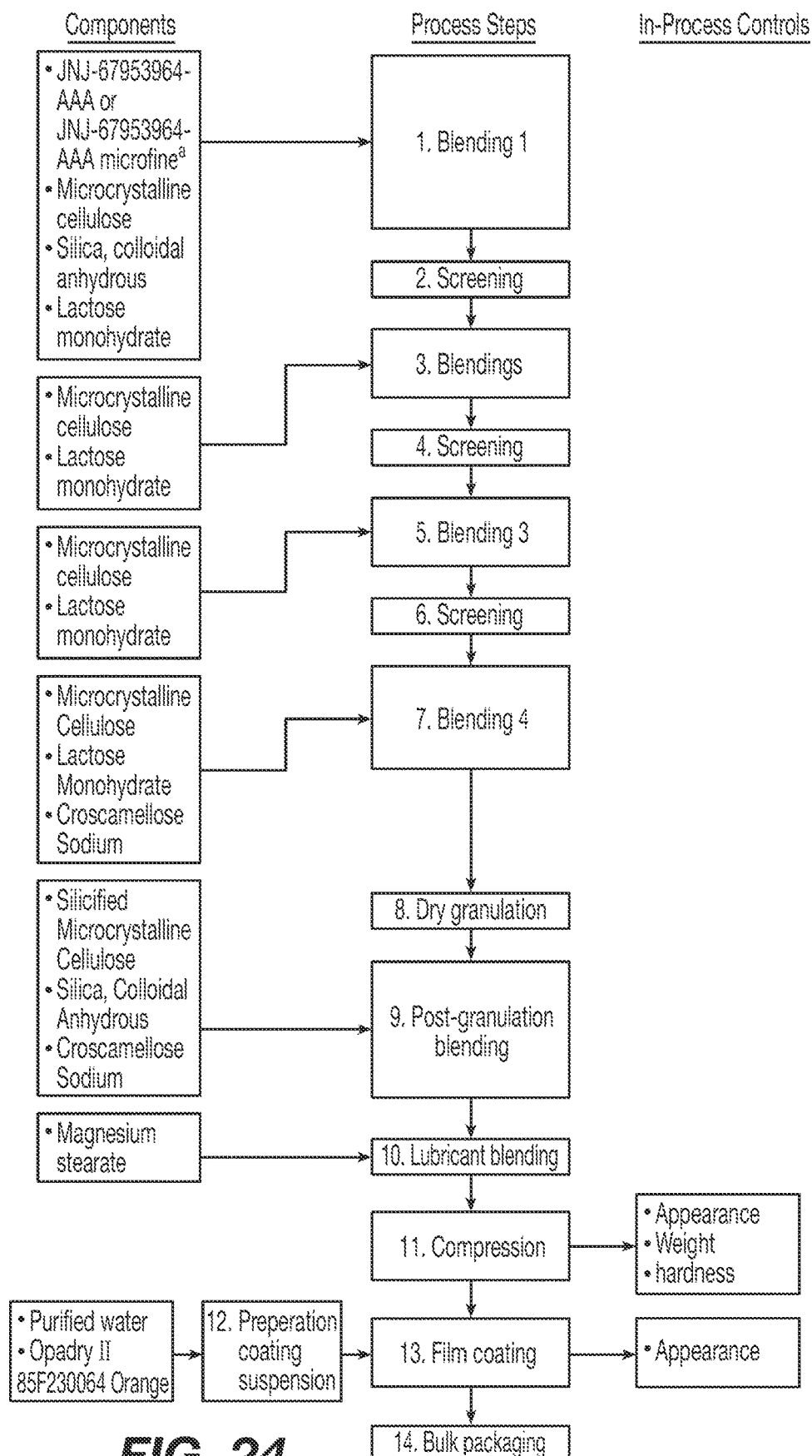
FIG. 24 is the flow chart for the process for preparing tablets containing aticaprant. In this figure, a refers to microfine, i.e., milled aticaprant.

Tablets containing aticaprant were prepared according to the scheme in FIG. 24 containing the components in Table 10.

TABLE 10

Qualitative and Quantitative Composition of the Aticaprant Tablet

| Component | Quantity (mg/tablet) | Quantity (mg/tablet) |
|---|---|---|
| Intragranular Phase: Core Tablet: Intragranular Phase: | | |
| Aticaprant (unmilled) or aticaprant microfine$^a$ (milled) | 5.00 | 10.00 |
| Microcrystalline cellulose | 30.00 | 60.00 |
| Lactose monohydrate$^b$ | 30.00 | 60.00 |
| Croscarmellose sodium | 2.50 | 5.00 |
| Silica, colloidal anhydrous | 0.50 | 1.00 |
| Extragranular Phase: | | |
| Silicified microcrystalline cellulose | 28.50 | 57.00 |
| Croscarmellose sodium | 2.50 | 5.00 |
| Silica, colloidal anhydrous | 0.50 | 1.00 |
| Magnesium Stearate$^c$ | 0.05 | 1.00 |
| Core Tablet Weight: | 100.00 | 200.00 |

TABLE 10-continued

Qualitative and Quantitative Composition of the Aticaprant Tablet

| Component | Quantity (mg/tablet) | Quantity (mg/tablet) |
|---|---|---|
| Film Coat: | | |
| Purified water$^d$ | 12.00$^d$ | 24.00$^d$ |
| Opadry II orange | 3.00 | 6.00 |
| Total Weight: | 103.00 | 206.00 |

$^a$"aticaprant microfine" is milled aticaprant (physically proceed in milling equipment).
$^b$From animal origin.
$^c$From vegetable source.
$^d$Removed during processing.

Tablets were prepared according to the following:
1. Mix the following, screened components in a blend using a suitable blender:
  a. Aticaprant or aticaprant microfine
  b. Microcrystalline cellulose
  c. Silica, colloidal anhydrous
  d. Lactose monohydrate
2. Screen the blend using a suitable screen.
3. Add the following screened components to the blend. Mix further using a suitable blender:
  a. Microcrystalline cellulose
  b. Lactose monohydrate
4. Screen the blend using a suitable screen.
5. Add the following screened components to the blend. Mix further using a suitable blender
  a. Microcrystalline cellulose
  b. Lactose monohydrate
6. Screen the blend using a suitable screen.
7. Add the following screened components to the blend. Mix further using a suitable blender:
Microcrystalline cellulose
Lactose monohydrate
Croscarmellose sodium
8. Make a dry granulate by using a suitable compaction technique.
9. Add the following screened components to the dry granulate and mix using a suitable blender:
  a. Silicified microcrystalline cellulose
  b. Croscarmellose sodium
  c. Silica, colloidal anhydrous
10. Add the following screened component to the blend and mix using a suitable blender
  a. Magnesium stearate
11. Compress the blend into core tablets using a suitable tablet press.
12. Suspend the coating powder in purified water using a suitable vessel.
13. Spray the coating suspension on the core tablets using a suitable coater.
14. Collect the film-coated tablets and package them in a suitable container.

Example 5—Testing of Tablets Containing Aticaprant

The tablets of Example 3 are tested to determine dissolution properties and chemical stability. See, Table 11 for dissolution conditions and Tables 12-13 for results.

TABLE 11

Dissolution Operating Conditions

| Parameter | Conditions |
|---|---|
| Apparatus | Paddle (USP Type 2, Ph. Eur., JP). |
| Dissolution Medium | 0.01M hydrochloric acid |
| Volume | 900 mL |
| Temperature | 37 ± 0.5° C. |
| Rotation Speed | 50 rpm |
| Analytical Finish | UHPLC with UV detection at 247 nm |

TABLE 12

| Characteristic | Acceptance | Criteria Result |
|---|---|---|
| Specificity | No interference with the peak of active or % dissolution of 100% placebo ≤2% | No interference |
| Accuracy | Recovery at the 20% concentration level of lowest dosage strength 20% ≤ X ≤ 50% = 75-125% | 100% |
| | Recovery at the 100% concentration level of lowest dosage strength ≥50% = 95-105% | 102% |
| | Recovery at the 100% concentration level of highest dosage strength ≥50% = 95-105% | 101% |
| | Recovery at the 120% concentration level of lowest dosage strength ≥50% = 95-105% | 101% |
| Precision-System Repeatability | % RSD of 5 injections of the same reference solution ≤2.0% | 0.3% |
| Linearity | % RSD of response factors ≤4% | 0.8% |
| | Correlation coefficient (R) ≥0.995 | 1.00 |
| Range | Linearity, accuracy, and precision criteria are fulfilled for the 20-120% range | Pass |
| Filtration recovery (Whatman Spartan RC 0.45 μm 30 mm) | Difference between % dissolution of filtered and unfiltered solution must be ≤2% for each of the 3 tested individual filters | 1% 0% 1% |
| Solution Stability | Concentration of active is within the range 97-103% of the initial value | |
| | Stock solutions stored in clear volumetric flasks at ambient conditions, 8 days | 101% |
| | Reference solutions stored in clear volumetric flasks in the refrigerator, 8 days/hours | 100% |
| | Reference solutions stored in clear volumetric flasks at ambient conditions, 8 days | 101% |
| | Sample solutions stored in clear unpierced pre-slit vials in the refrigerator, 7 days/hours | 100% |
| | Sample solutions stored in clear unpierced pre-slit vials at ambient conditions, 7 days | 101% |
| System Suitability | % RSD ≤2.0% | Pass |
| | Recovery reference 1 = 97.0-103.0% | Pass |
| | Recovery reference 2 = 98.0-102.0% | Pass |

TABLE 13

Dissolution (%) of Aticaprant Tablets

| Tablet 1 | Tablet 2 | Tablet 3 | Tablet 4 | Tablet 5 | Tablet 6 |
|---|---|---|---|---|---|
| 98 | 97 | 100 | 98 | 98 | 95 |

The chemical stability of the tablets is evaluated over a 28-day period using a Risk Based Predictive Stability (RiBPS) study. The stability protocols for the studies are provided in Tables 14-15.

TABLE 14

Storage Conditions and Testing Frequency for the Accelerated Stability Study

| Storage Time | 40° C./75% RH | 50° C./30% RH | 60° C./10% RH | 60° C./50% RH | 60° C./75% RH | 70° C./30% RH | 70° C./50% RH | 70° C./75% RH | 80° C./10% RH |
|---|---|---|---|---|---|---|---|---|---|
| 3 days | — | — | — | — | A | A | A | A | A |
| 7 days | — | — | A | A | A | A | A | A | A |
| 14 days | — | A | A | A | — | A | A[a] | A | A |
| 21 days | — | A | A | A | A[a] | A | A | A | — |
| 28 days | A[b] | A | A | A | A | — | — | — | — |

[a]duplicates; [b]triplicates; —: Not Tested; A = Assay and chromatographic purity

TABLE 15

Storage Conditions and Testing Frequency for the Accelerated Stability Study

| Storage Time | 5° C. | 50° C./10% RH | 50° C./30% RH | 60° C./10% RH | 60° C./50% RH | 70° C./30% RH | 70° C./50% RH | 80° C./10% RH | 80° C./50% RH |
|---|---|---|---|---|---|---|---|---|---|
| 3 days | — | — | — | — | A | A | A | A | A |
| 7 days | — | A | A | A | A | A | A | A | A |
| 14 days | — | A | A | A | — | A[a] | A | A | A |
| 21 days | A[b] | A | A | A | A[a] | A | A | — | — |

[a]duplicates; [b]triplicates; —: Not Tested; A = Assay and chromatographic purity The ICH stability protocol for is presented in Table 16.

TABLE 16

Storage Conditions and Testing Frequency for Stability Study

| Storage Time (months) | 5° C. | 25° C./ 60% RH | 30° C./ 75% RH | 40° C./ 75% RH | 50° C. | ICH Light[b] Unprotected | ICH Light[b] Protected (Primary pack) |
|---|---|---|---|---|---|---|---|
| Initial | — | A | — | — | — | A | (A) |
| 3 | A | (A) | A | A | A | — | — |
| 6 | — | (A) | A | A | — | — | — |
| 9 | — | (A) | A | — | — | — | — |
| 12 | (A) | A | A | — | — | — | — |
| 18 | — | (A) | A | — | — | — | — |
| 24 | (A) | A | A | — | — | — | — |
| 36 | (A) | A | A | — | — | — | — |

[b]Light ICH: CIE85-ID65, integrated near UV energy not less than 200 W*h/m$^2$, overall illumination not less than 1200 klux*h.
Tests performed: A = Appearance, assay, chromatographic purity, and dissolution; —: Not tested; Tests given in brackets are kept in reserve and are activated if stability information becomes relevant or if problems arise at the active time points.

During the RiBPS study, 3 main degradation products (RRT 0.399, RRT 0.466, and RRT 0.874) showed an increasing trend over the storage period. Levels of degradation ranged from 0.06% to 0.98% for RRT 0.399, from <0.05% to 0.39% for RRT 0.466, and from <0.05 to 0.99% for RRT 0.874.

The results of the RiBPS study showed that degradant RRT 0.466 is the shelf-life limiting attribute for the drug product.

The results demonstrated that for the drug product stored in open dish the probability to pass 12 months is 99% for the specification limit of 0.30% when stored at 25° C./60% RH and 30° C./75% RH.

Example 6

This was a multi-center, placebo-controlled, randomized, double-blind study in subjects with MDD who have had an inadequate response to SSRI/SNRI treatment. Aticaprant was evaluated as an adjunctive therapy; therefore, eligible subjects were maintained on their SSRI/SNRI treatment without change throughout the study. At least 50% of recruited subjects had to be anhedonic (as measured by SHAPS total score ≥20).

A. Objectives

The primary objective was to evaluate the efficacy of aticaprant compared to placebo when administered as adjunctive treatment in subjects with MDD partially responsive to SSRI/SNRI treatment in terms of reduction of symptoms of depression, as assessed by the change from baseline on the MADRS in non-responders during the placebo lead-in period.

The secondary objectives are:
  i. To evaluate the efficacy of aticaprant compared to placebo when administered as adjunctive treatment in subjects with MDD partially responsive to SSRI/SNRI treatment in terms of reduction of symptoms of depression, as assessed by the change from baseline on the MADRS in both responders and non-responders during the placebo lead-in period.
  ii. To investigate the overall safety and tolerability of treatment with adjunctive aticaprant in subjects with MDD when used in combination with a SSRI or SNRI.
  iii. To investigate the effect of aticaprant versus placebo on depression related anhedonia as assessed by the SHAPS.
  iv. To investigate the effect of aticaprant on symptoms of depression using the Clinical Global Impression-Severity (CGI-S), the patient reported Symptoms of Major Depressive Disorder Scale (SMDDS) and the self-assessment of treatment experience (SATE).
  v. To investigate the effect of aticaprant on symptoms of anxiety using the HAM-A and on core symptoms of anxiety using the HAM-A$_6$ subscale.
  vi. To assess the plasma PK of aticaprant in subjects with MDD and explore its relationship with efficacy and safety parameters.

Secondary exploratory objectives include:
  i. To explore the effect of aticaprant on aspects of cognitive and executive function using the CPFQ.
  ii. To explore mood-related biomarkers (including but not limited to growth factors, HPA axis markers, immune system activation, metabolic markers) and genetic/epigenetic variation that may be related to clinical response, nonresponse, or safety and tolerability parameters of aticaprant.

B. Study Design

For each subject, the study consisted of two phases: a screening phase of up to 5 weeks and a double-blind treatment phase lasting 11 weeks. See, FIG. 4.

Subjects with MDD who have had treatment initiated with a permitted SSRI/SNRI and have had an inadequate or only partial response to this treatment were screened. Assessments include the MINI, Antidepressant Treatment History Questionnaire (TRQ), and MADRS.

Figure 4:
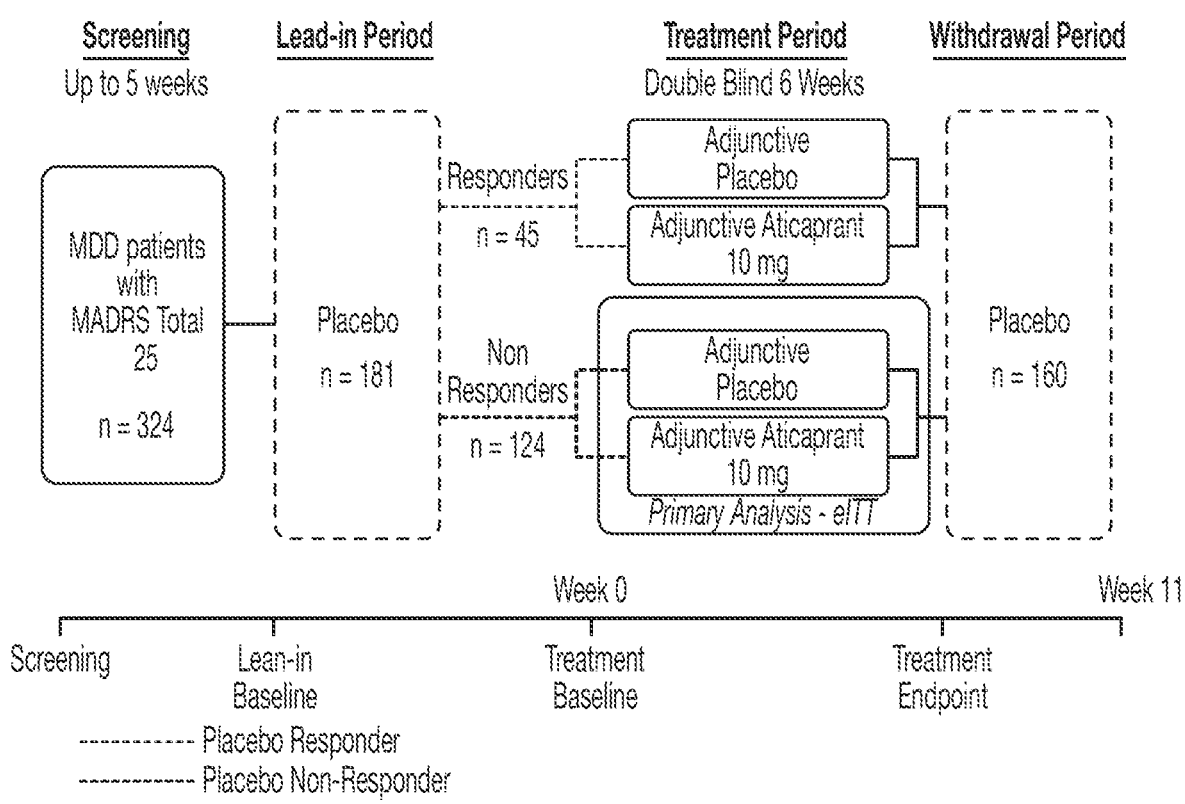
FIG. 4 is the trial design of Example 1.

The treatment phase consisted of 3 periods. A placebo lead-in period of concealed duration, after which subjects entered the double-blind treatment period when they were randomly assigned to 10 mg aticaprant (two 5 mg capsules) or continue placebo for 6 weeks. Each capsule contained aticaprant (5 mg), microcrystalline cellulose (94.95 mg), and magnesium stearate (0.05 mg) in a hard gelatin capsule. Subjects who completed the treatment period, entered the withdrawal period and were treated with placebo for the remaining time of the treatment phase. The total duration for each subject was approximately 16 weeks. There were 11 scheduled visits, including screening. An overall flow diagram is shown in FIG. 4.

Subjects were screened within 35 to 2 days prior to Day 1 to ascertain their eligibility per the inclusion and exclusion criteria. The symptoms of depression were assessed using the structured interview guide for the MADRS.

Double-Blind Treatment Phase

The duration of the double-blind treatment phase was 11 weeks divided into 3 periods. The subject received medication after completion of the visit on Day 1. The first dose was taken at home on Day 2. All medication was taken in fasting condition. At Visits 3, 4 and 5, the subjects were re-randomized to blind subjects the duration of the placebo lead-in period. During the double-blind phase, the subjects visited the center for out-patient visits every 1 to 2 weeks. See, Table 17.

Withdrawal period: Subjects who completed the double-blind treatment period prior to the end of Week 11 entered the withdrawal period where they were treated with placebo for the remaining time of the treatment phase.

C. Dosage and Administration

Aticaprant was supplied as 5-mg capsules. Placebo was supplied as matching capsules. All subjects took 2 capsules QD. The capsules were taken daily from Day 2 to Day 78 in fasting condition with some water (fasting for at least 4 hours before dosing). Medication was taken before breakfast. If the subject has forgotten to take the medication before breakfast, this was done before the next following meal, at the latest at dinner of the same day. If the subject

TABLE 17

Time and Events Schedule

| Phase | Screening | [a]Double-blind treatment phase | | | | | | | | | |
|---|---|---|---|---|---|---|---|---|---|---|---|
| Visit number | 1 | 2 | 3 | 4 | 5 | 6 | 7 | 8 | 9 | 10 | [b]11 or EW |
| Week (end of) | −5 to 0 | 0 | 1 | 2 | 3 | 4 | 6 | 7 | 8 | 9 | 11 |
| Day | −35 to −2 | 1 | 8 | 15 | 22 | 29 | 43 | 50 | 57 | 64 | 78 |
| Safety assessments | | | | | | | | | | | |
| Physical and neurological examination | X | X | | | | X | | | | | X |
| ASEX | | X | | | X | X | X | | | X | X |
| KSS | | X | | | X | X | X | | | X | X |
| Suicidality by C-SSRS | X | X | X | X | X | X | X | X | X | X | X |
| Dosing | | | | | | | | | | | |
| Randomization | | X | X | X | X | | | | | | |
| Supply new medication | | X | X | X | X | X | X | X | X | X | |
| Oral dose medication[d] | | Day 2 until and including Day 78[e] | | | | | | | | | |
| Meal after dosing | | X[l] | X[l] | X[l] | X[l] | X[l] | X[l] | X[l] | X[l] | X[l] | X[l] |
| Clinical Assessments | | | | | | | | | | | |
| Structured Interview Guide MADRS | X[j] | X | X | X | X | X | X | X | X | X | X |
| Structured Interview Guide SIGH-A | | X | X | X | X | X | X | X | X | X | X |
| CGI-S | | X | X | X | X | X | X | X | X | X | X |
| SMDDS | | X | | | X | X | X | | | X | |
| CPFQ | | X | | | X | X | X | | | X | |
| SHAPS | X | X | X | X | X | X | X | X | X | X | X |
| SATE[k] | | once weekly while at home | | | | | | | | | |
| Ongoing subject review | | | | | | | | | | | |
| Assessment of subject engagement[k] | X | up to 3 occasion when at home | | | | | | | | | |
| Adverse events | | Continuous | | | | | | | | | |
| Concomitant medication | | Continuous | | | | | | | | | |

EW = early withdrawal;
[a]Visits should be conducted ± 3 days of the scheduled day (based on Visit 2, not based on previous visit).
[b]If a subject discontinues treatment before the end of the double-blind treatment phase, EW visit should be completed.
[d]At home: In fasting condition. At clinic visit days: Use blisters dispensed at the previous visit. In fasting condition after completion of predose assessments.
[e]When Visit 11 is planned up to 3 days later, continue medication.
[j]During the first screening visit and by telephone up to 4 days before Visit 2, if 2 weeks or more elapse between the MADRS rating at screening and Visit 2.
[k]Using Q1.6-app on subjects' smartphone.
[l]Breakfast, lunch or dinner after drug intake at site.

Lead-in period: Subjects who successfully complete the baseline examination visit at the clinical site/unit, were treated with placebo for the entire duration of the lead-in period.

Treatment period: At the end of the lead-in period both placebo lead-in responders and placebo lead-in non-responders were randomized to receive either placebo or 10 mg aticaprant in a 1:1 ratio for 6 weeks. Subjects remained blinded to exact timing of the randomization, response criterion and drug treatment assignment for each subject.

remembered later than dinner, the dose of that day was omitted, and the subject took the dose before breakfast on the next day.

When Visit 11 was planned up to 3 days later, the subject continued medication until Visit 11.

The capsules were swallowed whole and not chewed, divided, dissolved or crushed. After having taken the medication, subjects did not to eat or drink for at least 30 minutes.

The first dose was taken in fasting condition on Day 2 of the double-blind phase. The dose of the medication was:

10 mg aticaprant: 2 capsules of 5 mg aticaprant

Placebo: 2 placebo capsules.

Medication dose was adjusted as needed to 5 mg QD based on the results of a blinded review of the safety data. When a dose reduction has been decided on, this only applied to new subjects and the dose of medication was:

5 mg aticaprant: 1 capsule of 5 mg aticaprant

Placebo: 1 placebo capsule.

As used herein, the Enriched ITT Analysis Set (eITT) is defined as all enrolled lead-in placebo non-responders who were randomized into a treatment period, received at least one dose of study medication in the treatment period and have at least one post-baseline MADRS assessment during the treatment period. Similarly, the Full ITT Analysis Set (fITT) is defined as all enrolled subjects who were randomized into a treatment period, received at least one dose of study medication in the treatment period and have at least one post-treatment baseline assessment of MADRS during the treatment period.

D. Clinical Assessments
   (i) Depression: Montgomery-Åsberg Depression Rating Scale (MADRS), Clinical Global Impression-Severity (CGI-S), Symptoms of Major Depressive Disorder Scale (SMDDS), and Self-assessment of treatment experience (SATE)
   (ii) Anhedonia: Snaith-Hamilton Pleasure Scale (SHAPS)
   (iii) Anxiety: Structured Interview Guide for the Hamilton Anxiety scale (SIGH-A) and HAM-A6
   (iv) Effects on Cognition: The Cognitive and Physical Functioning Questionnaire (CPFQ)
   (v) Safety assessments Standard safety assessments including physical and neurological examination, vital signs, 12-lead ECG, clinical chemistry, hematology, and urinalysis was performed. Based on observations of GI complaints in previous studies, a panel including PGI, PGII, G17 and Hp IgG was added to the clinical laboratory test panel to test for stomach mucosa status.

(vi) Suicidal ideation: C-SSRS
   (vii) Exploratory: CPFQ
   (viii) Central sedating effects: Karolinska Sleepiness Scale
   (ix) Sexual dysfunction: ASEX E. Patient Population Of 184 subjects, 169 were randomized into the treatment period and included in the safety population, while 166 subjects were considered for the full ITT population. Out of the 166 subjects in the full ITT population, 121 (73%) were lead-in placebo non-responders (enriched ITT population) and the remaining 45 (27%) were lead-in placebo responders. Of the 121 subjects in the enriched population, 112 (92.6%) were white and 84 (69.4%) were female. The mean age was 41.6 years, ranging from 19 to 64 years. All subjects had anhedonia (defined as SHAPS total score ≥20) at treatment baseline. A high anhedonia level (defined as SHAPS total score ≥38) was observed in 43.8% of the subjects. In general, the treatment groups were similar with respect to the baseline characteristics. Subject demographics for the eITT and safety analysis are provided in Tables 18 and 19.

TABLE 18

Summary of Demographics and Baseline Characteristics; Full Safety Analysis

| | Placebo (N = 84) | aticaprant 10 mg (N = 85) | Total (N = 169) |
|---|---|---|---|
| Age (Years) | | | |
| N | 84 | 85 | 169 |
| Mean (SD) | 42.1 (12.54) | 43.0 (12.81) | 42.6 (12.65) |
| Median | 43.5 | 43.0 | 43.0 |
| Range | (19; 64) | (21; 64) | (19; 64) |
| Gender | | | |
| N | 84 | 85 | 169 |
| Female | 62 (73.8%) | 60 (70.6%) | 122 (72.2%) |
| Male | 22 (26.2%) | 25 (29.4%) | 47 (27.8%) |
| Race | | | |
| N | 84 | 85 | 169 |
| American Indian or Alaska Native | 1 (1.2%) | 0 | 1 (0.6%) |
| Asian | 2 (2.4%) | 2 (2.4%) | 4 (2.4%) |
| Black or African American | 2 (2.4%) | 5 (5.9%) | 7 (4.1%) |
| White | 79 (94.0%) | 78 (91.8%) | 157 (92.9%) |
| Ethnicity | | | |
| N | 84 | 85 | 169 |
| Hispanic or Latino | 10 (11.9%) | 13 (15.3%) | 23 (13.6%) |
| Not Hispanic or Latino | 74 (88.1%) | 72 (84.7%) | 146 (86.4%) |
| Country | | | |
| N | 84 | 85 | 169 |
| Germany | 4 (4.8%) | 5 (5.9%) | 9 (5.3%) |
| Moldova | 15 (17.9%) | 14 (16.5%) | 29 (17.2%) |
| Russia | 25 (29.8%) | 21 (24.7%) | 46 (27.2%) |
| Ukraine | 9 (10.7%) | 7 (8.2%) | 16 (9.5%) |
| United Kingdom | 10 (11.9%) | 15 (17.6%) | 25 (14.8%) |
| United States | 21 (25.0%) | 23 (27.1%) | 44 (26.0%) |
| Baseline Height (cm) | | | |
| N | 84 | 85 | 169 |
| Mean (SD) | 167.4 (7.91) | 168.2 (8.64) | 167.8 (8.27) |
| Median | 167.5 | 167.6 | 167.6 |
| Range | (150; 183) | (152; 195) | (150; 195) |
| Baseline Weight (kg) | | | |
| N | 84 | 85 | 169 |
| Mean (SD) | 76.2 (14.73) | 78.7 (15.23) | 77.4 (14.99) |
| Median | 75.3 | 78.9 | 77.1 |
| Range | (47; 116) | (42; 119) | (42; 119) |
| Baseline BMI (kg/m$^2$) | | | |
| N | 84 | 85 | 169 |
| Mean (SD) | 27.2 (4.92) | 27.7 (4.56) | 27.5 (4.73) |
| Median | 26.6 | 28.1 | 27.6 |
| Range | (19; 35) | (18; 35) | (18; 35) |
| Presence of Anhedonia at Baseline | | | |
| N | 84 | 85 | 169 |
| No | 0 | 1 (1.2%) | 1 (0.6%) |
| Yes | 84 (100.0%) | 84 (98.8%) | 168 (99.4%) |
| Lead-in response status | | | |
| N | 84 | 85 | 169 |
| No | 62 (73.8%) | 62 (72.9%) | 124 (73.4%) |
| Yes | 22 (26.2%) | 23 (27.1%) | 45 (26.6%) |

TABLE 19

Summary of Demographics and Baseline Characteristics; eITT

| | Placebo (N = 61) | aticaprant 10 mg (N = 60) | Total (N = 121) |
|---|---|---|---|
| Age (Years) | | | |
| N | 61 | 60 | 121 |
| Mean (SD) | 41.6 (12.34) | 41.6 (12.78) | 41.6 (12.51) |
| Median | 43.0 | 40.5 | 42.0 |
| Range | (19; 64) | (21; 64) | (19; 64) |
| Gender | | | |
| N | 61 | 60 | 121 |
| Female | 42 (68.9%) | 42 (70.0%) | 84 (69.4%) |
| Male | 19 (31.1%) | 18 (30.0%) | 37 (30.6%) |
| Race | | | |
| N | 61 | 60 | 12 |
| Indian or Alaska Native | 1 (1.6%) | 0 | 1 (0.8%) |
| Asian | 2 (3.3%) | 1 (1.7%) | 3 (2.5%) |
| Black or African American | 2 (3.3%) | 3 (5.0%) | 5 (4.1%) |
| White | 56 (91.8%) | 56 (93.3%) | 112 (92.6%) |
| Ethnicity | | | |
| N | 61 | 60 | 121 |
| Hispanic or Latino | 3 (4.9%) | 7 (11.7%) | 10 (8.3%) |
| Not Hispanic or Latino | 58 (95.1%) | 53 (88.3%) | 111 (91.7%) |
| Country | | | |
| N | 61 | 60 | 121 |
| Germany | 4 (6.6%) | 4 (6.7%) | 8 (6.6%) |
| Moldova | 15 (24.6%) | 14 (23.3%) | 29 (24.0%) |
| Russia | 19 (31.1%) | 18 (30.0%) | 37 (30.6%) |
| Ukraine | 7 (11.5%) | 5 (8.3%) | 12 (9.9%) |
| United Kingdom | 6 (9.8%) | 10 (16.7%) | 16 (13.2%) |
| United States | 10 (16.4%) | 9 (15.0%) | 19 (15.7%) |
| Baseline Height (cm) | | | |
| N | 61 | 60 | 121 |
| Mean (SD) | 168.1 (8.19) | 167.3 (8.10) | 167.7 (8.13) |
| Median | 168.0 | 166.3 | 167.0 |
| Range | (151; 183) | (152; 186) | (151; 186) |
| Baseline Weight (kg) | | | |
| N | 61 | 60 | 121 |
| Mean (SD) | 74.7 (14.19) | 76.8 (15.12) | 75.7 (14.63) |
| Median | 74.2 | 77.1 | 75.6 |
| Range | (47; 116) | (42; 119) | (42; 119) |
| Baseline BMI (kg/m$^2$) | | | |
| N | 61 | 60 | 121 |
| Mean (SD) | 26.4 (4.67) | 27.3 (4.36) | 26.9 (4.52) |
| Median | 25.7 | 27.8 | 26.7 |
| Range | (19; 35) | (18; 35) | (18; 35) |
| Presence of Anhedonia at Baseline | | | |
| N | 61 | 60 | 121 |
| No | 0 | 0 | 0 |
| Yes | 61 (100.0%) | 60 (100.0%) | 121 (100.0%) |
| Lead-in response status | | | |
| N | 61 | 60 | 121 |
| No | 61 (100.0%) | 60 (100.0%) | 121 (100.0%) |
| Yes | 0 | 0 | 0 |

E. Evaluations of Efficacy

At the end of the lead-in period, response status of the subjects was assessed according to the double-blind response criteria based on reduction in MADRS relative to lead-in baseline. Both lead-in placebo responders and lead-in placebo non-responders were randomly assigned in a 1:1 ratio to either aticaprant or placebo in the treatment period. The randomization was stratified by lead-in response status (non-responders: <30% reduction from baseline in MADRS total score at the end of the lead-in period vs responders: ≥30% reduction from baseline at the end of the lead-in period) and presence/absence of anhedonia (presence defined as SHAPS total score ≥20).

Treatment duration: The study consisted of two periods: a screening phase of up to 5 weeks and a double-blind treatment phase of 11 weeks. The double-blind treatment phase of the trial consisted of 3 periods. The first period was a placebo lead-in of 3 weeks, after which subjects entered the treatment period when they were randomly assigned to aticaprant or continuation on placebo for 6 weeks. Subjects who successfully completed the treatment period were treated with placebo during a 2-week withdrawal period, i.e., Period 3. The total duration for each subject was approximately 16 weeks.

Primary analysis set for efficacy: The efficacy analysis is based on the eITT set defined as all enrolled lead-in placebo non-responders who were randomized into the treatment period, received at least one dose of medication, and have at least one post-baseline MADRS assessment during the treatment period. The primary analysis set is used for all efficacy endpoints.

Secondary analysis set for efficacy: A secondary analysis set is the fITT set defined as all enrolled subjects who were randomized into the treatment period, received at least one dose of medication, and have at least one post-baseline MADRS assessment during the treatment period. The secondary analysis set is used for all efficacy endpoints to examine the effect in the general population, which may be useful for designing subsequent studies in the development program.

Analysis set for safety: The safety analysis is based on the full safety analysis set, defined as all enrolled subjects who received at least one dose of medication in the treatment period.

The efficacy endpoints were presented for both the eITT and the fITT.

Level of significance: The analysis of primary efficacy endpoint was performed at a significance level of 0.20 (one-sided). The analysis of secondary efficacy endpoints was performed at a significance level of 0.20 (two-sided). No adjustment for multiple comparisons was performed.

Figure 5:
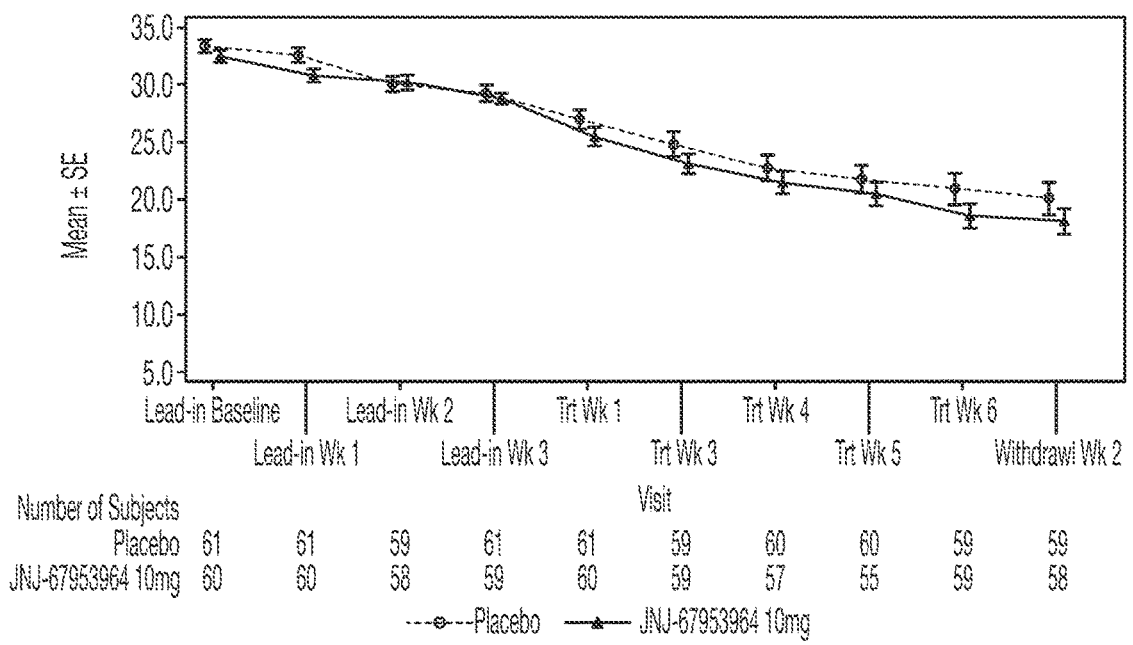
FIG. 5 is a line graph showing the MADRS (Montgomery-Åsberg Depression Rating Scale) total score: least squares mean changes from baseline (±SE) during the treatment period for the enriched intent-to-treat (eITT) analysis set.
Figure 8:
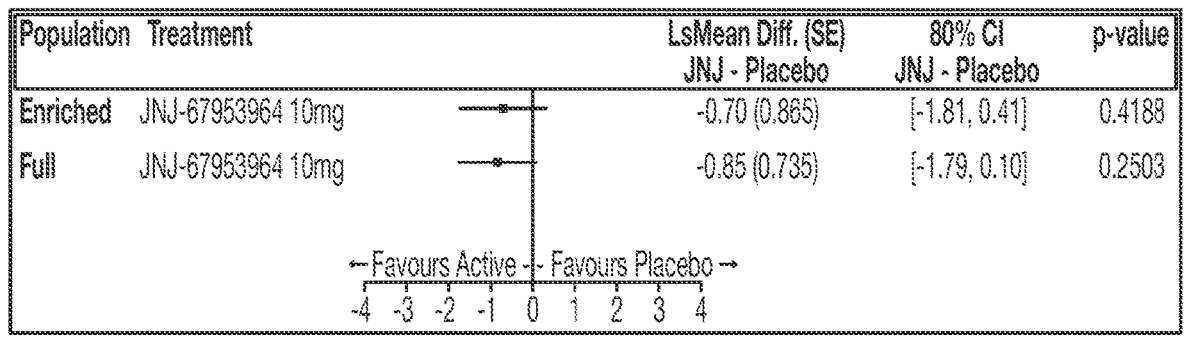
FIG. 8 is a plot showing SHAPS total score changes at treatment week 6 for enriched and full population: MMRM (Mixed-effects Model for Repeated Measures) Results—estimated LSMeans and comparison versus placebo
Figure 9:
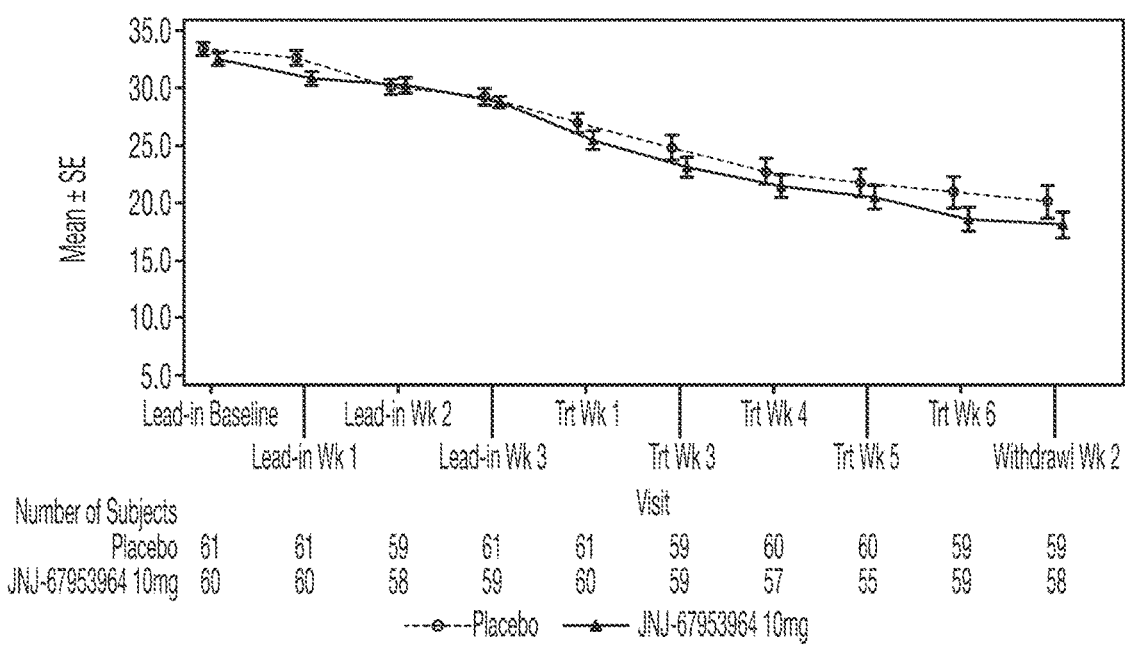
FIG. 9 is a line graph showing MADRS total score: mean values (±SE) over time for the eITT analysis set.

F. Results (i) Primary Endpoint: Change from Treatment Baseline in MADRS Total Score at Treatment Week 6 in Non-Responders during Placebo Lead-in Period Enriched ITT Analysis Set The mean (SD) MADRS total score at treatment baseline was 29.0 (4.61), ranging from 19 to 41. See, FIG. 5. The mean change from treatment baseline (SD) in MADRS total score at treatment week 6 was −10.2 (8.44) for aticaprant and −8.2 (8.53) for placebo. The observed effect size was 0.23. See Tables 20-22 and FIG. 8.

TABLE 20

Summary of Baseline Psychiatry Rating Scales at the Start of the Lead-in and Treatment Periods; eITT Analysis Set

| | | MADRS Total Score | | | SHAPS Total Score | |
|---|---|---|---|---|---|---|
| | N | Mean (SD) | Median (Range) | N | Mean (SD) | Median (Range) |
| Lead-in Baseline | | | | | | |
| Placebo | 61 | 33.4 (4.25) | 34.0 (26; 42) | 61 | 38.0 (6.28) | 38.0 (22; 55) |
| Aticaprant | 60 | 32.5 (4.18) | 32.0 (25; 45) | 60 | 38.3 (5.66) | 38.0 (21; 53) |
| Total | 121 | 32.9 (4.22) | 33.0 (25; 45) | 121 | 38.1 (5.96) | 38.0 (21; 55) |
| Treatment Baseline | | | | | | |
| Placebo | 61 | 29.2 (5.47) | 29.0 (19; 41) | 61 | 36.8 (5.75) | 37.0 (23; 50) |
| Aticaprant | 60 | 28.7 (3.58) | 28.5 (21; 36) | 60 | 36.4 (5.16) | 36.5 (20; 49) |
| Total | 121 | 29.0 (4.61) | 29.0 (19; 41) | 121 | 36.6 (5.45) | 37.0 (20; 50) |

TABLE 21

MADRS Total Score: Mean Changes to Placebo During the Treatment Period; eITT Analysis Set

| Analysis Visit Treatment | N | Mean Change from Baseline (SD) | Mean Change to Placebo (SD pooled) | 90% CI for Mean Change to Placebo | Effect Size |
|---|---|---|---|---|---|
| Treatment Week 1 | | | | | |
| Placebo | 61 | −2.2 (3.73) | | | |
| Aticaprant | 60 | −3.3 (5.21) | −1.1 (4.52) | [−2.4, 0.3] | −0.24 |
| Treatment Week 3 | | | | | |
| Placebo | 59 | −4.3 (5.99) | | | |
| Aticaprant | 59 | −5.7 (6.38) | −1.4 (6.18) | [−3.3, 0.5] | −0.22 |
| Treatment Week 4 | | | | | |
| Placebo | 60 | −6.4 (6.66) | | | |
| Aticaprant | 57 | −7.3 (7.35) | −0.9 (7.00) | [−3.1, 1.2] | −0.14 |
| Treatment Week 5 | | | | | |
| Placebo | 60 | −7.4 (7.15) | | | |
| Aticaprant | 55 | −8.4 (7.36) | −1.1 (7.25) | [−3.3, 1.2] | −0.14 |
| Treatment Week 6 | | | | | |
| Placebo | 59 | −8.2 (8.53) | | | |
| Aticaprant | 59 | −10.2 (8.44) | −2.0 (8.49) | [−4.6, 0.6] | −0.23 |

Negative change from baseline indicates improvement. Negative change to Placebo indicates favorable aticaprant effect. Negative effect size favors aticaprant; positive effect size favors Placebo.

TABLE 22

MADRS Total Score: MMRM Results - Estimated LS Means and Comparison versus Placebo; eITT Analysis Set

| Analysis Visit Treatment | N | Mean (SD) | Mean (SD) | LSMean (SE) | LSMean Difference (SE)\ Treatment Placebo | 60% Confidence Interval on Difference | p-value[a] |
|---|---|---|---|---|---|---|---|
| Treatment Week 1 | | | | | | | |
| Placebo | 61 | 26.9 (6.77) | −2.2 (3.73) | −2.0 (0.92) | | | |
| aticaprant | 60 | 25.4 (5.93) | −3.3 (5.21) | −3.2 (0.93) | −1.2 (1.24) | [−2.28, −0.19] | 0.1604 |
| Treatment Week 3 | | | | | | | |
| Placebo | 59 | 24.8 (8.25) | −4.3 (5.99) | −4.2 (0.92) | | | |
| aticaprant | 59 | 23.1 (6.58) | −5.7 (6.38) | −5.6 (0.93) | −1.5 (1.25) | [−2.55, −0.44] | 0.1159 |
| Treatment Week 4 | | | | | | | |
| Placebo | 60 | 22.7 (9.10) | −6.4 (6.66) | −6.2 (0.92) | | | |
| aticaprant | 57 | 21.5 (7.49) | −7.3 (7.35) | −7.3 (0.93) | −1.1 (1.25) | [−2.19, −0.09] | 0.1811 |
| Treatment Week 5 | | | | | | | |
| Placebo | 60 | 21.7 (9.54) | −7.4 (7.15) | −7.2 (0.92) | | | |
| aticaprant | 55 | 20.5 (7.44) | −8.4 (7.36) | −8.7 (0.94) | −1.5 (1.25) | [−2.60, −0.48] | 0.1103 |
| Treatment Week 6 | | | | | | | |
| Placebo | 59 | 20.9 (10.54) | −8.2 (8.53) | −8.0 (0.92) | | | |
| aticaprant | 59 | 18.6 (8.14) | −10.2 (8.44) | −10.1 (0.93) | −2.1 (1.25) | [−3.20, −1.09] | 0.0443 |

[a] One-sided test for no difference between treatments from a MMRM model with subject as random effect; country, treatment, time and time-by-treatment interaction as factors; and baseline MADRS total score as continuous covariate. An AR(1) variance-covariance matrix was employed Based on the results of a MMRM model with subject as random effect; country, treatment, time and time-by-treatment interaction as factors; and baseline MADRS total score as continuous covariate a significant positive efficacy signal was detected for aticaprant versus placebo at the one-sided 0.20 significance level. The estimated LS mean difference at treatment week 6 between aticaprant and placebo was −2.1 with 80% 1-sided CI upper limit of −1.09. The corresponding p-value was 0.044. The treatment effect was larger in the fITT than in the eITT population: −3.1 with 80% 1-sided CI upper limit of −2.2 (p=0.002). The effect size was 0.36 and 0.23, respectively. See, FIGS. 2 and 3.

Full ITT Analysis Set

Figure 7:
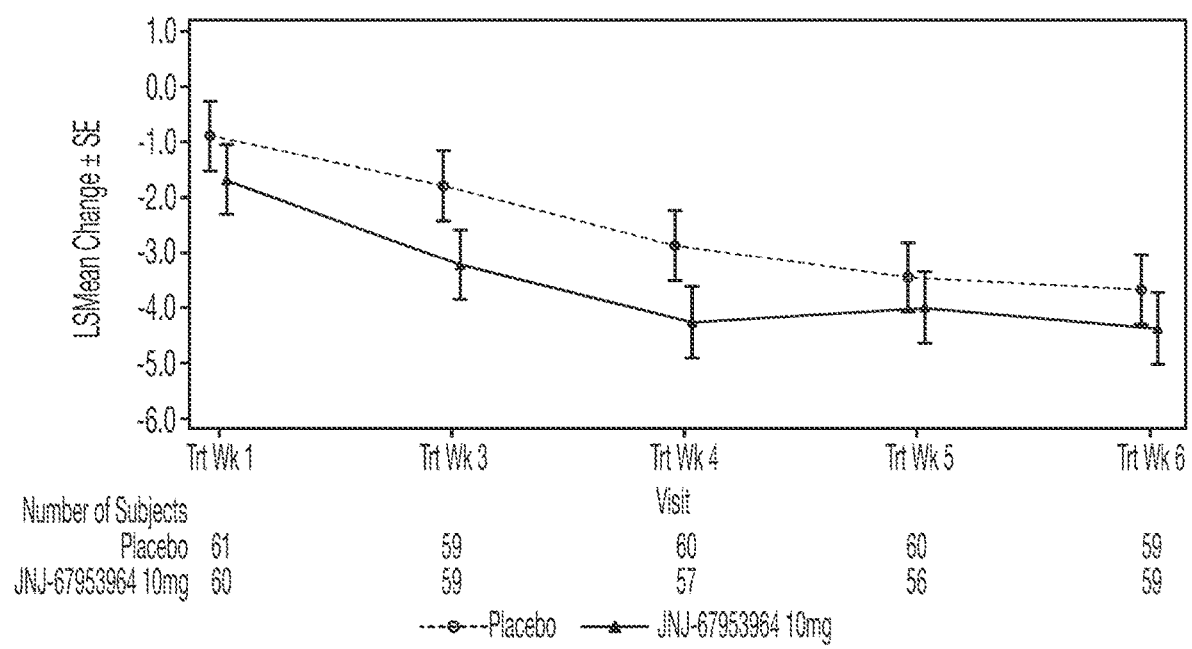
FIG. 7 is a line graph showing SHAPS (Snaith-Hamilton Pleasure Scale) total score: least squares mean changes from baseline (±SE) during the treatment period for the eITT analysis set.

The mean (SD) baseline MADRS total score at treatment baseline was 25.3 (7.86), ranging from 0 to 41. See, FIGS. 7A and 7B. The mean changes from treatment baseline in MADRS total score at Treatment Week 6 for fITT were smaller than for eITT: −9.7 (8.02) for aticaprant and −6.6 (8.57) for placebo. The observed effect size was 0.36. These results illustrate a statistical superiority over placebo with a durability of effect with the greatest difference seen at week 6. See, Table 23.

TABLE 23

Summary of Baseline Psychiatry Rating Scales at the Start of the Lead-in and Treatment Periods; fITT Analysis Set

| | MADRS Total Score | | | | SHAPS Total Score | | | |
|---|---|---|---|---|---|---|---|---|
| | N | Mean (SD) | Median (Range) | | N | Mean (SD) | Median (Range) | |

Lead-in Baseline

| | | | | | | | | |
|---|---|---|---|---|---|---|---|---|
| Placebo | 83 | 32.8 (4.25) | 33.0 (26; 42) | | 83 | 37.8 (6.01) | 38.0 (22; 55) | |
| Aticaprant | 83 | 32.4 (4.27) | 32.0 (21; 45) | | 83 | 37.3 (6.23) | 38.0 (14; 53) | |
| Total | 166 | 32.6 (4.25) | 32.0 (21; 45) | | 166 | 37.6 (6.11) | 38.0 (14; 55) | |

Treatment Baseline

| | | | | | | | | |
|---|---|---|---|---|---|---|---|---|
| Placebo | 83 | 25.7 (7.73) | 26.0 (10; 41) | | 83 | 36.3 (5.44) | 36.0 (23; 50) | |
| Aticaprant | 83 | 24.8 (8.02) | 27.0 (0; 36) | | 83 | 35.0 (5.85) | 36.0 (14; 49) | |
| Total | 166 | 25.3 (7.86) | 26.5 (0; 41) | | 166 | 35.6 (5.67) | 36.0 (14; 50) | |

Figure 6:
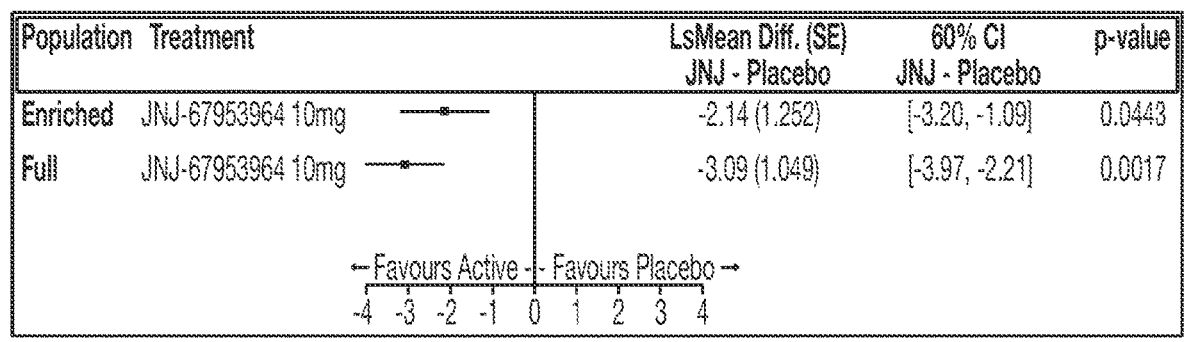
FIG. 6 is a plot showing MADRS total score changes at treatment week 6 for enriched and full population: MMRM results—estimated LS means and comparison versus placebo.

Significant effect for aticaprant versus placebo in fITT population was also detected. The estimated LS mean difference at treatment week 6 between aticaprant and placebo was −3.1 with 80% 1-sided CI upper limit of −2.21. The corresponding p-value was 0.002. See, Tables 24-25 and FIG. 6.

TABLE 24

MADRS Total Score: MMRM Results - Estimated LS Means and Comparison versus Placebo; fITT Analysis Set

| | | | | Change from Baseline | | | |
|---|---|---|---|---|---|---|---|
| Analysis Visit Treatment | N | Mean (SD) | Mean LSMean (SD) | LSMean (SE) | Difference (SE)\ Treatment Placebo | 60% Confidence Interval on Difference | p-value[a] |

Treatment Week 1

| | | | | | | | |
|---|---|---|---|---|---|---|---|
| Placebo | 83 | 24.0 (8.12) | −1.8 (4.00) | −1.7 (0.78) | | | |
| aticaprant | 83 | 21.7 (8.78) | −3.1 (4.81) | −3.2 (0.77) | −1.6 (1.03) | [−2.44, −0.70] | 0.0653 |

Treatment Week 3

| | | | | | | | |
|---|---|---|---|---|---|---|---|
| Placebo | 81 | 22.2 (9.28) | −3.4 (6.50) | −3.4 (0.78) | | | |
| aticaprant | 80 | 20.0 (8.53) | −5.1 (6.74) | −5.2 (0.78) | −1.9 (1.04) | [−2.74, −0.99] | 0.0368 |

Treatment Week 4

| | | | | | | | |
|---|---|---|---|---|---|---|---|
| Placebo | 82 | 20.8 (9.24) | −4.9 (7.02) | −4.8 (0.78) | | | |
| aticaprant | 78 | 17.9 (9.32) | −7.2 (7.02) | −7.3 (0.78) | −2.5 (1.04) | [−3.34, −1.59] | 0.0093 |

Treatment Week 5

| | | | | | | | |
|---|---|---|---|---|---|---|---|
| Placebo | 82 | 19.2 (9.89) | −6.4 (7.16) | −6.3 (0.78) | | | |
| aticaprant | 76 | 16.7 (9.47) | −8.3 (7.48) | −8.7 (0.78) | −2.4 (1.05) | [−3.24, −1.47] | 0.0125 |

Treatment Week 6

| | | | | | | | |
|---|---|---|---|---|---|---|---|
| Placebo | 81 | 19.0 (10.35) | −6.6 (8.57) | −6.5 (0.78) | | | |
| aticaprant | 77 | 15.9 (9.09) | −9.7 (8.02) | −9.6 (0.79) | −3.1 (1.05) | [−3.97, −2.21] | 0.0017 |

[a]One-sided test for no difference between treatments from a MMRM model with subject as random effect; country, treatment, time and time-by-treatment interaction as factors; and baseline MADRS total score as continuous covariate. An AR(1) variance-covariance matrix was employed

TABLE 25

MADRS (Montgomery-Åsberg Depression Rating Scale) Total Score: Mean Changes to Placebo During the Treatment Period; fITT Analysis Set

| Analysis Visit Treatment | N | Mean Change to Placebo (SD pooled) | 90% CI for Mean Change to Placebo | Effect Size |
|---|---|---|---|---|

Treatment Week 1

| | | | | |
|---|---|---|---|---|
| Placebo | 83 | | | |
| Aticaprant | 83 | −1.3 (4.43) | [−2.4, −0.2] | −0.29 |

Treatment Week 3

| | | | | |
|---|---|---|---|---|
| Placebo | 81 | | | |
| Aticaprant | 80 | −1.7 (6.62) | [−3.4, 0.0] | −0.26 |

Treatment Week 4

| | | | | |
|---|---|---|---|---|
| Placebo | 82 | | | |
| Aticaprant | 78 | −2.3 (7.02) | [−4.1, −0.4] | −0.32 |

Treatment Week 5

| | | | | |
|---|---|---|---|---|
| Placebo | 82 | | | |
| Aticaprant | 76 | −1.9 (7.31) | [−3.9, −0.0] | −0.26 |

Treatment Week 6

| | | | | |
|---|---|---|---|---|
| Placebo | 81 | | | |
| Aticaprant change from | 77 | −3.0 (8.31) | [−5.2, −0.8] | −0.36 |

Negative change from baseline indicates improvement. Negative change to Placebo indicates favorable aticaprant effect. Negative effect size favors aticaprant; positive effect size favors Placebo.

COVID-19 Impact on Primary Efficacy Assessment

Supplementary analysis was conducted using the same MMRM model as described for the primary analysis on all the data collected prior to 15 Mar. 2020 (estimated date of the COVID-19 lockdowns in most of the countries participating in the trial). Seventeen percent of the subjects in fITT and 19% in eITT population had at least one of the MADRS assessment excluded from the model due to COVID-19 impact. Results of the analysis corroborated the findings of the primary efficacy analysis in both: eITT and fITT populations. LSMeans difference estimate was −3.0 (80% 1-sided CI upper limit of −1.88) for eITT and −3.4 (80% 1-sided CI upper limit of −2.51) for fITT.

(ii) Secondary Endpoints

MADRS Remission Rates Over Treatment Period

Figure 11:
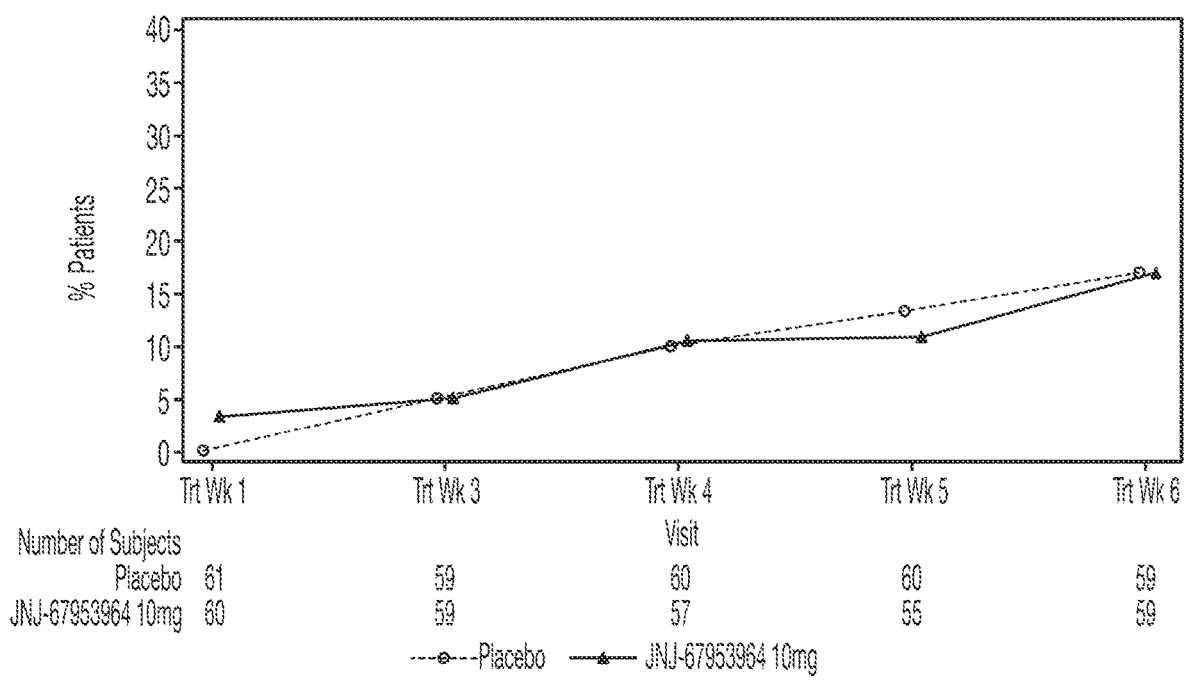
FIG. 11 is a line graph showing MADRS total score: percentage of subjects with remission of depressive symptoms (total score ≤10) during the treatment period for the eITT analysis set.
Figure 12:
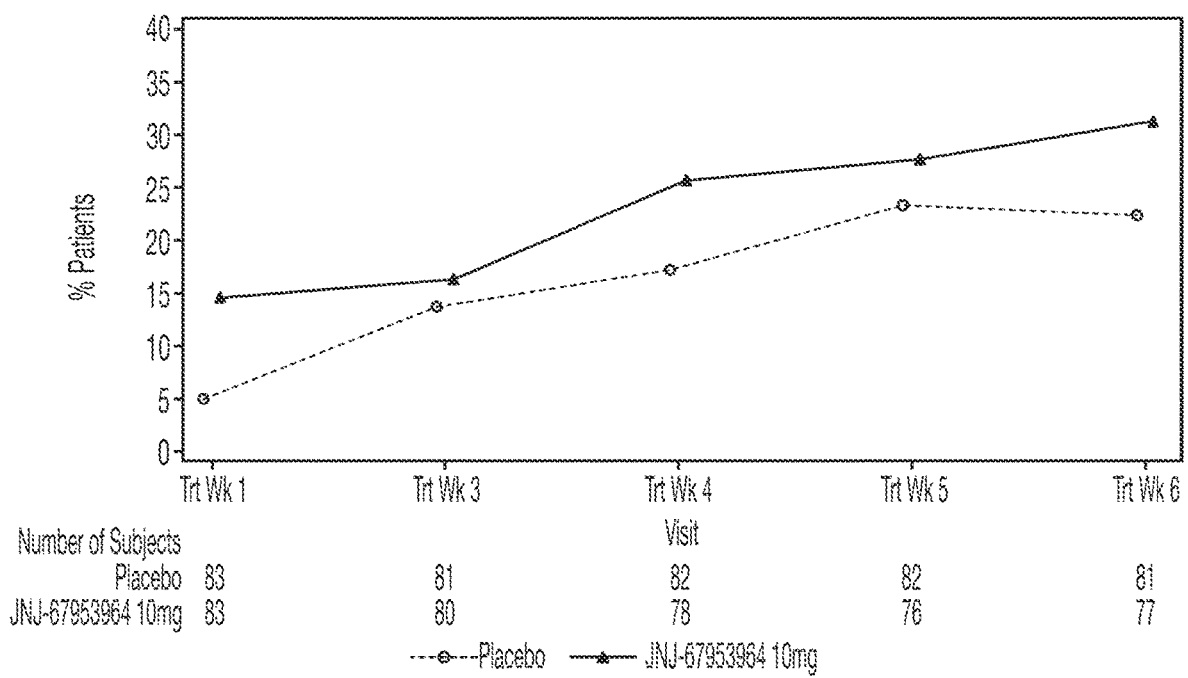
FIG. 12 is a line graph showing MADRS total score: percentage of subjects with remission of depressive symptoms (total score ≤10) during the treatment period for the fITT analysis set.
Figure 13:
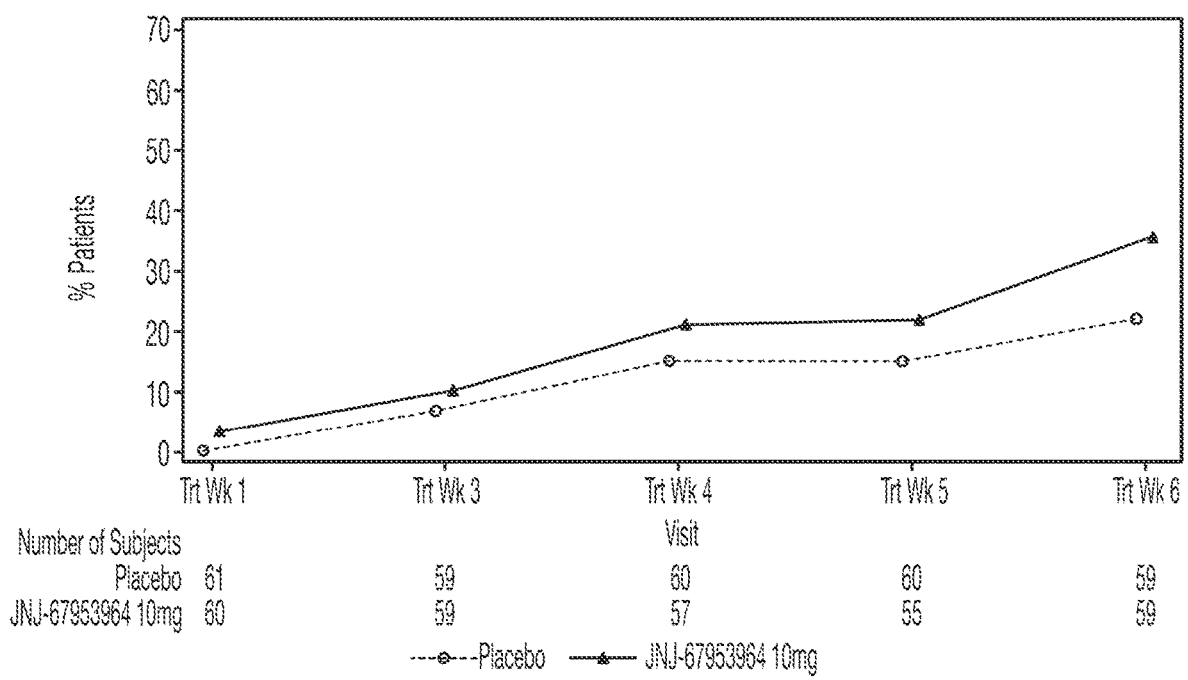
FIG. 13 is a line graph showing MADRS total score: percentage of responders (≥30% improvement from baseline) during the treatment period for the eITT analysis set.
Figure 14:
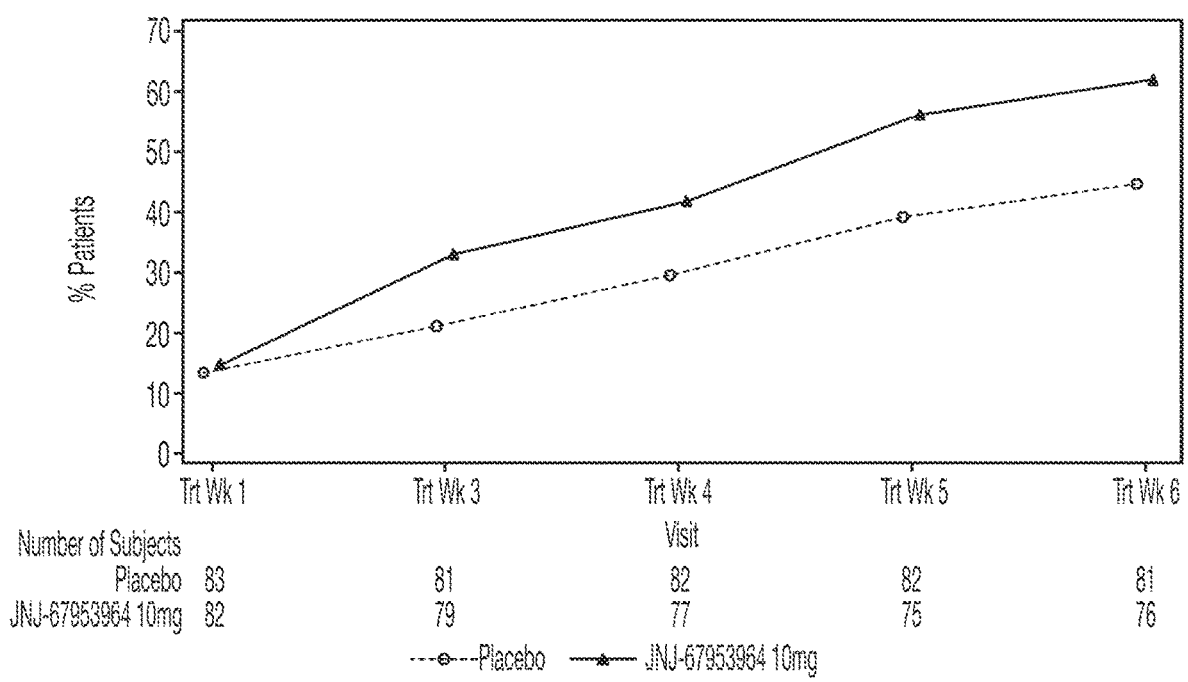
FIG. 14 is a line graph showing MADRS total score: percentage of responders (≥30% improvement from baseline) during the treatment period for the fITT analysis set.
Figure 15:
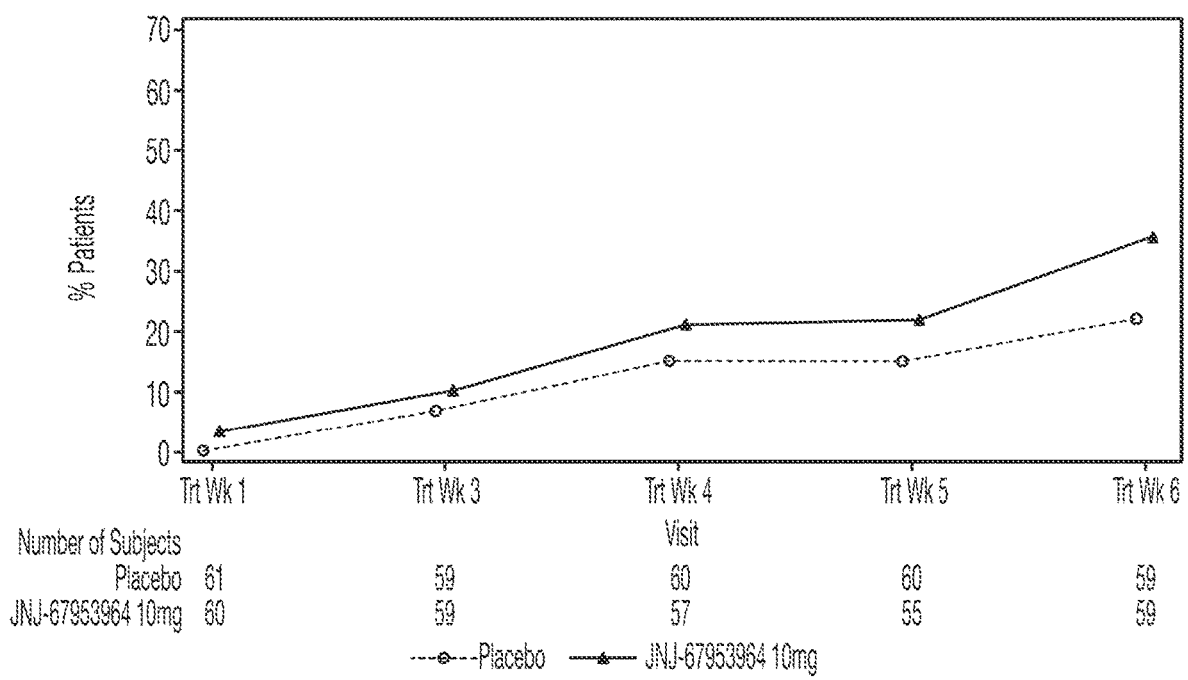
FIG. 15 is a line graph showing MADRS total score: percentage of responders (≥50% improvement from baseline) during the treatment period for the eITT analysis set.
Figure 16:
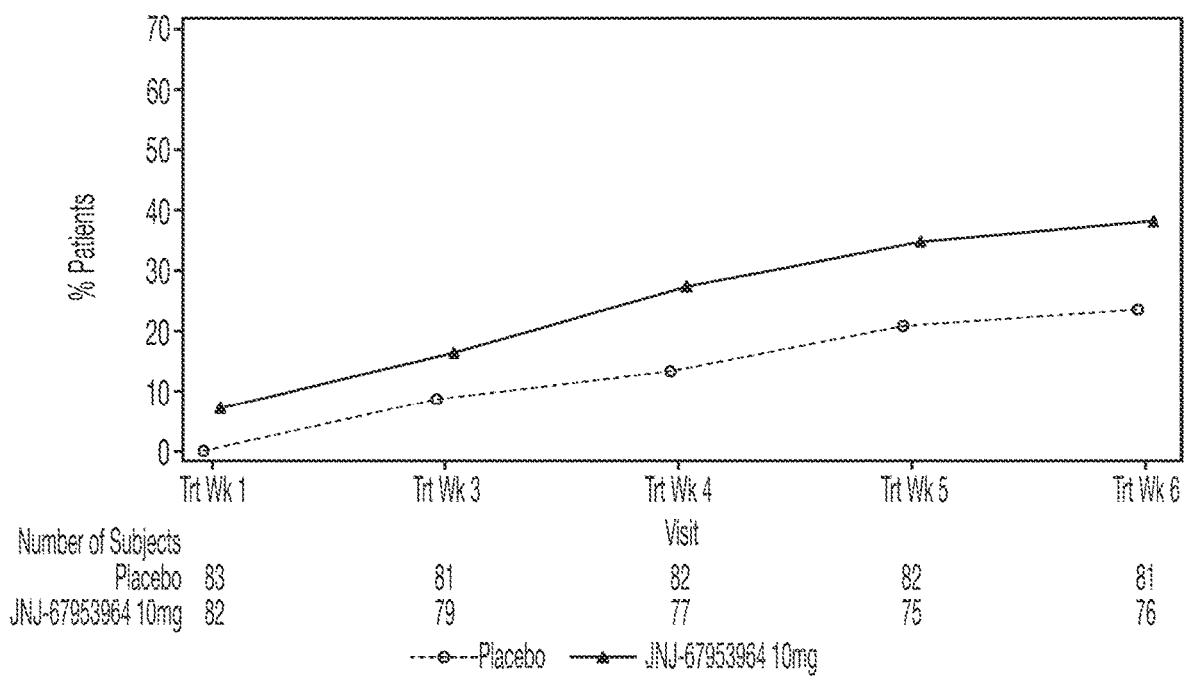
FIG. 16 is a line graph showing MADRS total score: percentage of responders (≥50% improvement from baseline) during the treatment period for the fITT analysis set.

At Treatment Week 6 the percentage of subjects with MADRS remission (MADRS total score≤10) in the eITT population was 16.9% for aticaprant and 16.9% for placebo. Treatment week 6 remission rates in fITT population were 31.2% for aticaprant and 22.2% for placebo. For both populations (eITT and fITT), no significant treatment differences were detected at treatment week 6 using Chi-square test (2-sided p=0.999 and p=0.203, respectively). See, FIGS. 11 and 12.

MADRS Response Rates (at Least 30% Improvement) Over Treatment Period

The percentage of subjects with ≥30% improvement in MADRS total score at treatment week 6 in the eITT population was 57.6% for aticaprant and 45.8% for placebo. Treatment week 6 response rates in fITT population were 61.8% for aticaprant and for 44.4% placebo. For both populations, treatment differences at Treatment Week 6 were significant at 20% 2-sided significance level (Chi-square test: p=0.197 for eITT and p=0.029 for fITT).

MADRS Response Rates (at Least 50% Improvement) Over Treatment Period

The percentage of subjects with ≥50% improvement in MADRS total score at treatment week 6 in the eITT population was 35.6% for aticaprant and 22.0% for placebo. Treatment week 6 response rates in fITT population were 38.2% for aticaprant and 23.5% for placebo. For both populations, treatment differences at treatment week 6 were significant at 20% 2-sided significance level (Chi-square test: p=0.104 for eITT and p=0.046 for fITT). See, Table 26 and FIGS. 13-16.

TABLE 26

Change from Treatment Baseline in MADRS Total Score at Treatment Week 6 in Both Responders and Non-Responders during Placebo Lead-in Period

| End point values | Placebo | aticaprant 10 milligrams (mg) |
|---|---|---|
| Number of subjects analyzed Units: score on a scale | 81 | 77 |
| Measure Type: Least Squares Mean (Standard Error) | −6.5 ± 0.78 | −9.6 ± 0.79 |
| P-value | | =0.0017 |
| Parameter type | | Least Squares Mean Difference |
| Point estimate | | −3.1 |
| Confidence interval | | |
| level | | 80% |
| sides | | 1-Sided |
| lower limit | | — |
| upper limit | | −2.21 |
| Variability estimate | | Standard Error of the mean |
| Dispersion value | | 1.05 |

Changes in SHAPS Total Score from Treatment Baseline to Treatment Week 6

Enriched ITT Analysis Set

In eITT population, in a subgroup of subjects with high anhedonia level (baseline SHAPS total score ≥38), larger differences between aticaprant placebo at Treatment Week 6 were observed than in subjects with low anhedonia level (20≤ baseline SHAPS total score <38). The effect size was 0.38 and 0.11, respectively.

Figure 17:
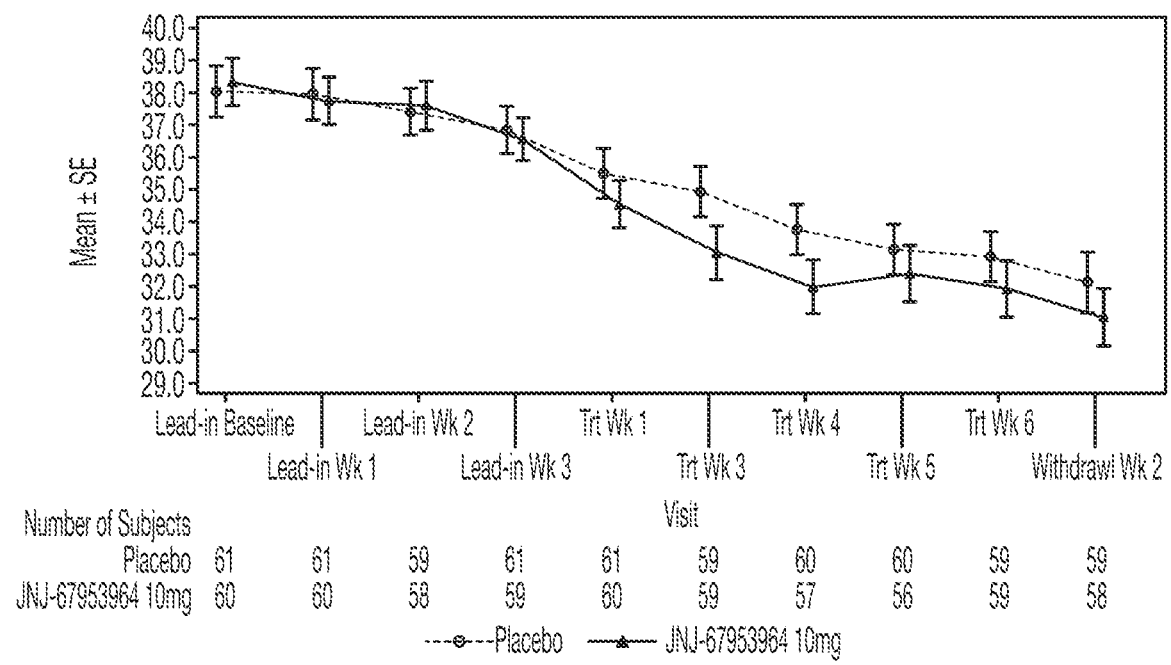
FIG. 17 is a line graph showing SHAPS total score: mean values (±SE) over time for the eITT analysis set.
Figure 37:
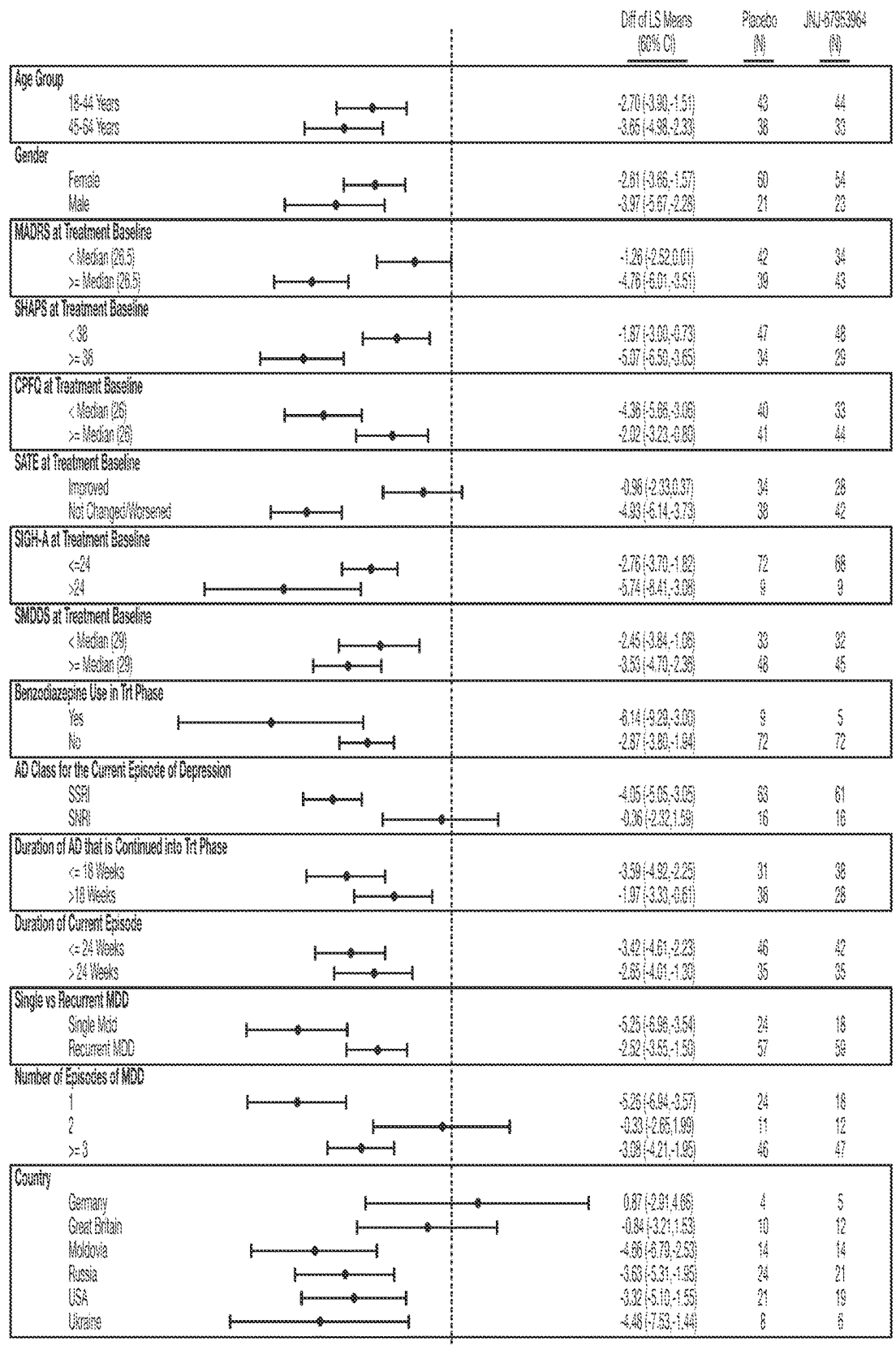
FIG. 37 is a plot showing MADRS total score: difference of LSMeans (60% at Weeks 6 by different subgroups for the fITT analysis set. In this plot, <17 indicates mild severity; 18-24 indicates mild to moderate severity, and 25-30 indicates moderate to severe.

The mean (SD) SHAPS total score at treatment baseline was 36.6 (5.45), ranging from 20 to 50. The mean change from treatment baseline (SD) in SHAPS total score at treatment week 6 was −4.6 (6.23) for aticaprant and −4.2 (5.04) for placebo. The observed effect size was 0.07. See, Table 27 and FIGS. 17 and 37.

TABLE 27

SHAPS Total Score: Mean Changes to Placebo During the Treatment Period; eITT Analysis Set

| Analysis Visit Treatment | N | Mean Change from Baseline (SD) | Mean Change to Placebo (SD pooled) | 90% CI for Mean Change to Placebo | Effect Size |
|---|---|---|---|---|---|
| Treatment Week 1 | | | | | |
| Placebo | 61 | −1.3 (3.17) | | | |
| aticaprant | 60 | −1.9 (4.30) | −0.6 (3.77) | [−1.7, 0.6] | −0.15 |
| Treatment Week 3 | | | | | |
| Placebo | 59 | −2.2 (4.65) | | | |
| aticaprant | 59 | −3.4 (5.25) | −1.2 (4.96) | [−2.8, 0.3] | −0.25 |
| Treatment Week 4 | | | | | |
| Placebo | 60 | −3.3 (4.47) | | | |
| aticaprant | 57 | −4.5 (5.89) | −1.2 (5.21) | [−2.8, 0.4] | −0.23 |
| Treatment Week 5 | | | | | |
| Placebo | 60 | −3.9 (4.88) | | | |
| aticaprant | 56 | −4.3 (6.07) | −0.4 (5.49) | [−2.1, 1.3] | −0.08 |
| Treatment Week 6 | | | | | |
| Placebo | 59 | −4.2 (5.04) | | | |
| aticaprant | 59 | −4.6 (6.23) | −0.4 (5.66) | [−2.1, 1.3] | −0.07 |

Negative change from baseline indicates improvement. Negative change to Placebo indicates favorable aticaprant effect. Negative effect size favors aticaprant; positive effect size favors Placebo.

Figure 18:
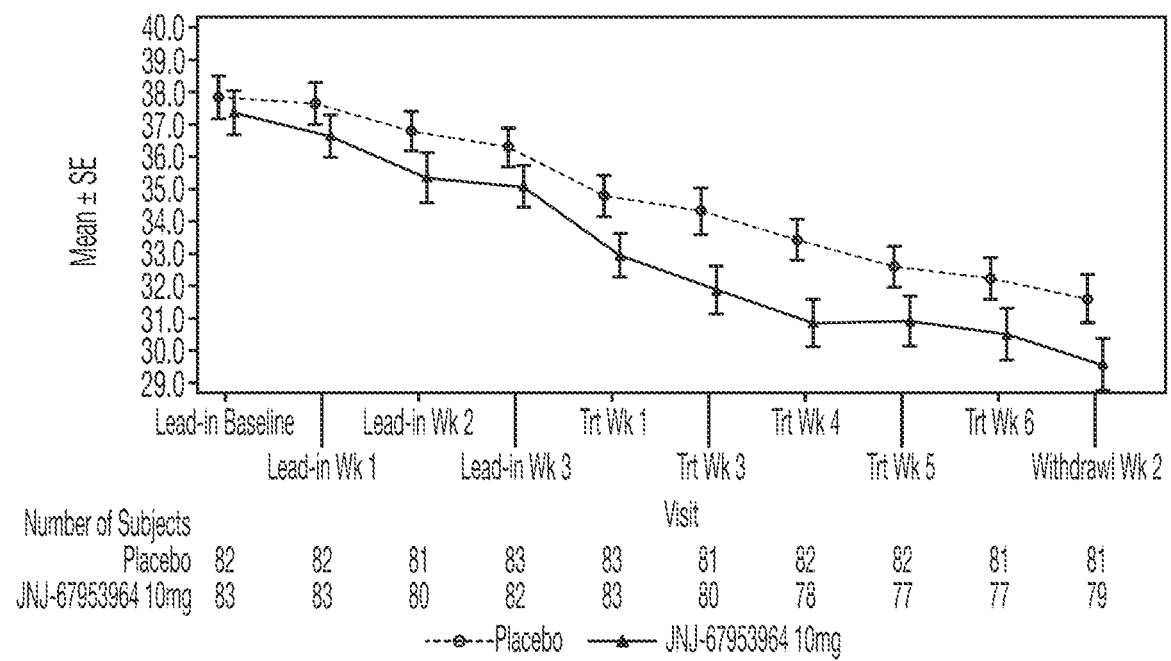
FIG. 18 is a line graph showing SHAPS total score: mean values (±SE) over time for the fITT analysis set.

Changes in SHAPS total score were analyzed with the same MMRM model used for MADRS total score. The estimated LS Mean difference with 80% 2-sided CI at treatment week 6 between aticaprant and placebo was −0.7 [−1.81, 0.41]. See, FIG. 7 and Tables 28 and 29 and FIG. 18. The corresponding p-value was 0.419.

TABLE 28

SHAPS Total Score: MMRM Results - Estimated LS Means and Comparison versus Placebo; eITT Analysis Set

| Analysis Visit Treatment | N | Mean (SD) | Change from Baseline Mean (SD) | LSMean (SE) | LSMean Difference (SE)\ Treatment Placebo | 60% Confidence Interval on Difference | p-value[a] |
|---|---|---|---|---|---|---|---|
| Treatment Week 1 | | | | | | | |
| Placebo | 61 | 35.5 (6.00) | −1.3 (3.17) | −0.9 (0.63) | | | |
| aticaprant | 60 | 34.5 (5.63) 5 | −1.9 (4.30) | −1.7 (0.64) | −0.8 (0.86) | [−1.90, 0.31] | 0.3542 |

TABLE 28-continued

SHAPS Total Score: MMRM Results - Estimated LS Means and Comparison versus Placebo; eITT Analysis Set

| Analysis Visit Treatment | N | Mean (SD) | Mean (SD) | LSMean (SE) | LSMean Difference (SE)\ Treatment Placebo | 60% Confidence Interval on Difference | p-value[a] |
|---|---|---|---|---|---|---|---|
| Treatment Week 3 | | | | | | | |
| Placebo | 59 | 34.9 (6.09) | −2.2 (4.65) | −1.8 (0.64) | | | |
| aticaprant | 59 | 33.0 (6.39) | −3.4 (5.25) | −3.2 (0.64) | −1.4 (0.86) | [−2.53, −0.31] | 0.1005 |
| Treatment Week 4 | | | | | | | |
| Placebo | 60 | 33.7 (5.89) | −3.3 (4.47) | −2.9 (0.63) | | | |
| aticaprant | 57 | 32.0 (6.24) | −4.5 (5.89) | −4.3 (0.64) | −1.4 (0.86) | [−2.48, −0.26] | 0.1131 |
| Treatment Week 5 | | | | | | | |
| Placebo | 60 | 33.1 (5.88) | −3.9 (4.88) | −3.5 (0.64) | | | |
| aticaprant | 56 | 32.4 (6.61) | −4.3 (6.07) | −4.0 (0.64) | −0.5 (0.87) | [−1.65, 0.57] | 0.5332 |
| Treatment Week 6 | | | | | | | |
| Placebo | 59 | 32.9 (6.04) | −4.2 (5.04) | −3.7 (0.64) | | | |
| aticaprant | 59 | 31.9 (6.60) | −4.6 (6.23) | −4.4 (0.64) | −0.7 (0.87) | [−1.81, 0.41] | 0.4188 |

[a] two-sided test for no difference between treatments from a MMRM model with subject as random effect; country, treatment, time and time-by-treatment interaction as factors; and baseline SHAPS total score as continuous covariate. An AR(1) variance-covariance matrix was employed.

TABLE 29

SHAPS Total Score: MMRM Results - Estimated LS Means and Comparison versus Placebo; fITT Analysis Set

| Analysis Visit Treatment | N | Mean (SD) | Mean (SD) | LSMean (SE) | LSMean Difference (SE)\ Treatment Placebo | 60% Confidence Interval on Difference | p-value[a] |
|---|---|---|---|---|---|---|---|
| Treatment Week 1 | | | | | | | |
| Placebo | 83 | 34.8 (5.86) | −1.5 (3.57) | −1.0 (0.54) | | | |
| aticaprant | 83 | 32.9 (6.09) | −2.0 (4.05) | −1.9 (0.54) | −1.0 (0.72) | [−1.88, −0.02] | 0.1888 |
| Treatment Week 3 | | | | | | | |
| Placebo | 81 | 34.3 (6.36) | −2.2 (5.11) | −1.7 (0.54) | | | |
| aticaprant | 80 | 31.9 (6.54) | −3.2 (5.07) | −3.1 (0.54) | −1.4 (0.73) | [−2.32, −0.45] | 0.0580 |
| Treatment Week 4 | | | | | | | |
| Placebo | 82 | 33.4 (5.70) | −3.0 (4.41) | −2.5 (0.54) | | | |
| aticaprant | 78 | 30.8 (6.37) | −4.2 (5.70) | −4.1 (0.55) | −1.6 (0.73) | [−2.51, −0.63] | 0.0321 |
| Treatment Week 5 | | | | | | | |
| Placebo | 82 | 32.6 (5.63) | −3.8 (4.76) | −3.3 (0.55) | | | |
| aticaprant | 77 | 30.9 (6.76) | −4.3 (5.70) | −4.1 (0.55) | −0.8 (0.73) | [−1.71, 0.17] | 0.2912 |

TABLE 29-continued

SHAPS Total Score: MMRM Results - Estimated LS Means and Comparison versus Placebo; fITT Analysis Set

| | | | | Change from Baseline | | |
|---|---|---|---|---|---|---|
| Analysis Visit Treatment | N | Mean (SD) | Mean (SD) | LSMean (SE) | LSMean Difference (SE)\ Treatment Placebo | 60% Confidence Interval on Difference | p-value[a] |

| | | | | | | |
|---|---|---|---|---|---|---|
| Treatment Week 6 | | | | | | |
| Placebo | 81 | 32.2 (5.81) | −4.2 (4.98) | −3.7 (0.55) | | |
| aticaprant two-sided test | 77 | 30.5 (6.98) | −4.7 (5.91) | −4.5 (0.55) | −0.8 (0.73) | [−1.79, 0.10] | 0.2503 |

[a]two-sided test for no difference between treatments from a MMRM model with subject as random effect; country, treatment, time and time-by-treatment interaction as factors; and baseline SHAPS total score as continuous covariate. An AR(1) variance-covariance matrix was employed The estimated LS mean differences with 80% 2-sided CI at treatment week 6 between aticaprant and placebo was −0.8 [−1.79, 0.10]. The corresponding p-value was 0.250. See, FIGS. 7 and 8.

Full ITT Analysis Set

Similar trend was observed in fITT population and differences were larger in magnitude than those observed in eITT population. The effect size was 0.51 and 0.29, respectively. The mean (SD) baseline SHAPS total score at treatment baseline was 35.6 (5.67), ranging from 14 to 50. The mean changes from treatment baseline in SHAPS total score at treatment week 6 for fITT population were similar to changes in eITT: −4.7 (5.91) for aticaprant and −4.2 (4.98) for placebo. The observed effect size was 0.08. See, Table 30.

TABLE 30

SHAPS Total Score: Mean Changes to Placebo During the Treatment Period; fITT Analysis Set

| Analysis Visit Treatment | N | Mean Change from Baseline (SD) | Mean Change to Placebo (SD pooled) | 90% CI for Mean Change to Placebo | Effect Size |
|---|---|---|---|---|---|
| Treatment Week 1 | | | | | |
| Placebo | 83 | −1.5 (3.57) | | | |
| aticaprant | 83 | −2.0 (4.05) | −0.6 (3.82) | [−1.5, 0.4] | −0.15 |
| Treatment Week 3 | | | | | |
| Placebo | 81 | −2.2 (5.11) | | | |
| aticaprant | 80 | −3.2 (5.07) | −1.0 (5.09) | [−2.4, 0.3] | −0.20 |
| Treatment Week 4 | | | | | |
| Placebo | 82 | −3.0 (4.41) | | | |
| aticaprant | 78 | −4.2 (5.70) | −1.2 (5.08) | [−2.5, 0.1] | −0.23 |
| Treatment Week 5 | | | | | |
| Placebo | 82 | −3.8 (4.76) | | | |
| aticaprant | 77 | −4.3 (5.70) | −0.5 (5.24) | [−1.8, 0.9] | −0.09 |

TABLE 30-continued

SHAPS Total Score: Mean Changes to Placebo During the Treatment Period; fITT Analysis Set

| Analysis Visit Treatment | N | Mean Change from Baseline (SD) | Mean Change to Placebo (SD pooled) | 90% CI for Mean Change to Placebo | Effect Size |
|---|---|---|---|---|---|
| Treatment Week 6 | | | | | |
| Placebo | 81 | −4.2 (4.98) | | | |
| aticaprant | 77 | −4.7 (5.91) | −0.5 (5.45) | [−1.9, 1.0] | −0.08 |

Negative change from baseline indicates improvement. Negative change to Placebo indicates favorable aticaprant effect. Negative effect size favors aticaprant; positive effect size favors Placebo.

Changes in MADRS Total Score from Treatment Baseline to Treatment Week 6 by Anhedonia Level at Baseline Enriched ITT Analysis Set In subgroup of subjects with high anhedonia level (SHAPS total score ≥38) at treatment baseline, n=53, larger differences between aticaprant and placebo at treatment Week 6 were observed than in subjects with low anhedonia level (20≤ baseline SHAPS total score <38), n=65: −3.4 with 90% 2-sided CI of [−7.5, 0.7] and −0.9 with 90% 2-sided CI of [−4.2, 2.5], respectively (Table 31). The observed effect size was 0.38 and 0.11, respectively.

TABLE 31

MADRS (Montgomery-Åsberg Depression Rating Scale) Total Score: Mean Changes to Placebo During the Treatment Period by Anhedonia Level at Treatment Baseline; eITT Analysis Set

| Analysis Visit Treatment | N | Mean Change from Baseline (SD) | Mean Change to Placebo (SD pooled) | Level 90% CI for Mean Change to Placebo | Effect size |
|---|---|---|---|---|---|
| Low anhedonia Treatment Week 1 | | | | | |
| Placebo | 34 | −1.8 (3.43) | | | |
| aticaprant | 34 | −2.3 (5.03) | −0.5 (4.30) | [−2.2, 1.2] | −0.12 |
| Treatment Week 3 | | | | | |
| Placebo | 32 | −4.8 (5.70) | | | |
| aticaprant | 33 | −4.9 (5.99) | −0.1 (5.85) | [−2.5, 2.4] | −0.01 |

TABLE 31-continued

MADRS (Montgomery-Åsberg Depression Rating Scale) Total Score: Mean Changes to Placebo During the Treatment Period by Anhedonia Level at Treatment Baseline; eITT Analysis Set

| Analysis Visit Treatment | N | Mean Change from Baseline (SD) | Mean Change to Placebo (SD pooled) | 90% CI for Mean Change to Placebo | Effect size |
|---|---|---|---|---|---|
| Treatment Week 4 | | | | | |
| Placebo | 33 | −6.5 (6.16) | | | |
| aticaprant | 32 | −6.4 (7.40) | 0.0 (6.80) | [−2.8, 2.9] | 0.01 |
| Treatment Week 5 | | | | | |
| Placebo | 33 | −7.6 (6.80) | | | |
| aticaprant | 29 | −7.2 (6.46) | 0.3 (6.65) | [−2.5, 3.2] | 0.05 |
| Treatment Week 6 | | | | | |
| Placebo | 32 | −8.3 (8.25) | | | |
| aticaprant | 33 | −9.2 (8.01) | −0.9 (8.13) | [−4.2, 2.5] | −0.11 |
| High anhedonia Treatment Week 1 | | | | | |
| Placebo | 27 | −2.7 (4.08) | | | |
| aticaprant | 26 | −4.6 (5.25) | −1.8 (4.69) | [−4.0, 0.3] | −0.39 |
| Treatment Week 3 | | | | | |
| Placebo | 27 | −3.6 (6.35) | | | |
| aticaprant | 26 | −6.7 (6.83) | −3.0 (6.59) | [−6.1, 0.0] | −0.46 |
| Treatment Week 4 | | | | | |
| Placebo | 27 | −6.3 (7.34) | | | |
| aticaprant | 25 | −8.5 (7.26) | −2.2 (7.30) | [−5.6, 1.2] | −0.30 |
| Treatment Week 5 | | | | | |
| Placebo | 27 | −7.1 (7.67) | | | |
| aticaprant | 26 | −9.7 (8.18) | −2.6 (7.93) | [−6.3, 1.0] | −0.33 |
| Treatment Week 6 | | | | | |
| Placebo | 27 | −8.1 (9.01) | | | |
| aticaprant | 26 | −11.5 (8.95) | −3.4 (8.98) | [−7.5, 0.7] | −0.38 |

Low Anhedonia level (SHAPS Total Score at Treatment Baseline >= 20 and < 38), High Anhedonia level (SHAPS Total Score at Treatment Baseline >= 38). The MADRS Total Score ranges from 0 to 60, with higher scores indicating greater severity of depression.

Full ITT Analysis Set

A similar trend was observed in fITT population. The differences were larger in magnitude compared to eITT population: −4.6 with 90% 2-sided CI of [−8.4, −0.8] for subjects with high anhedonia level (n=63) and −2.3 with 90% 2-sided CI of [−5.0, 0.4] for subjects with low anhedonia level (n=94). See, Table 32. The observed effect size was 0.51 and 0.29, respectively.

TABLE 32

MADRS (Montgomery-Åsberg Depression Rating Scale) Total Score: Mean Changes to Placebo During the Treatment Period by Anhedonia Level at Treatment Baseline; fITT Analysis Set

| Analysis Visit Treatment | N | Mean Change from Baseline (SD) | Mean Change to Placebo (SD pooled) | 90% CI for Mean Change to Placebo | Effect size |
|---|---|---|---|---|---|
| Low anhedonia Treatment Week 1 | | | | | |
| Placebo | 49 | −1.3 (4.17) | | | |
| aticaprant | 52 | −2.4 (4.59) | −1.0 (4.39) | [−2.5, 0.4] | −0.24 |
| Treatment Week 3 | | | | | |
| Placebo | 47 | −3.6 (6.04) | | | |
| aticaprant | 49 | −4.1 (6.67) | −0.5 (6.37) | [−2.7, 1.7] | −0.08 |

TABLE 32-continued

MADRS (Montgomery-Åsberg Depression Rating Scale) Total Score: Mean Changes to Placebo During the Treatment Period by Anhedonia Level at Treatment Baseline; fITT Analysis Set

| Analysis Visit Treatment | N | Mean Change from Baseline (SD) | Mean Change to Placebo (SD pooled) | 90% CI for Mean Change to Placebo | Effect size |
|---|---|---|---|---|---|
| Treatment Week 4 | | | | | |
| Placebo | 48 | −4.9 (6.53) | | | |
| aticaprant | 48 | −6.4 (6.77) | −1.5 (6.65) | [−3.8, 0.8] | −0.23 |
| Treatment Week 5 | | | | | |
| Placebo | 48 | −6.6 (6.82) | | | |
| aticaprant | 45 | −7.3 (6.90) | −0.7 (6.86) | [−3.1, 1.7] | −0.10 |
| Treatment Week 6 | | | | | |
| Placebo | 47 | −6.5 (8.11) | | | |
| aticaprant | 47 | −8.8 (7.48) | −2.3 (7.80) | [−5.0, 0.4] | −0.29 |
| High anhedonia Treatment Week 1 | | | | | |
| Placebo | 34 | −2.4 (3.71) | | | |
| aticaprant | 30 | −4.4 (5.04) | −2.0 (4.38) | [−3.8, −0.1] | −0.45 |
| Treatment Week 3 | | | | | |
| Placebo | 34 | −3.1 (7.17) | | | |
| aticaprant | 30 | −6.9 (6.66) | −3.8 (6.94) | [−6.7, −0.9] | −0.54 |
| Treatment Week 4 | | | | | |
| Placebo | 34 | −4.8 (7.75) | | | |
| aticaprant | 29 | −8.6 (7.32) | −3.8 (7.56) | [−7.0, −0.6] | −0.50 |
| Treatment Week 5 | | | | | |
| Placebo | 34 | −6.2 (7.72) | | | |
| aticaprant | 30 | −10.2 (8.04) | −4.0 (7.87) | [−7.3, −0.7] | −0.51 |
| Treatment Week 6 | | | | | |
| Placebo | 34 | −6.8 (9.30) | | | |
| aticaprant | 29 | −11.3 (8.69) | −4.6 (9.03) | [−8.4, −0.8] | −0.51 |

Low Anhedonia level (SHAPS Total Score at Treatment Baseline >= 20 and < 38), High Anhedonia level (SHAPS Total Score at Treatment Baseline >= 38). The MADRS Total Score ranges from 0 to 60, with higher scores indicating greater severity of depression.

This data illustrates that segmentation into high vs low anhedonia had a benefit for treating MDD: higher treatment effect for aticaprant. Further, the placebo response was lower in patients with high anhedonia, as compared to low anhedonia.

Change from Treatment Baseline in CGI-S Total Score at Treatment

TABLE 33

Change from Treatment Baseline in CGI-S Total Score at Treatment

| End point values | Placebo | aticaprant 10 milligrams (mg) |
|---|---|---|
| Number of subjects analyzed Units: Scores on a scale | 59 | 59 |
| Measure Type: Arithmetic Mean (SD) | −0.76 ± 0.858 | −0.92 ± 1.039 |

Change from Treatment Baseline in SMDDS Total Score at Treatment Week 6

TABLE 34

Change from Treatment Baseline in SMDDS Total Score at Treatment Week

| End point values | Placebo | aticaprant 10 milligrams (mg) |
|---|---|---|
| Number of subjects analyzed Units: Scores on a scale | 59 | 59 |
| Measure Type: Arithmetic Mean (SD) | −8.49 ± 9.567 | −8.03 ± 9.957 |

Number of Subjects with SATE Score at Treatment Week 6

TABLE 35

Number of Subjects with SATE Score at Treatment Week 6

| End point values | Placebo | aticaprant 10 milligrams (mg) |
|---|---|---|
| Number of subjects analyzed Units: subjects | 61 | 60 |
| Overall Depression (Got worse) (n = 40, 30) | 1 | 0 |
| Overall Depression (Not changed) (n = 40, 30) | 12 | 9 |
| Overall Depression (Improved) (n = 40, 30) | 27 | 21 |
| Depression Worsened (Slightly worse) (n = 1, 0) | 1 | 0 |
| Depression Worsened (Much worse) (n = 1, 0) | 0 | 0 |
| Depression Worsened (Very much worse) (n = 1, 0) | 0 | 0 |
| Depression Slightly improved (n = 27, 21) | 13 | 15 |
| Depression Much improved (n = 27, 21) | 11 | 6 |
| Depression Very Much Improved (n = 27, 21) | 3 | 0 |

Change from Treatment Baseline in HAM-A6 Total Score at Treatment Week 6

TABLE 36

Change from Treatment Baseline in HAM-A6 Total Score at Treatment Week 6

| End point values | Placebo | aticaprant 10 milligrams (mg) |
|---|---|---|
| Number of subjects analyzed Units: scores on a scale | 59 | 59 |
| Measure Type: Arithmetic Mean (SD) | −2.19 ± 2.837 | −2.73 ± 2.651 |

These data show a greater improvement in HAMA6 score in aticaprant treated patients vs. placebo.

Change from Treatment Baseline in Structured Interview Guide for the SIGH-A Score at Treatment Week 6

TABLE 37

Change from Treatment Baseline in Structured Interview Guide for the SIGH-A score at Treatment Week 6

| End point values | Placebo | aticaprant 10 milligrams (mg) |
|---|---|---|
| Number of subjects analyzed Units: scores on a scale | 59 | 59 |
| Measure Type: Arithmetic Mean (SD) | −5.37 ± 6.549 | −5.85 ± 5.369 |

Maximum Plasma Concentration ($C_{max}$) of Aticaprant $C_{max}$ is defined as maximum plasma concentration of aticaprant. The eITT population included all enrolled lead-in placebo non-responders who were randomized into a treatment period, received at least 1 dose of study medication, and had at least 1 post-baseline MADRS assessment during the treatment period. Here 'N' (number of subjects analyzed) includes the number of subjects evaluable for this endpoint. Here 'n' (number analyzed) included all subjects evaluable for specified time point categories.

TABLE 38

$C_{max}$ of Aticaprant (10 mg)

| Number of subjects analyzed | 58 |
|---|---|
| Units: nanograms per milliliter (ng/ml) | |
| Measure Type: Arithmetic Mean (SD) | |
| Week 1 (n = 56) | 32.7 ± 10.9 |
| Week 3 (n = 56) | 33.5 ± 11.1 |
| Week 6 (n = 56) | 34.3 ± 11.1 |

No statistical analyses of this end point.

(iii) Safety Endpoints

Overall, in full safety analysis set 40/85 (47.1%) of subjects in the aticaprant group and 30/84 (35.7%) of subjects in the placebo group experienced at least one TEAE during the treatment period. See, Table 39.

TABLE 39

Overall Summary of Treatment-Emergent Adverse Events During the Treatment Period; Full Safety Analysis Set

| | Placebo (N = 84) n (%) | aticaprant 10 mg (N = 85) n (%) | Overall (N = 169) n (%) |
|---|---|---|---|
| Subjects with 1 or more TEAE | 30 (35.7) | 40 (47.1) | 70 (41.4) |
| Total subjects affected by non-serious adverse events | 9 (10.7%) | 23 (27.1%) | |
| Subjects with drug-related TEAE [a] | 13 (15.5) | 20 (23.5) | 33 (19.5) |
| Subjects with TEAE leading to death | 0 | 0 | 0 |
| Subjects with 1 or more serious TEAE | 1 (1.2) | 0 | 1 (0.6) |
| Subjects with TEAE leading to discontinuation of agent | 1 (1.2) | 1 (1.2) | 2 (1.2) |

[a] Drug relationships of possible, probable, and very likely are included in this category. Subjects are presented by the treatment received during the Treatment period.

The most common TEAEs during the treatment period were headache (experienced by 10/85 subjects—11.8% in the aticaprant group and by 6/84 subjects—7.1% in the placebo group) and diarrhea (experienced by 7/85 subjects—8.2% in the aticaprant group and by 2/84 subjects—2.4% in the placebo group). See, Table 40.

TABLE 40

Treatment-Emergent Adverse Events by Body System or Organ Class and Dictionary-Derived Term in >= 5% of Subjects in Either Treatment Group During the Treatment Period; Full Safety Analysis Set

| Body System Preferred Term | Placebo (N = 84) n (%) | aticaprant 10 mg (N = 85) n (%) | Overall (N = 169) n (%) |
|---|---|---|---|
| Total no. Subjects with Adverse Events | 30 (36) | 40 (47) | 70 (41) |
| Infections And Infestations | 9 (11) | 13 (15) | 22 (13) |
| Nasopharyngitis | 2 (2) | 5 (6) | 7 (4) |
| Nervous System Disorders | 9 (11) | 13 (15) | 22 (13) |

TABLE 40-continued

Treatment-Emergent Adverse Events by Body
System or Organ Class and Dictionary-Derived
Term in >= 5% of Subjects in Either Treatment Group
During the Treatment Period; Full Safety Analysis Set

| Body System<br>Preferred Term | Placebo<br>(N = 84)<br>n (%) | aticaprant<br>10 mg<br>(N = 85)<br>n (%) | Overall<br>(N = 169)<br>n (%) |
|---|---|---|---|
| Headache | 6 (7) | 10 (12) | 16 (10) |
| Gastrointestinal Disorders | 9 (11) | 12 (14) | 21 (12) |
| Diarrhea | 2 (2) | 7 (8) | 9 (5) |
| Skin And Subcutaneous Tissue Disorders | 3 (4) | 6 (7) | 9 (5) |
| Pruritus | 0 | 5 (6) | 5 (3) |

Percentages calculated with the number of subjects in each group as denominator. Reported dictionary version: MedDRA 22.1. Subjects are presented by the treatment received during the Treatment period.

There were 2 subjects in total who discontinued during the treatment period due to treatment-emergent adverse events: 1 subject in the aticaprant 10 group due to diarrhea, nausea, vomiting and headache, and another subject in placebo group due to acute calculous cholecystitis.

Overall, 17/169 subjects experienced TEAEs of special interest during the treatment period: 13/85 (15.3%) in the aticaprant group and 4/84 (4.8%) in the placebo group. The most common treatment-emergent adverse events during the treatment phase were headache and diarrhea. The most common TEAE of special interest during the treatment period were diarrhea and pruritus (experienced by 5/85 subjects—5.9% in the aticaprant group and by 0/84 subjects in the placebo group). Further 1 patient in the placebo group (1.19%) experienced acute cholecystitis, as compared to 0 patients receiving aticaprant. See, Table 41.

TABLE 41

Treatment-Emergent Adverse Events of Special Interest
During the Treatment Period; Full Safety Analysis Set

| Body System<br>Preferred Term | Placebo<br>(N = 84)<br>n (%) | aticaprant<br>10 mg<br>(N = 85)<br>n (%) | Overall<br>(N = 169)<br>n (%) |
|---|---|---|---|
| Total no. Subjects with Adverse Events of Special Interest | 4 (4.8) | 13 (15.3) | 17 (10.1) |
| Gastrointestinal Disorders | 4 (4.8) | 9 (10.6) | 13 (7.7) |
| deaths causally related to treatment/all | | | |
| Diarrhea | 2 (2.4) | 7 (8.2) | 9 (5.3) |
| Abdominal Pain Upper | 2 (2.4) | 0 | 2 (1.2) |
| Dyspepsia | 1 (1.2) | 1 (1.2) | 2 (1.2) |
| Abdominal Pain | 0 | 1 (1.2) | 1 (0.6) |
| Skin And Subcutaneous Tissue Disorders | 0 | 5 (5.9) | 5 (3.0) |
| Pruritus | 0 | 5 (5.9) | 5 (3.0) |

Percentages calculated with the number of subjects in each group as denominator. Reported dictionary version: MedDRA 22.1. Subjects are presented by the treatment received during the Treatment period.

Two serious adverse events occurred. One subject in the placebo group experienced acute calculous cholecystitis during the treatment period and other subject suicidal ideation during the lead-in period. Both subjects discontinued due to these AEs.

No deaths were reported.

(iv) Anhedonia Analysis

Patients in the larger fITT group maintained baseline level of depression and anhedonia severity consistent with the eITT group. See, Tables 42-44.

TABLE 42

Frequency of Subjects with Anhedonia at
Treatment Baseline; fITT Analysis Set

| | N | No Anhedonia (SHAPS Total Score <20) Baseline/Day 22 | Anhedonia (SHAPS Total Score >=20) |
|---|---|---|---|
| Placebo | 83 | 0 | 83 (100%) |
| aticaprant | 83 | 1 (1.2%) | 82 (98.8%) |
| Total | 166 | 1 (0.6%) | 165 (99.4%) |

Anhedonia classification is based on calculated SHAPS total score at Visit Day 22

Figure 19:
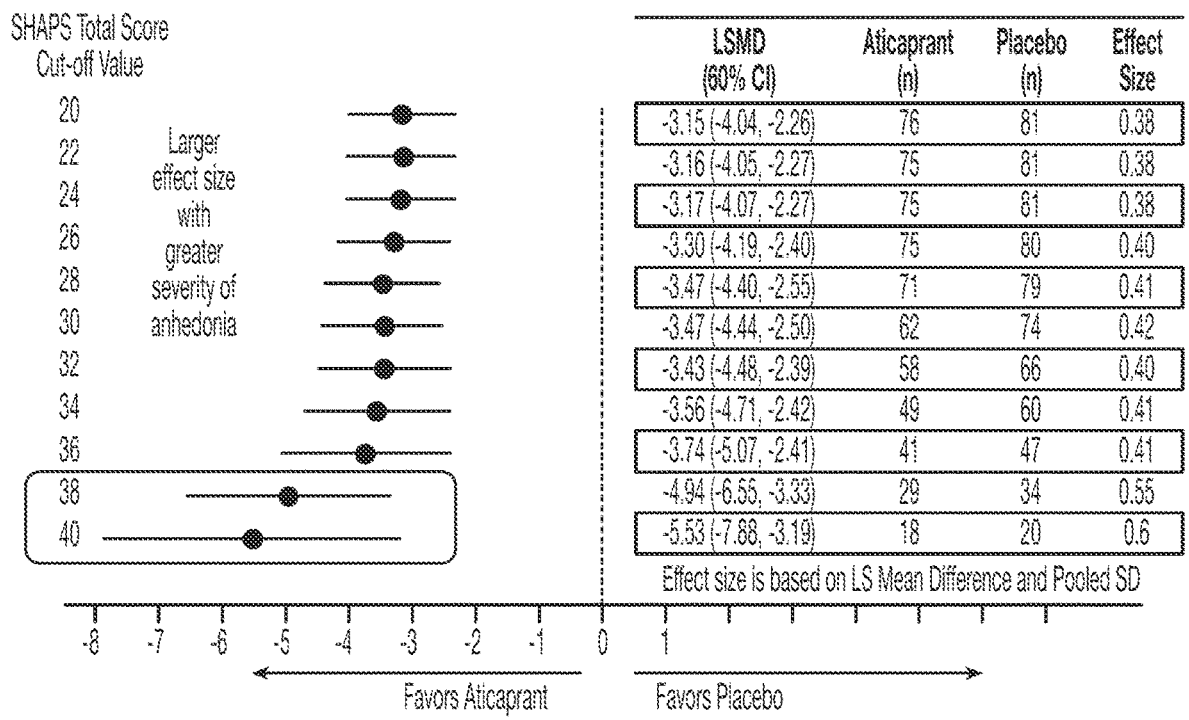
FIG. 19 illustrates the MADRS change from baseline by anhedonia severity.

The results illustrate that treatment effect is larger in patients with more anhedonia at baseline. See, FIG. 19.

TABLE 43

Frequency of Subjects with Different Level of Anhedonia at
Treatment Baseline and Treatment Week 6; eITT Analysis Set

| | N | No Anhedonia (SHAPS Total Score < 20) | Low Level of Anhedonia (20 <= SHAPS Total Score < 38) | High Level of Anhedonia (SHAPS Total Score >= 38) |
|---|---|---|---|---|
| Treatment Baseline | | | | |
| Placebo | 61 | 0 | 34 (55.74%) | 27 (44.26%) |
| aticaprant | 60 | 0 | 34 (56.67%) | 26 (43.33%) |
| Total | 121 | 0 | 68 (56.2%) | 53 (43.8%) |
| Treatment Week 6 | | | | |
| Placebo | 59 | 0 | 46 (77.97%) | 13 (22.03%) |
| aticaprant | 59 | 3 (5.08%) | 48 (81.36%) | 8 (13.56%) |
| Total | 118 | 3 (2.54%) | 94 (79.66%) | 21 (17.8%) |

Anhedonia classification is based on re-calculated SHAPS total score at analysis visits Treatment Baseline and Treatment Week 6.

TABLE 44

Frequency of Subjects with Different Level of Anhedonia at
Treatment Baseline and Treatment Week 6; fITT Analysis Set

| | N | No Anhedonia (SHAPS Total Score < 20) | Low Level of Anhedonia (20 >= SHAPS Total Score <38) | High Level of Anhedonia (SHAPS Total Score >= 38) |
|---|---|---|---|---|
| Treatment Baseline | | | | |
| Placebo | 83 | 0 | 49 (59.04%) | 34 (40.96%) |
| aticaprant | 83 | 1 (1.2%) | 52 (62.65%) | 30 (36.14%) |
| Total | 166 | 1 (0.6%) | 101 (60.84%) | 64 (38.55%) |
| Treatment Week 6 | | | | |
| Placebo | 81 | 0 | 66 (81.48%) | 15 (18.52%) |
| aticaprant | 77 | 7 (9.09%) | 62 (80.52%) | 8 (10.39%) |
| Total | 158 | 7 (4.43%) | 128 (81.01%) | 23 (14.56%) |

Anhedonia classification is based on re-calculated SHAPS total score at analysis visits Treatment Baseline and Treatment Week 6.

Figure 20A:
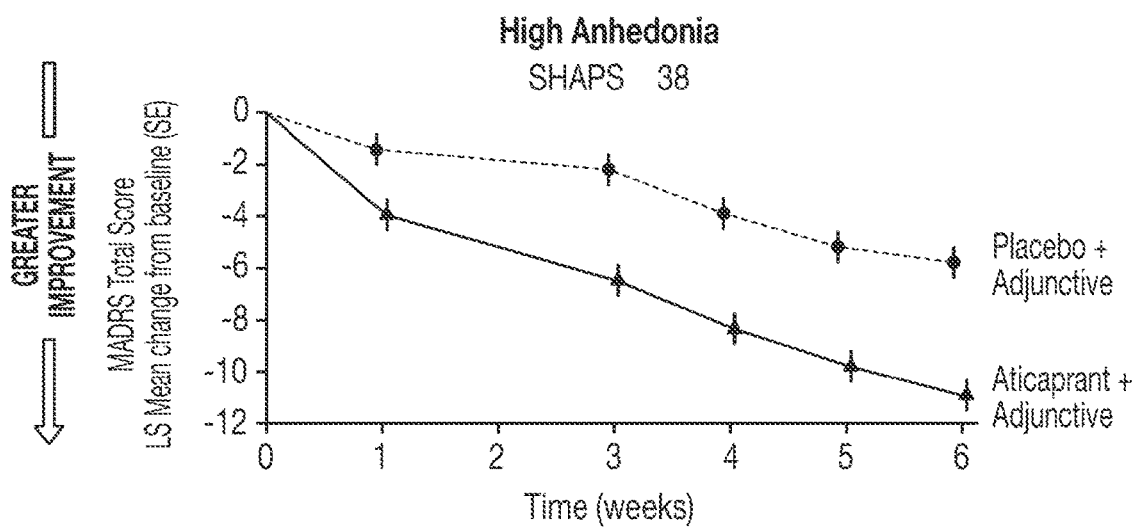
FIG. 20-A is a line graph showing MADRS change from baseline for patients with high anhedonia, i.e., SHAPS ≥38.
Figure 20B:
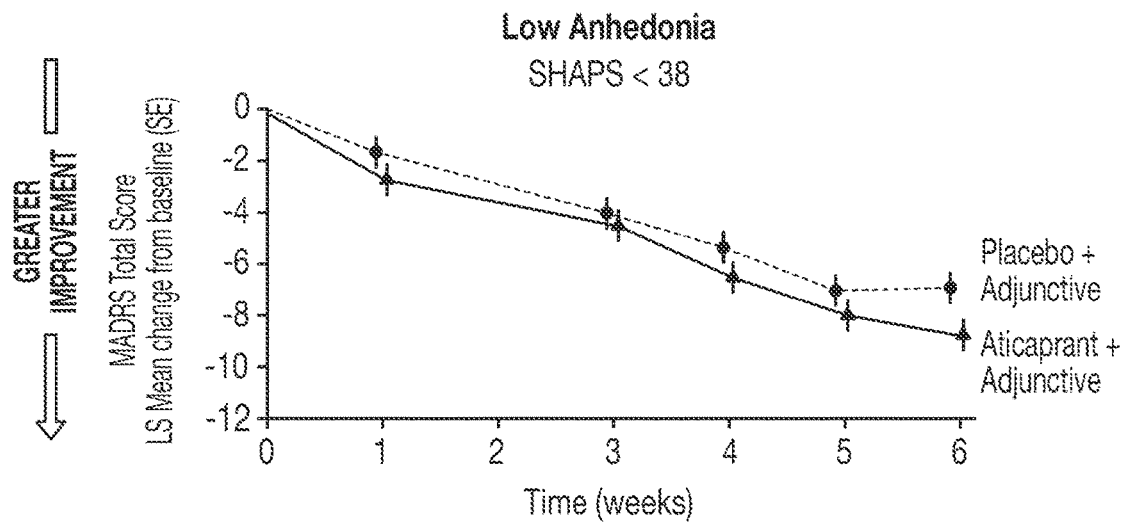
Figure 21:
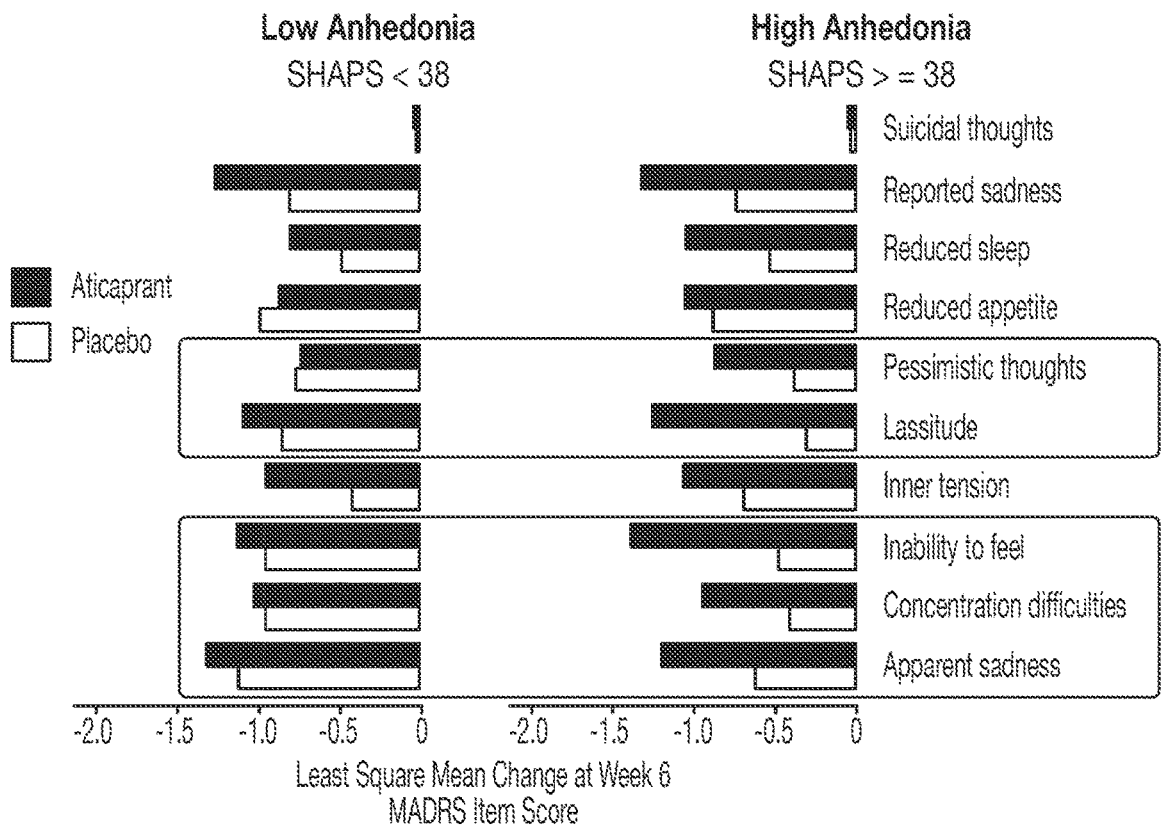
FIG. 21 is bar graph showing the comparison of MADRS in patients having low and high anhedonia.

The results illustrate that the treatment effect is larger in patients with more anhedonia at baseline. See, FIGS. 20-A and 20-B. In FIG. 20-A, i.e., the high anhedonia group, the placebo+oral antidepressant group shows less placebo response as compared to the low anhedonia group in FIGS. 7-8. Similarly the treatment effect of the aticaprant+oral antidepressant group is higher in the high anhedonia group as compared to the low anhedonia group. Overall the effect size is larger at every single time point (from week 1 onwards) in the high anhedonia group. The LSMD in the high anhedonia group is more than double that of the low anhedonia group at week 6. Further, when looking at the symptom level, greater improvement in items related to anhedonia and dysphoria in subgroup with high anhedonia vs low anhedonia. See, FIG. 21.

(v) Weight Change

At the lead-in baseline timepoint, the mean weight for subjects in the placebo group was 76.17 kg compared to 78.66 in the aticaprant group. After 6 weeks in the double-blind treatment phase, the mean weight in the placebo group was 75.75 kg compared to 78.57 kg in the aticaprant group. This indicates that the weight in both groups remained relatively stable over the 6-week double blind treatment period. This is unexpected because other adjunctive treatments for MDD result in a mean weight increase. See, Thase M, et al. J Clin Psych. 2015: 76(9), 1224-1231; Thase, J Clin Psych. 2015, 76(9): 1232-1240; El Khalili, Int J Neuropsychopharmacol. 2010, 13, 917-932; Marcus, J. Clin. Psychopharmacol. 2008, 28:156-165; Berman, J. Clin. Psychiatry 2007; 68:843-853; Berman, American College of Neuropsychopharmacology, 2008, Annual Meeting Abstracts (Scottsdale, Ariz, Dec. 7-11, 2008). Nashville, Tenn, ACNP, 2008; Earley, American College of Neuropsychopharmacology, 2007, Annual Meeting Abstracts (Boca Raton, Fla, Dec. 9-13, 2007). Nashville, TN, ACNP, 2007). See, Table 45.

TABLE 45

Mean weight by treatment group (kg)

| weight | Placebo n = 84 | Aticaprant n = 85 |
|---|---|---|
| Screening, mean (SE) | 76.39 (1.61) | 78.42 (1.65) |
| Lead-in Baseline, mean (SE) | 76.17 (1.61) | 78.66 (1.65) |
| Withdrawal Baseline, mean (SE) | 75.75 (1.62) | 78.57 (1.71) |
| Absolute Change (Withdrawal—Lead-in) | −0.42 | −0.09 |
| Relative % Change | −0.55% | −0.11% |

(vi) Completion Rate

Patients who passed the screening phase entered a lead in phase followed by a double-blind phase. Patients who responded to placebo during the lead in phase were labelled as non-responders. Patients who did not respond to placebo were labelled as non-responders. The double-blind treatment phase then continued for an additional 6 weeks, after which patients entered a withdrawal period.

Of the 121 subjects in the enriched population (60 in aticaprant and 61 in placebo group), 117 (96.7%) completed the study. The overall completion rate for the full ITT analysis set is 95%. This contrasts with completion rates of approximately 85% for studies of adjunctive aripiprazole (Pae, CNS Drugs, 2011; 25, 109-127) and 45-62% for adjunctive quetiapine (El Khalili cited above). In total 4 subjects (3.3%) discontinued the study: 2 subjects in placebo and 2 subjects in aticaprant treatment group. See, Tables 46 and 47.

TABLE 46

Completion/Early Withdrawal Information; eITT Analysis Set

| | Placebo (N = 61) | aticaprant 10 mg (N = 60) | Total (N = 121) |
|---|---|---|---|
| Subject Completed Treatment/Trial | | | |
| Completed | 59 (96.7%) | 58 (96.7%) | 117 (96.7%) |
| Withdrawn | 2 (3.3%) | 2 (3.3%) | 4 (3.3%) |
| Reason For Withdrawal/Termination | | | |
| Lack of Efficacy | 0 | 1 (1.7%) | 1 (0.8%) |
| Non-compliance with drug | 0 | 1 (1.7%) | 1 (0.8%) |
| Withdrawal by subject | 1 (1.6%) | 0 | 1 (0.8%) |
| Other | 1 (1.6%) | 0 | 1 (0.8%) |

Percentages calculated with the number of subjects in each group as denominator.

TABLE 47

Completion/Early Withdrawal Information; Full Safety Analysis Set

| | Placebo (N = 84) | aticaprant 10 mg (N = 85) | Total (N = 169) |
|---|---|---|---|
| Subject Completed Treatment/Trial | | | |
| Completed | 81 (96.4%) | 79 (92.9%) | 160 (94.7%) |
| Withdrawn | 3 (3.6%) | 6 (7.1%) | 9 (5.3%) |
| Reason For Withdrawal/Termination | | | |
| Adverse event | 1 (1.2%) | 1 (1.2%) | 2 (1.2%) |
| Lack of Efficacy | 0 | 2 (2.4%) | 2 (1.2%) |
| Non-compliance with drug | 0 | 1 (1.2%) | 1 (0.6%) |
| Protocol deviation | 0 | 1 (1.2%) | 1 (0.6%) |
| Withdrawal by subject | 1 (1.2%) | 0 | 1 (0.6%) |
| Other | 1 (1.2%) | 1 (1.2%) | 2 (1.2%) |

Percentages calculated with the number of subjects in each group as denominator.

(vii) Sexual Functioning

Impairments in sexual functioning is a common side effect of antidepressant treatment and can be very upsetting to patients and their sexual partners. Major depression itself is associated with increased sexual dysfunction, and many of the pharmacological treatments are known to worsen sexual functioning even further. In a large survey of nearly 5000 patients in France, it was estimated that in untreated patients with MDD, the prevalence of sexual dysfunction was 65%. The prevalence of sexual dysfunction increased to 71% for patients treated with antidepressant therapy.

Sexual pleasure is an important component of hedonic tone. The brain reward circuitry is controlled by several areas: nucleus accumbens, ventral tegmental area and the amygdala. It is hypothesized that treatment with kappa opioid receptors may restore the normal homeostatic balance in patients with overactivation. Treatment with aticaprant could potentially improve symptoms of anhedonia. Other symptoms associated with the reward circuitry includes: sexual pleasure, lack of interest and lack of enjoyment.

Patients had their sexual functioning measured using a standard, well accepted rating scale: ASEX. See, Table 48.

TABLE 48

ASEX scores by treatment group

|  | Placebo<br>n = 84 | Aticaprant<br>n = 85 |
|---|---|---|
| Baseline | 22.04 | 21.26 |
| Endpoint | 21.36 | 19.79 |
| Absolute Change | −0.68 | −1.47 |
| Relative % Change | −3.09% | −6.91% |

Figure 22:
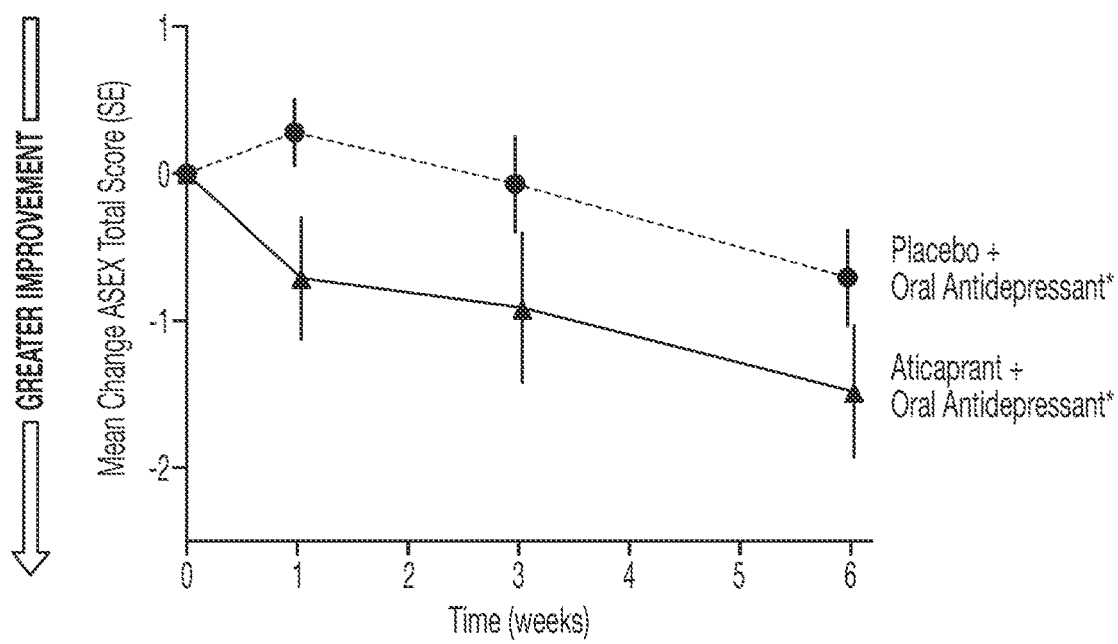
FIG. 22 is a line graph showing the ASEX total score mean change from baseline.

The mean change from treatment baseline (SD) in ASEX total score to week 6 was −1.5 (4.02) points for aticaprant compared to −0.7 (2.98) points for placebo. A lower score on the ASEX indicates improvement. The score reduction at week 6 was greater in the aticaprant group compared to placebo. This is unexpected because adjunctive treatments with other agents are expected to worsen sexual functioning, i.e., increase in ASEX score over time. See, FIG. 22.

Figure 23:
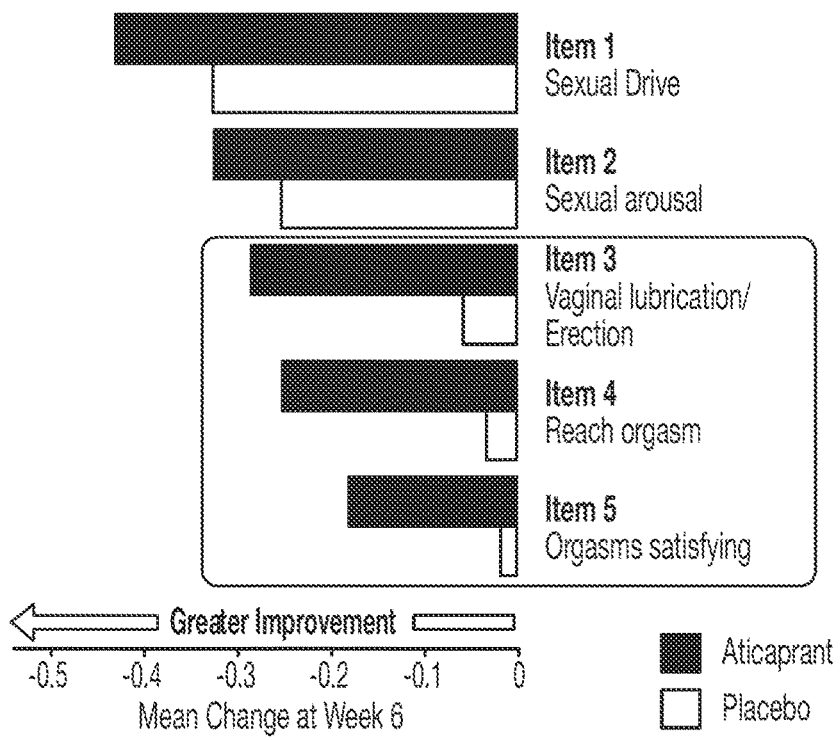
FIG. 23 is a bar graph showing ASEX item level change total score mean change from baseline.

Patients receiving aticaprant had notable improvements in sexual functioning. An examination of individual item level changes was also conducted and revealed that the greatest changes were seen in items related to consummatory pleasure: orgasm satisfying, reach orgasm and vaginal lubrication/erection. Most of the improvements seen in items 3, 4 and 5 of FIG. 23.

(viii) Onset of Effect

Figure 10A:
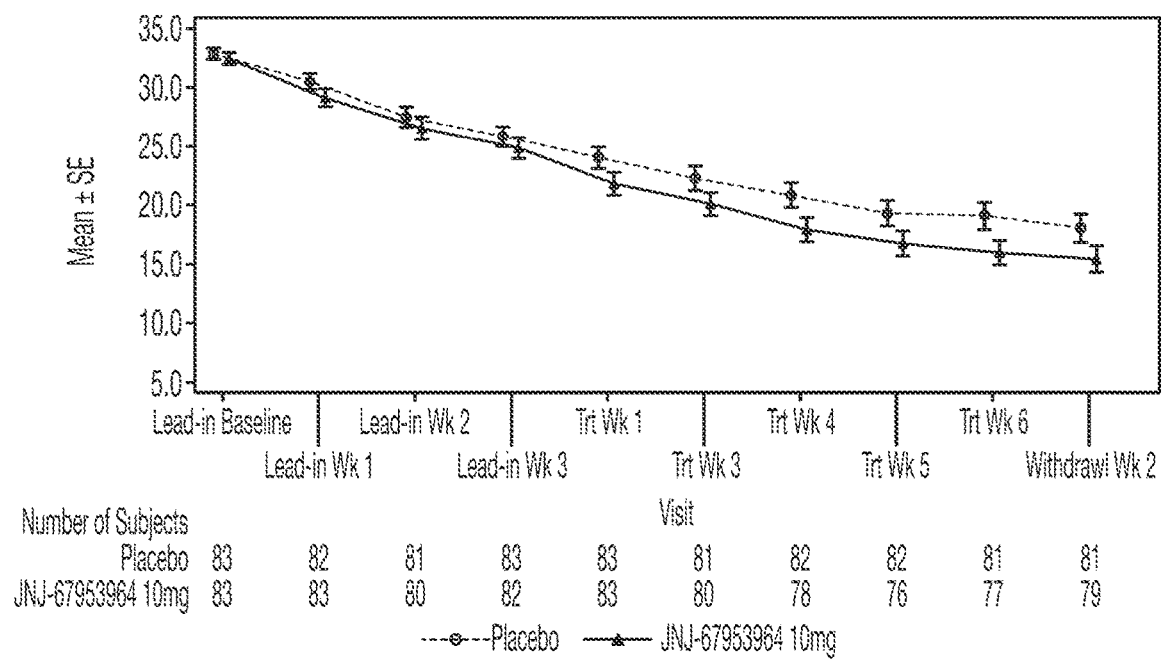
FIG. 10-A is a line graph showing MADRS total score: mean values (±SE) over time for the full intent-to-treat (fITT) analysis set.
Figure 10B:
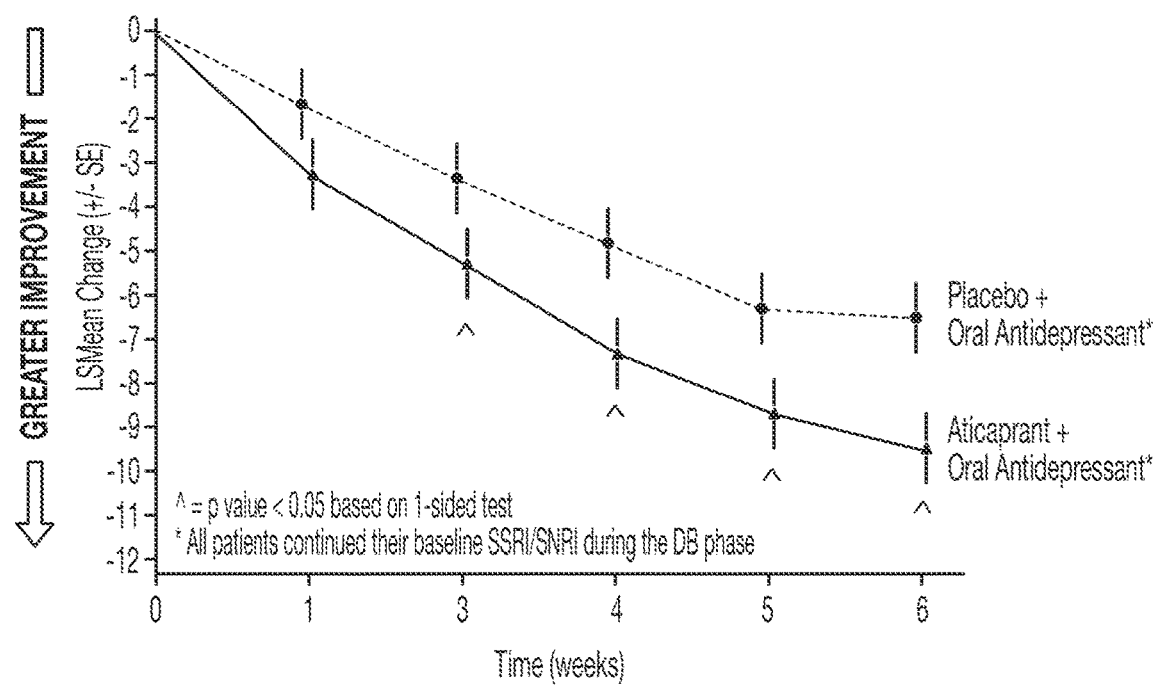

The onset of effect for aticaprant can be estimated from the study. FIG. 10-B depicts the least squares mean change from baseline. A significant treatment effect favoring aticaprant was seen as early as week 3. At this point, aticaprant showed a statistically superior effect compared to placebo.

Example 7—Single Dose Aticaprant as Adjunctive Antidepressant Therapy

Figure 34:
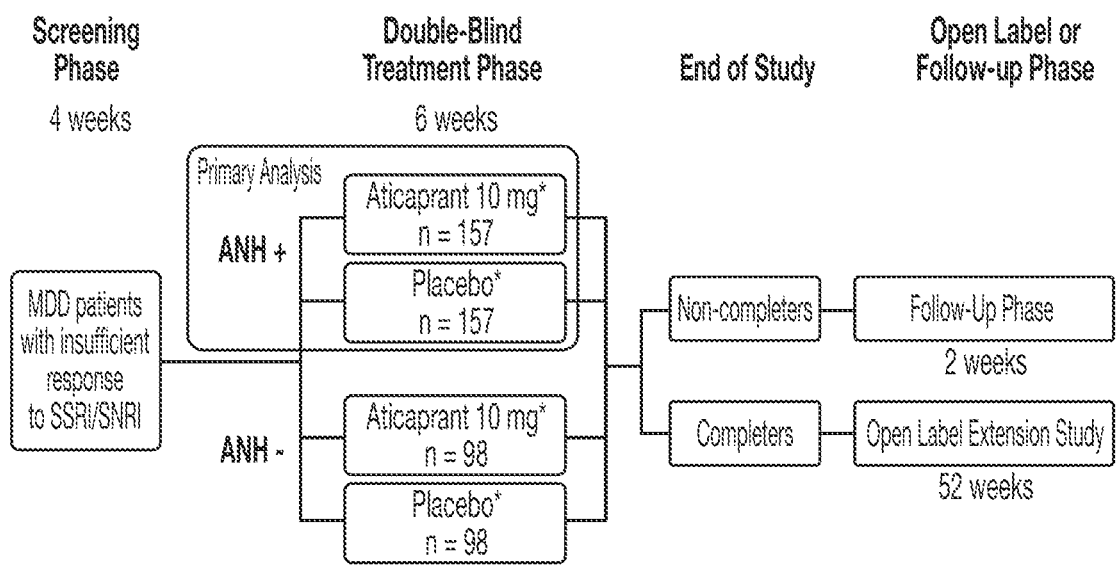
FIG. 34 is the study scheme for Example 7. All patients will continue their oral antidepressant SSRI/SNRI during the entire study. Approximately an additional 34 elderly participants will be randomized.

Study Design: A 6-week, multicenter, double-blind, randomized, placebo-controlled study to assess the efficacy, safety, and tolerability of aticaprant in adult and elderly subjects (18 to 74 years) who have MDD with prominent anhedonia (MDD ANH+), and who have had an inadequate response to a SSRI or a serotonin and SNRI in the current depressive episode. See, FIG. 34.

For all subjects, this study will consist of 3 phases: an eligibility screening phase (up to 4 weeks prior to first dose administration), a double-blind treatment phase of 6 weeks, and a follow-up of 1-2 weeks. Subjects who have completed the double-blind phase may participate in an open-label long-term safety study.

Sample Size and Randomization: Approximately 544 subjects with MDD with prominent anhedonia (MDD ANH+) and without prominent anhedonia (MDD ANH−) will be randomized in a 1:1 ratio to adjunctive placebo or aticaprant to achieve a minimum of 314 adult subjects meeting predefined criteria for MDD ANH+ eligible to be included in the primary analysis. Randomization will be stratified by study site, age group (adults [<65 years], elderly [≥65 years]), baseline anhedonia, and baseline MADRS total score. All subjects will continue their baseline antidepressant (SSRI/SNRI) during the entire study.

Doses and Administration All eligible subjects will receive aticaprant or placebo in addition to their baseline SSRI/SNRI which will be continued during the entire study. Study medication will be taken daily.

Inclusion Criteria:

1. Age of 18 to 74 years (inclusive).
2. Be medically stable on the basis of physical examination (including a brief neurological examination), medical history, vital signs (including blood pressure), and 12-lead ECG performed at screening and baseline. If there are any abnormalities that are not specified in the inclusion and exclusion criteria, their significance must be determined.
3. Be medically stable on the basis of clinical laboratory tests performed at screening. If the results of the serum chemistry panel, hematology, or urinalysis are outside the normal reference ranges, retesting of an abnormal lab values that may lead to exclusion will be allowed once during the screening phase.
4. Meet DSM-5 diagnostic criteria for recurrent or single episode MDD, without psychotic features (DSM-5 296.22, 296.23, 296.32, or 296.33), based upon clinical assessment and SCID-CT. Subjects 65 years of age or older must have had the first onset of depression prior to 55 years of age. The length of the current depressive episode must be ≤18 months.
5. Have had an inadequate response to at least 1 but no more than 2 antidepressants (SSRI/SNRI), administered at an adequate dose and duration in the current episode of depression. An inadequate response is defined as 26% to <50% reduction in depressive symptom severity and overall good tolerability, as assessed by the MGH-ATRQ. An adequate trial is defined as an antidepressant treatment for at least 6 weeks (and no greater than 12 months in the current episode) at or above the stable therapeutic dose specified in the MGH-ATRQ, must include the subject's current antidepressant treatment. If the subject has received 2 SSRI/SNRI treatments of sufficient dose and duration in the current episode, and has shown ≤25% improvement to both, then the subject would not qualify based on exclusion criterion (first exclusion criterion).
6. Current major depressive episode, depression symptom severity, presence of anhedonia and antidepressant treatment response in the current depressive episode must be confirmed. Is receiving and tolerating well any one of the following SSRI or SNRI for depressive symptoms, in any formulation and available in the participating country: citalopram, duloxetine, escitalopram, fluvoxamine, fluoxetine, milnacipran, levomilnacipran, paroxetine, sertraline, venlafaxine, desvenlafaxine at a stable dose (at therapeutic dose level) for at least 6 weeks, and for no greater than 12 months in the current episode, at screening. The above SSRI/SNRI needs to be approved for the treatment of MDD. Subjects using fluvoxamine as baseline SSRI and have normal renal and hepatic function are admitted.
7. HDRS-17 total score ≥22 at start of the screening and must not demonstrate a clinically significant improvement (which is defined as an improvement of >20% on their HDRS-17 total score) from the start to end of screening (from the first to the last independent HDRS-17 rating).
8. Symptoms of anhedonia based on clinical assessment and confirmed by a positive response for anhedonia (MDE symptoms Item 2) on the SCID-CT at screening and baseline (Day 1 prior to randomization).
9. BMI between 18 and 40 kg/m$^2$ (inclusive).
10. Outpatient at screening.
11. A woman of childbearing potential must have a negative highly sensitive serum (β-hCG) pregnancy test at screening and a negative urine pregnancy test predose on Day 1 of the double-blind phase prior to randomization.
12. Contraceptive use by men or women should be consistent with local regulations regarding the use of contraceptive methods for subjects in clinical studies.
13. A woman must be either:
    Postmenopausal
    Permanently sterile
    Of childbearing potential and practicing a highly effective method of contraception (failure rate of <1% per year when used consistently and correctly).
14. A woman must not to donate eggs (ova, oocytes) or freeze for future use for the purposes of assisted reproduction during the study and for a period of at least 1 month after receiving the last dose of study medication.

Inclusion Criteria:

15. During the study and for a minimum of 1 spermatogenesis cycle (defined as approximately 3 months) after receiving the last dose of study medication, a man:
    who is sexually active with a woman of childbearing potential must use a barrier method of contraception (e.g., condom with spermicidal foam/gel/film/cream/suppository) and his female partner must use a highly effective method of contraception.
    who is sexually active with a woman who is pregnant must use a condom.
    must not to donate sperm.

Exclusion Criteria:

1. History of treatment-resistant MDD, defined as a lack of response to 2 or more adequate antidepressant treatments in the current episode, as indicated by no or minimal improvement ($\leq 25\%$ improvement) when treated with an antidepressant of adequate dose (per MGH-ATRQ) and duration (at least 6 weeks).
2. Current or prior DSM-5 diagnosis of a psychotic disorder or MDD with psychotic features, bipolar or related disorders (confirmed by the SCID-CT), intellectual disability (DSM-5 diagnostic codes 317, 318.0, 318.1, 318.2, 315.8, and 319), autism spectrum disorder, borderline personality disorder, antisocial personality disorder, histrionic personality disorder, narcissistic personality disorders or somatoform disorders.
3. Current active DSM-5 diagnosis of obsessive-compulsive disorder, post-traumatic stress disorder, anorexia nervosa, or bulimia nervosa.
4. Primary DSM-5 diagnosis of panic disorder, generalized anxiety disorder, social anxiety disorder, or specific phobia which has been the primary focus of psychiatric treatment within the past 2 years. These are allowed as secondary diagnoses if MDD is the primary focus of treatment.
5. History or evidence of clinically meaningful noncompliance with current antidepressant therapy.
6. History of moderate to severe substance use disorder including alcohol use disorder according to DSM-5 criteria within 6 months before screening or positive test results for alcohol and/or drugs of abuse (e.g., opiates [including methadone], cocaine, amphetamines, methamphetamines, cannabinoids, CBD, barbiturates, MDMA) at screening or at baseline. One retest during screening is allowed. Tobacco and caffeine use are not exclusionary.
7. Has within the last 5 years received any prior antidepressant treatment with ketamine/esketamine, electroconvulsive therapy, vagal nerve stimulation, or a deep brain stimulation device. Subjects who previously had taken up to 2 doses of ketamine/esketamine and did not continue (e.g., did not benefit from the treatment or experienced tolerability issues) can be considered for enrollment.
8. Homicidal ideation/intent or has suicidal ideation with some intent to act within 3 months prior to the start of the screening phase, per clinical judgment or based on the C-SSRS, corresponding to a response of "Yes" on Item 4 (active suicidal ideation with some intent to act, without specific plan) or Item 5 (active suicidal ideation with specific plan and intent) for suicidal ideation on the C-SSRS, or a history of suicidal behavior within the past year prior to the start of the screening phase. Subjects reporting suicidal ideation with intent to act or suicidal behavior prior to the start of the double-blind treatment phase should be excluded.
9. Cognitive impairment that would render the informed consent invalid or limit the ability of the subject to comply with the study requirements. Subject has neurodegenerative disorder (e.g., Alzheimer's disease, vascular dementia, Parkinson's disease with clinical evidence of cognitive impairment) or evidence of MCI. Subjects of age $\geq 65$ years: has a MMSE <25 or <23 for those subjects with less than high school equivalent education.
10. Current or history of seizures (uncomplicated childhood febrile seizures with no sequelae are not exclusionary).

Exclusion Criteria:

11. Clinically significant ECG abnormalities at screening or Day 1 prior to randomization that may jeopardize the subjects' safety or the integrity of the study defined as:
    During screening and/or Day 1, a QT interval corrected according to Fridericia's formula (QTcF): $\geq 450$ msec (males); $\geq 470$ msec (females).
    Evidence of second- and third-degree atrioventricular block.
    Features of new ischemia.
    Other clinically important arrhythmia or cardiac abnormalities.
12. History of, or symptoms and signs suggestive of, liver cirrhosis (e.g., esophageal varices, ascites, and increased prothrombin time) OR ALT or AST values >3 × the ULN or total bilirubin >1.5 × the ULN in the screening phase. Repeat of screening test for abnormal ALT and AST is permitted during the screening period there is an alternative explanation for the out of range value.
13. For elevations in bilirubin if the elevation in bilirubin is consistent with Gilbert's disease, the subject may participate.
14. Positive test result for drugs of abuse (e.g., barbiturates, methadone, opiates, cocaine, PCP, MDMA, and amphetamine/methamphetamine) at the start of the screening phase or Day 1 of the double-blind treatment phase prior to randomization.
15. Subjects who have a positive test result at screening due to prescribed psychostimulants taken for any indication must discontinue the medication at least 2 weeks before Day 1 of the double-blind treatment phase (prior to randomization). The result of the Day 1 (prior to randomization) test for drugs of abuse must be negative for the subject to be randomized. Subjects who have a positive test result at screening due to prescribed/over-the-counter opiates or barbiturates may be permitted to continue in the screening phase if the medication is discontinued at least 1 week or 5 half-lives, whichever is longer, before Day 1 of the double-blind treatment phase (prior to randomization). The result of the Day 1 (prior to randomization) test for drugs of abuse must be negative for the subject to be randomized.
    Intermittent use of cannabinoids prior to the start of the screening phase is not exclusionary as long as the subject does not meet the criteria for substance use disorder.
    A positive test for cannabinoids at the start of the screening phase is not exclusionary; however, a positive test result for cannabinoids predose on Day 1 of the double-blind treatment phase is exclusionary.
16. Taking a total daily dose of benzodiazepines greater than the equivalent of 6 mg/day of lorazepam at the start of the screening phase.
17. Recent (last 3 months) history of, or current signs and symptoms of:
    Severe renal insufficiency (creatinine clearance <30 mL/min)
    Clinically significant or unstable cardiovascular, respiratory, gastrointestinal, neurologic, hematologic, rheumatologic, immunologic or endocrine disorders.
    Uncontrolled Type 1 or Type 2 diabetes mellitus. Subjects with Type 1 or Type 2 diabetes mellitus who are controlled (hemoglobin A1c $\leq 8.0\%$ and glucose $\leq 150$ mg/dL at screening) may be eligible to participate if otherwise medically healthy, and if on a stable regimen of glucose-lowering medications for at least 2 months prior to screening).
18. Current signs/symptoms of hypothyroidism or hyperthyroidism. For subjects with a history of thyroid disease and for subjects who, regardless of thyroid history have the TSH value out of range, a $FT_4$ test will be conducted. If the FT4 value is abnormal and considered to be clinically significant the subject is not eligible.
19. Subjects with a pre-existing history of thyroid disease/disorder who are treated with thyroid hormones need to be on a stable dosage for 3 months prior to the start of the screening phase. Subjects taking thyroid supplementation for antidepressant purposes are not allowed. Has Cushing's Disease, Addison's Disease, primary amenorrhea, or other evidence of significant medical disorders of the hypothalamic-pituitary-adrenal axis.
20. Significant medical illness, particularly unstable medical problem.
21. Ongoing psychological treatments (e.g., Cognitive Behavior Therapy, Interpersonal Psychotherapy, Psychodynamic Psychotherapy etc.), initiated within 6 weeks prior to start of screening. A subject who has been receiving ongoing psychological treatment for a period of greater than 6 weeks is eligible, if psychological treatment to be of stable duration and frequency.

| Exclusion Criteria: |
| --- |
| 22. Significant medical illness, particularly unstable medical problem.
23. Clinically-relevant GI complaints per clinical judgment (unless symptoms of Axis I disorder) at screening or baseline or history of documented gastric disease (including but not limited to documented peptic ulcer disease, gastritis [including atrophic gastritis], upper GI bleeding, Barret's esophagus, Crohn disease, ulcerative colitis, GI precancerous conditions or any other clinically-relevant GI disease irritable bowel syndrome).
24. Requires chronic use of a PPIs. A history of chronic NSAID or aspirin use. (Low dose aspirin e.g., in cardiovascular disease prevention is allowed).
25. History of malignancy within 5 years before the start of the screening phase (exceptions are squamous and basal cell carcinomas of the skin and carcinoma in situ of the cervix, or malignancy that is considered cured with minimal risk of recurrence)
26. Known allergies, hypersensitivity, intolerance, or contraindications to aticaprant and/or its excipients.
27. Taken any prohibited therapies that would not permit dosing on Day 1.
28. Received an investigational drug (including investigational vaccines) or used an invasive investigational medical device within 60 days before the start of the screening phase, or has participated in 2 or more MDD or other psychiatric condition clinical interventional studies (with different investigational medication) in the previous 1 year before the start of the screening phase, or is currently enrolled in an investigational interventional study.
29. A woman who is pregnant, breastfeeding, or planning to become pregnant while enrolled or within 6 weeks after the last dose of the study medication.
30. Plans to father a child while enrolled or within 90 days after the last dose of study intervention.
31. Diagnosis of acquired immunodeficiency syndrome. Human immunodeficiency virus testing is not required.
32. Any condition or situation/circumstance for which participation would not be in the best interest of the subject (e.g., compromise the well-being) or that could prevent, limit, or confound the protocol specified assessments. |

A. Efficacy Objectives and Endpoints

The assessment of primary and secondary (key and other) endpoints will be conducted on the FAS which includes adult (not elderly) subjects with MDD ANH+ who took at least 1 dose of study medication.

Primary: To evaluate the efficacy of aticaprant compared with placebo as adjunctive therapy to an antidepressant (SSRI or SNRI) in improving depressive symptoms in adult subjects with MDD ANH+ and inadequate response to the current antidepressant, as assessed by the change from baseline in the MADRS total score from Day 1 (pre-randomization) to end of the 6-week double-blind treatment phase (Day 43):

Change from baseline to Day 43 in the MADRS total score.

Key Secondary: To assess efficacy of aticaprant compared with placebo in adult subjects with MDD ANH+ as adjunctive therapy to an antidepressant on patient-reported assessment of anhedonia outcomes:

Change from baseline to Day 43 in the Dimensional Anhedonia Rating Scale (DARS) total score.

Other Secondary: To assess the efficacy of aticaprant compared with placebo in adult subjects with MDD ANH+ as adjunctive therapy on the following:

Proportion of responders at Day 43 (≥50% reduction in MADRS total score).

Proportion of subjects with remission of depressive symptoms, defined as a MADRS total score≤12 at Day 43.

Change from baseline to Day 43 in MADRS 6

Change from baseline to Day 43 in PHQ-9 total score.

Change from baseline to Day 43 in SHAPS total score.

Change from baseline to Day 43 in symptoms of anxiety using the GAD-7.

Exploratory: To assess the efficacy of aticaprant compared with placebo in adult subjects with MDD ANH+, and all MDD subjects (adult and elderly subjects with MDD ANH+ and MDD ANH−) as adjunctive therapy on the following:

Change from baseline over time in the MADRS total score.

Change from baseline over time in MADRS anhedonia items factor score.

Change from baseline over time in patient-reported outcomes of anhedonia (SHAPS, DARS).

Change from baseline over time in PHQ-9 total score.

Change from baseline to Day 43 in health-related quality of life and health status, as assessed by the EQ-5D-5L questionnaire.

Change from baseline to Day 43 in the SDS total score.

Change from baseline over time in the CGI-S score.

Change from baseline over time in symptoms of anxiety using the GAD-7.

Change from baseline over time in depressive symptoms using the PGI-S.

Change from baseline to Day 43 in patient-reported sexual functioning using the ASEX.

To assess the efficacy of aticaprant compared with placebo in adult subjects with MDD ANH− as adjunctive therapy on the following:

Change from baseline over time in MADRS total score.

Change from baseline over time in DARS total score.

Safety Objectives (All): The following safety endpoints will be assessed separately for the adult and elderly subjects; the safety analysis set for each age group will include all randomized subjects who have received at least one dose of study medication:

AEs including AESI. An AE can be any unfavorable and unintended sign (including an abnormal finding), symptom, or disease temporally associated with the use of a medicinal (investigational or non-investigational) product, whether or not related to that medicinal (investigational or non-investigational) product. TEAEs were AEs with onset during the treatment phase that has worsened since baseline. The full safety analysis set included all enrolled subjects who received at least 1 dose of study medication in the treatment period.

Vital signs

ECG, Laboratory Values

Weight/BMI

Suicidality assessment using the C-SSRS

Withdrawal symptoms assessment using the PWC-20

B. Concomitant Therapies and Prohibited Therapies

Background therapy: All subjects will continue their baseline antidepressant (SSRI/SNRI) during the entire study. The following antidepressants are permitted: citalopram, duloxetine, escitalopram, fluvoxamine, fluoxetine, milnacipran, levomilnacipran, paroxetine, sertraline, venlafaxine, and desvenlafaxine. Subjects will only continue one of these allowed antidepressants at an adequate and tolerated dose (i.e., monotherapy) during the study. No changes in antidepressant or dose are permitted from screening until the end of the study.

Prohibited therapies: Subjects must not use the following medications or food supplements prior to or during the study, as indicated, except to treat an AE or breakthrough symptoms, preferably after the EOT visit:

MAOIs within 4 weeks before screening until the first follow-up visit.

Antipsychotic drugs from at least 14 days before Day 1 until the first follow-up visit.

Hypnotic drugs or food supplements (from at least 7 days prior to Day 1 until the first follow-up visit), including but not limited to benzodiazepines, non-benzodiazepine hypnotics (e.g., zolpidem, zopiclone, zaleplon, eszopiclone, suvorexant and ramelteon), sedating antihistamines including over-the-counter hypnotics (e.g., diphenhydramine, doxylamine, and hydroxyzine), and melatonin/agomelatine.

Subjects who were taking benzodiazepines and/or permitted non-benzodiazepine sleep medications during the screening phase can continue these medications (at dosages equal to or less than the equivalent of 6 mg/day of lorazepam) during the double-blind treatment phase. No dose increases beyond the equivalent of 6 mg/day of lorazepam, or new benzodiazepine medications are permitted during the double-blind treatment phase.

Non-SSRI/SNRI antidepressants (e.g., doxepin, trazodone, mirtazapine, bupropion, tricyclic antidepressants, agomelatine, and SAMe) from at least 7 days before Day 1 until the first follow-up visit.

Any form of new psychotherapy or change in current psychotherapy is prohibited during the screening and double-blind phase.

Opiates and mood stabilizers (e.g., lithium and anticonvulsants) from at least 7 days prior to Day 1 until the first follow-up visit.

Stimulants (e.g., dexamphetamine, methylphenidate, dexmethylphenidate), oral systemic steroids, and appetite suppressants (ephedrine), and isoxsuprine from at least 7 days before Day 1 until EOT.

Magnetic and electrical stimulation therapies: electroconvulsive therapy, vagal nerve stimulation, deep brain stimulations, TMS of any type, or DCS or electrical stimulation, from screening to End-of-Study visit. TMS or DCS or electrical stimulation use prior to screening is not exclusionary.

T3, thyroid hormone or other thyroid function supplementation prescribed for depression.

These medications are allowed when given to control pre-existing thyroid disease/disorder.

Ketamine or esketamine within 5 years prior to and during the study (up to 2 doses are allowed in lifetime prior to screening).

Psychedelics (e.g., psilocybin).

Memantine.

Other investigational drugs within 30 days prior to and during the study.

Figure 35:
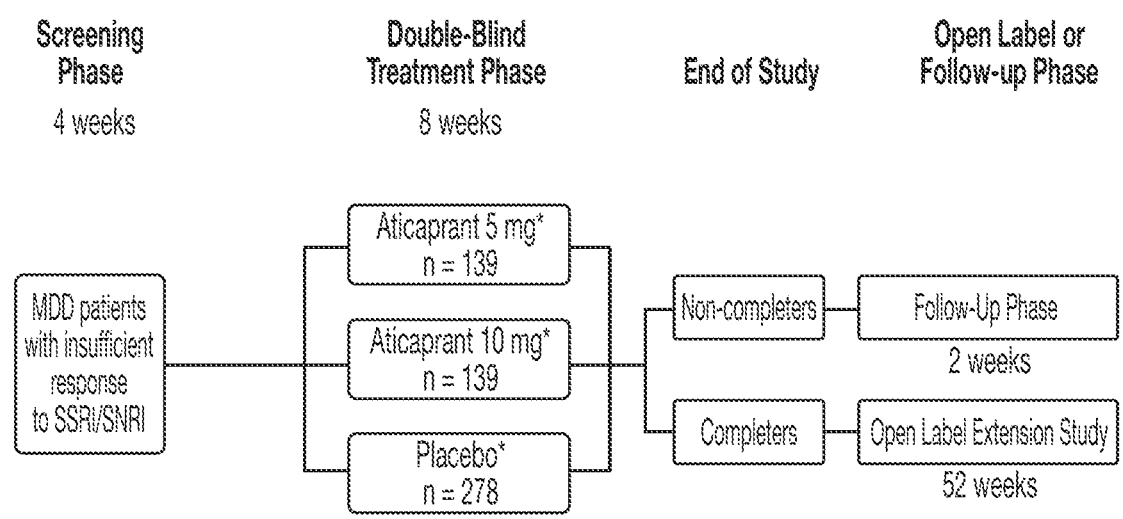
FIG. 35 is the study scheme for Example 8. All patients will continue their oral antidepressant SSRI/SNRI during the entire study. Approximately an additional 68 elderly participants will be randomized.
Figure 36:
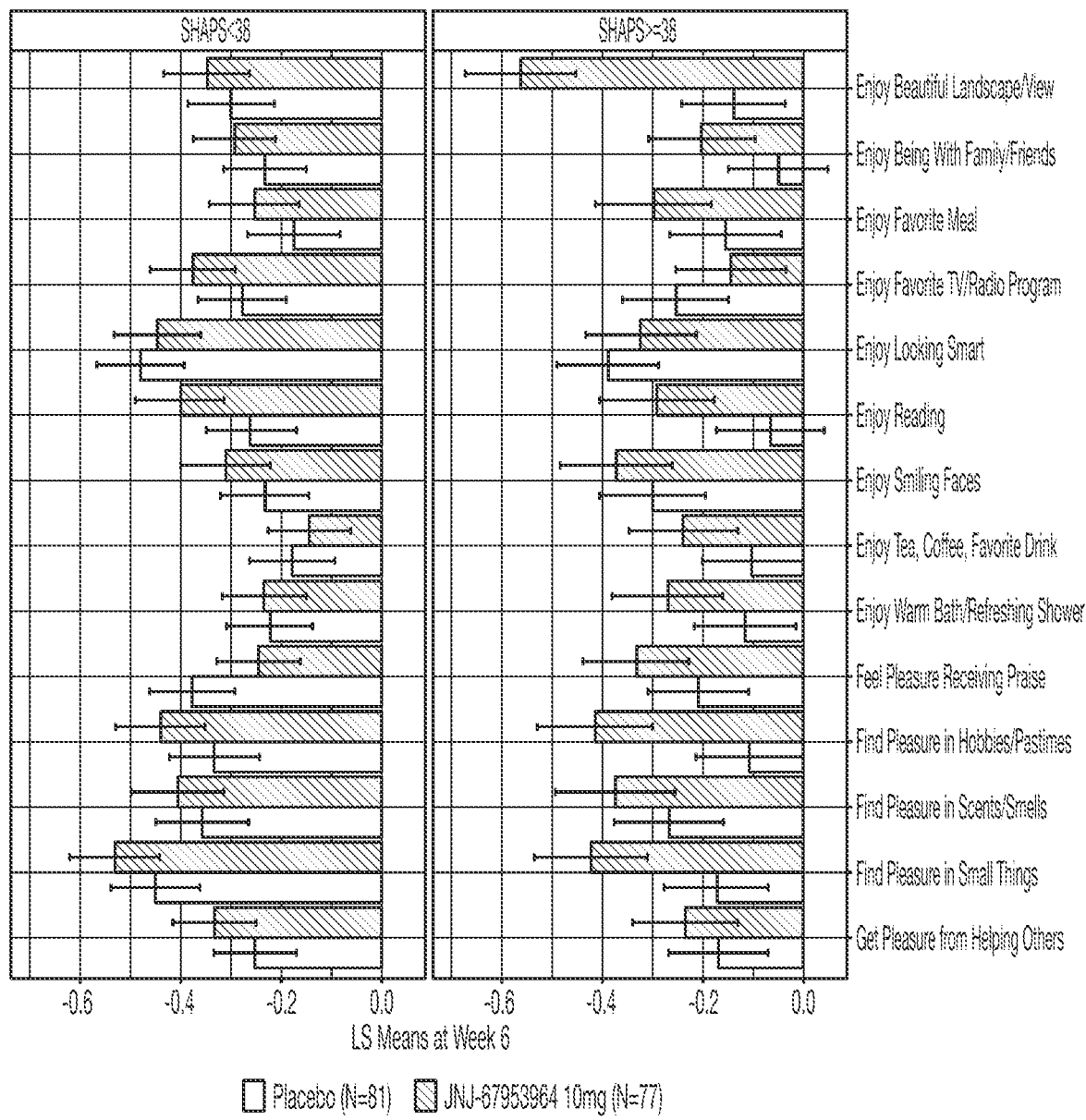
FIG. 36 is a bar graph showing the SHAPS items: LS means for change from baseline at week 6 by baseline SHAPS total score for the fITT analysis set. In this figure and going from top to bottom, the bars alternatively refer to placebo or aticaprant. For example, the first bar refers to aticaprant, the second bar refers to placebo, the third bar refers to aticaprant, etc.

Example 8—a Randomized, Double-Blind, Multicenter, Placebo-Controlled Study to Evaluate the Efficacy, Safety, and Tolerability of Fixed Doses of Aticaprant 5 mg and 10 mg as Adjunctive Therapy in Adult and Elderly Subjects with MDD with Prominent Anhedonia and Inadequate Response to Current Antidepressant Therapy Study Design: An 8-week, multicenter, double-blind, randomized, placebo-controlled study to assess the efficacy, safety, and tolerability of aticaprant in adult and elderly subjects (18 to 74 years) who have MDD with prominent anhedonia and who have had an inadequate response to a SSRI or a SNRI in the current depressive episode. See, FIG. 35.

For all subjects, this study will consist of 3 phases:

an eligibility screening phase (up to 4 weeks prior to first dose administration), a double-blind treatment phase of 8 weeks, and a follow-up phase of 1-2 weeks.

Approximately 624 subjects (randomized in a 2:1:1 ratio to placebo, aticaprant 5 mg, and aticaprant 10 mg) will be enrolled in the study. This enrolment is targeted to achieve a minimum of 556 adult subjects with MDD with prominent anhedonia and approximately 68 elderly subjects (≥65 years) with MDD with prominent anhedonia.

Subjects who have completed the double-blind treatment phase may participate in an open-label long-term safety study.

Sample Size and Randomization: Approximately 624 adult (<65 years) and elderly (≥65 years) subjects with MDD with prominent anhedonia will be randomized in a 2:1:1 ratio to adjunctive placebo, 5-mg aticaprant, or 10-mg aticaprant to achieve a minimum of 556 adult subjects meeting predefined criteria for MDD with prominent anhedonia eligible to be included in the primary efficacy analysis set. Randomization will be stratified by study site, age group (adult, elderly) and baseline MADRS total score. All subjects will continue their baseline antidepressant (SSRI/SNRI) during the entire study.

Doses and Administration: All eligible subjects will receive aticaprant 5 mg, aticaprant 10 mg or placebo in addition to their baseline SSRI/SNRI which will be continued during the entire study. Study medication will be taken daily.

| Inclusion Criteria: |
| --- |
| 1. Age of 18 to 74 years (inclusive). |
| 2. Medically stable on the basis of physical examination (including a brief neurological examination), medical history, vital signs (including blood pressure), and 12-lead ECG performed at screening and baseline. |
| 3. Medically stable on the basis of clinical laboratory tests performed at screening. If the results of the serum chemistry panel, hematology, or urinalysis are outside the normal reference ranges, retesting of an abnormal lab values that may lead to exclusion will be allowed once during the screening phase. |
| 4. Meet DSM-5 diagnostic criteria for recurrent or single episode MDD, without psychotic features (DSM-5 296.22, 296.23, 296.32, or 296.33), based upon clinical assessment and confirmed by the SCID-CT. Subjects 65 years of age or older must have had the first onset of depression prior to 55 years of age. The length of the current depressive episode must be ≤18 months. |
| 5. Symptoms of anhedonia based on clinical assessment and confirmed by a positive response for anhedonia (MDE symptoms Item 2) on the SCID-CT at screening and baseline (Day 1 prior to randomization). |
| 6. SHAPS total score of ≥38 at screening and baseline (Day 1 prior to randomization) corresponding to prominent (high level) of anhedonia. |
| 7. Inadequate response to at least 1 but no more than 2 antidepressants (SSRI/SNRI), administered at an adequate dose and duration in the current episode of depression. An inadequate response is defined as 26% to <50% reduction in depressive symptom severity and overall good tolerability, as assessed by the MGH-ATRQ. An adequate trial is defined as an antidepressant treatment for at least 6 weeks (and no greater than 12 months in the current episode) at or above the stable therapeutic dose specified in the MGH-ATRQ, must include the subject's current antidepressant treatment. If the subject has received 2 SSRI/SNRI treatments of sufficient dose and duration in the current episode, and has shown ≤25% improvement to both, then the subject would not qualify based on exclusion criterion (first exclusion criterion). |

| Inclusion Criteria: |
| --- |

8. The current major depressive episode, depression symptom severity, presence of anhedonia and antidepressant treatment response in the current depressive episode, must be confirmed. Is receiving and tolerating well any one of the following SSRI or SNRI for depressive symptoms, in any formulation and available in the participating country citalopram, duloxetine, escitalopram, fluvoxamine, fluoxetine, milnacipran, levomilnacipran, paroxetine, sertraline, venlafaxine, desvenlafaxine at a stable dose (at therapeutic dose level) for at least 6 weeks, and for no greater than 12 months in the current episode, at screening. The SSRI/SNRI needs to be approved for the treatment of MDD.
9. HDRS-17 total score ≥22 at start of the screening and must not demonstrate a clinically significant improvement (which is defined as an improvement of >20% on their HDRS-17 total score) from the start to end of screening (from the first to the last independent HDRS-17 rating).
10. BMI between 18 and 40 kg/m² (inclusive).
11. Outpatient at screening.
12. A woman of childbearing potential must have a negative highly sensitive serum (β human chorionic gonadotropin [β-hCG]) pregnancy test at screening and a negative urine pregnancy test predose on Day 1 of the double-blind phase prior to randomization.
13. Contraceptive use by men or women should be consistent with local regulations regarding the use of contraceptive methods for subjects in clinical studies.
14. A woman must be either:
    Postmenopausal: A postmenopausal state is defined as no menses for 12 months without an alternative medical cause. A high FSH level in the postmenopausal range based on the reference range of the central laboratory may be used to confirm a postmenopausal state in women not using hormonal contraception or hormonal replacement therapy, however in the absence of 12 months of amenorrhea, a single FSH measurement is insufficient.
    Permanently sterile
    Of childbearing potential and practicing a highly effective method of contraception (failure rate of <1% per year when used consistently and correctly).
    Remains on a highly effective method and for at least 1 month after the last dose of study medication.
    A woman must not donate eggs (ova, oocytes) or freeze for future use for the purposes of assisted reproduction during the study and for a period of at least 1 month after receiving the last dose of study medication.
    During the study and for a minimum of 1 spermatogenesis cycle (defined as approximately 3 months) after receiving the last dose of study medication, a man (a) who is sexually active with a woman of childbearing potential must use a barrier method of contraception and his female partner must use a highly effective method of contraception; (b) who is sexually active with a woman who is pregnant must use a condom; (c) must not donate sperm.

| Exclusion Criteria: |
| --- |

1. History of treatment-resistant MDD, defined as a lack of response to 2 or more adequate antidepressant treatments in the current episode, as indicated by no or minimal improvement (≤25% improvement) when treated with an antidepressant of adequate dose (per MGH-ATRQ) and duration (at least 6 weeks).
2. Current or prior DSM-5 diagnosis of a psychotic disorder or MDD with psychotic features, bipolar or related disorders (confirmed by the SCID-CT), intellectual disability (DSM-5 diagnostic codes 317, 318.0, 318.1, 318.2, 315.8, and 319), autism spectrum disorder, borderline personality disorder, antisocial personality disorder, histrionic personality disorder, narcissistic personality disorders or somatoform disorders.
3. Current active DSM-5 diagnosis of obsessive-compulsive disorder, post-traumatic stress disorder, anorexia nervosa, or bulimia nervosa.

| Exclusion Criteria: |
| --- |

4. Primary DSM-5 diagnosis of panic disorder, generalized anxiety disorder, social anxiety disorder, or specific phobia which has been the primary focus of psychiatric treatment within the past 2 years. These are allowed as secondary diagnoses if MDD is the primary focus of treatment.
5. History or evidence of clinically meaningful noncompliance with current antidepressant therapy.
6. History of moderate to severe substance use disorder including alcohol use disorder according to DSM-5 criteria within 6 months before screening or positive test results for alcohol and/or drugs of abuse (e.g., opiates [including methadone], cocaine, amphetamines, methamphetamines, cannabinoids, CBD, barbiturates, MDMA) at screening or at baseline. One retest during screening is allowed. Tobacco and caffeine use are not exclusionary.
7. Has within the last 5 years received any prior antidepressant treatment with ketamine/esketamine, electroconvulsive therapy, vagal nerve stimulation, or a deep brain stimulation device. Subjects who previously had taken up to 2 doses of ketamine/esketamine and did not continue (e.g., did not benefit from the treatment or experienced tolerability issues) can be considered for enrollment.
8. Homicidal ideation/intent or has suicidal ideation with some intent to act within 3 months prior to the start of the screening phase, per clinical judgment or based on the C-SSRS, corresponding to a response of "Yes" on Item 4 (active suicidal ideation with some intent to act, without specific plan) or Item 5 (active suicidal ideation with specific plan and intent) for suicidal ideation on the C-SSRS, or a history of suicidal behavior within the past year prior to the start of the screening phase. Subjects reporting suicidal ideation with intent to act or suicidal behavior prior to the start of the double-blind treatment phase should be excluded.
9. Cognitive impairment that would render the informed consent invalid or limit the ability of the subject to comply with the study requirements. Subject has neurodegenerative disorder (e.g., Alzheimer's disease, vascular dementia, Parkinson's disease with clinical evidence of cognitive impairment) or evidence of MCI. Subjects of age ≥65 years: has a MMSE <25 or <23 for those subjects with less than high school equivalent education.
10. Current or history of seizures (uncomplicated childhood febrile seizures with no sequelae are not exclusionary).
11. Clinically significant electrocardiogram (ECG) abnormalities at screening or Day 1 prior to randomization that may jeopardize the subjects' safety or the integrity of the study defined as:
    During screening and/or Day 1, a QT interval corrected according to Fridericia's formula (QTcF): ≥450 msec (males); ≥470 msec (females).
    Evidence of second- and third-degree atrioventricular block.
    Features of new ischemia.
    Other clinically important arrhythmia or cardiac abnormalities.
12. History of, or symptoms and signs suggestive of, liver cirrhosis (e.g., esophageal varices, ascites, and increased prothrombin time) OR ALT or AST values ≥3 × the ULN or total bilirubin >1.5 × the ULN in the screening phase. Repeat of screening test for abnormal ALT and AST is permitted during the screening period provided there is an alternative explanation for the out of range value.
13. For elevations in bilirubin if the elevation in bilirubin is consistent with Gilbert's disease, the subject may participate in the study.
14. Positive test results for drugs of abuse (e.g., barbiturates, methadone, opiates, cocaine, PCP, MDMA, and amphetamine/methamphetamine) at the start of the screening phase or Day 1 of the double-blind treatment phase prior to randomization.
15. Subjects who have a positive test result at screening due to prescribed psychostimulants taken for any indication must discontinue the medication at least 2 weeks before Day 1 of the double-blind treatment phase (prior to randomization). The result of the Day 1 (prior to randomization) test for drugs of abuse must be negative for the subject to be randomized. Otherwise, subjects who have a positive test result at screening due to prescribed/over-the-counter opiates or barbiturates may be permitted to continue in the screening phase if the medication is discontinued at least 1 week or 5 half-lives, whichever is longer, before Day 1 of the double-blind treatment phase (prior to randomization). The result of the Day 1 (prior to randomization) test for drugs of abuse must be negative for the subject to be randomized.

| Exclusion Criteria: |
|---|
| 16. Intermittent use of cannabinoids prior to the start of the screening phase is not exclusionary as long as the subject does not meet the criteria for substance use disorder. A positive test for cannabinoids at the start of the screening phase is not exclusionary; however, a positive test result for cannabinoids predose on Day 1 of the double-blind treatment phase is exclusionary. |
| 17. Taking a total daily dose of benzodiazepines greater than the equivalent of 6 mg/day of lorazepam at the start of the screening phase. |
| 18. Recent (last 3 months) history of, or current signs and symptoms of:<br>Severe renal insufficiency (creatinine clearance <30 mL/min)<br>Clinically significant or unstable cardiovascular, respiratory, gastrointestinal, neurologic, hematologic, rheumatologic, immunologic or endocrine disorders.<br>Uncontrolled Type 1 or Type 2 diabetes mellitus. Subjects with Type 1 or Type 2 diabetes mellitus who are controlled (hemoglobin A1c ≤8.0% and glucose ≤150 mg/dL at screening) may be eligible to participate if otherwise medically healthy, and if on a stable regimen of glucose-lowering medications for at least 2 months prior to screening). |
| 19. Current signs/symptoms of hypothyroidism or hyperthyroidism. For subjects with a history of thyroid disease and for subjects who, regardless of thyroid history have the TSH value out of range, a $FT_4$ test will be conducted. If the FT4 value is abnormal and considered to be clinically significant the subject is not eligible. |
| 20. Subjects with a pre-existing history of thyroid disease/disorder who are treated with thyroid hormones need to be on a stable dosage for 3 months prior to the start of the screening phase. Subjects taking thyroid supplementation for antidepressant purposes are not allowed. |
| 21. Cushing's Disease, Addison's Disease, primary amenorrhea, or other evidence of significant medical disorders of the hypothalamic-pituitary-adrenal axis. |
| 22. Significant medical illness, particularly unstable medical problem |
| 23. Ongoing psychological treatments (e.g., Cognitive Behavior Therapy, Interpersonal Psychotherapy, Psychodynamic Psychotherapy etc.), initiated within 6 weeks prior to start of screening. A subject who has been receiving ongoing psychological treatment for a period of greater than 6 weeks is eligible. |
| 24. Significant medical illness, particularly unstable medical problem. |
| 25. Clinically-relevant GI complaints (unless symptoms of Axis I disorder) at screening or baseline or history of gastric disease (including but not limited to documented peptic ulcer disease, gastritis [including atrophic gastritis], upper GI bleeding, Barret's esophagus, Crohn's disease, ulcerative colitis, GI precancerous conditions or any other clinically-relevant GI disease irritable bowel syndrome). |
| 26. Requires chronic use of a PPIs. A history of chronic NSAID or aspirin use. (Low dose aspirin e.g., in cardiovascular disease prevention is allowed). |
| 27. History of malignancy within 5 years before the start of the screening phase (exceptions are squamous and basal cell carcinomas of the skin and carcinoma in situ of the cervix, or malignancy that is considered cured with minimal risk of recurrence). |
| 28. Known allergies, hypersensitivity, intolerance, or contraindications to aticaprant and/or its excipients. |
| 29. Has taken any prohibited therapies that would not permit dosing on Day 1. |
| 30. Taking a total daily dose of benzodiazepines greater than the equivalent of 6 mg/day of lorazepam at the start of the screening phase. |
| 31. Received an investigational drug (including investigational vaccines) or used an invasive investigational medical device within 60 days before the start of the screening phase, or has participated in 2 or more MDD or other psychiatric condition clinical interventional studies (with different investigational medication) in the previous 1 year before the start of the screening phase, or is currently enrolled in an investigational interventional study. |
| 32. A woman who is pregnant, breastfeeding, or planning to become pregnant while enrolled in this study or within 6 weeks after the last dose of the study medication. |
| 33. Plans to father a child while enrolled in this study or within 90 days after the last dose of study intervention. |
| 34. Diagnosis of acquired immunodeficiency syndrome. Human immunodeficiency virus testing is not required for this study. |
| 35. Any condition or situation/circumstance for which participation would not be in the best interest of the subject (e.g., compromise the well-being) or that could prevent, limit, or confound the protocol specified assessments. |

A. Efficacy Objectives and Endpoints

The assessment of primary and secondary (key and other) endpoints will be conducted on the full analysis set (FAS) which includes adult (not elderly) subjects with MDD with prominent anhedonia who took at least 1 dose of study medication.

Primary: Evaluate the efficacy of 2 fixed doses of aticaprant (5 mg and 10 mg) compared with placebo as adjunctive therapy to an antidepressant (SSRI or SNRI) in improving depressive symptoms in adult subjects (18-64 years) with MDD with prominent anhedonia and inadequate response to the current antidepressant Change from baseline to Day 43 in the MADRS total score.

Key Secondary: To assess efficacy of aticaprant 10 mg compared with placebo in adult subjects with MDD with prominent anhedonia as adjunctive therapy to an antidepressant on patient-reported assessment of anhedonia outcomes:

Change from baseline to Day 43 in the Dimensional Anhedonia Rating Scale (DARS) total score.

Other Secondary: Assess the efficacy of aticaprant compared with placebo as adjunctive therapy to an antidepressant (SSRI or SNRI) in adult subjects with MDD with prominent anhedonia:

Proportion of responders at Day 43 and Day 57 (≥50% reduction in MADRS total score).

Proportion of subjects with remission of depressive symptoms, defined as a MADRS total score≤12 at Day 43 and Day 57.

Change from baseline to Day 43 and Day 57 in MADRS-6

Change from baseline to Day 43 and Day 57 in Patient Health Questionnaire, 9-Item (PHQ-9) total score.

Exploratory: To assess the efficacy of aticaprant compared with placebo in adult subjects with MDD with prominent anhedonia as adjunctive therapy on the following:

Change from baseline over time in the MADRS total score.

Change from baseline over time in MADRS anhedonia items factor score.

Change from baseline over time in patient-reported outcomes of anhedonia (SHAPS, DARS).

Change from baseline over time in PHQ-9 total score.

Change from baseline to Day 43 in health-related quality of life and health status, as assessed by the EQ-5D-5L questionnaire.

Change from baseline to Day 43 in the Sheehan Disability Scale (SDS) total score.

Change from baseline over time in the CGI-S score.

Change from baseline over time in symptoms of anxiety using the GAD-7.

Change from baseline over time in depressive symptoms using the PGI-S.

Change from baseline to Day 43 in patient-reported sexual functioning using the ASEX.

Safety Objectives (All): The following safety endpoints will be assessed separately for the adult and elderly subjects;

the safety analysis set for each age group will include all randomized subjects who have received at least one dose of study medication:

AEs including AESI
Vital signs
ECG
Laboratory Values
Weight/BMI
Suicidality assessment using the C-SSRS
Withdrawal symptoms assessment using the PWC-20

Other Objectives (Exploratory):

To identify diagnostic biomarkers and to investigate changes in MDD-related biomarkers in relation to clinical response on depression symptoms and anhedonia upon monotherapy with aticaprant.

To identify genetic and other factors that may influence the pharmacokinetics (PK), safety, or tolerability of aticaprant.

B. Concomitant Therapies and Prohibited Therapies

Background therapy: All subjects will continue their baseline antidepressant (SSRI/SNRI) during the entire study. The following antidepressants are permitted: citalopram, duloxetine, escitalopram, fluvoxamine, fluoxetine, milnacipran, levomilnacipran, paroxetine, sertraline, venlafaxine, and desvenlafaxine. Subjects will only continue one of these allowed antidepressants at an adequate and tolerated dose (i.e., monotherapy) during the study. No changes in antidepressant or dose are permitted from screening until the end of the study.

Prohibited Therapies:

Subjects must not use the following medications or food supplements prior to or during the study, as indicated, except to treat an AE or breakthrough symptoms, preferably after the EOT visit:

MAOIs within 4 weeks before screening until the first follow-up visit.

Antipsychotic drugs from at least 14 days before Day 1 until the first follow-up visit.

Hypnotic drugs or food supplements (from at least 7 days prior to Day 1 until the first follow-up visit), including but not limited to benzodiazepines, non-benzodiazepine hypnotics (e.g., zolpidem, zopiclone, zaleplon, eszopiclone, suvorexant and ramelteon), sedating antihistamines including over-the-counter hypnotics (e.g., diphenhydramine, doxylamine, and hydroxyzine), and melatonin. Subjects who were taking benzodiazepines and/or permitted non-benzodiazepine sleep medications during the screening phase can continue these medications (at dosages equal to or less than the equivalent of 6 mg/day of lorazepam) during the double-blind treatment phase. No dose increases beyond the equivalent of 6 mg/day of lorazepam, or new benzodiazepine medications are permitted during the double-blind treatment phase.

Non-SSRI/SNRI antidepressants (e.g., doxepin, trazodone, mirtazapine, bupropion, tricyclic antidepressants, agomelatine, and SAMe) from at least 7 days before Day 1 until the first follow-up visit.

Any form of new psychotherapy or change in current psychotherapy is prohibited during the screening and double-blind phase of this study.

Opiates and mood stabilizers (e.g., lithium and anticonvulsants) from at least 7 days prior to Day 1 until the first follow-up visit.

Stimulants (e.g., dexamphetamine, methylphenidate, dexmethylphenidate), oral systemic steroids, and appetite suppressants (ephedrine), and isoxsuprine from at least 7 days before Day 1 until EOT.

Magnetic and electrical stimulation therapies: electroconvulsive therapy, vagal nerve stimulation, deep brain stimulations, TMS of any type, or DCS or electrical stimulation, from screening to End-of-Study visit. TMS or DCS or electrical stimulation use prior to screening is not exclusionary.

T3, thyroid hormone or other thyroid function supplementation prescribed for depression. These medications are allowed when given to control pre-existing thyroid disease/disorder.

Ketamine or esketamine within 5 years prior to and during the study (up to 2 doses are allowed in lifetime prior to screening).

Psychedelics (e.g., psilocybin).

Memantine.

Other investigational drugs within 30 days prior to and during the study.

Example 9

This is a Phase 1, open-label, single dose, multicenter, 4-part study in healthy adult participants.

A total of approximately 80 qualified healthy adult participants are planned to be enrolled in this study: 24 participants each are to be enrolled to ensure at least 20 participants in each part complete all required PK assessments. Eligible participants can be enrolled in more than one part of the study if sufficient wash-out period is completed between periods by participants.

Potential participants will be screened from Day −28 to Day −2 to determine participants' eligibility for study participation. For Part 1, qualified participants will be admitted on Day −1 of each treatment period and will remain in-house for the total duration of the treatment (Day −1 until Day 5, with single-dose treatment on Day 1 and 96 hours of PK), whereas for Part 2, PK sampling will be done up to 120 hours (Day 6). Each dosed participant will have a safety follow-up on Day 10 to Day 14 after last dose of the study intervention.

Part 1

Figure 25:
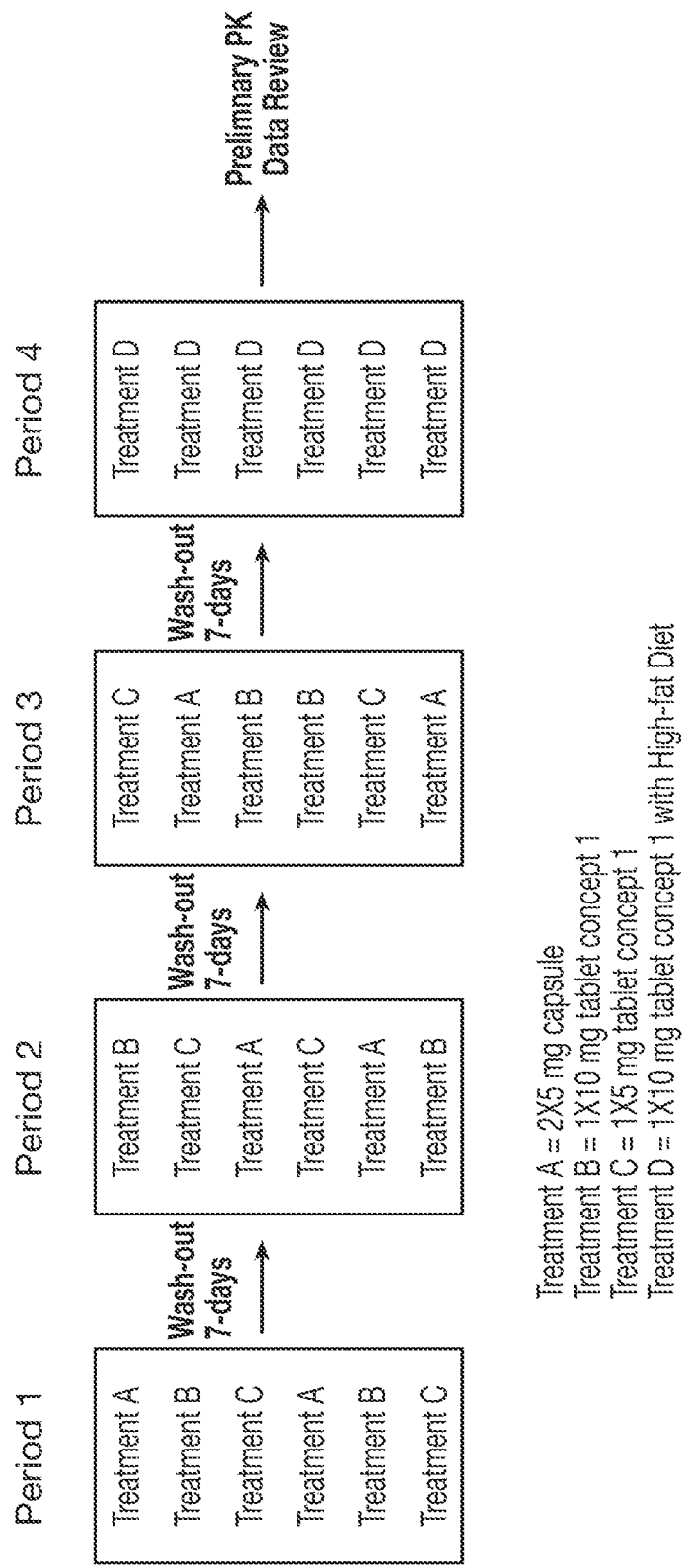
FIG. 25 is the schematic overview of part 1 of the study. In this figure, Treatment A=2×5 mg capsule; Treatment B=1×10 mg tablet concept 1; Treatment C=1×5 mg tablet concept 1; Treatment D=1×10 mg tablet concept 1 with high-fat diet.

The Part 1 of the study involves determination of relative bioavailability for tablet (Formulation Concept 1, i.e., unmilled aticaprant formulation, see Table 10) and capsule formulations (see Example 6, study design, for description of capsule formulation) and dose proportionality and food effect for tablet formulation (Formulation Concept 1) in healthy adult participants (FIG. 25). Part 1 will consist of Subpart 1A and Subpart 1B consisting of a total of 4 periods. Subpart 1A is a randomized, open label, 3-way crossover, 3-period study to be conducted in 24 healthy participants to evaluate the relative bioavailability of a single dose of 10 mg aticaprant administered as 1×10 mg oral tablet (Formulation Concept 1) under fasted conditions (Treatment B) compared to 10 mg aticaprant administered as 2×5 mg oral capsules under fasted conditions (Treatment A) and to evaluate the dose proportionality of a single dose of 5 mg aticaprant administered as 1×5 mg oral tablet (Formulation Concept 1) under fasted conditions (Treatment C) compared to the potential Phase 3 oral tablet (Formulation Concept 1) under fasted conditions (1×10 mg, Treatment B; Table 49). Participants will be assigned to 1 of 6 treatment sequences (Table 51) and will be administered the 3 treatments in a 3-way crossover. The same 24 participants who complete Subpart 1A will be enrolled in Subpart 1B. Subpart 1B consists of a fourth period to evaluate the food effect of a single dose of 10 mg aticaprant administered as 1×10 mg oral tablet (Formulation Concept 1) under fed conditions (Treatment D; Table 50 and Table 52). A preliminary PK analysis will be conducted at the end of the food effect part (Subpart 1B) for all the periods from Part 1 and will include the food effect data.

TABLE 49

Study Treatment Regimens in Subpart 1A

| Treatment | Formulation | Dose | Food |
|---|---|---|---|
| A | 5 mg oral capsule | 10 mg (2 × 5 mg) | Fasted |
| B | Formulation Concept 1 (10 mg oral tablet) | 10 mg (1 × 10 mg) | Fasted |
| C | Formulation Concept 1 (5 mg oral tablet) | 5 mg (1 × 5 mg) | Fasted |

Treatment A: 2 × 5 mg oral capsule administered in the morning, after at least 10-hour overnight fasting
Treatment B: 1 × 10 mg Formulation Concept 1 administered in the morning, after at least 10-hour overnight fasting
Treatment C: 1 × 5 mg Formulation Concept 1 administered in the morning, after at least 10-hour overnight fasting

TABLE 50

Study Treatment Regimen in Subpart 1B

| Treatment | Formulation | Dose | Food |
|---|---|---|---|
| D | Formulation Concept 1 (10 mg oral tablet) | 10 mg (1 × 10 mg) | Fed |

Treatment D: 1 × 10 mg Formulation Concept 1 administered in the morning approximately 30 minutes after the start of a standardized high-fat breakfast following at least 10-hour overnight fasting

TABLE 51

Treatment Sequences in Subpart 1A

| | Treatment Periods | | |
|---|---|---|---|
| Sequence | 1 | 2 | 3 |
| Sequence 1 (n = 4) | A | B | C |
| Sequence 2 (n = 4) | B | C | A |
| Sequence 3 (n = 4) | C | A | B |
| Sequence 4 (n = 4) | A | C | B |
| Sequence 5 (n = 4) | B | A | C |
| Sequence 6 (n = 4) | C | B | A |

Treatment A: 2 × 5 mg oral capsule administered in the morning, after at least 10-hour overnight fasting;
Treatment B: 1 × 10 mg Formulation Concept 1 administered in the morning, after at least 10-hour overnight fasting
Treatment C: 1 × 5 mg Formulation Concept 1 administered in the morning, after at least 10-hour overnight fasting

TABLE 52

Treatment Sequence in Subpart 1B

| Sequence | Treatment Period 4 |
|---|---|
| All Sequences from Subpart 1A (n = 24) | D |

Treatment D: 1 × 10 mg Formulation Concept 1 administered in the morning approximately 30 minutes after the start of a standardized high-fat breakfast following at least 10-hour overnight fasting Primary Objectives:

To evaluate the relative oral bioavailability of potential Phase 3 tablet concept formulations (unmilled API formulation concept; 1×10 mg) compared with the oral capsule formulation (2×5 mg) of aticaprant when administered as a single oral dose of 10 mg aticaprant in healthy adult participants under fasting conditions.

To evaluate the dose proportionality of potential Phase 3 tablet concept formulation (unmilled API formulation concept; 1×5 mg) relative to the potential Phase 3 tablet concept formulation (unmilled API formulation concept; 1×10 mg) of aticaprant when administered in healthy adult participants under fasting conditions.

To evaluate the PK of a single oral dose of potential Phase 3 tablet concept formulation (unmilled API formulation concept; 1×10 mg) of aticaprant in healthy adult participants under fasting and fed (high-fat meal) conditions.

Secondary Objectives:

To assess the safety and tolerability of oral doses of aticaprant in healthy adult participants.

Part 2

Figure 26:
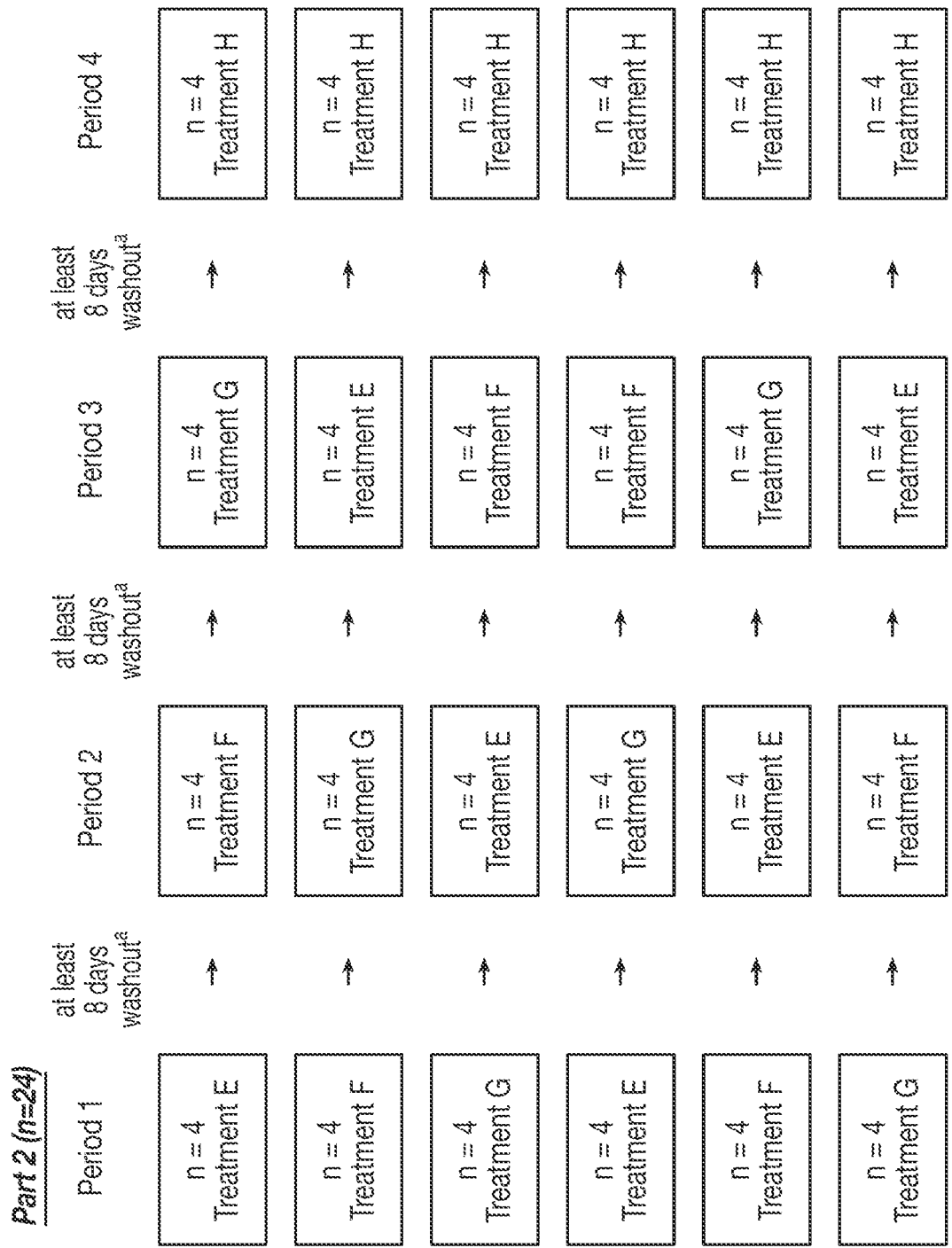
FIG. 26 is the schematic overview of part 2 of the study. In this figure, a) Day 1 of a treatment period is the first day of the washout period. Treatment E: 2×5 mg oral capsule administered in the morning, after at least 10-hour overnight fasting. Treatment F: 1×10 mg Formulation Concept 2 administered in the morning, after at least 10-hour overnight fasting. Treatment G: 1×5 mg Formulation Concept 2 administered in the morning, after at least 10-hour overnight fasting. Treatment H: 1×10 mg Formulation Concept 2 administered in the morning approximately 30 minutes after the start of a standardized high-fat breakfast following at least 10-hour overnight fasting
Figure 27:
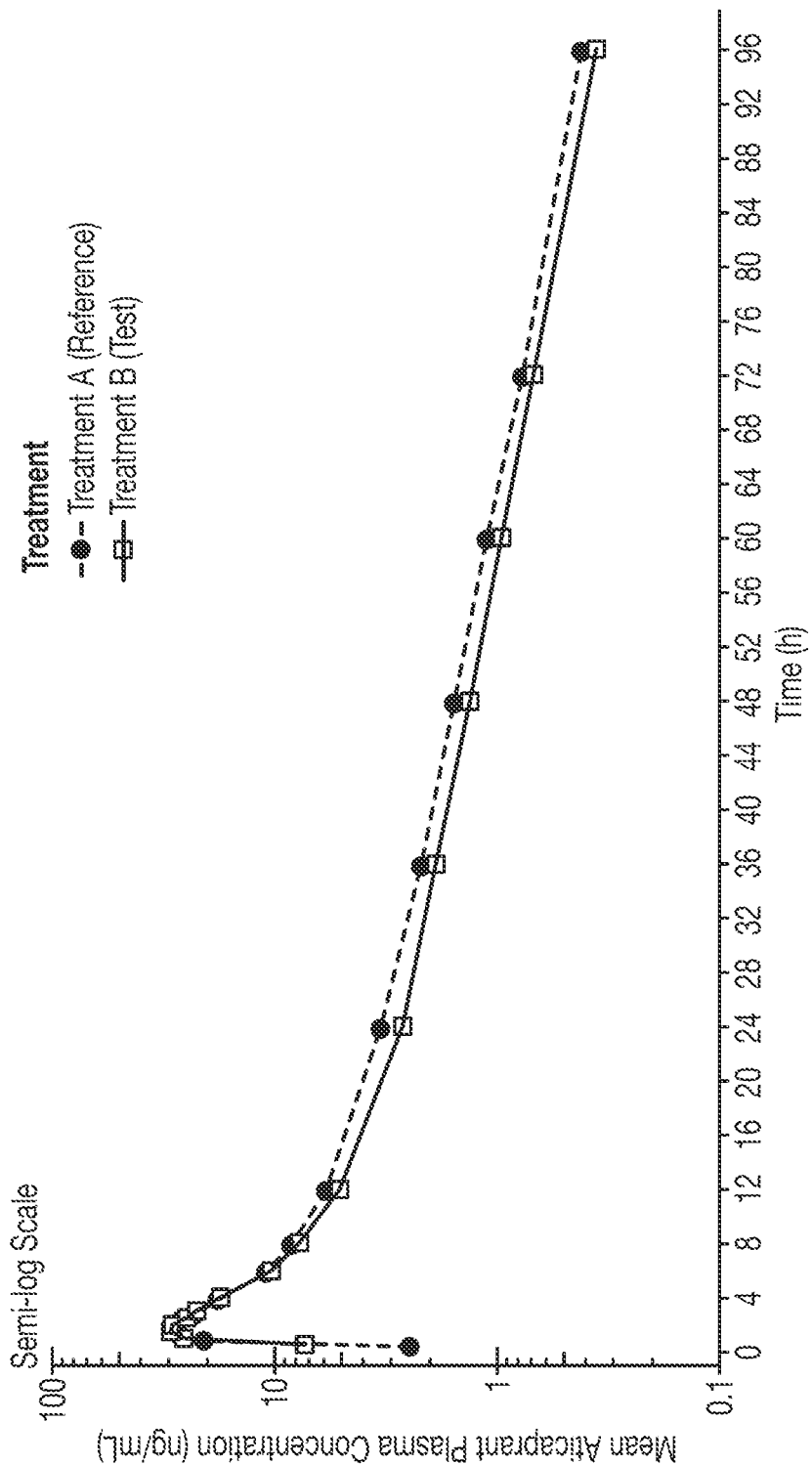
FIGS. 27 and 28 show the relative bioavailability results for aticaprant PK profiles relative to BA.
Figure 28:
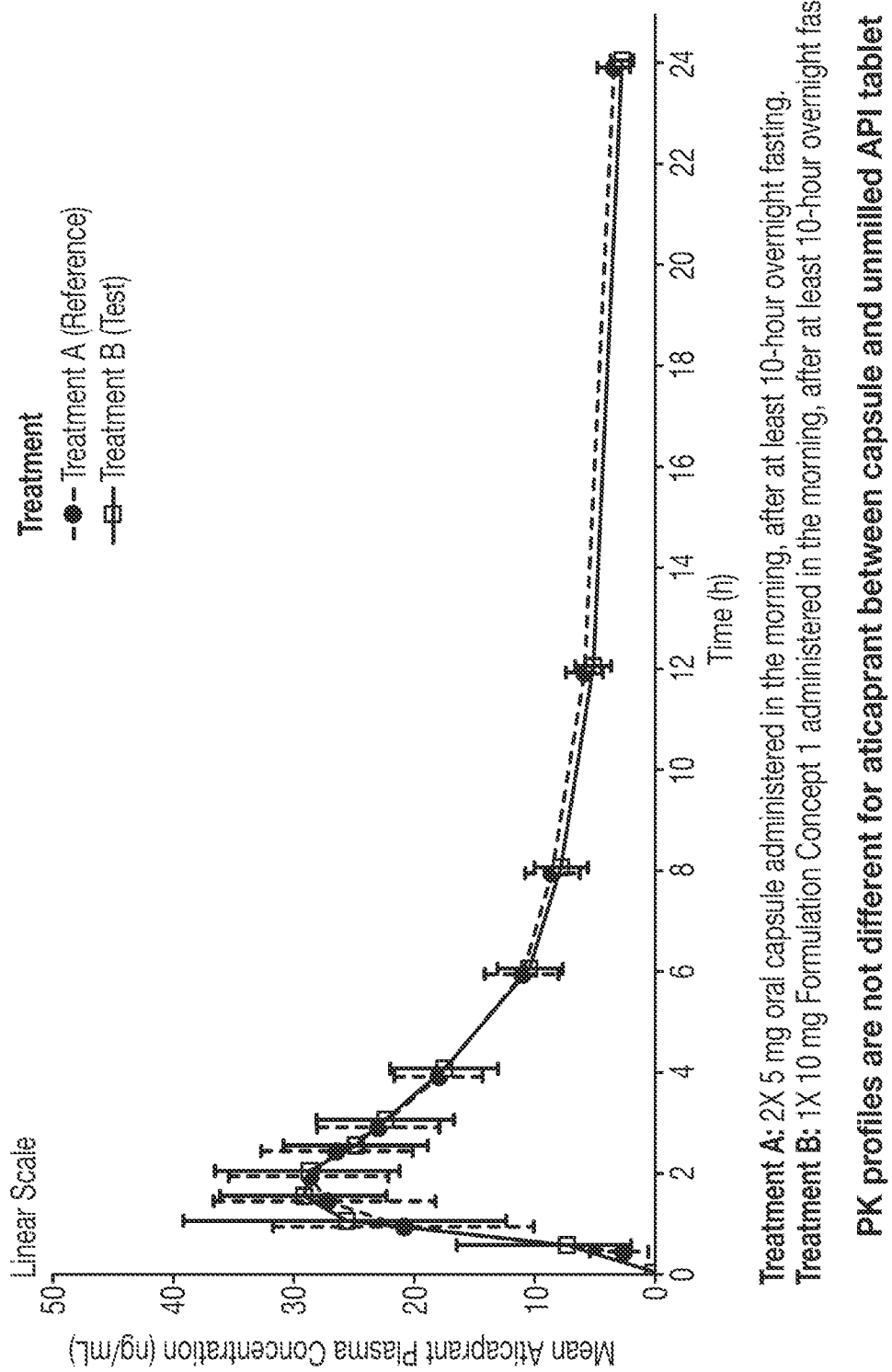
Figure 29:
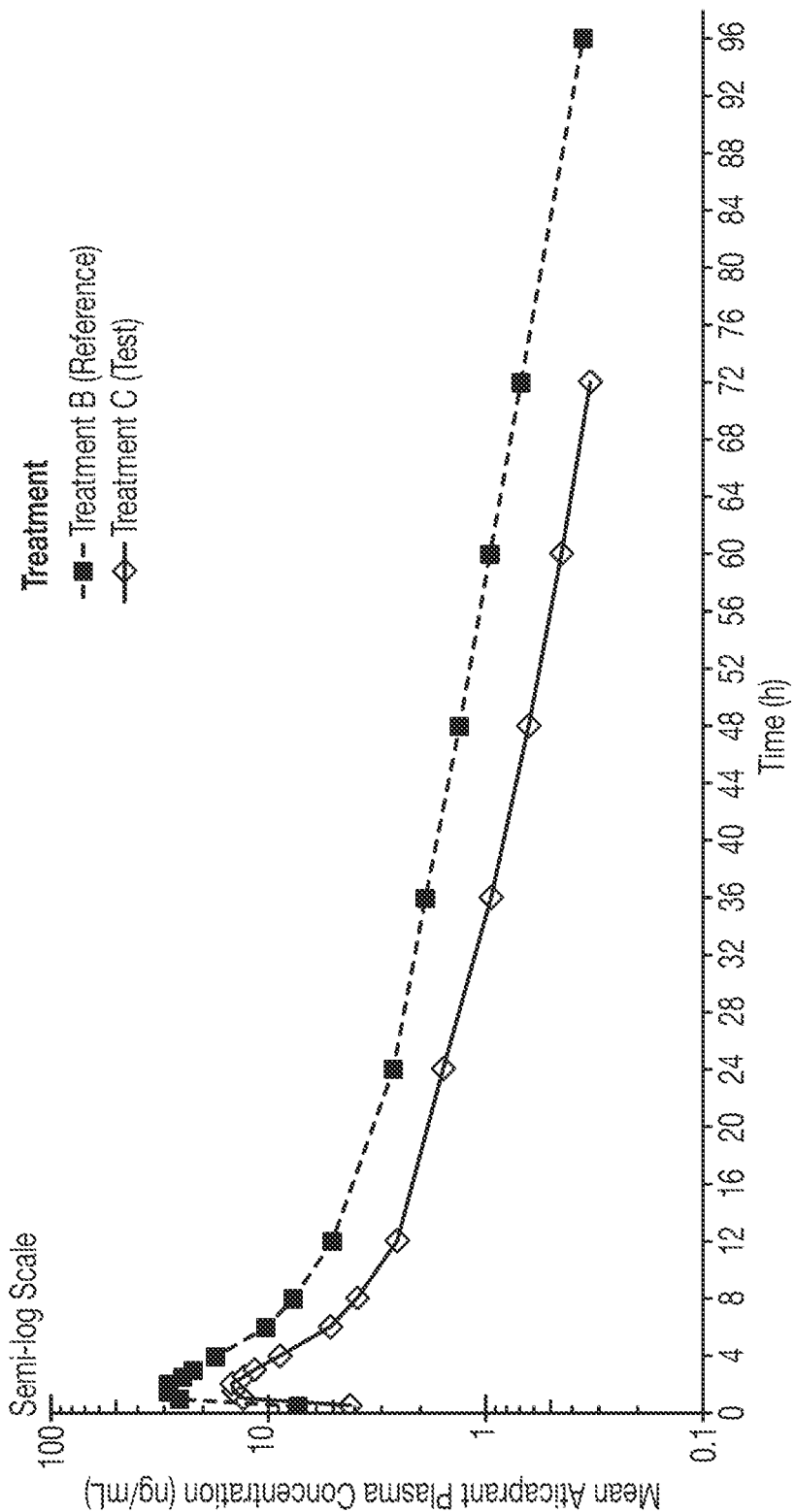
FIGS. 29 and 30 show the relative bioavailability results for aticaprant PK profile, dose-proportionality.
Figure 30:
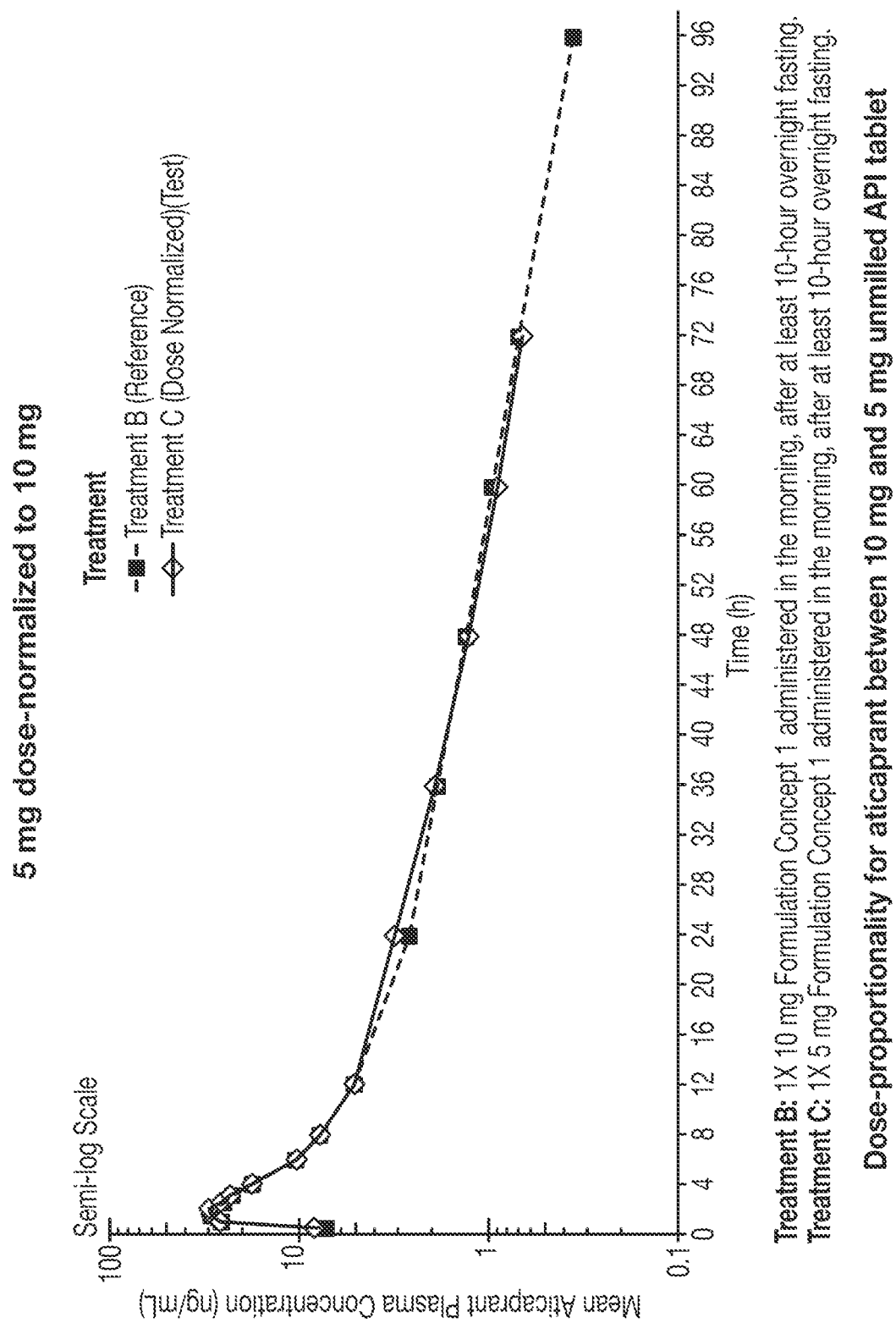
Figure 31:
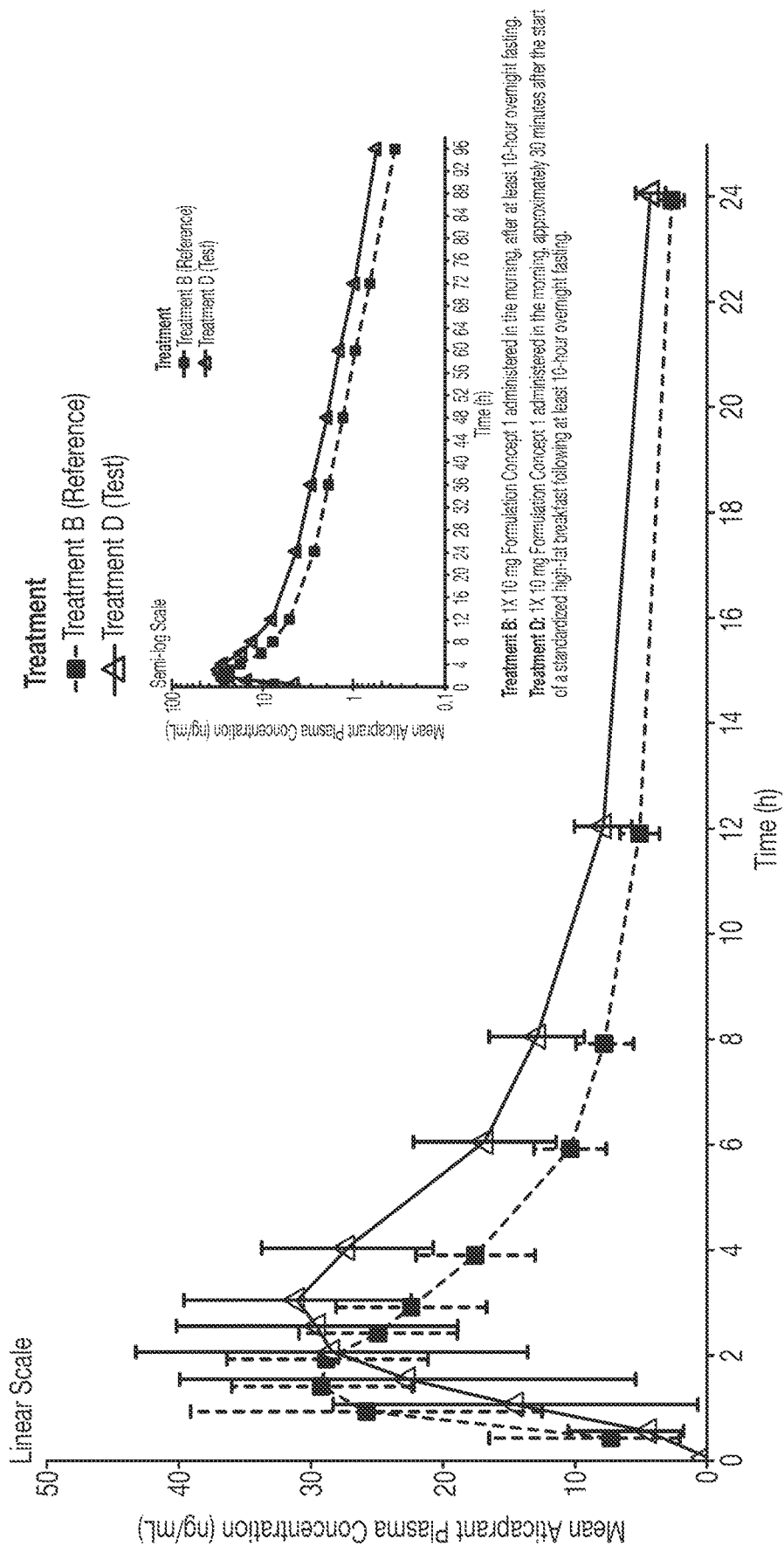
FIGS. 31-33 show the relative bioavailability results for aticaprant PK profile, food effect.
Figure 32:
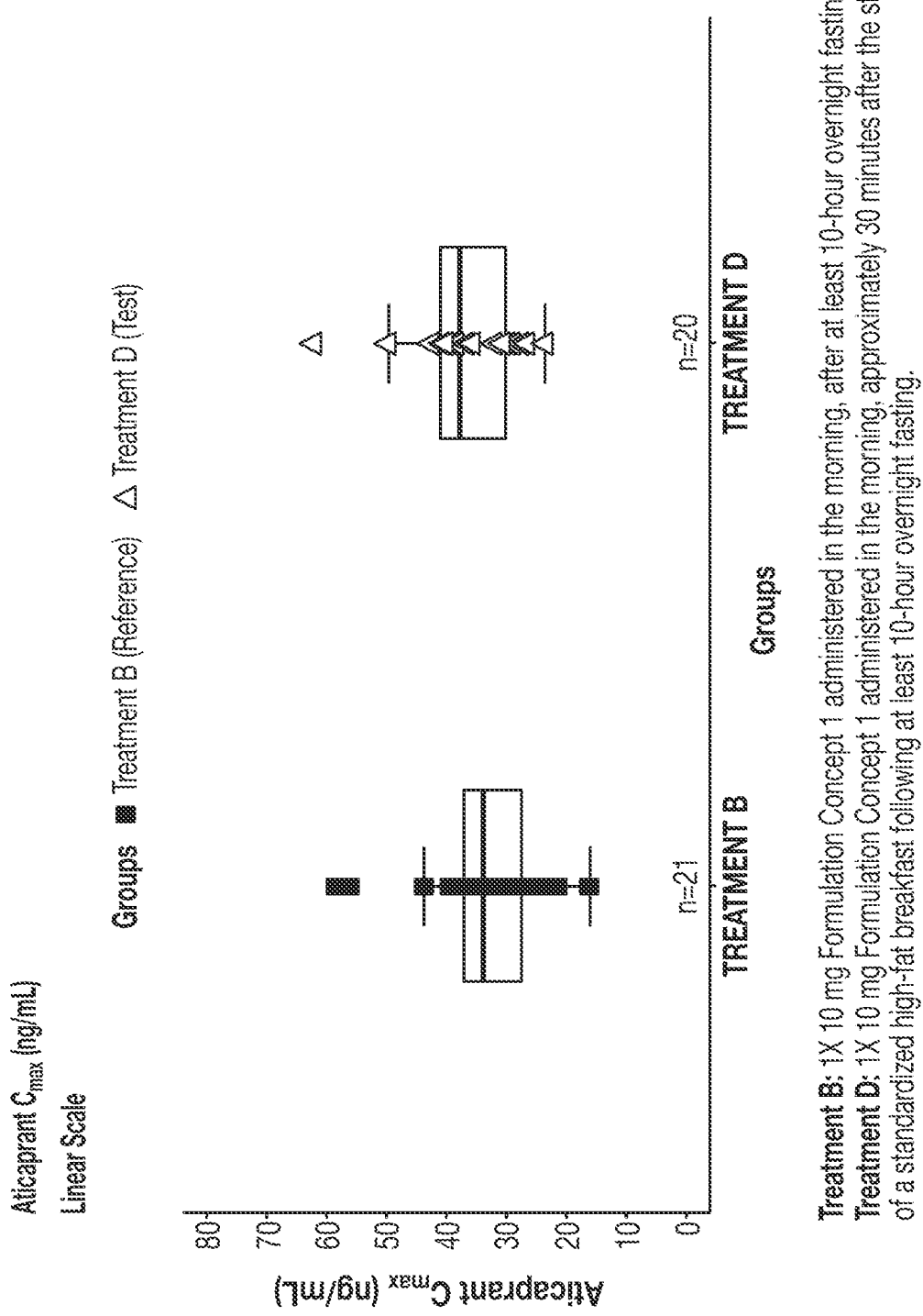
Figure 33:
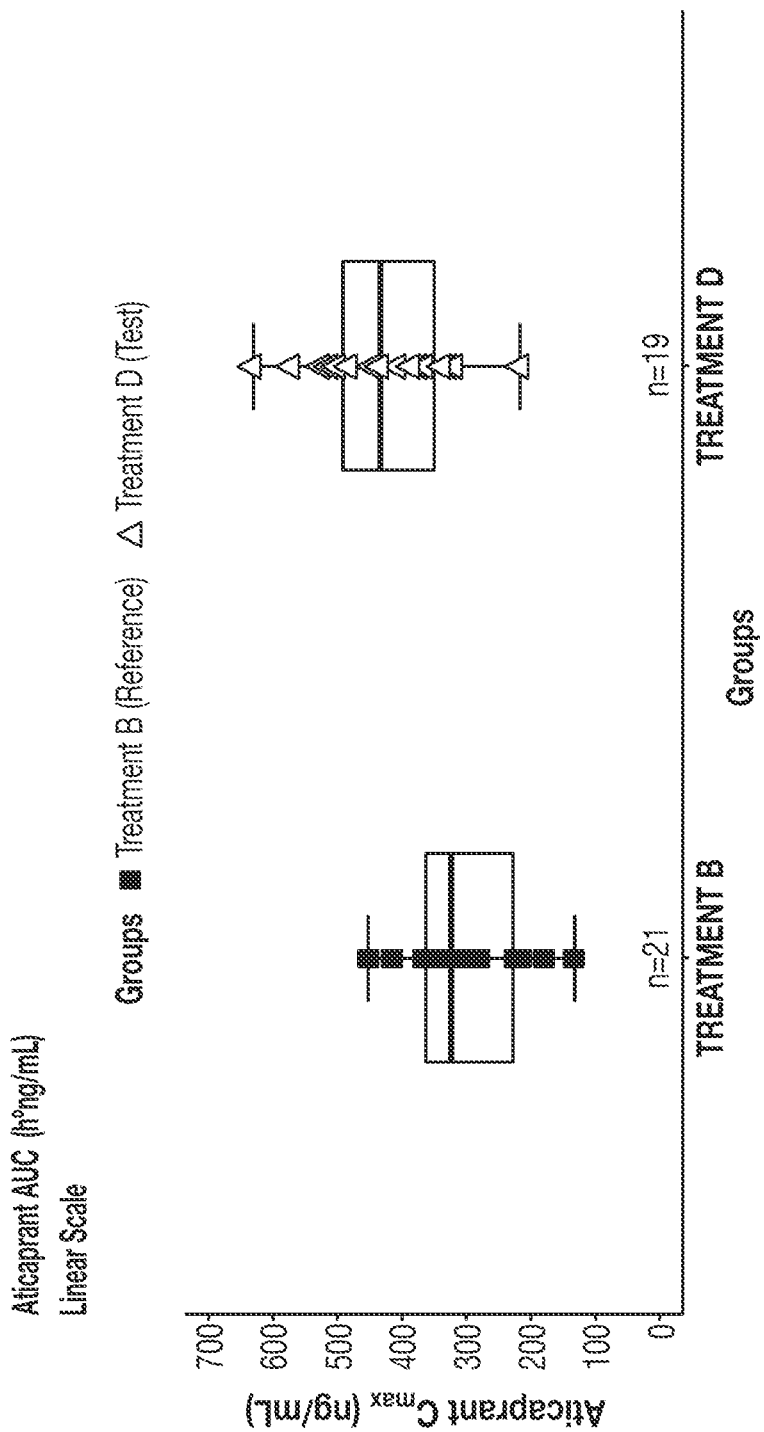

The Part 2 of the study involves determination of relative bioavailability for tablet (Formulation Concept 2, i.e., milled (microfine) aticaprant formulation; see Table 10) and capsule formulations (see Example 6, study design, for description of capsule formulation) and dose proportionality and food effect for tablet formulation (Formulation Concept 2) in healthy adult participants (FIG. 26). Part 2 will consist of Subpart 2A and Subpart 2B consisting of a total of 4 periods. Subpart 2A is a randomized, open label, 3-way crossover, 3-period study to be conducted in 24 healthy participants to evaluate the relative bioavailability of a single dose of 10 mg aticaprant administered as 1×10 mg oral tablet (Formulation Concept 2) under fasted conditions (Treatment F) compared to 10 mg aticaprant administered as 2×5 mg oral capsules under fasted conditions (Treatment E) and to evaluate the dose proportionality of a single dose of 5 mg aticaprant administered as 1×5 mg oral tablet (Formulation Concept 2) under fasted conditions (Treatment G) compared to the potential Phase 3 oral tablet (Formulation Concept 2) under fasted conditions (1×10 mg, Treatment F; Table 53). Participants will be assigned to 1 of 6 treatment sequences (Table 55) and will be administered the 3 treatments in a 3-way crossover. The same 24 participants who complete Subpart 2A will be enrolled in Subpart 2B. Subpart 2B consists of a fourth period to evaluate the food effect of a single dose of 10 mg aticaprant administered as 1×10 mg oral tablet (Formulation Concept 2) under fed conditions (Treatment H; Tables 54 and 56). A preliminary PK analysis will be conducted at the end of the food effect part (Subpart 2B) for all the periods from Part 2 and will include the food effect data.

TABLE 53

Study Treatment Regimens in Subpart 2A

| Treatment | Formulation | Dose | Food |
|---|---|---|---|
| E | 5 mg oral capsule | 10 mg (2 × 5 mg) | Fasted |
| F | Formulation Concept 2 (10 mg oral tablet) | 10 mg (1 × 10 mg) | Fasted |
| G | Formulation Concept 2 (5 mg oral tablet) | 5 mg (1 × 5 mg) | Fasted |

Treatment E: 2 × 5 mg oral capsule administered in the morning, after at least 10-hour overnight fasting
Treatment F: 1 × 10 mg Formulation Concept 2 administered in the morning, after at least 10-hour overnight fasting
Treatment G: 1 × 5 mg Formulation Concept 2 administered in the morning, after at least 10-hour overnight fasting

TABLE 54

Study Treatment Regimen in Subpart 2B

| Treatment | Formulation | Dose | Food |
|---|---|---|---|
| H | Formulation Concept 2 (10 mg oral tablet) | 10 mg (1 × 10 mg) | Fed |

Treatment H: 1 × 10 mg Formulation Concept 2 administered in the morning approximately 30 minutes after the start of a standardized high-fat breakfast following at least 10-hour overnight fasting

TABLE 55

Treatment Sequences in Subpart 2A

| | Treatment Periods | | |
|---|---|---|---|
| Sequence | 1 | 2 | 3 |
| Sequence 1 (n = 4) | E | F | G |
| Sequence 2 (n = 4) | F | G | E |
| Sequence 3 (n = 4) | G | E | F |
| Sequence 4 (n = 4) | E | G | F |
| Sequence 5 (n = 4) | F | E | G |
| Sequence 6 (n = 4) | G | F | E |

Treatment E: 2 × 5 mg oral capsule administered in the morning, after at least 10-hour overnight fasting
Treatment F: 1 × 10 mg Formulation Concept 2 administered in the morning, after at least 10-hour overnight fasting
Treatment G: 1 × 5 mg Formulation Concept 2 administered in the morning, after at least 10-hour overnight fasting

TABLE 56

Treatment Sequences in Subpart 2B

| Sequence | Treatment Period 4 |
|---|---|
| All Sequences from Subpart 2A (n = 24) | E |

Treatment H: 1 × 10 mg Formulation Concept 2 administered in the morning approximately 30 minutes after the start of a standardized high-fat breakfast following at least 10-hour overnight fasting Primary Objectives:

To evaluate the relative oral bioavailability of potential Phase 3 tablet concept formulations (milled aticaprant formulation concept; 1×10 mg) compared with the oral capsule formulation (2×5 mg) of aticaprant when administered as a single oral dose of 10 mg aticaprant in healthy adult participants under fasting conditions.

To evaluate the dose proportionality of potential Phase 3 tablet concept formulation (milled API formulation concept; 1×5 mg) relative to the potential Phase 3 tablet concept formulation (milled aticaprant formulation concept; 1×10 mg) of aticaprant when administered in healthy adult participants under fasting conditions.

To evaluate the PK of a single oral dose of potential Phase 3 tablet concept formulation (milled aticaprant formulation concept; 1×10 mg) of aticaprant in healthy adult participants under fasting and fed (high-fat meal) conditions.

Additional Points

For each individual participant, there will be a washout period of at least 7 days for Part 1 and at least 8 days for Part 2 between subsequent intakes of the study intervention. Day 1 of a treatment period (day of study intervention intake) is the first day of the washout period (also in between the study parts, if applicable).

Participants will be fasting in Part 1A and Part 2A. Participants will have been fed in Parts 1B and 2B. For a fasted condition, participants will fast (nothing to eat or drink except noncarbonated water) overnight for at least 10 hours before and until 4 hours after study intervention administration during each fasted treatment period. Approximately, 4 hours post-dose and after the 4-hour PK sampling, a standard lunch will be served at the study-site. Intake of water is allowed until 2 hours before the intake of the study intervention. Thereafter, water intake is only allowed for study intervention intake and for breakfast, if applicable. Drinking of water is allowed ad libitum from approximately 2 hours after dosing. For a fed condition, participants will consume, after an overnight fast (at least 10 hours), a standardized high-fat breakfast within a 20-minute period. A high-fat (approximately 50 percent of total caloric content of the meal) and high-calorie (approximately 800 to 1000 calories) meal is recommended for food effect bioavailability studies (e.g., 2 strips of fried bacon, 2 eggs fried in butter, 4 ounces [120 gram] hash brown potatoes fried in butter, 2 buttered pieces of whole wheat bread, and 240 mL whole milk). Study intervention will be administered approximately 30 minutes after the start of the breakfast.

In Parts 1 and 2, plasma concentrations will be determined for aticaprant. Blood samples for determination of plasma concentrations of aticaprant will be collected predose and at the postdose time points starting on Day 1 as indicated in the Tables 57-58.

Parts 1 and 2, of the study will start at any time, irrespective of other parts of the study.

For Parts 1 and 2, the study will consist of a screening phase (within 28 days before study intervention administration), an open-label treatment phase (Day −1 until Day 5, with single-dose treatment on Day 1 and at least 96 hours of PK for Part 1 and 120 hours of PK (Day 6) for Part 2).

TABLE 57

Part 1 Schedule of Activities

| Phase | Screening | | Open-Label (washout of 7 days between each administration of study intervention) For Part 1: Periods 1-4 | | | | | | | | | | | |
|---|---|---|---|---|---|---|---|---|---|---|---|---|---|---|
| Study Day | Days −28 to −2 | Day −1 | Day 1 | | | | | | | | | | | |
| Time | | | Predose | −30 m | 0 | +30 m | +1 h | +1 h 30 m | +2 h | +2 h 30 m | +3 h | +4 h | +6 h | +8 h | +12 h |
| Inclusion/exclusion criteria | X | X | | | | | | | | | | | | | |
| Medical history | X | | | | | | | | | | | | | | |
| Demographic information | X | | | | | | | | | | | | | | |
| Physical examination | X | X | | | | | | | | | | | | | |
| Height | X | | | | | | | | | | | | | | |

TABLE 57-continued

Part 1 Schedule of Activities

| Phase | Screening | | Open-Label (washout of 7 days between each administration of study intervention) For Part 1: Periods 1-4 | | | | | | | | | | | | |
|---|---|---|---|---|---|---|---|---|---|---|---|---|---|---|---|
| Study Day | Days −28 | Day | | | | | | | Day 1 | | | | | | |
| Time | to −2 | −1 | Predose | −30 m | 0 | +30 m | +1 h | +1 h 30 m | +2 h | +2 h 30 m | +3 h | +4 h | +6 h | +8 h | +12 h |
| Weight | X | X | | | | | | | | | | | | | |
| BMI | X | | | | | | | | | | | | | | |
| Body temperature | X | X | | | | | | | | | | | | | |
| 12-Lead ECG[a] | X | X | | | | | | | X | | | X | | X | |
| Vital signs (supine BP, pulse / heart rate)[a,o] | X | X | | | | | | | X | | | | | X | |
| Serology (HIV, HBsAg, and hepatitis C virus antibody) | X | | | | | | | | | | | | | | |
| Urine drug screen | X | X | | | | | | | | | | | | | |
| Alcohol screen[p] | X | X | | | | | | | | | | | | | |
| Urine cotinine test | X | X | | | | | | | | | | | | | |
| Hematology, chemistry, and urinalysis[a] | X | X | | | | | | | | | | | | | |
| Suicidality by C-SSRS[a,k] | X | X | | | | | | | | | | | | | |
| Severe acute respiratory syndrome coronavirus 2 (SARS-COV-2) test[j] | | X | | | | | | | | | | | | | |
| FSH[f] | X | | | | | | | | | | | | | | |
| Serum beta-HCG[b] | X | | | | | | | | | | | | | | |
| Urine pregnancy test[b] | | X | | | | | | | | | | | | | |
| Admission to clinical unit | | X | | | | | | | | | | | | | |
| Randomization to sequence[c] | | | X | | | | | | | | | | | | |
| High-fat breakfast[d] | | | | X | | | | | | | | | | | |
| Oral dose aticaprant[e] | | | | | X | | | | | | | | | | |
| Blood sample for PK; sample for aticaprant[a] | | | X | | X | X | X | X | X | X | X | X | X | X | X |
| Lunch[g] | | | | | | | | | | | | | X | | |
| Residence in clinical unit | | | | | Continuous | | | | | | | | | | |
| Adverse events | | | | | Continuous | | | | | | | | | | |
| Concomitant medication | | | | | Continuous | | | | | | | | | | |

TABLE 57

Part 1 Schedule of Activities

| Phase | Open-Label (washout of 7 days between each administration of study intervention) For Part 1: Periods 1-4 | | | | End-of-Study (Day 10 to Day 14) or Early Withdrawal |
|---|---|---|---|---|---|
| Study Day | Day 2 | Day 3 | Day 4 | Day 5 | |
| Time | +24 h +36 h | +48 h +60 h | +72 h | +96 h | |
| Physical examination | | | | | X |
| Weight | | | | X | X |
| Body temperature | | | | X | X |
| 12-Lead ECG[a] | | X | X | | X |
| Vital signs (supine BP, pulse/heart rate )[a,o] | X | X | | X | X |
| Hematology, chemistry, and urinalysis[a] | X | | | X | X |
| Suicidality by C-SSRS[a,k] | | | | X | X |

TABLE 57-continued

Part 1 Schedule of Activities

| Phase | Open-Label (washout of 7 days between each administration of study intervention) For Part 1: Periods 1-4 | | | | | End-of-Study (Day 10 to Day 14) or Early Withdrawal |
|---|---|---|---|---|---|---|
| Study Day | Day 2 | Day 3 | Day 4 | | Day 5 | |
| Time | +24 h +36 h | +48 h +60 h | +72 h | | +96 h | |
| Serum beta-HCG[b] | | | | | | X |
| Blood sample for PK; sample for aticaprant[a] | X X | X X | X | | X | |
| Discharge from clinical unit | | | | | X | |
| Residence in clinical unit | | Continuous | | | | |
| Adverse events | | | Continuous | | | |
| Concomitant medication | | | Continuous | | | |

TABLE 58

Part 2 Schedule of Activities

| Phase | Screening Days | | Open-Label (washout of 8 days between each administration of study intervention) For Part 2: Periods 1-4 | | | | | | | | | | | | |
|---|---|---|---|---|---|---|---|---|---|---|---|---|---|---|---|
| Study Day | −28 to −2 | Day −1 | Day 1 | | | | | | | | | | | | |
| Time | | | Predose | −30 m | 0 | +30 m | +1 h | +1 h 30 m | +2 h | +2 h 30 m + | +3 h | +4 h | +6 h | +8 h | +12 h |
| Inclusion/exclusion criteria | X | X | | | | | | | | | | | | | |
| Medical history | X | | | | | | | | | | | | | | |
| Demographic information | X | | | | | | | | | | | | | | |
| Physical examination | X | X | | | | | | | | | | | | | |
| Height | X | | | | | | | | | | | | | | |
| Weight | X | X | | | | | | | | | | | | | |
| BMI | X | | | | | | | | | | | | | | |
| Body temperature | X | X | | | | | | | | | | | | | |
| 12-Lead ECG[a] | X | X | | | | | | | X | | | X | | X | |
| Vital signs (supine BP, pulse/heart rate)[a,o] | X | X | | | | | | | X | | | | | X | |
| Serology (HIV, HBsAg, and hepatitis C virus antibody) | X | | | | | | | | | | | | | | |
| Urine drug screen | X | X | | | | | | | | | | | | | |
| Alcohol screen[p] | X | X | | | | | | | | | | | | | |
| Urine cotinine test | X | X | | | | | | | | | | | | | |
| Hematology, chemistry, and urinalysis[(a)] | X | X | | | | | | | | | | | | | |
| Suicidality by C-SSRS[a,k] | X | X | | | | | | | | | | | | | |
| Severe acute respiratory syndrome coronavirus 2 (SARS-COV-2) test[j] | | X | | | | | | | | | | | | | |
| ESH[f] | X | | | | | | | | | | | | | | |
| Serum beta-HCG[b] | X | | | | | | | | | | | | | | |
| Urine pregnancy test[b] | | X | | | | | | | | | | | | | |
| Admission to clinical unit | | X | | | | | | | | | | | | | |
| Randomization to sequence[c] | | | X | | | | | | | | | | | | |
| High-fat breakfast[d] | | | | X | | | | | | | | | | | |

TABLE 58-continued

Part 2 Schedule of Activities

| Phase | Screening Days | Open-Label (washout of 8 days between each administration of study intervention) For Part 2: Periods 1-4 | | | | | | | | | | | | | |
|---|---|---|---|---|---|---|---|---|---|---|---|---|---|---|---|
| Study Day | −28 | Day | | | | | | Day 1 | | | | | | | |
| Time | to −2 | −1 | Predose | −30 m | 0 | +30 m | +1 h | +1 h 30 m | +2 h | +2 h 30 m + | +3 h | +4 h | +6 h | +8 h | +12 h |
| Oral dose aticaprante | | | | | X | | | | | | | | | | |
| Blood sample for PK; sample for aticaprant[a] | | X | | | | X | X | X | X | X | X | X | X | x | X |
| Lunch[g] | | | | | | | | | | | | X | | | |
| Residence in clinical unit | | | | | | Continuous | | | | | | | | | |
| Adverse events | | | | | | Continuous | | | | | | | | | |
| Concomitant medication | | | | | | Continuous | | | | | | | | | |

TABLE 58

Part 2 Schedule of Activities

| Phase | Open-Label (washout of 8 days between each administration of study intervention) For Part 2: Periods 1-4 | | | | | | End-of-Study (Day 10 |
|---|---|---|---|---|---|---|---|
| Study Day | Day 2 | Day 3 | Day 4 | Day 5 | Day 6 | | to Day 14) or |
| Time | 4 h +2 | 6 h +3 | 8 h + 4 | 0 h + 6 | 2 h + 7 | 6 h + 9 | 0 h + 12 | Early Withdrawal |
| Physical examination | | | | | | | X |
| Weight | | | | X | X | | X |
| Body temperature | | | | X | X | | X |
| 12-Lead ECG[a] | | X | | X | X | X | X |
| Vital signs (supine BP, pulse/heart rate)[a,o] | X | X | | X | X | | X |
| Hematology, chemistry, and urinalysis[a] | X | | | | X | | X |
| Suicidality by C-SSRSask | | | | | X | | X |
| Serum beta-HCG [b] | | | | | | | X |
| Blood sample for PK; sample for aticaprant[a] | X | X | X | X | X | X | X |
| Discharge from clinical unit | | | | | | X | |
| Residence in clinical unit | | Continuous | | | | | |
| Adverse events | | | Continuous | | | | |
| Concomitant medication | | | Continuous | | | | |

For Tables 57-58:
(a) When scheduled procedures coincide, they should preferably take place in the following order: 12-lead ECG, vital signs (supine blood pressure, pulse/heart rate), blood/CSF draws for PK, or laboratory measurements, and C-SSRS.
(b) For all female participants.
(c) Period 1 only.
(d) Only in the period with dosing in fed condition. Standardized high-fat breakfast should be consumed within a 20-minute period.
(e) After at least 10-hour overnight fasting, study intervention will be administered in the morning in fasting condition where dosing is under fasting condition and 30 minutes after breakfast for the periods where dosing is under fed condition.
(f) For all postmenopausal women, FSH is done to confirm post-menopausal state in women without an alternative medical cause.
(g) After collection of the 4-hour PK blood sample and/or CSF sample.
(h) 6 mL additional blood will be collected prior to dosing in each participant for experimental work related to protein binding of parent and metabolites.
(i) Additional severe acute respiratory syndrome coronavirus 2 (SARS-CoV-2) tests may be performed per site-specific guidelines or practice.

(j) There are 2 versions of the C-SSRS. A baseline/screening version of the C-SSRS will be completed at screening, and subsequently a since-your-last-visit version of the C-SSRS will be completed predose on Day −1, prior to discharge on Day 5 of each treatment period (for Part 1) and prior to discharge on Day 6 of each treatment period (for Part 2), and at end-of-study or early withdrawal.

(k) After discharge from clinic, participants may be contacted telephonically for assessment of adverse events.

(l) Free as well as total plasma concentrations of aticaprant will be assayed.

(m)

(n) Blood pressure, pulse/heart rate, and respiratory rate will be measured after 5 minutes rest in a supine position.

(o) Either urine alcohol test or alcohol breath test will be used for alcohol screen per site-specific guidelines or practice.

(p) Prior to the insertion of the spinal catheter.

(q) Catheter tip will be used for culture analyses whenever a catheter is kept in a place for more than 24 hours.

A. Study Population

A total of approximately 80 qualified healthy adult participants are planned to be enrolled in this study: 24 participants each are to be enrolled in Parts 1 and 2 to ensure at least 20 participants in each part complete all required PK assessments. Eligible participants can be enrolled in more than one part of study if sufficient wash-out period is completed between periods by participants.

Screening for eligible participants will be performed within 28 days before administration of the study intervention.

(i) Inclusion Criteria

Each potential participant must satisfy all of the following criteria to be enrolled in the study:

For All Participants

Age
Healthy male and female participants between 18 and 55 years of age, inclusive.
Type of Participant and Disease Characteristic
Healthy on the basis of physical examination, medical history (screening only), vital signs, and 12-lead ECG performed at screening and admission to the clinical unit on Day −1 of the first treatment period. Minor abnormalities in ECG, which are not considered to be of clinical significance are acceptable.
Healthy on the basis of clinical laboratory tests performed at screening and at admission to the study center. If the results of the serum chemistry panel, hematology, or urinalysis are outside the normal reference ranges, the participant may be included. If the results of the serum chemistry panel, hematology, or urinalysis are outside the normal reference ranges, retesting of an abnormal lab value(s) that may lead to exclusion will be allowed once during the screening phase. At screening and baseline (Period 1, Day −1), ALT, AST, alkaline phosphatase and bilirubin must be within 1.5 times of upper limit of normal range and not clinically significant.
Weight
BMI (weight [kg]/height$^2$ [m]$^2$) between 18 and 29.9 kg/m$^2$ (inclusive), and body weight not less than 50 kg.
Sex and Contraceptive/Barrier Requirements
Male or female
All women participants must have a negative highly sensitive serum β-hCG pregnancy test at screening and all women participants must have a negative urine pregnancy test on Day −1 of each treatment period.

-continued

A woman must be
a. Not of childbearing potential
b. Of childbearing potential and
   Practicing a highly effective method of contraception (failure rate of <1% per year when used consistently and correctly) and agrees to remain on a highly effective method while receiving study intervention and until 90 days after last dose-the end of relevant systemic exposure.
A woman must agree not to donate eggs (ova, oocytes) or freeze for future use for the purposes of assisted reproduction during the study and for a period of at least 90 days after receiving the last dose of study intervention.
During the study and for a minimum of 1 spermatogenesis cycle (defined as approximately 3 months) after receiving the last dose of study intervention:
A male participant must agree to use a barrier method of contraception (e.g., condom) when engaging in any activity that allows for passage of ejaculate to another person.
A male participant who is sexually active with a woman who is pregnant must use a condom.
Male participants should also be advised of the benefit for a female partner to use a highly effective method of contraception as condom may break or leak.
A male participant must agree not to donate sperm for the purpose of reproduction during the study and for a minimum of 1 spermatogenesis cycle (defined as approximately 3 months) after receiving the last dose of study intervention.

Other Inclusions

Blood pressure (after the participant is [supine] for 5 minutes) between 90 mmHg and 140 mmHg systolic, inclusive, and no higher than 90 mmHg diastolic at screening and Day −1 of each treatment period.
A 12-lead ECG consistent with normal cardiac conduction and function, at screening and Day −1 of each treatment period, including:
Sinus rhythm
Heart rate between 40 and 100 beats per minute, extremes included
QTc interval ≤450 ms for males, ≤470 for females (corrected cf. Fridericia 1920; ICH E14 2005)
QRS interval of <120 ms
PR interval <210 ms
Morphology consistent with healthy cardiac conduction and function (ii) Exclusion Criteria Any potential participant who meets any of the following criteria will be excluded from participating in the study:
For All Participants:

Medical Conditions
History of or current significant medical illness including (but not limited to) cardiac arrhythmias or other cardiac disease, hematological disease, lipid abnormalities, bronchospastic respiratory disease, diabetes mellitus, renal or hepatic insufficiency, thyroid disease, neurologic or psychiatric disease, seizure disorder (uncomplicated childhood febrile seizures with no sequelae are not exclusionary) Parkinson's disease, infection, hypertension, vascular disorder, significant pulmonary disease, or any other illness.
History of malignancy within 5 years before screening (exceptions are squamous and basal cell carcinomas of the skin and carcinoma in situ of the cervix, or malignancy, which is considered cured with minimal risk of recurrence).
Known allergies, hypersensitivity, or intolerance to aticaprant or its excipients.
Presence of LBBB, AV block (second degree or higher), or a permanent pacemaker or implantable cardioverter defibrillator.
Clinically relevant GI complaints per clinical judgment at screening or baseline or history of documented gastric disease (including but not limited to documented peptic ulcer disease, gastritis [including atrophic gastritis], upper GI bleeding, Barret's esophagus, Crohn disease, ulcerative colitis, GI precancerous conditions or any other clinically relevant GI disease irritable bowel syndrome).
Participant has current or past homicidal ideation/intent within the last 6 months, or has current or past suicidal ideation with some -continued intent to act within 6 months prior to the start of the screening phase, corresponding to a response of "Yes" on Item 4 (active suicidal ideation with some intent to act, without specific plan) or Item 5 (active suicidal ideation with specific plan and intent) for suicidal ideation on the C-SSRS, or a history of suicidal behavior within the past year prior to the start of the screening phase. Participants reporting suicidal ideation with intent to act or suicidal behavior on Day −1 prior to the start of the treatment should be excluded.
Serology positive for HbsAg, HCV antibodies or HIV antibodies at screening.
Prior/Concomitant Therapy
Contraindications to the use of aticaprant or similar class of drugs (not limited to drugs such as mu-antagonists, kappa-antagonists) per local prescribing information.
Participant requires chronic use of a PPIs.
History of chronic NSAID or aspirin use. (Low dose aspirin e.g., in cardiovascular disease prevention is allowed).
Taken any disallowed therapies, Concomitant Therapy before the planned first dose of study intervention.
Use of any prescription or nonprescription medication (including vitamins, herbal supplements, and mineral supplements), except for paracetamol, hormone-based contraceptives and hormonal replacement therapy within 14 days before the first dose of the study intervention is scheduled until completion of the study.
Prior/Concurrent Clinical Study Experience
Received an investigational intervention (including investigational vaccines) or used an invasive investigational medical device within at least 1 month, before the planned first dose of study intervention or is currently enrolled in an investigational study.
Pregnant, or breast-feeding, or planning to become pregnant while enrolled in this study or within 1 month after the last dose of study intervention.
Plans to father a child while enrolled in this study or within 3 months after the last dose of study intervention.
Diagnostic Assessments
Had major surgery, (e.g., requiring general anesthesia) within 12 weeks before screening, or will not have fully recovered from surgery, or has surgery planned during the time the participant is expected to participate in the study.
History of substance or alcohol use disorder according to DSM-5 criteria within 6 months before Screening or positive test result(s) for alcohol, nicotine metabolites or drugs of abuse (including barbiturates, opioids [including methadone], cocaine, cannabinoids, amphetamines, methamphetamines, hallucinogens such as PCP and LSD, and benzodiazepines) at Screening or Day −1 of each treatment period.

Other Exclusions

Donated blood or blood products or plasma or had substantial loss of blood (more than 500 mL) within 3 months before the first administration of study intervention in each part of the study or intention to donate blood or blood products during the study.

Unable to swallow solid, oral dosage forms whole with the aid of water (participants may not chew, divide, dissolve, or crush the study intervention).

History of smoking or use of nicotine-containing substances within the previous 3 months prior to screening, as determined by medical history or participant's verbal report.

Vulnerable participants (e.g., a person kept in detention).

Drinks, on average, more than 8 cups of tea/coffee/cocoa/cola or other caffeinated beverages per day.

Clinically significant acute illness within 7 days prior to study intervention administration.

History of clinically significant drug and/or food allergies.

(iii) Meals and Dietary Restrictions

1. Participants may not consume any food or beverages containing, grapefruit juice, Seville oranges (including any orange marmalade), or quinine (e.g., tonic water) from 48 hours (72 hours in the case of grapefruit juice and Seville oranges) before the first dose of study intervention until the last dose of study intervention.

2. No water will be allowed within 2 hours before study intervention with the exception of 240 mL of noncarbonated water to take the oral study intervention and water given with high-fat breakfast. No water is allowed until 2 hours after dosing, after which time, water is allowed ad libitum.

3. Must not consume any foods or drinks (including additional salt or sugar) other than those provided by the study site personnel during domiciled inpatient periods.

4. Must refrain from the use of any methylxanthine-containing products, (e.g., chocolate bars or beverages, energy drinks if it contains methylxanthine, coffee, teas, or colas) from 48 hours before administration of study intervention and during confinement, and also must avoid excessive use of caffeine (i.e., no more than approximately 500 mg/day, as contained in 5 cups of tea or coffee or 8 cans of cola) for the entire study period (including the screening period and follow-up visit).

5. May not consume food containing poppy seeds during the study starting 72 hours before screening or 72 hours before admission to study site in each treatment period (in order to avoid false positive urine drug test for codeine).

Caffeine, Alcohol, Tobacco, and Drugs of Abuse

1. Smoking cigarettes (or equivalent) and/or the use of nicotine-based products is not allowed from 3 months prior to screening until completion of the follow-up visit.

2. The use of alcohol should be limited to the absolute minimum. Best is to use no alcohol at all from the first screening visit until the follow-up visit. If any alcohol is taken, up to 2 standard drinks consumptions daily, will be allowed. A standard drink is defined as: a 350 mL glass of 5% ABV beer, a 150 mL glass of 12% ABV wine, or a 45 mL glass of a 40% ABV (80 proof) spirit.

Activity

1. Strenuous exercise may affect study specified assessments and safety laboratory results; for this reason, strenuous exercise should be avoided within 48 hours before all planned study visits and during stays in the CRC. Prior exercise will be allowed if the participant's serum creatinine concentration is within the normal range. Minor abnormalities, which are not considered to be of clinical relevance, are acceptable.

2. Participants will be advised not to donate blood for at least 3 months after completion of the study or to participate in an investigational drug study for at least 1 month after completion of the study.

B. Study Intervention

All study intervention will be taken in the morning on Day 1 of each treatment period with 240 mL of noncarbonated water. Study intervention must be swallowed whole and not chewed, divided, dissolved, or crushed.

For each participant, all doses must be administered at approximately the same time.

Participants receiving study intervention in the fasted condition will fast overnight for at least 10 hours.

Participants receiving study intervention in the fed condition will fast overnight (at least 10 hours) followed by the consumption of a high-fat breakfast within a 20-minute period. The high-fat breakfast will be the same on the day of dosing in the fed period (Period 4 for Part 1 and Part 2).

Study intervention will be administered approximately 30 minutes after the start of the breakfast.

Noncarbonated water will be allowed up to 2 hours before study intervention administration. Participants will continue fasting until at least 4 hours after study intervention administration. At approximately 2 hours after dosing (but not earlier), drinking of water is allowed ad-libitum onwards. A standardized lunch will be served on Day 1 for all participants after collection of the 4-hour PK blood sample. Participant can resume their normal diet after 4 hours.

The exact composition of breakfast and the lunch will be recorded. The lunch will be the same in all intervention periods. The exact start and end time of breakfast, as well as the start time of lunch will be recorded, together with any deviation regarding the timing of the meals.

Aticaprant will be supplied for this study as 5 mg capsule and 5 mg and 10 mg tablet formulation.

Concomitant Therapy

Prestudy therapies administered up to 30 days before first dose of study intervention must be recorded at screening.

All therapies (prescription or over-the-counter medications, including vaccines, vitamins, herbal supplements; non-pharmacologic therapies such as electrical stimulation, acupuncture, special diets, exercise regimens, or other specific categories of interest) different from the study intervention must be recorded. Recorded information will include a description of the type of therapy, duration of use, dosing regimen, route of administration, and indication. Modification of an effective preexisting therapy should not be made for the explicit purpose of entering a participant into the study.

All concomitant therapies that are considered to be a CYP inhibitor or inducer or a transport inhibitor or inducer are disallowed during the study and disallowed for at least 1 month before receiving the first intake of study intervention.

Throughout the study, prescription or nonprescription medication (including vitamins and herbal supplements) other than the study intervention are prohibited, except for paracetamol. Throughout the study, a maximum of 3 doses per day of 500 mg paracetamol, and no more than 3 g per week, will be allowed for the treatment of headache or other pain.

Women using hormonal contraceptives as a means of birth control must continue to use the same hormonal contraceptives throughout the study. Women using hormone replacement therapy must continue to use the same hormone replacement therapy throughout the study.

C. Study Assessments

Tables 59-60 summarize the frequency and timing of PK measurements applicable to this study.

If multiple assessments are scheduled for the same timepoint, they should preferably take place in the following order: 12-lead ECG, vital signs (supine blood pressure, pulse/heart rate), blood/CSF draws for PK or laboratory measurements, and C-SSRS. Blood collections for PK assessments should be kept as close to the specified time as possible. Other measurements may be done earlier than specified timepoints, if needed.

For each participant, the maximum amount of blood drawn from each participant will not exceed 500 mL.

The total volume of CSF collected per participant enrolled in CSF PK will not exceed 52.3 mL which is considered to be acceptable considering the daily CSF production rate.

TABLE 59

Volume of Blood to be Collected From Each Participant (Part 1)

| Type of Sample | Volume per Sample (mL) | No. of Samples per Participant | Approximate Total Volume of Blood (mL)[a] |
|---|---|---|---|
| Pharmacokinetic samples | 4 mL | 68 | 272 |
| Loss by use of indwelling intravenous cannula | 1 mL | 68 | 68 |
| Approximate Total[c] | | | 442 |

[a]Calculated as number of samples multiplied by amount of blood per sample.
b.
[c]Repeat or unscheduled samples may be taken.
Note:
An indwelling intravenous cannula may be used for blood sample collection. If a mandarin (obturator) is used, blood loss due to discard is not expected.

TABLE 60

Volume of Blood to be Collected From Each Participant (Part 2)

| Type of Sample | Volume per Sample (mL) | No. of Samples per Participant | Approximate Total Volume of Blood (mL)[a] |
|---|---|---|---|
| Pharmacokinetic samples | 4 mL | 72 | 288 |
| Loss by use of indwelling intravenous cannula | 1 mL | 72 | 72 |
| Approximate Total[c] | | | 462 |

[a]Calculated as number of samples multiplied by amount of blood per sample.
b.
[c]Repeat or unscheduled samples may be taken.
Note:
An indwelling intravenous cannula may be used for blood sample collection. If a mandarin (obturator) is used, blood loss due to discard is not expected.

(i) Vital Signs

Body temperature, pulse/heart rate, respiratory rate, blood pressure will be assessed.

Blood pressure and pulse/heart rate measurements will be assessed with a completely automated device consisting of an inflatable cuff and an oscillatory detection system. All values will be registered on a built-in recorder so that measurements are observer-independent. Blood pressure and pulse/heart rate measurements will be recorded after 5 minutes rest in a quiet setting without distractions (e.g., television, cell phones) in a supine position.

(ii) Electrocardiograms

During the collection of ECGs, participants should be in a quiet setting without distractions (e.g., television, cell phones). Participants should rest in a supine position for at least 5 minutes before ECG collection and should refrain from talking or moving arms or legs. If blood sampling or vital sign measurement is scheduled for the same time point as ECG recording, they should preferably take place in the following order: 12-lead ECG, vital signs (supine blood pressure, pulse/heart rate), blood/CSF draws for PK, or laboratory measurements, and C-SSRS.

(iii) Columbia Suicide Severity Rating Scale (C-SSRS)

The C-SSRS is a measure of the spectrum of suicidal ideation and behavior that was developed to assess severity and track suicidal events through any treatment studies. It is a clinical interview to assess the risk of treatment-emergent suicidal ideation/behavior.

There are 2 versions of the C-SSRS. A baseline/screening version of the C-SSRS will be completed at screening, and subsequently a since-your-last-visit version of the C-SSRS will be completed predose on Day −1, prior to discharge on Day 5 of each treatment period (for Part 1), prior to discharge on Day 6 of each treatment period (for Part 2) and at end-of-study or early withdrawal.

(iv) Fundoscopy

Fundoscopy is a form of examination of the fundus of the eye. The WelchAllyn® PanOptic™ Ophthalmoscope (model 11810) is used according to the internal standard operating procedure.

(v) Pharmacokinetics

Plasma and CSF samples will be used to evaluate the PK of aticaprant.

Evaluations

Blood samples (4 mL each) for determination of aticaprant plasma concentrations will be collected at the time points indicated in Tables 59-60.

Analytical Procedures

During the study, serial blood samples (4 mL each) for determination of aticaprant plasma concentrations, will be collected at the time points as indicated in Tables 59-60.

Plasma samples will be analyzed to determine concentrations of aticaprant using a validated, specific, and sensitive Liquid chromatography coupled to tandem mass spectrometry (LC-MS/MS) method.

Parameters

The following plasma PK parameters of aticaprant will be determined. A noncompartmental model with extravascular input will be used for the pharmacokinetic analysis.

Based on the individual concentration-time data, using the actual sampling times, the following PK parameters will be derived for aticaprant:

| | |
|---|---|
| $C_{max}$ | Maximum observed plasma concentration |
| $T_{max}$ | The actual sampling time to reach $C_{max}$ |
| $AUC_{last}$ | area under the plasma concentration-time curve from 0 to t last hours postdosing, calculated by trapezoidal summation (time t last is the time of the last quantifiable concentration $C_{last}$) |
| $AUC\infty$ | $AUC_{last}$ extrapolated to infinity, calculated as $AUC_{last} + C_{last}/\lambda z$ |
| $t^{1/2}$ | Terminal half-life, defined as $0.693/\lambda_z$ |
| $\lambda_z$ | Elimination rate constant, determined by linear regression of the terminal points of the log-linear plasma concentration-time curve |
| CL/F | Apparent clearance (assessed for aticaprant) |
| Vd/F | Apparent volume of distribution (assessed for aticaprant) |

The following requirements should be met for an acceptable calculation of $t_{1/2}$, $\lambda_z$, and $AUC_\infty$:

A) at least 3 data points are used in the calculation, otherwise $t_{1/2}$, $\lambda_z$ and $AUC_\infty$ are not assessable.

B) coefficient of determination ($r^2$ adj) is at least 0.90.

If requirement (B) is not met, $t_{1/2}$, $\lambda_z$, and $AUC_\infty$ will be reported as approximations.

Actual sampling times will be checked for major aberrations. In case a major aberration occurs for an actual sampling time of >20.00% deviation from the scheduled time, this plasma concentration will be excluded from descriptive statistics in the plasma concentration table.

Sample Size Determination

The intra-participant coefficient of variation (CV) for PK parameters ($AUC_\infty$ and $C_{max}$) is estimated to be between 8.3% and 10.4% for $AUC_\infty$ and between 14.4% and 24.3% for $C_{max}$. Thus, an intra-participant CV of 25% was used for this sample size justification.

With the selected intra-participant CV of 25% and N=20 or 24 completers, the limits where the point estimate of the ratio of geometric means for PK parameters ($AUC_\infty$ and $C_{max}$) in relative bioavailability (test formulation versus reference formulation), food effect (fed versus fasted condition), and dose proportionality with normalized PK parameters will fall are given in Table 61.

TABLE 61

Precision Estimates for Relative Bioavailability, Dose Proportionality, and Food Effect of Study Subpart 1A, Subpart 1B, Subpart 2A, Subpart 2B

| Study Part | Purpose | N | Lower Limit (%) | Upper Limit (%) |
|---|---|---|---|---|
| Subpart 1A, and/or Subpart 2A | Relative Bioavailability and/or Dose Proportionality | 20 | 87.7 | 114.0 |
| | | 24 | 88.7 | 112.7 |
| Subpart 1B, Subpart 2B | Food Effect | 20 | 87.4 | 114.4 |
| | | 24 | 88.5 | 113.0 |

Lower and Upper limit are given as % of true ratio of means with 90% confidence.

24 participants will be enrolled to ensure 20 participants complete the study. If 20 participants do not complete the study, additional participants can be recruited.

Populations for Analysis Sets

For purposes of analysis, the following populations are defined:

| Population | Description |
|---|---|
| Enrolled | All participants who sign the consent and not screen failures. |
| Randomized | All participants who were randomized in the study |
| Pharmacokinetics | All randomized participants who take at least 1 dose of study intervention and have at least one estimated PK parameter. |

Statistical Analyses

The statistical analysis plan will be finalized prior to DBL and it will include a more technical and detailed description of the statistical analyses described in this section. This section is a summary of the planned statistical analyses of the most important endpoints.

Initial Participant Characteristics

For all participants who received at least one dose of study intervention, descriptive statistics (mean, standard deviation, median, minimum, and maximum) will be performed for age, BMI, weight, and height. Sex and race will be listed and tabulated.

Pharmacokinetic Analyses

Data will be listed for all participants with available plasma concentrations per intervention. All concentrations below the limit of quantification (LOQ) or missing data will be labeled as such in the concentration data listings. Concentrations below the LOQ will be treated as zero in the summary statistics and for the calculation of pharmacokinetic parameters. All participants and samples excluded from analysis will be clearly documented in the clinical study report.

Factors that may influence the plasma concentrations (e.g., vomiting, high predose concentration) will be checked. Reasons for exclusion of a participant or a sample from the analysis include, but are not limited to, the following:

Predose aticaprant plasma concentrations higher than 5% of $C_{max}$

Vomiting (within 3 hours post-dose under fasting conditions and 8 hours post-dose under fed conditions) after study intervention administration for immediate-release products. (Considering median $T_{max}$ of 1.5 hours under fasting conditions and median $T_{max}$ of 4 hours under fed conditions)

If the % $AUC_{\infty,ex}$ exceeds 20% for a given participant, that participant will be excluded from the statistical analysis of $AUC_\infty$ Too few data (greater than 10% missing values per each participant)

Noncompliance with study procedures affecting pharmacokinetics (e.g., comedication)

All participants and samples excluded from the analysis will be clearly documented in the study report.

For each intervention, descriptive statistics, including arithmetic mean, standard deviation (SD), coefficient of variation (CV), geometric mean, median, minimum, and maximum will be calculated for the aticaprant plasma concentrations at each sampling time and for all PK parameters of aticaprant.

For relative bioavailability, graphical representations of the results will include (but are not limited to) the following graphs for aticaprant:

Log-linear and linear-linear plasma concentration-time profiles for each individual Log-linear and linear-linear plasma concentration-time profiles for the mean values per intervention Log-linear and linear-linear plasma concentration-time profiles for the median values per intervention Log-linear and linear-linear overlay plots of the individual plasma concentration-time profiles for each intervention A graphical comparison of the individual and mean (±SD) primary PK parameters of aticaprant for each intervention For dose proportionality, graphical representations of the results will include (but are not limited to) the following graphs for aticaprant:

Log-linear and linear-linear plasma concentration-time profiles for each individual, for all dose levels.

Overlay graph with the observed mean plasma concentration-time profiles on a log-linear and linear-linear scale for all dose levels. Overlay graph with the mean dose-normalized plasma concentration-time profiles on a log-linear and linear-linear scale.

A graph with the observed individual values of $C_{max}$, $AUC\infty$, $AUC_{last}$ and/or AUC truncated to a common time point versus the dose;

A graph with the observed dose-normalized individual values of $C_{max}$, $AUC\infty$, $AUC_{last}$ and/or AUC truncated to a common time point versus the dose;

The primary objective of the statistical analysis will be to estimate the relative bioavailability of aticaprant test formulations with respect to aticaprant reference formulations, dose proportionality of aticaprant test formulations, and the effect of food on the PK of aticaprant test formulations.

The primary parameters of interest for the statistical analysis will be the log-transformed estimated AUCs, $AUC_{last}$, $AUC_\infty$, and $C_{max}$. The $AUC_\infty$ will be rejected as primary parameter for a group if more than half of the participants do not have a reliable value. If one of PK parameter of interest is not estimable for a given participant in one or more periods, the participant's data will not be included in the statistical analysis of that particular PK parameter.

For the relative bioavailability and dose proportionality in Subpart 1A (i.e., only the first 3 periods will be included in this analysis), after dose-normalized $AUC_{last}$, $AUC_\infty$, and $C_{max}$ for Treatment C, a mixed-effects model that includes treatment, period, and treatment sequence as fixed effects, and participant as a random effect will be used to estimate the least squares means and intra-participant variance. Using these estimated least squares means and intra-participant variance, the point estimate and 90% confidence intervals for the difference in means on a log scale between Treatment B (Test) and Treatment A (Reference), and between Treatment C (Test) and Treatment B (Reference) will be constructed. The limits of the confidence intervals will be back-transformed using antilogarithms to obtain 90% confidence intervals for the ratios of the mean AUCs and $C_{max}$ of the test to reference formulation (Treatment B/Treatment A and Treatment C/Treatment B). For the relative bioavailability and dose proportionality in Subpart 2A, similar analyses will be carried out for Treatment E, Treatment F, and Treatment G.

For the food effect in both Subpart 1B (Treatment D versus Treatment B) and Subpart 2B (Treatment H versus Treatment F), mixed-effects models will be fit to the data with the logarithm of PK parameters as the dependent variable, treatment (fed versus fasted) as a fixed effect, and participant as a random effect. Using these estimated least squares means and intra-participant variance from the mixed-effects models, the point estimate and 90% confidence intervals for the difference in means on a log scale between Treatment D (fed) and Treatment B (fasted), and Treatment H (fed) and Treatment F (fasted) will be constructed. The limits of the confidence intervals will be back-transformed using antilogarithms to obtain 90% confidence intervals for the corresponding ratios of the mean AUCs and $C_{max}$ under fed to fasted conditions.

D. Results

This study included two parts with similar study design to investigate two different tablet formulation concepts with part 1 (unmilled API tablet) and part 2 (milled API tablet). Within each part, the evaluations included relative bioavailability of immediate-release tablet formulation (1×10 mg) versus API in capsule formulation (2×5 mg), dose-proportionality between 10 and 5 mg tablet strengths, and food effect assessment at 10 mg of tablet strength. Each part consisted of a subpart A and subpart B with a total of 4 periods. Subpart A was a randomized, open label, 3-way crossover, 3-period study conducted in 24 healthy participants to evaluate the relative bioavailability of a single dose of 10 mg aticaprant administered as 1×10 mg oral tablet under fasted conditions compared to 10 mg aticaprant administered as 2×5 mg oral capsules under fasted conditions and to evaluate the dose proportionality of a single dose of 5 mg aticaprant administered as 1×5 mg oral tablet under fasted conditions compared to the 1×10 mg oral tablet under fasted conditions. The same 24 participants who completed subpart A were enrolled in subpart B which consisted of a fourth period to evaluate the food effect of a single dose of 10 mg aticaprant administered as 1×10 mg oral tablet under fed conditions.

The PK analysis results for part 1 (unmilled API tablet formulation) including the PK parameters across treatments and statistical comparisons between treatments of interest are shown in Tables 62-65. Table 62 summarizes PK parameters across treatments in Part 1. Table 63 shows the statistical comparison results of the relative bioavailability of a 1×10 mg unmilled API tablet with 2×5 mg API in capsule formulation. Table 64 shows the statistical comparison results of the dose-proportionality between 1×10 mg unmilled API tablet and 1×5 mg unmilled API tablet formulation. Table 65 shows the statistical comparison results of food effect assessment with 1×10 mg unmilled API tablet when administered in the presence of high-fat diet to that of fasted condition. The results of the PK parameters were comparable between unmilled API tablet (1×10 mg) and API in capsule (2×5 mg) formulation and the statistical assessment using calculated geometric mean ratios indicated that these two formulations are comparable and within the BE limits of criteria. A dose-proportionality was established between 10 and 5 mg unmilled API tablet formulation strengths based on dose-dependent increase in PK parameters, a comparison of dose-normalized PK parameters and statistical assessment of calculated geometric mean ratios being within BE limits of 0.8 to 1.25. Finally, unmilled API tablet formulation showed ~40% increase in AUC when 10 mg given in the presence of high-fat diet compared to fasted condition administration as evident from geometric mean ratio calculated for AUC.

The PK analysis results for part 2 (milled API tablet formulation) including the PK parameters across treatments and statistical comparisons between treatments of interest are shown in Tables 66-73. Table 70 summarizes PK parameters across treatments in Part 2. Table 71 shows the statistical comparison results of the relative bioavailability of a 1×10 mg milled API tablet with 2×5 mg API in capsule formulation. Table 72 shows the statistical comparison results of the dose-proportionality between 1×10 mg milled API tablet and 1×5 mg milled API tablet formulation. Table 73 shows the statistical comparison results of food effect assessment with 1×10 mg milled API tablet when administered in the presence of high-fat diet to that of fasted condition. The results of the PK parameters were comparable between milled API tablet (1×10 mg) and API in capsule (2×5 mg) formulation and the statistical assessment using calculated geometric mean ratios indicated that these two formulations are comparable and within the BE limits of criteria. A dose-proportionality was established between 10 and 5 mg milled API tablet formulation strengths based on dose-dependent increase in PK parameters, a comparison of dose-normalized PK parameters and statistical assessment of calculated geometric mean ratios being within BE limits of 0.8 to 1.25. Finally, milled API tablet formulation showed ~30% increase in AUC when 10 mg given in the presence of high-fat diet compared to fasted condition administration as evident from geometric mean ratio calculated for AUC.

In summary, both the milled and unmilled API tablet formulations of 1×10 mg showed similar comparable exposures for aticaprant as those were observed with 10 mg reference API in capsule formulation (2×5 mg API in capsules) and were bioequivalent. A dose-proportionality was observed between 10 and 5 mg tablet formulation strengths of each of the tablet formulation concepts of unmilled and milled API. A modest food effect of ~30% (milled API tablet) and ~40% (unmilled API tablet) increase in AUC was observed at 10 mg with a slightly delayed median $T_{max}$ of 2.00 hours (milled API tablet) and 2.75 hours (unmilled API tablet) in presence of high-fat diet vs. 1.5 hours in the fasted condition administration. A 40% food effect is not considered clinically relevant for many drugs given it is part of PK variability and no safety concerns exist at higher aticaprant exposures. Aticaprant can therefore be administered with or without food.

(i) PK Parameters

TABLE 66

Summarized PK Parameters of Aticaprant

| Pharmacokinetic Parameters of Aticaprant (mean [SD], $t_{max}$: median [range]) | Treatment | | | | |
|---|---|---|---|---|---|
| | A | B | C | C Dose Normalized | D |
| n | 23 | 21 | 21 | 21 | 20 |
| $C_{max}$ (ng/mL) | 31.2 (6.90) | 34.1 (10.0) | 17.0 (4.48) | 33.9 (8.97) | 37.7 (9.18) |
| $t_{max}$ (h) | 1.50 (1.00-2.50) | 1.50 (1.00-2.00) | 1.50 (1.00-3.00) | — | 2.75 (1.00-4.00) |
| $AUC_{last}$ (h * ng/mL) | 304 (77.7) | 283 (76.2) | 143 (39.9) | 286 (79.7) | 398 (87.6) |
| $AUC_\infty$ (h * ng/mL) | 315 (83.7)[a] | 301 (80.1) | 155 (43.2) | 309 (86.4) | 425 (101)[b] |
| $\lambda_z$ (1/h) | 0.030 (0.010)[a] | 0.029 (0.010) | 0.035 (0.017) | — | 0.031 (0.010)[b] |
| $t_{1/2}$ (h) | 26.3 (10.2)[a] | 26.6 (8.12) | 24.7 (11.2) | — | 24.5 (8.05)[b] |
| CL/F (L/h) | 34.5 (11.6)[a] | 36.2 (12.5) | 35.8 (14.4) | — | 25.0 (6.83)[b] |
| Vd/F (L) | 1248 (546)[a] | 1335 (448) | 1150 (394) | — | 835 (187)[b] |

Treatment A: 2 × 5 mg oral capsule administered in the morning, after at least 10-hour overnight fasting Treatment B: 1 × 10 mg Formulation Concept 1 administered in the morning, after at least 10-hour overnight fasting Treatment C: 1 × 5 mg Formulation Concept 1 administered in the morning, after at least 10-hour overnight fasting Treatment D: 1 × 10 mg Formulation Concept 1 administered in the morning approximately 30 minutes after the start of a standardized high-fat breakfast following at least 10-hour overnight fasting

[a] n = 21,

[b] n = 19

5 mg dose normalized to 10 mg (ii) Relative BA Assessment

1×10 mg unmilled API tablet concept may show similar exposures for aticaprant as those were observed with 10 mg reference API in capsule formulation (2×5 mg API in capsules)

TABLE 67

Relative BA Testing (10 mg Tablet vs. 10 mg reference capsule) - Summarized statistical results for Estimated Ratio of Means and 90% Confidence Interval : Treatment B/Treatment A-Aticaprant-For completers (Relative Bioavailability); Phamacokinetics Data Analysis Set

| Analyte | PK Parameter | N | | Treatment | | Geometric Means | | |
|---|---|---|---|---|---|---|---|---|
| | | A (Reference) | B (Test) | A (Reference) | B (Test) | Ratio of Geometric Means (%) | 90% CI (%) | Intra-participant CV (%) |
| Aticaprant | $C_{max}$ | 20 | 20 | 30.2 | 32.8 | 108.64 | 99.25-118.92 | 17.0 |
| | $AUC_{last}$ | 20 | 20 | 291 | 271 | 93.31 | 87.41-99.62 | 12.2 |
| | $AUC_\infty$ | 19 | 19 | 305 | 287 | 94.14 | 88.19-100.49 | 11.9 |

Note:
Log transformed PK parameters were analyzed by mixed model analysis of variance with treatment, sequence, and period as fixed effects, and participant in sequence as a random effect and the results were back-transformed using anti-logarithm.
Participants who completed all treatment periods and for which an evaluable PK parameter could be obtained in all treatment periods are included in the analysis.
N: number of participants who completed the study and for which an evaluable PK parameter could be obtained.
Intra-participant CV(%) = 100* (sqrt(exp(MSE)-1).
Treatment A: 2 × 5 mg oral capsule administered in the morning, after at least 10-hour overnight fasting (Reference)
Treatment B: 1 × 10 mg Formulation Concept 1 administered in the morning, after at least 10-hour overnight fasting (Test)

(iii) Dose-Proportionality

Dose-proportionality may be observed between 1×10 mg unmilled API tablet vs. 1×5 mg unmilled API tablet

TABLE 68

Dose-proportionality testing (10 mg Tablet vs. 5 mg tablet) - Summarized statistical results for Estimated Ratio of Means and 90% Confidence Interval: Treatment B/Treatment A-ATICPARANT-For completers (Dose proportionality); Pharmacokinetics Data Analysis Set

| Analyte | PK Parameter | N | | Treatment | | Geometric Means | | |
|---|---|---|---|---|---|---|---|---|
| | | B (Reference) | C (Test) | B (Reference) | C (Test) | Ratio of Geometric Means (%) | 90% CI (%) | Intra-participant CV (%) |
| Aticaprant | $C_{max}$ | 20 | 20 | 32.8 | 33.5 | 102.12 | 93.23-111.86 | 17.0 |
| | $AUC_{last}$ | 20 | 20 | 271 | 280 | 103.20 | 96.63-110.23 | 12.2 |
| | $AUC_\infty$ | 19 | 19 | 287 | 299 | 103.93 | 97.34-110.98 | 11.9 |

Note:
Log transformed PK parameters were analyzed by mixed model analysis of variance with treatment, sequence, and period as fixed effects, and participant in sequence as a random effect and the results were back-transformed using anti-logarithm.
Participants who completed all treatment periods and for which an evaluable PK parameter could be obtained in all treatment periods are included in the analysis.
N: number of participants who completed the study and for which an evaluable PK parameter could be obtained.
Intra-participant CV(%) = 100* (sqrt(exp(MSE)-1).
Treatment B: 1 × 10 mg Formulation Concept 1 administered in the morning, after at least 10-hour overnight fasting (Reference)
Treatment C: 1 × 5 mg Formulation Concept 1 administered in the morning, after at least 10-hour overnight fasting (Test)
5 mg dose normalized to 10 mg (iv) Food-Effect Food effect (high-fat diet) was observed for 10 mg unmilled API tablet (~44% increase in AUC) with delayed $T_{max}$ to ~3 hours in presence of high-fat diet vs. 1.5 hours in the absence of high-fat diet.

TABLE 69

Food Effect testing (10 mg Tablet vs. 10 mg tablet in presence of high-fat diet) -
Summarized statistical results for Estimated Ratio of Means and 90% Confidence Interval for
Aticaprant: Treatment D/Treatment B-For completers (Food Effect); Pharmacokinetics Data
Analysis Set

| Analyte | PK Parameter | N Treatment B (Reference) | N Treatment D (Test) | Geometric Means B (Reference) | Geometric Means D (Test) | Ratio of Geometric Means (%) | 90% CI (%) | Intra-participant CV (%) |
|---|---|---|---|---|---|---|---|---|
| Aticaprant | $C_{max}$ | 20 | 20 | 32.6 | 36.6 | 112.49 | 100.49-125.93 | 20.9 |
|  | $AUC_{last}$ | 20 | 20 | 270 | 388 | 144.01 | 135.53-153.02 | 11.1 |
|  | $AUC_\infty$ | 19 | 19 | 287 | 413 | 143.84 | 135.29-152.94 | 10.9 |

Note:
Log transformed PK parameters were analyzed by mixed model analysis of variance with treatment as fixed effect and participant as a random effect and the results were back-transformed using anti-logarithm.
Participants who completed all treatment periods and for which an evaluable PK parameter could be obtained in all treatment periods are included in the analysis.
N: number of participants who completed the study and for which an evaluable PK parameter could be obtained.
Intra-participant CV(%) = 100* (sqrt(exp(MSE)-1).
Treatment B: 1 × 10 mg Formulation Concept 1 administered in the morning, after at least 10-hour overnight fasting (Reference)
Treatment D: 1 × 10 mg Formulation Concept 1 administered in the morning approximately 30 minutes after the start of a standardized high-fat breakfast following at least 10-hour overnight fasting (Test)

TABLE 70

Summarized PK Parameters of Aticaprant in Part 2

| Pharmacokinetic Parameters of Aticaprant (mean [SD], $t_{max}$: median [range]) | E | F | G | G Dose Normalized | H |
|---|---|---|---|---|---|
| n | 22 | 22 | 23 | 23 | 21 |
| $C_{max}$ (ng/mL) | 31.7 (9.41) | 32.4 (7.39) | 17.4 (5.81) | 34.7 (11.6) | 34.0 (9.99) |
| $t_{max}$ (h) | 2.00 (1.00-6.00) | 1.50 (1.00-2.50) | 1.00 (1.00-4.00) |  | 2.00 (1.00-6.00) |
| $AUC_{last}$ (h * ng/mL) | 308 (108) | 297 (123) | 157 (80.1) | 314 (160) | 388 (135) |
| $AUC_\infty$ (h * ng/mL) | 307 (80.8)[a] | 318 (148) | 154 (37.0)[a] | 308 (74.1)[a] | 388 (81.7)[b] |
| $\lambda_z$ (1/h) | 0.024 (0.006)[a] | 0.024 (0.007) | 0.030 (0.013)[a] |  | 0.025 (0.009)[b] |
| $t_{1/2}$ (h) | 30.5 (6.98)[a] | 31.0 (8.05) | 26.6 (9.45)[a] |  | 30.8 (8.27)[b] |
| % $AUC_{\infty, ex}$ (%) | 5.02 (2.06)[a] | 5.50 (3.17) | 6.93 (2.25)[a] |  | 4.92 (2.51)[c] |
| CL/F (L/h) | 34.8 (9.82)[a] | 35.8 (12.1) | 34.7 (10.7)[a] |  | 27.0 (6.38)[b] |

[a] n = 21,
[b] n = 19,
[c] n = 20

Treatment E: 2 × 5 mg oral capsule administered in the morning, after at least 10-hour overnight fasting
Treatment F: 1 × 10 mg Formulation Concept 2 administered in the morning, after at least 10-hour overnight fasting
Treatment G: 1 × 5 mg Formulation Concept 2 administered in the morning, after at least 10-hour overnight fasting
Treatment H: 1 × 10 mg Formulation Concept 2 administered in the morning approximately 30 minutes after the start of a standardized high-fat breakfast following at least 10-hour overnight fasting Participant 100029, Treatment F (incomplete profile) and 100031 (vomiting) hence excluded

TABLE 71

Statistical comparison results of the relative bioavailability of a 1 × 10 mg milled API tablet
(test) with 2 × 5 mg API in capsule formulation (reference).
Summarized statistical results for Estimated Ratio of Means and 90% Confidence Interval:
Treatment F/Treatment E - Aticaprant - For completers (Relative Bioavailability); Pharmacokinetics
Data Analysis Set

| Analyte | PK Parameter | N Treatment E (Reference) | N Treatment F (Test) | Geometric Means E (Reference) | Geometric Means F (Test) | Ratio of Geometric Means (%) | 90% CI (%) | Intra-participant CV (%) |
|---|---|---|---|---|---|---|---|---|
| Aticaprant | $C_{max}$ | 21 | 21 | 30.2 | 30.9 | 102.30 | 94.30-110.97 | 15.6 |

TABLE 71-continued

Statistical comparison results of the relative bioavailability of a 1 × 10 mg milled API tablet (test) with 2 × 5 mg API in capsule formulation (reference).
Summarized statistical results for Estimated Ratio of Means and 90% Confidence Interval: Treatment F/Treatment E - Aticaprant - For completers (Relative Bioavailability); Pharmacokinetics Data Analysis Set

| Analyte | PK Parameter | N Treatment | | | | Geometric Means | | |
|---|---|---|---|---|---|---|---|---|
| | | E (Reference) | F (Test) | E (Reference) | F (Test) | Ratio of Geometric Means (%) | 90% CI (%) | Intra-participant CV (%) |
| | $AUC_{last}$ | 21 | 21 | 291 | 274 | 94.31 | 89.93-98.90 | 9.1 |
| | $AUC_\infty$ | 20 | 20 | 297 | 279 | 93.66 | 89.58-97.93 | 8.3 |

Note:
Log transformed PK parameters were analyzed by mixed model analysis of variance with treatment, sequence, and period as fixed effects, and participant in sequence as a random effect and the results were back-transformed using anti-logarithm.
Participants who completed all treatment periods and for which an evaluable PK parameter could be obtained in all treatment periods are included in the analysis.
N: number of participants who completed the study and for which an evaluable PK parameter could be obtained.
Intra-participant CV(%) = 100* (sqrt(exp(MSE)-1).
Treatment E: 2 × 5 mg oral capsule administered in the morning, after at least 10-hour overnight fasting (Reference)
Treatment F: 1 × 10 mg Formulation Concept 2 administered in the morning, after at least 10-hour overnight fasting (Test).

TABLE 72

Statistical comparison results of the dose-proportionality between 1 × 10 mg milled API tablet (reference) and 1 × 5 mg milled API tablet formulation (test).
Summarized statistical results for Estimated Ratio of Means and 90% Confidence Interval: Treatment G/Treatment F- ATICAPTANT- For completers (Dose proportionality); Pharmacokinetics Data Analysis Set

| Analyte | PK Parameter | N Treatment | | | | Geometric Means | | |
|---|---|---|---|---|---|---|---|---|
| | | F (Reference) | G (Test) | F (Reference) | G (Test) | Ratio of Geometric Means (%) | 90% CI (%) | Intra-participant CV (%) |
| Aticaprant | $C_{max}$ | 21 | 21 | 30.9 | 32.5 | 105.13 | 96.97-113.98 | 15.6 |
| | $AUC_{last}$ | 21 | 21 | 274 | 285 | 104.15 | 99.35-109.19 | 9.1 |
| | $AUC_\infty$ | 20 | 20 | 279 | 296 | 106.40 | 101.79-111.22 | 8.3 |

Note:
Log transformed PK parameters were analyzed by mixed model analysis of variance with treatment, sequence, and period as fixed effects, and participant in sequence as a random effect and the results were back-transformed using anti-logarithm.

Participants who completed all treatment periods and for which an evaluable PK parameter could be obtained in all treatment periods are included in the analysis.

N: number of participants who completed the study and for which an evaluable PK parameter could be obtained.

Intra-participant CV(%) = 100* (sqrt(exp(MSE)-1).

Treatment F: 1 × 10 mg Formulation Concept 2 administered in the morning, after at least 10-hour overnight fasting (Reference)

Treatment G: 1 × 5 mg Formulation Concept 2 administered in the morning, after at least 10-hour overnight fasting (Test)

Note:

Treatment G, Dose Normalized to 10 mg

Participants 100029 (incomplete PK profile) and 100031 (vomiting) from treatment F were excluded from the analysis.

TABLE 73

Statistical comparison results of food effect assessment with 1 × 10 mg milled API tablet when administered in the presence of high-fat diet (test) to that of fasted condition administration (reference) - Summarized statistical results for Estimated Ratio of Means and 90% Confidence Interval for Aticaprant: Treatment H/Treatment F- For completers (Food Effect); Pharmacokinetics Data Analysis Set

| | | N Treatment | | | | Geometric Means | | |
|---|---|---|---|---|---|---|---|---|
| | | | | | | Ratio of Geometric | | Intra-participant |
| Analyte | PK Parameter | F (Reference) | H (Test) | F (Reference) | H (Test) | Means (%) | 90% CI (%) | CV (%) |
| Aticaprant | $C_{max}$ | 20 | 20 | 31.3 | 33.5 | 107.30 | 97.03-118.66 | 18.6 |
| | $AUC_{last}$ | 20 | 20 | 279 | 377 | 134.90 | 128.72-141.39 | 8.6 |
| | $AUC_\infty$ | 19 | 19 | 280 | 379 | 135.55 | 129.65-141.72 | 7.9 |

Note:
Log transformed PK parameters were analyzed by mixed model analysis of variance with treatment, sequence, and period as fixed effects, and participant in sequence as a random effect and the results were back-transformed using anti-logarithm.
Participants who completed all treatment periods and for which an evaluable PK parameter could be obtained in all treatment periods are included in the analysis.
N: number of participants who completed the study and for which an evaluable PK parameter could be obtained.
Intra-participant CV(%) = 100* (sqrt(exp(MSE)-1).
Participant 100031 (vomiting) from treatment F excluded from the analysis.

What is claimed is:

1. A pharmaceutical composition in the form an oral tablet comprising about 5 mg to about 10 mg of aticaprant, wherein the oral tablet comprises a core tablet having an intragranular and extragranular phase, wherein:
   the intragranular phase comprises the aticaprant, a filler, a disintegrant, and a glidant;
   the extragranular phase comprises a filler, a disintegrant, and a lubricant; and
   the ratio of intragranular to extragranular phase is between about 1.5 and about 3 by weight.

2. The pharmaceutical composition of claim 1, wherein the intragranular phase comprises one or more of: an aticaprant to filler ratio of about 0.01 and about 1 by weight; an aticaprant to disintegrant ratio of about 0.5 to about 8 by weight; and an aticaprant to glidant ratio of about 1 to about 10 by weight.

3. The pharmaceutical composition of claim 2, wherein the extragranular phase comprises one or more of: a filler to disintegrant ratio of about 20 to about 80 by weight; and a filler to lubricant ratio of about 5 to about 100 by weight.

4. The pharmaceutical composition of claim 3, wherein the filler in the intragranular and the extragranular phase is, independently, microcrystalline cellulose, lactose monohydrate, or silicified microcrystalline cellulose, or a combination thereof.

5. The pharmaceutical composition of claim 4, wherein the disintegrant in the intragranular and the extragranular phase is, independently, croscarmellose sodium.

6. The pharmaceutical composition of claim 5, wherein the glidant is silica, colloidal anhydrous.

7. The pharmaceutical composition of claim 1, wherein the intragranular phase comprises about 50 to about 70 mg microcrystalline cellulose, about 50 to about 70 mg lactose monohydrate, about 4 to about 6 mg croscarmellose sodium, and about 1 to about 3 mg silica, colloidal anhydrous; and wherein the extragranular phase comprises about 50 to about 70 mg silicified microcrystalline cellulose, about 4 to about 6 mg croscarmellose sodium, and about 1 to about 3 mg magnesium stearate.

8. The pharmaceutical composition of claim 1, wherein the intragranular phase comprises about 60 mg microcrystalline cellulose, about 60 mg lactose monohydrate, about 5 mg croscarmellose sodium, and about 2 mg silica, colloidal anhydrous; and wherein the extragranular phase comprises about 57 mg silicified microcrystalline cellulose, about 5 mg croscarmellose sodium, and about 2 mg magnesium stearate.

9. The pharmaceutical composition of claim 1, wherein the composition has a pharmacokinetic (PK) profile comprising one or more of the following parameters after administration of the composition to a human after at least a 10-hour fast (dose-normalized to 10 mg):
   a. a mean $C_{max}$ between about 30 and 40 ng/ml;
   b. a mean $AUC_{infinity}$ between about 300 and 430 h*ng/ml;
   c. a mean $AUC_{last}$ between about 280 and 430 h*ng/ml;
   d. a median $t_{max}$ between about 1 to 4 hours.

10. The pharmaceutical composition of claim 9, wherein the mean $C_{max}$ is between about 30 and 35 ng/mL.

11. The pharmaceutical composition of claim 9, wherein the mean $AUC_{infinity}$ is between about 300 and 320 h*ng/mL.

12. The pharmaceutical composition of claim 9, wherein the mean $AUC_{last}$ is between about 280 and 310 h*ng/mL.

13. The pharmaceutical composition of claim 9, wherein the median $t_{max}$ is about 1.5 hours.

14. The pharmaceutical composition of claim 1, wherein the composition has a dissolution profile comprising a Q value of between about 60% and 90% at 45 minutes, under the following dissolution operating conditions:
   Apparatus: Paddle (USP Type 2, Ph. Eur., JP)
   Dissolution medium: 0.01 M hydrochloric acid
   Volume: 900 mL
   Temperature: 37+/−0.5 degrees Celsius
   Rotation Speed: 50 rpm
   Analytical Finish: UHPLC with UV detection at 247 nm.

15. The pharmaceutical composition of claim 14, wherein the Q value is between about 70% and 80% at 45 minutes.

16. The pharmaceutical composition of claim 14, wherein the Q value is about 75% at 45 minutes.

17. The pharmaceutical composition of claim 1, wherein the oral tablet comprises a film coat.

18. The pharmaceutical composition of claim 17, wherein the ratio of the film coat to core tablet is between about 0.03 to about 10 by weight.

19. The pharmaceutical composition of claim 18, wherein the film coat comprises a coating powder.

* * * * *